(12) United States Patent
Clark et al.

(10) Patent No.: US 6,645,775 B1
(45) Date of Patent: Nov. 11, 2003

(54) INSULIN-LIKE GROWTH FACTOR AGONIST MOLECULES

(75) Inventors: Ross G. Clark, Auckland (NZ); Henry B. Lowman, El Granada, CA (US); Iain C. A. F. Robinson, St. Albans (GB)

(73) Assignee: Genentech, Inc., South San Francisco, CA (US)

( * ) Notice: Subject to any disclaimer, the term of this patent is extended or adjusted under 35 U.S.C. 154(b) by 349 days.

(21) Appl. No.: 09/723,931

(22) Filed: Nov. 28, 2000

Related U.S. Application Data

(60) Division of application No. 09/052,888, filed on Mar. 31, 1998, now Pat. No. 6,251,865, which is a continuation-in-part of application No. 08/825,852, filed on Apr. 4, 1997, now Pat. No. 6,121,416.

(51) Int. Cl.[7] ..................... G01N 33/543; C07K 16/00; C07K 7/08
(52) U.S. Cl. ..................... 436/518; 435/7.1; 530/391.1; 530/391.3; 530/326
(58) Field of Search .......................... 436/518; 435/7.1; 530/391.1, 391.3, 326

(56) References Cited

U.S. PATENT DOCUMENTS

| | | |
|---|---|---|
| 4,411,890 A | 10/1983 | Momany |
| 4,876,242 A | 10/1989 | Applebaum et al. |
| 4,988,675 A | 1/1991 | Froesch et al. |
| 5,068,224 A | 11/1991 | Fryklund et al. |
| 5,077,276 A | 12/1991 | Ballard et al. |
| 5,093,317 A | 3/1992 | Lewis et al. |
| 5,106,832 A | 4/1992 | Froesch et al. |
| 5,126,324 A | 6/1992 | Clark et al. |
| 5,164,370 A | 11/1992 | Ballard et al. |
| 5,187,151 A | 2/1993 | Clark et al. |
| 5,202,119 A | 4/1993 | Clark et al. |
| 5,206,235 A | 4/1993 | Fisher et al. |
| 5,210,017 A | 5/1993 | Carlsson et al. |
| 5,223,409 A | 6/1993 | Ladner et al. |
| 5,273,961 A | 12/1993 | Clark |
| 5,374,620 A | 12/1994 | Clark et al. |
| 5,466,670 A | 11/1995 | Dunger et al. |
| 5,470,828 A | 11/1995 | Ballard et al. |
| 5,534,617 A | 7/1996 | Cunningham et al. |
| 5,569,648 A | 10/1996 | Lewis et al. |
| 5,593,844 A | 1/1997 | Carlsson et al. |
| 5,597,797 A | 1/1997 | Clark |
| 5,622,932 A | 4/1997 | DiMarchi et al. |
| 5,652,214 A | 7/1997 | Lewis et al. |
| 5,703,045 A | 12/1997 | Lewis et al. |
| 5,714,460 A | 2/1998 | Gluckman et al. |
| 5,776,897 A | 7/1998 | Lewis et al. |

FOREIGN PATENT DOCUMENTS

| | | |
|---|---|---|
| EP | 128733 | 12/1984 |
| EP | 135094 | 3/1985 |
| EP | 230869 | 8/1987 |
| EP | 288451 | 10/1988 |
| EP | 294021 | 12/1988 |
| EP | 369943 | 5/1990 |
| EP | 375438 | 6/1990 |
| EP | 379338 | 7/1990 |
| EP | 681842 | 11/1995 |
| EP | 742228 | 11/1996 |
| EP | 965596 | 12/1999 |
| WO | WO 89/05822 | 6/1989 |
| WO | WO 89/08667 | 9/1989 |
| WO | WO 89/09268 | 10/1989 |
| WO | WO 89/09792 | 10/1989 |
| WO | WO 91/03253 | 3/1991 |
| WO | WO 92/11865 | 7/1992 |
| WO | WO 92/15679 | 9/1992 |
| WO | WO 93/08826 | 5/1993 |
| WO | WO 93/20836 | 10/1993 |
| WO | WO 93/23071 | 11/1993 |
| WO | WO 93/25219 | 12/1993 |
| WO | WO 94/04569 | 3/1994 |
| WO | WO 94/16722 | 8/1994 |
| WO | WO 94/16723 | 8/1994 |
| WO | WO 95/07697 | 3/1995 |
| WO | WO 95/17422 | 6/1995 |
| WO | WO 95/17423 | 6/1995 |
| WO | WO 96/01124 | 1/1996 |
| WO | WO 96/15148 | 5/1996 |
| WO | WO 96/33216 | 10/1996 |
| WO | WO 96/37514 | 11/1996 |
| WO | WO 96/40189 | 12/1996 |
| WO | WO 96/40750 | 12/1996 |
| WO | WO 97/37010 | 10/1997 |
| WO | WO 97/39032 | 10/1997 |
| WO | WO 00/23469 | 4/2000 |

OTHER PUBLICATIONS

Alberts et al. *Molecular Biology of the Cell*, 3rd edition, New York:Garland Publishing, Inc. pp. 119 (1994).

Bach and Rechler, "Insulin–like Growth Factor Binding Proteins" *Diabetes Reviews* 3:38–61 (1995).

Ballard et al., "Does IGF–I Ever Act Through the Insulin Receptor?" *The Insulin–like Growth Factors and Their Regulatory Proteins*, Baxter, eds., Amsterdam: Elsevier pp. 131–138 (1994).

Bar et al., "Tissue localization of perfused endothelial cell IGF binding protein is markedly altered by association with IGF–I" *Endocrinology* 127(6):3243–3245 (1990).

(List continued on next page.)

*Primary Examiner*—David S. Romeo
(74) *Attorney, Agent, or Firm*—Janet E. Hasak, Esq.; Heller Ehrman White & McAuliffe, LLP

(57) ABSTRACT

Compounds are provided that inhibit the interaction of an IGF with any one of its binding proteins and not to a human IGF receptor. These IGF agonist compounds, which include peptides, are useful to increase serum and tissue levels of active IGFs in a mammal.

4 Claims, 44 Drawing Sheets

OTHER PUBLICATIONS

Bass et al., "Hormone Phage: An Enrichment Method for Variant Proteins with Altered Binding Properties" *Proteins: Structure, Function, and Genetics* 8(4):309–314 (1990).

Baxter & Martin, "Binding Proteins for Insulin–Like Growth Factors in Adult Rat Serum. Comparison With Other Human and Rat Binding Proteins" *Biochem. & Biophys. Res. Comm.* 147(1):408–415 (1987).

Baxter et al., "Structural determinants for binary and ternary complex formation between insulin–like growth factor–I (IGF–I) and IGF binding protein–3" *Journal of Biological Chemistry* 267(1):60–65 (Jan. 5, 1992).

Baxter, "Physiological Roles of IGF Binding Proteins" *Modern Concepts of Insulin–like Growth Factors*, Spencer, eds., Elsevier, New York pp. 371–380 (1991).

Baxter, "The somatomedins: insulin–like growth factors" *Advances in Clinical Chemistry* 25:49–115 (1986).

Baxter, R., "The Insulin–Like Growth Factors and Their Binding Proteins" *Comp. Biochem. Physiol.* 91B(2):229–235 (1988).

Bayne et al., "Structural analogs of human insulin–like growth factor I with reduced affinity for serum binding proteins and the type 2 insulin–like growth factor receptor" *Journal of Biological Chemistry* 263:6233–6239 (1988).

Bayne et al., "The C region of human insulin–like growth factor (IGF) I is required for high affinity binding to the type 1 IGF receptor" *Journal of Biological Chemistry* 264(19):11004–11008 (Jul. 5, 1989).

Bayne et al., "The roles of tyrosines 24, 31, and 60 in the high affinity binding of insulin–like growth factor–I to the type I insulin–like growth factor receptor" *Journal of Biological Chemistry* 265(26):15648–15652 (Sep. 15, 1990).

Binkert et al., "Cloning, sequence analysis and expression of a cDNA encoding a novel insulin–like growth factor binding protein (IGFBP–2)" *EMBO Journal* 8:2497–2502 (1989).

Binoux, M., "Donnees recentes sur les somatomedines (Insulin–like growth factors)" *Annales d'Endocrinologie* 41:157–192 (1980).

Bondy, C., "Clinical uses of insulin–like growth factor I" *Annals of Internal Medicine* 120:593–601 (1994).

Bowers, C. Y., "GH Releasing Peptides—Structure and Kinetics" *J. Pediatr. Endocrinology* 6(1):21–31 (1993).

Bowie et al., "Deciphering the Message in Protein Sequences: Tolerance to Amino Acid Substitutions" *Science* 247:1306–1310 (1990).

Brandt et al., "Role of natriuretic peptide clearance receptor in in vivo control of C–type natriuretic peptide" *American Journal of Physiology* 269(1 Pt 2):H326–H331 (Jul. 1995).

Brewer et al., "Cloning, Characterization, and Expression of a Human Insulin–Like Growth Factor Binding Protein" *Biochem. & Biophys. Res. Comm.* 152(3):1289–1297 (1988).

Brinkman et al., "Isolation and characterization of a cDNA encoding the low molecular weight insulin–like growth factor binding protein (IBP–1)" *The EMBO J.* 7:2417–2423 (1988).

Carlsson et al., "Growth Hormone and Growth in Diabetic Rats: Effects of Insulin and Insulin–Like Growth Factor–I Infusions" *J. Endocrinol.* 122:661–670 (1989).

Cascieri et al., "Analysis of the interaction of IGF–I analogs with the IGF–I receptor and IGF binding proteins" *Advances in Experimental Medicine & Biology* 343:33–40 (1993).

Cascieri et al., "Mutants of human insulin–like growth factor I with reduced affinity for the type 1 insulin–like growth factor receptor" *Biochemistry* 27(9):3229–3233 (May 3, 1988).

Cascieri et al., "Structural analogs of human insulin–like growth factor (IGF) I with altered affinity for type 2 IGF receptors" *Journal of Biological Chemistry* 264:2199–2202 (1989).

Charlton et al., "Growth hormone–deficient dwarfism in the rat: a new mutation" *J. of Endocrinology* 119:51–58 (1988).

Cheetham et al., "The Effects of Recombinant Human Insulin–like Growth Factor I on Growth Hormone Secretion in Adolescents With Insulin Dependent Diabetes Mellitus" *Clin. Endocrinol.* 40:515–522 (1994).

Cheetham et al., "The Effects of Recombinant Insulin–like Growth Factor I Administration on Growth Hormone Levels and Insulin Requirements in Adolescents With Type 1 (Insulin–dependent) Diabetes Mellitus" *Diabetologia* 36:678–681 (1993).

Chen et al., "Recombinant human IGF–I infusion results in transient improvement in nitrogen balance: evidence for IGF–I autoregulation" *US Endocrine Meeting* (Abstract 1596) pp. 449 (1993).

Clark et al., "Growth–Responses to Patterned GH Delivery" *Endocrine* 3:717–723 (1995).

Clark et al., "Insulin–Like Growth Factor–1 and Growth Hormone (GH) Have Distinct and Overlapping anabolic Effects in GH–Deficient Rats" *Endocrine* 3:297–304 (1995).

Clemmons and Van Wyk, "Somatomedin: physiological control and effects on cell proliferation" *Handbook Exp. Pharmacol.* 57:161–208 (1981).

Clemmons et al., "Competition for binding to insulin–like growth factor (IGF) binding protein–2, 3, 4, and 5 by the IGFs and IGF analogs" *Endocrinology* 131(2):890–895 (Aug. 1992).

Clemmons et al., "Discrete Alterations of the Insulin–like Growth Factor I Molecule Which Alter Its Affinity for Insulin–like Growth Factor–binding Proteins Result in Changes in Bioactivity" *Journal of Biological Chemistry* 265(21):12210–12216 (1990).

Cwirla et al., "Peptides on phage: a vast library of peptides for identifying ligands" *Proc. Natl. Acad. Sci. USA* 87(16):6378–6382 (1990).

Devlin et al., "Random peptide libraries: a source of specific protein binding molecules" *Science* 249:404–406 (1990).

Duerr et al., "Insulin–like growth factor–1 enhances ventricular hypertrophy and function during the onset of experimental cardiac failure" *J. Clin. Invest.* 95:619–627 (1995).

Elahi et al., "Hemodynamic and metabolic responses to human insulin–like growth factor I (IGF–I) in men" *Modern Concepts of Insulin–Like Growth Factors*, Spencer, EM, ed., New York:Elsevier Science Publ. Co. pp. 219–224 (1991).

Fielder et al., "Differential long–term effects of insulin–like growth factor–I (IGF–I) growth hormone (GH), and IGF–I plus GH on body growth and IGF binding proteins in hypophysectomized rats" *Endocrinology* 137:1913–1920 (1996).

Franklin et al., "Insulin–Like Growth Factor I Preserves Renal Function Postoperatively" *Am. J. Physiol.* 272:F257–F259 (1997).

Froesch et al., "Metabolic and Therapeutic Effects of Insulin–Like Growth Factor I" *Horm. Res.* 42:66–71 (1994).

Furnsinn et al., "Insulin–Like Growth Factor–I Inhibits Insulin and Amylin Secretion in Conscious Rats" *Endocrinology* 135(5):2144–2149 (1994).

Geysen et al., "A priori delineation of a peptide which mimics a discontinuous antigenic determinant" *Molecular Immunology* 23(7):709–715 (1986).

Ghazzi et al., "Cardiac and glycemic benefits of troglitazone treatment in NIDDM" *Diabetes* 46:433–439 (1997).

Giebel et al., "Screening of cyclic peptide phage libraries identifies ligands that bind streptavidin with high affinities" *Biochemistry* 34:15430–15435 (1995).

Guler et al., "Effects of Insulin–like Growth Factor I in Man" *Acta Paediatr. Scand.* 367:52–54 (Suppl. 1990).

Guler et al., "Effects of recombinant insulin–like growth factor I on insulin secretion and renal function in normal human subjects" *Proc. Natl. Acad. Sci. USA* 86:2868–2872 (Apr. 1989).

Guler et al., "Insulin–like growth factor I increases glomerular filtration rate and renal plasma flow in man" *Acta Endocrinologica* 121:101–106 (1989).

Guler et al., "Recombinant human insulin–like growth factor 1 stimulates growth and has distinct effects on organ size in hypophysectomized rats" *Proc. Natl. Acad. Sci. USA* 85:4889–4893 (1988).

Guler et al., "Short–term metabolic effects of recombinant human insulin–like growth factor I in healthy adults" *New England J. of Medicine* 317(3):137–140 (1987).

Hammerman and Miller, "The growth hormone insulin–like factor axis in kidney revisited" *Am. J. Physiol.* 265:F1–F14 (1993).

Hammerman and Miller, "Therapeutic use of growth factors in renal failure" *J. Am. Soc. Nephrol.* 5:1–11 (1994).

Hampton et al., "Purification and Characterization of an Insulin–like Growth Factor II Variant from Human Plasma" *Journal of Biological Chemistry* 264(32):19155–19160 (Nov. 15, 1989).

Hartman et al., "A low dose euglycemic infusion of recombinant human insulin–like growth factor I rapidly suppresses fasting–enhanced pulsatile growth hormone secretion in humans" *J. Clin. Invest.* 91:2453–2462 (1993).

Hasegawa et al., "The free form of insulin–like growth factor I increases in circulation during normal human pregnancy" *J. Clin. Endocrinol. Metabol.* 80:3284–3286 (1995).

Heding et al., "Biosensor measurement of the binding of insulin–like growth factors I and II and their analogues to the insulin–like growth factor–binding protein–3" *Journal of Biological Chemistry* 271(24):13948–13952 (Jun. 14, 1996).

Hirschberg et al., "Effects of insulin–like growth factor I on renal function in normal men"0 *Kidney International* 43:387–397 (1993).

Hizuka et al., "Measurement of free form of insulin–like growth factor I in human plasma" *Growth Regulation* 1:51–55 (1991).

Humbel, "Insulin–like growth factors I and II" *European Journal of Biochemistry* 190:445–462 (1990).

Jabri et al., "Adverse effects of recombinant human insulin–like growth factor I in obese insulin–resistant type II diabetic patients" *Diabetes* 43:369–374 (1994).

Johnson et al., "Underexpression of β cell high $K_m$ glucose transporters in noninsulin–dependent diabetes" *Science* 250:546–549 (1990).

Jones et al., "Insulin–Like Growth Factors and Their Binding Proteins: Biological Actions" *Endocrine Reviews* 16(1):3–34 (1995).

Juul et al., "Serum concentrations of free and total insulin–like growth factor–I, IGF binding proteins –1 and –3 and IGFBP–3 protease activity in boys with normal or precocious puberty" *Clin. Endocrinology* 44:515–523 (1996).

Kay et al., "An M13 phage library displaying random 38–amino–acid peptides as a source of novel sequences with affinity to selected targets" *Gene* 128:59–65 (1993).

Kerr et al., "Effect of Insulin–like Growth Factor 1 on the Responses to and Recognition of Hypoglycemia" *Diabetes: American Diabetes Association (ADA), San Antonio, Texas, Jun. 20–23, 1992* (abstract #225), 52nd Annual Meeting edition 41(supp 1):60A (Jun. 1992).

Kerr et al., "Effect of Insulin–like Growth Factor–1 on the Responses to and Recognition of Hypoglycemia in Humans" *J. Clin. Invest.* 91:141–147 (1993).

Kletzien et al., "Enhancement of adipocyte differentiation by an insulin–sensitizing agent" *Molecular Pharmacology* 41(2):393–398 (Feb. 1992).

Kupfer et al., "Enhancement of the anabolic effects of growth hormone and insulin–like growth factor I by use of both agents simultaneously" *J. Clin Invest.* 91:391–396 (1993).

Kuzuya et al., "Trial of insulinlike growth factor I therapy for patients with extreme insulin resistance syndromes" *Diabetes* 42:696–705 (1993).

Lassalle et al., "ESM–1 is a novel human endothelial cell–specific molecule expressed in lung and regulated by cytokines" *Journal of Biological Chemistry* 271:20458–20464 (1996).

Leahy et al., "Insulin–Like Growth Factor–I at Physiological Concentrations is a Potent Inhibitor of Insulin Secretion" *Endocrinology* 126(3):1593–1598 (1990).

Lee et al., "Insulin–Like Growth Factor (IGF) Binding Protein Complementary Deoxyribonucleic Acid from Human HEP G2 Hepatoma Cells: Predicted Protein Sequence Suggests an IGF Binding Domain Different from Those of the IGF–I and IGF–II Receptors" *Mol. Endocrinol.* 2(5):404–411 (1988).

Lee et al., "Regulation and function of insulin–like growth factor–binding protein–1" *Proc. Soc. Exp. Biol. & Med.* 204:4–29 (1993).

Leung et al., "Growth hormone receptor and serum binding protein: purification, cloning and expression" *Nature* 330:537–543 (1987).

Lewitt and Baxter, "Insulin–like growth factor–binding protein–1: a role in glucose counterregulation?" *Mol. Cell. Endocrinology* 79(1–3):C147–C152 (1991).

Lewitt et al., "Bioavailability of insulin–like growth factors (IGFs) in rats determined by the molecular distribution of human IGF–binding protein–3" *Endocrinology* 133:1797–1801 (1993).

Lewitt et al., "Insulin–like Growth Factor–binding Protein–1 Modulates Blood Glucose Levels" *Endocrinology* 129 (4):2254–2256 (1991).

Lieberman et al., "Anabolic effects of recombinant insulin–like growth factor I in AIDS–associated cachexia" *US Endocrine Meeting* (Abstract 1664) pp. 466 (1993).

Lieberman et al., "Anabolic effects of recombinant insulin–like growth factor–I in cachectic patients with the acquired immunodeficiency syndrome" *J. Clin. Endocrinol. and Metab.* 78(2):404–410 (1994).

Lieberman et al., "Effects of recombinant human insulin–like growth factor–I (rhIGF–I) on total and free IGF–I concentrations, IGF–binding proteins, and glycemic response in humans" *J. Clin. Endocrinol. and Metab.* 75(1)30–36 (1992).

Livnah et al., "Functional mimicry of a protein hormone by a peptide agonist: the EPO receptor complex at 2.8 A" *Science* 273(5274):464–471 (Jul. 26, 1996).

Loddick et al., "Displacement of insulin–like growth factors from their binding proteins as a potential treatment for stroke" *Proc. Natl. Acad. Sci. USA* 95(4):1894–1898 (Feb. 17, 1998).

Lowman et al., "Molecular mimics of insulin–like growth factor 1 (IGF–1) for inhibiting IGF–1: IGF–binding protein interactions" *Biochemistry* 37(25):8870–8878 (1998).

Maack et al., "Physiological Role of Silent Receptors of Atrial Natriuretic Factor" *Science* 238:675–678 (Oct. 30, 1987).

Martin & Baxter, "Insulin–like Growth Factor–binding Protein from Human Plasma. Purification and Characterization" *Journal of Biological Chemistry* 261(19):8754–8760 (1986).

McLafferty et al., "M13 bacteriophage displaying disulfide–constrained microproteins" *Gene* 128:29–36 (1993).

Miller et al., "Effects of IGF–I on renal function in end–stage chronic renal failure" *Kidney International* 46:201–207 (1994).

Morrow et al., "Recombinant Human (rh) IGF–1 Reverses Hyperglycemia and Improved Insulin Sensitivity in Severe Insulin Resistance" *Diabetes—53rd Annual Meeting, Jun. 12–15, 1993* (abstract No. 269) 42:83A (Suppl. 1 1993).

O'Neil et al., "Identification of novel peptide antagonists for GPIIb/IIIa from a conformationally constrained phage peptide library" *Proteins: Structure, Function, and Genetics* 14:509–515 (1992).

O'Shea and Layish, "Growth hormone and the kidney: a case presentation and review of the literature" *J. Am. Soc. Nephrol.* 3:157–161 (1992).

O'Shea et al., "Effects of IGF–I on renal function in patients with chronic renal failure" *Am. J. Physiol.* 264:F917–F922 (1993).

Oh et al., "Characterization of the affinities of insulin–like growth factor (IGF)–binding proteins 1–4 for IGF–I, IGF–II, IGF–I/insulin hybrid, and IGF–I analogs" *Endocrinology* 132:1337–1344 (1993).

Oh et al., "Synthesis and characterization of insulin–like growth factor–binding protein (IGFBP)–7. Recombinant human mac25 protein specifically binds IGF–I and –II" *Journal of Biological Chemistry* 271:30322–30325 (1996).

Oldenburg et al., "Peptide ligands for a sugar–binding protein isolated from a random peptide library" *Proc. Natl. Acad. Sci.* 89:5393–5397 (1992).

Peterkofsky et al., "Elevated Activity of Low Molecular Weight Insulin–Like Growth Factor–Binding Proteins in Sera of Vitamin C–Deficient and Fasted Guinea Pigs" *Endocrinology* 128(4):1769–1779 (1991).

Quin et al., "Acute Response to Recombinant Insulin–like Growth Factor I in a Patient with Mendenhall's Syndrome" *New England J. of Medicine* 323:1425–1426 (1990).

Rinderknecht and Humbel, "Polypeptides with nonsuppressible insulin–like and cell–growth promoting activities in human serum: isolation, chemical characterization, and some biological properties of forms I and II" *Proc. Natl. Acad. Sci. USA* 73(7):2365–2369 (1976).

Rinderknecht and Humbel, "The amino acid sequence of human insulin–like growth factor I and its structural homology with proinsulin" *Journal of Biological Chemistry* 253(8):2769–2776 (1978).

Ross et al., "The Role of Insulin, Growth Hormone and IGF–I as Anabolic Agents in the Critically Ill" *Intensive Care Med.* 19(2):S54–S57 (Suppl. 1993).

Rudinger, J., "Characteristics of the Amino Acids as Components of a Peptide Hormone Sequence" *Peptide Hormones*, J.A. Parsons, Baltimore:University Park Press pp. 1–7 (1976).

Saad et al., "Low–doses of Insulin–like Growth Factor–I Improve Insulin Sensitivity" *Diabetologia* (Abstract 152) 37:A40 (Supp. 1 1994).

Schalch et al., "Short–Term Effects of Recombinant Human Insulin–Like Growth Factor I on Metabolic Control of Patients with Type II Diabetes Mellitus" *J. of Clinical Endocrinology & Metabolism* 77(6):1563–1568 (1993).

Schalch et al., "Short–term metabolic effects of recombinant human insulin–like growth factor I (rhIGF–I) in type II diabetes mellitus" *Modern Concepts of Insulin–Like Growth Factors,* Spencer, ed., New York:Elsevier Science Publ. Co. pp. 705–713 (1991).

Schoen et al., "Growth Hormone Secretagogues" *Annual Reports in Medicina Chemistry: Section IV—Immunology, Endocrinology & Metabolic Diseases*, William K. Hagmann, Chapter 19, vol. 28:177–186 (1993).

Schoenle et al., "Recombinant human insulin–like growth factor I(rhIGF I) reduces hyperglycaemia in patients with extreme insulin resistance" *Diabetologia* 34:675–679 (1991).

Scott and Smith, "Searching for peptide ligands with an epitope library" *Science* 249:386–390 (1990).

Sherwin et al., "Metabolic Effects of Insulin–like Growth Factor I in Normal Humans" *Horm. Res.* 41:97–101 (Suppl. 2 1994).

Skottner et al., "Growth responses in a mutant dwarf rat to human growth hormone and recombinant human insulin–like growth factor I" *Endocrinology* 124(5):2519–2526 (1989).

Smith, "Filamentous fusion phage: novel expression vectors that display cloned antigens on the virion surface" *Science* 228 (4705):1315–1317 (1985).

Stern et al., "Insulin resistance and pancreatic insulin release in the genetically obese Zucker rat" *Proc. Soc. Exp. Biol. Med.* 139:66–69 (1972).

Suikkari et al., "Insulin regulates the serum levels of low molecular weight insulin–like growth factor–binding protein" *J. Clin. Endocrinology Metabol.* 66:266–272 (1988).

Swisshelm et al., "Enhanced expression of an insulin growth factor–like binding protein (mac25) in senescent human mammary epithelial cells and induced expression with retinoic acid" *Proc. Natl. Acad. Sci.* 92:4472–4476 (1995).

Takano et al., "Effects of sc Administration of Recombinant Human Insulin–like Growth Factor I (IGF–I) on Normal Human Subjects" *Endocrinol. Japan* 37(2):309–317 (1990).

Tanner et al., "Comparative rapidity of response of height, limb muscle and limb fat to treatment with human growth hormone in patients with and without growth hormone deficiency" *Acta Endocrinologica* 84:681–696 (1977).

Underwood et al., "Regulation of somatomedin–c/insulin–like growth factor I by nutrients" *Hormone Res.* 24:166–176 (1986).

Usala et al., "Brief report: treatment of insulin–resistant diabetic ketoacidosis with insulin–like growth factor I in an adolescent with insulin–dependent diabetes" *New England J. of Medicine* 327(12):853–857 (1992).

Uthne et al., "Effects of human somatomedin preparations on membrane transport and protein synthesis in the isolated rat diaphram" *J. Clin. Endocrinol. Metab.* 39(3):548–554 (1974).

Van Wyk et al., "The somatomedins: a family of insulinlike hormones under growth hormone control" *Recent Prog. Horm. Res.* 30:259–318 (1974).

Vlachopapadopoulou et al., "Metabolic and Clinical Response to Recombinant Human Insulin–like Growth Factor I in Myotonic Dystrophy—A Clinical Research Center Study" *J. Clin. Endo. Metab.* 80(12):3715–3723 (1995).

Wells and Lowman, "Rapid Evolution of Peptide and Protein Binding Properties in Vitro" *Curr. Opin. Struct. Biol.* 2:597–604 (1992).

Wilton et al., "Treatment with recombinant human insulin–like growth factor I of children with growth hormone receptor deficiency (Laron syndrome)" *Acta Paediatr Supp* 383:137–142 (1992).

Wood et al., "Cloning and expression of the growth hormone–dependent insulin–like growth factor–binding protein" *Molecular Endocrinology* 2:1176–1185 (1988).

Wood et al., "Crystal structure analysis of deamino–oxytocin: conformational flexibility and receptor binding" *Science* 232:633–636 (1986).

Wrighton et al., "Small peptides as potent mimetics of the protein hormone erythropoietin" *Science* 273:458–463 (1996).

Yamauchi et al., "Purification and molecular cloning of prostacyclin–stimulating factor from serum–free conditioned medium of human diploid fibroblast cells" *Biochemical Journal* 303(Part 2):591–598 (1994).

Zenobi et al., "Effects of insulin–like growth factor–I on glucose tolerance, insulin levels, and insulin secretion" *J. Clin. Invest.* 89:1908–1913 (1992).

Zenobi et al., "Insulin–like growth factor–I improves glucose and lipid metabolism in type 2 diabetes mellitus" *J. Clin. Invest.* 90:2234–2241 (1992).

FIG. 1

Nucleotide and Amino Acid Sequence of the LamB Signal Sequence and IGF-I (Y24L,Y31A)

plasmid IGFMI
length: 5115 (circular)

```
   1 GAATTCAACT TCTCCATACT TTGGATAAGG AAATACAGAC ATGAAAAATC TCATTGCTGA GTTGTTATTT AAAAAGAAGA AGAGTCGAAT
     CTTAAGTTGA AGAGGTATGA AACCTATTCC TTTATGTCTG TACTTTTTAG AGTAACGACT CAACAATAAA TTCGAACGG TCTCAGCTTA

101 GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
     CTTGACACAC GCGTCCATCT TCGAAACCTC TAATAGCAGT GACGTTACGA AGCGTTATAC CGCGTTTTAC TGGTTGTGC CAACTAACTA GTCCATCTCC

201 GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
     CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCACG AGTGTCATAA ATAGTCGCTT GCCGAGACTT ATAGTCGCTT TGTTTTTATT TTTTAATGTA GTACGCAAGT
     TTTTCAATTA GAAAAGTGT CGACAGTGT TCAACAGTAT TATCAGCGAA CGGCTCTGAA ACAAAAATAA AAAATTACAT CATGCGTTCA

401 TCACGTAAAA AGGGTATCTA GAATTATGAT GATTACTCTG CGCAAACTTC CTCTGGCGGT ATGTCGCGCA GCGGGCGTAA GGCCATGGCC
 1   AGTGCATTTT TCCCATAGAT CTTAATACTA CTAATGAGAC GCGTTTGAAG GAGACCGCCA TACAGCGCGT CGCCCGCATT CCGGTACCGG
     .            MetMe tIleThrLeu ArgLysLeuP roLeuAlaVa lAlaValAla AlaGlyValM nAlaMetAla

501 GGTCCCGAAA CTCTGTGCGG TGCTGAACTG GTTGACGTCG TGCAGTTCGT ATGTGGTGAT CGAGGCTTCC TGTTCAACAA ACCGACTGGG GCTGGATCCT
 26  CCAGGGCTTT GAGACACGCC ACGACTTGAC CAACTGCAGC ACGTCAAGCA TACACCACTA GCTCCGAAGG ACAAGTTGTT TGGCTGACCC CGACCTAGGA
     GlyProGluT hrLeuCysGl yAlaGluLeu ValAspAlaL euGlnPheVa lCysGlyAsp ArgGlyPheL euPheAsnLy sProThrGly AlaGlySerSer

601 CCTCTCGTCG TGCTCCCCAG ACTGGTATTG TTGACGAATG CTGCTTTCGT TCTTGCGACC TCTGTTGTGT ACGCAGCAGA TGCGTCGTCT GAAAATGTAT TGCGCTCCCC TGAAACCCGC
 60  GGAGAGCAGC ACGAGGGGTC TGACCATAAC AACTGCTTAC GACGAAAGCA AGAACCTGG ACGACGACGT ACGCAGCACA CCTTTACTA ACGCGAGGGG ACTTTGGCCG
     SerArgAr gAlaProGln ThrGlyIleV alAspGluLy sCysPheArg SerCysAspL euCysAspL euArgArgLe uGluMetTyr CysAlaProL euLysProAla

701 TAGAAGCTCC TAGAAATTGT CGCGCCGG TTGCCGCTCG GCGTTTTTA TTGTTAACTC ATGTTTGACA GCTTATCATC GATAAGCTTT AATGCGGTAG
 93  ATCTTCGAGG ATTGCTAAC GA ATGCGGGGCC AACGGGCGCC CGCAAAAAAT AACAATTGAG TACAAACTGT CGAATAGTAG CTATTCGAAA TTACGCCATC
     LysSerAla Am*

801 TTTATCACAG TTAAATTGCT AACGCAGTCA GGCACCGTGT ATGAAATCTA ACAATGCGCT CATCGTCATC CTCGGCACCG TCACCCTGGA TGCTGTAGGC
     AAATAGTGTC AATTTAACGA TTGCGTCAGT CCGTGGCACA TACTTTAGAT TGTTACGCGA GTAGCAGTAG GAGCCGTGGC AGTGGGACCT ACGACATCCG

901 ATAGGCTTGG TTATGCCGGT ACTGCCGGGC CTCTTGCGGG ATATCGTCCA TTCCGACAGC ATCGCCAGTC AGGCTCAAGG ACTATGGGCT GCTGCTAGCC CTATATGCGT
     TATCCGAACC AATACGGCCA TGACGGCCCA GAGAACGCCC TATAGCAGGT AAGGCTGTCG TAGCGGTCAG TCCGAGTTCC TGATACCGA CGACGATCGC GATATACGCA

1001 TGATGCAATT TCTATGCGCA CCCGTTCTCG GAGCACTGTC TAACGCCGCC GGCGCCGCCC CAGTCCTGCT CGCTTCGCTA CTTGGAGCCA CTATCGACTA
     ACTACGTTAA AGATACGCGT GGGCAAGAGC CTCGTGACAG ATTGCGGCGG CCGCGGCGGG GTCAGGACGA GCGAAGCGAT GAACCTCGGT GATAGCTGAT
```

FIG. 3A

```
1101  CGCGATCATG GCGACCACAC CCGTCCTCTG GATCCTCTAC GCCGACGCA TCGTGGCCGG CATCACCGGC GCCACAGGTG CGGTTGCTGG CGCCTATATC
      GCGCTAGTAC CGCTGGTGTG GGCAGGACAC CTAGGAGATG CGGCCTGCGT AGCACCGCC CGTAGTGGCCG CGTGTCCAC GCCAACGACC GCGGATATAG

1201  GCCGACATCA CCGATGGGGA AGATCGGGCT CGCCACTTCG GGCTCATGAG TCGTTGTTTC GGCGTGGGTA TGGTGGCAGG CCCCTGGGCC GGGGGACTGT
      CGGCTGTAGT GGCTACCCCT TCTAGCCCGA GCGGTGAAGC CCGAGTACTC AGCAACAAAG CCGCACCCAT ACCACCGTCC GGGGCACCGG CCCCCTGACA

1301  TGGGCGCCAT CTCCTTGCAT GCACCATTCC TTGCGGCGGC GGTGCTCAACC GGCCTCAACC TACTACTGGG CTGCTTCCTA ATGCAGGAGT CGCATAAGGG
      ACCCGCGGTA GAGGAACGTA CGTGGTAAGG AACGCCGCCG CCACGAGTTG CCGGAGTTGG ATGATGACCC GACGAAGAT TACGTCCTCA GCGTATTCCC

1401  AGAGCGTCGA CCGATGCCCT TGAGAGCCTT CAAACCCAGTC GGTGGGCGCG AGCTCCTTCC GGGCATGACT ATCGTCGCCG CACTTATGAC TGTCTTCTTT
      TCTCGCAGCT GGCTACGGGA ACTCTCGGAA GTTGGGTCAG CCACCCGCGC TCGAGGAAGG CCCGTACTGA TAGCAGCGGC GTGAATACTG ACAGAAGAAA

1501  ATCATGCAAC TCGTAGGACA GGTGCCGGCA GCGCTCTGGG TCATTTTCGG CGAGGACCGC TTTCGCTGAA GCGCGACGAT GATCGGCCTG TCGCTTGCGG
      TAGTACGTTG AGCATCCTGT CCACGGCCGT CGCGAGACCC AGTAAAAGCC GCTCCTGGCG AAAGCGACTT CGCGCTGCTA CTAGCCGGAC AGCGAACGCC

1601  TATTCGGAAT CTTGCACGCC CTCGCCTCAA TGGTCCCGCC ACCAAACGTT TCGGCGAGAA GCAGGCCATT ATCGCCCGGCA TGGCGCCGA ACCCGCGGCT
      ATAAGCCTTA GAACGTGCGG GAGCGAGTTC GGAAGCAGTG TGGTTTGCAA AGCCGCTCTT CGTCCGGTAA TAGCGGCCCGT ACCGGCGGCT

1701  CGCGCTGGGC TACGTCTTGC TGGCGTTCGC GACGCGAGGC TGGATGGCCT TCCCCATTAT GATTCTTCTC GCTTCCGGCG GCATCGGGAT GCCCGCGTTG
      GCGCGACCCG ATGCAGAACG ACCGCAAGCG CTGCGCTCCG ACCTACCGGA AGGGGTAATA CTAAGAAGAG CGAAGGCCGC CGTAGCCCTA CGGGCGCAAC

1801  CAGGCCATGC TGTCCAGGCA GGTAGATGAC GACCATCAGG GACAGCTTCA AGGATCGCTC CCAGCTCTTA GCGGCTCTTA CCAGCCTAAC TTCGATCACT GACCGCTGA
      GTCCGGTACG ACAGGTCCGT CCATGCTACTG CTGTCGAAGT TCCTAGCGAG GGTTAGGAGT CGCCGAGAAT GGTCGGATTG AAGCTAGTGA CCTGGCGACT

1901  TCGTCACGGC GATTTATGCC GCCTCGGGCA GCACATGGAA TGGATTGTGAG AACCTAACATC GCGCCGCCCT ATACCTTGTC TGCCTCCCCG CGTTGCGTCG
      AGCAGTGCCG CTAAATACGG CGGAGCCGCT CGTGTACCTT GCCCAACCGT ACCTAACATG CGCCGGGGA TATGGAACAG ACGGAGGGGC GCAACGCAGC

2001  CGGTGCATGG AGCCGGGCCA CCTCGACCTG CGGCGCACCT CGCTAACGGA TTCACCACTC CAAGAATTGG AGCCAATCAA TTCTTGCGGA
      GCCACGTACC TCGGCCCCGT GGAGCTGGAC GCCGCGTGGA GCGATTGCCT AAGTGGTAGG GTTCTTAACC TCGGTTAGTT AAGAACGCCT

2101  GAACTGTGAA TGCGCAAACC AACCCTTGGC AGAACATATC GCCATCTCCA GCAGCCGCAC GCGGCGATC TCGGGCAGCG TTGGGTCCTG
      CTTGACACTT ACGCGTTTGG TTGGGAACCG TCTTGTATAG CGGTAGAGGT CGTCGGCGTG CGCCGGTAG AGCCCGTCGC AACCCAGGAC

2201  GCCACGGGTG CGCATGATCG TGCTCCTGTC GTTGAGGACC CGGCTAGGCT GGCGGGGGTTG CCTTACTGGT TAGCAGAATG ACGGAGGCGA AATCACCGAT
      CGGTGCCCAC GCGTACTAGC ACGAGGACAG CAACTCCTGG CCGATCCGA CCGCCCCAAC GGAATGACCA ATCGTCTTAC TGCCTCTCGT TTAGTGGCTA

2301  ACGTGAAGCG ACTGCTGCTG CAAAACGTCT GCGACCTGAG GGCGACCCTG CAACAACATG GGTTTCCGTG TTTCGTAAAG TCTGGAAACG CGGAAGTCAG
      TGCACTTCGC TGACGACGAC GTTTTGCAGA CGCTGGACTC CCGCTGGGAC GTTGTTGTAC CCAAGGCAC AAAGCATTTC AGACCTTTGC GCCTTCAGTC

2401  CGCCCTGCAC CATTATGTTC CGGATCTGCA TCGCAGGATG CCCTGTGAA CACCTACATC TGTATTAACG AAGCGCTGGC ATTGACCCTG
      GCGGGACGTG GTAATACAAG GCCTAGACGT AGCGTCCTAC GACGACGAT GGGACACCTT GTGGATGTAG ACATAATTGC TTCGCGACCG TAACTGGGAC
```

FIG. 3B

```
2501  AGTGATTTTT CTCTGGTCCC GCCGCATCCA TACCGCCAGT TGTTTACCCT CACAACGTTC CAGTAACCGG GCATGTTCAT CATCAGTAAC CCGTATCGTG
      TCACTAAAAA GAGACCAGGG CGGCGTAGGT ATGGCGGTCA ACAAATGGGA GTGTTGCAAG GTCATTGGCC CGTACAAGTA GTAGTCATTG GGCATAGCAC

2601  AGCATCCCTCT CTCGTTTCAT CGGTATCATT ACCCCATGA ACAGAAATTC CCCCTTACAC GGAGGCATCA AGTGACCAAA CAGGAAAAAA CCGCCCTTAA
      TCGTAGGAGA GAGCAAAGTA GCCATAGTAA TGGGGGTACT TGTCTTTAAG GGGGAATGTG CCTCCGTAGT TCACTGGTTT GTCCTTTTT  GGCGGGAATT

2701  CATGGCCCGC TTTATCAGAA GCCAGACATT AACGCTTCTG GAGAAACTCA ACGAGCTGGA CGGGATGAA  CAGGCAGACA TCTGTGAATC GCTTCACGAC
      GTACCGGGCG AAATAGTCTT CGGTCTGTAA TTGCGAAGAC CTCTTTGAGT TGCTCGACCT GCCCTACTTT GTCCGTCTGT AGACACTTAG CGAAGTGCTG

2801  CACGCTGATG AGTTTTACCG CAGCTGCCTC GCGCGTTTCG GTGATGACGG TGAAAACCTC TGACACATGC AGCTCCCGGA GACGGTCACA GCTTGTCTGT
      GTGCGACTAC TCGAAATGGC GTCGACGGAG CGCGCAAAGC CACTACTGCC ACTTTTGGAG ACTGTGTACG TCGAGGGCCT CTGCCAGTGT CGAACAGACA

2901  AAGCGGATGC CGGGAGCAGA CAAGCCCGTC AGGGCGCGTC AGCGGGTGTT GGGGCGCAGC CATGACCCAG TCACGTAGCG ATAGCGGAGT
      TTCGCCTACG GCCCTCGTCT GTTCGGGCAG TCCGCGCAG  CCCCCACAA  CCGGCACGTCG GTACTGGGTC AGTGCATCGC TATCGCCTCA

3001  GTATACTGGC TTAACTAGCC GGCATCAGAG CAGATTGTAC TGAGAGTGCA TGTGAAATAC CGCACAGATG CGTAAGGAGA AAATACCGCA
      CATATGACCG AATTGATCGG CCGTAGTCTC GTCTAACATG ACTCTCACGT ACACTTTATG GCGTGTCTAC GCATTCCTCT TTTATGGCGT

3101  TCAGGCGCTC TTCCGCTTCC ACTCGCTGCG CTCGGTCGTT CGGCTGCGGC AGCTCACTCA AAGGCCGTAA TACGGTTATC
      AGTCCGCGAG AAGGCGAAGG TGAGCGACGC GAGCCAGCAA GCCGACGCCG TCGAGTGAGT TTCCGGCATT ATGCCAATAG

3201  CACAGAATCA GGGGATAACG CAGGAAAGAA CATGTGAGCA AAAGGCCAGC GAACCGTAAA AAGGCCGCGT TGCTGGCGTT TTTCCATAGG
      GTGTCTTAGT CCCCTATTGC GTCCTTTCTT GTACACTCGT TTTCCGGTCG CTTGGCATTT TTCCGGCGCA ACGACCGCAA AAAGGTATCC

3301  CTCCGCCCCC CTGACGAGCA TCACAAAAAT CGACGCTCAA GTCAGAGGTG GCGAAACCCG ACAGGACTAT AAAGATACCA GGCGTTTCCC CCTGGAAGCT
      GAGGCGGGGG GACTGCTCGT AGTGTTTTTA GCTGCGAGTT CAGTCTCCAC CGCTTTGGGC TGTCCTGATA TTTCTATGGT CCGCAAAGGG GGACCTTCGA

3401  CCCTCGTGCG CTCTCCTGTT CCGACCCTGC CGCTTACCGG ATACCTGTCC GCCTTTCTCC CTTCGGGAAG CGTGGCGCTT TCTCATAGCT CACGCTGTAG
      GGGAGCACGC GAGAGGACAA GGCTGGGACG GCGAATGGCC TATGGACAGG CGGAAAGAGG GAAGCCCTTC GCACCGCGAA AGAGTATCGA GTGCGACATC

3501  GTATCTCAGT TCGGTGTAGG TCGTTCGCTC CAAGCTGGGC TGTGTGCACG AACCCCCCGT TCAGCCCGAC CGCTGCGCCT TATCCGGTAA CTATCGTCTT
      CATAGAGTCA AGCCACATCC AGCAAGCGAG GTTCGACCCG ACACACGTGC TTGGGGGGCA AGTCGGGCTG GCGACGCGGA ATAGGCCATT GATAGCAGAA

3601  GAGTCCAACC CGGTAAGACA CGACTTATCG CCACTGGCAG CAGCCACTGG TAACAGGATT AGCAGAGCGA GGTATGTAGG CGGTGCTACA GAGTTCTTGA
      CTCAGGTTGG GCCATTCTGT GCTGAATAGC GGTGACCGTC GTCGGTGACC ATTGTCCTAA TCGTCTCGCT CCATACATCC GCCACGATGT CTCAAGAACT

3701  AGTGGTGGCC TAACTACGGC TACACTAGAA GGACAGTATT TGGTATCTGC GCTCTGCTGA AGCCAGTTAC CTTCGGAAAA AGAGTTGGTA GCTCTTGATC
      TCACCACCGG ATTGATGCCG ATGTGATCTT CCTGTCATAA ACCATAGACG CGAGACGACT TCGGTCAATG GAAGCCTTTT TCTCAACCAT CGAGAACTAG
```

FIG. 3C

```
3801 CGGCAAACAA ACCACCGCTG GTAGCGGTGG TTTTTTTGTT TGCAAGCAGC AGATTACGCG CAGAAAAAAA GGATCTCAAG AAGATCCTTT GATCTTTTCT
     GCCGTTTGTT TGGTGGCGAC CATCGCCACC AAAAAAACAA ACGTTCGTCG TCTAATGCGC GTCTTTTTTT CCTAGAGTTC TTCTAGGAAA CTAGAAAAGA

3901 ACGGGGTCTG ACGCTCAGTG GAACGAAAAC TCACGTTAAG GGATTTTGGT CATGAGATTA TCAAAAAGGA TCTTCACCTA GATCCTTTTA AATTAAAAAT
     TGCCCCAGAC TGCGAGTCAC CTTGCTTTTG AGTGCAATTC CCTAAAACCA GTACTCTAAT AGTTTTTCCT AGAAGTGGAT CTAGGAAAAT TTAATTTTTA

4001 GAAGTTTTAA ATCAATCTAA AGTATATATG GTCTGACAGT TACCAATGCT TAATCAGTGA GGCACCTATC TCAGCGATCT GTCTATTTCG
     CTTCAAAATT TAGTTAGATT TCATATATAC CAGACTGTCA ATGGTTACGA ATTAGTCACT CCGTGGATAG AGTCGCTAGA CAGATAAAGC

4101 TTCATCCATA GTTGCCTGAC TCCCCGTCGT GTAGATAACT ACGATACGGG AGGGCTTACC ATCTGGCCCC AGTGCTGCAA TGATACCGCG AGACCACGC
     AAGTAGGTAT CAACGGACTG AGGGGCAGCA CATCTATTGA TGCTATGCCC TCCCGAATGG TAGACCGGGG TCACGACGTT ACTATGGCGC TCTGGTGCG

4201 TCACCGGCTC CAGATTTATC AGCAATAAAC CAGCCAGCCG GAAGGGCCGA GCGCAGAAGT GGTCCTGCAA CTTTATCCGC CTCCATCCAG TCTATTAATT
     AGTGGCCGAG GTCTAAATAG TCGTTATTTG GTCGGTCGGC CTTCCCGGCT CGCGTCTTCA CCAGGACGTT GAAATAGGCG GAGGTAGGTC AGATAATTAA

4301 GTTGCCGGGA AGCTAGAGTA AGTAGTTCGC CAGTTAATAG TTTGCGCAAC GTTGTTGCCA TTGCTGCAGG CATCGTGGTG TCACGCTCGT CGTTTGGTAT
     CAACGGCCCT TCGATCTCAT TCATCAAGCG GTCAATTATC AAACGCGTTG CAACAACGGT AACGACGTCC GTAGCACCAC AGTGCGAGCA GCAAACCATA

4401 GGCTTCATTC AGCTCCGGTT CCCAACGATC AAGGCGAGTT ACATGATCCC CATGTTGTGC AAAAAAGCG GTTAGCTCCT CATCCGTAAG GATCGTTGTC
     CCGAAGTAGG TCGAGGCCAA GGGTTGCTAG TTCCGCTCAA TGTACTAGGG GTACAACAC GTTTTTTTCGC CAATCGAGGA GTAGGCATTC CTAGCAACAG

4501 AGAAGTAAGT TGGCCGCAGT GTTATCACTC ATGGCGGGCG ATATGCGGCG GTATGGTATGT CTCTTGCCCGG TCTTACCGCT ACTGTCATGC GTGACTGGTG
     TCTTCATTCA ACCGGCGTCA CAATAGTGAG TACCAATACC CATACGCCGC CATACCATATCA GAGAACGGGCC AGAATGGCGA TGACAGTACG CACTGACCAC

4601 AGTACTCAAC CAAGTCATTC TGAGAATAGT GTATGCGGCG ACCGAGTTGC TCTTGCCCGG TCTTACCGCT GTTGAGATCC AACCTAGG GCGCCACATA GCAGAACTTT
     TCATGAGTTG GTTCAGTAAG ACTCTTATCA CATACGCCGC TGGCTCAACG AGAACGGGCC AGAATGGCGA CAACTCTAGG TCAAGCTACA CGTCTTGAAA

4701 AAAAGTGCTC ATCATTGGAA AACGTTCTTC TGGCAAGGAA AGCAAAAC AGGAAGGCAA AATGCCGCAA AAAAGGGAAT GCGCACCAAC TGCACCCAAC
     TTTTCACGAG TAGTAACCTT TTGCAAGAAG ACCGTTCCTT TCGTTTTG TCCTTCCGTT TTACGGCGTT TTTCCCTTA ACGTGGGTTG ACGTGGGTTG

4801 TGATCTTCAG CATCTTTAC AATAAACAGC GTTCTCGGGT ATTGCAAGGA CTCGTGGTT CAAAGACCCA CTCCTGGT GAGCAAGGCAA AAGGGCAGCA CGGAAAATGTT
     ACTAGAAGTC GTAGAAGATG AAAGTGGTCG CAACTGTTT GACGTGCTT GAGTTCCCGTTT TGAGATCCTT GCTGAGCCAA AAGTTCCCGGTT GCCCTTACAA

4901 GAATACTCAT ACTCTTCCTT TTTCAATATT ATTGAAGCAT TAACTTCGTA TATCAGGGT TATTGTCTCA TGAGCGGATA CATATTTGAA TGTATTTAGA AAATAAACA
     CTTATGAGTA TGAGAAGGAA AAAGTTATAA TAACTTCGTA AATGTGCCA ATAACAGAGT ACTCGCCTAT GTATAACTT ACATAAATCT TTTTATTTGT

5001 AATAGGGGTT TTCCCCGAAA CCGCGCACAT AGTGCCTAAG GACGTCTAAG AAACCATTAT TATCATGACA TTAACCTATA AAAATAGGCG TATCACGAGG
     TTATCCCCAA AAGGGGCTTT GGCGCGTGTA TCACGGATTC CTGCAGATTC TTTGGTAATA ATAGTACTGT AATTGGATAT TTTATCCGC ATAGTGCTCC

5101 CCCTTTCGTC TTCAA
     GGGAAAGCAG AAGTT
```

FIG. 3D

—□— Control    —●— IGF-Mutant

- ● — IGF-1 (150 μg, tid)
- □ — IGF Mutant (150 μg, tid)
- ○ — IGF Mutant (50 μg, tid)
- ▲ — Excipient Control ☐ IGF-1 (150 μg, tid)  ☒ IGF-Mutant (150 μg, tid)
☒ IGF-Mutant (50 μg, tid)  ■ Control

```
plasmid t4.g8
length: 5140 (circular)

1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
     CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

101 GAACTGTGTG CGCAGGTAGA CGCTTTGGAG ATTATCGTCA CTGCAATGCT TCGCAATATG GCCGAAAATG GCCAACAGCG ACCAACAGCG GTTGATTGAT CAGGTAGAGG
     CTTGACACAC GCGTCCATCT TCGAAACCTC TAATAGCAGT GACGTTACGA AGCGTTATAC CGGTTGTCGC TGGTTGTCGC CAACTAACTA GTCCATCTCC

201 GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
     CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

301 AAAAGTTAAT CTTTTCAACA GCTGTCATAA GCCGAGACTT ATAGTCGCTT TGTTTTTATT TTTTAATGTA GTACGCAAGT
     TTTTCAATTA GAAAAGTTGT CGACAGTATT TCAACAGTGC CGGCTCTGAA TATCAGCGAA ACAAAAATAA AAAATTACAT CATGCGTTCA

401 TCACGTAAAA AGGGTATCTA GAGGTTGAGG TGATTTTATG AAAAAGAATA TTTTCTTTAT TCTTGCATCT ATGTTCGTTT TTTCTATTGC TACAAATGCC
     AGTGCATTTT TCCCATAGAT CTCCAACTCC ACTAAAATAC TTTTTCTTAT AGCGTAAAGA AGAACGTAGA TACAAGCAAA AAAGATAACG ATGTTTACGG

501 TATGCATCTG GTACCGCCAT GGCTGATCCG AACCGTTTCC GCGGTAAAGA TCTGGCAGGT TCACCAGGTG GAGGATCCGG AGGAGGCGCC GAGGGTGACG
     ATACGTAGAC CATGGCGGTA CCGACTAGGC TTGGCAAAGG CGCCATTTCT AGACCGTCCA AGTGGTCCAC CTCCTAGGCC CTCCCGCGG CTCCCACTGC
   1            SerG lyThrAlaMe tAlaAspPro AsnArgPheA rgGlyLysAs pLeuAlaGly SerProGlyG lyGlySerGl yGlyGlyAla GluGlyAspAsp

601 ATCCCGCAAA AGCGGCCTTT AACTCCCTGC AAGCCTCAGC GACCGAATAT ATCGGTTATG CGTTGTTGTC GGTTGTCGCG ATTGTCGCCG CAACTATCGG
     TAGGGCGTTT TCGCCGGAAA TTGAGGGACG TTCGGAGTCG CTGGCTTATA TAGCCAATAC GCACCCGCTA CCAACAACAG TAACAGCGGC GTTGATAGCC
  33 ProAlaLy sAlaAlaPhe AsnSerLeuG lnAlaSerAl aThrGluTyr IleGlyTyrA laTrpAlaVal laTrpAlaVal IleValGlyA lAThrIleGly

701 TATCAAGCTG TTTAAGAAAT TCACCTCGAA AGCAAGCTGA TAAACCGATA CAATTAAAGG CTCCTTTTGG AGCCTTTTTT TTTGGAGATT TTCAACGTGA
     ATAGTTCGAC AAATTCTTTA AGTGGAGCTT TCGTTCGACT ATTTGGCTAT GTTAATTTCC GAGGAAAACC TCGGAAAAAA AAACCTCTAA AAGTTGCACT
  66 IleLysLeu PheLysLysP heThrSerLy sAlaSer

801 AAAAATTATT ATTCGCAATT CCTTTAGTTG TTCCTTTCTA TTCTCACTCC GCTGAAACTG TTGAAAGTTG TTTAGCAAAA CCCATACAG AAAATTCATT
     TTTTTAATAA TAAGCGTTAA GGAAATCAAC AAGGAAAGAT AAGAGTGAGG CGACTTTGAC AACTTTCAAC AAATCGTTTT GGGTATGTC TTTTAAGTAA

901 TACTAACGTC TGGAAAGACC ACAAAACTTT AGATCGTTAC GCTAACTATG AGGGTTGTCT ACAGGCGTTG TAGTTTGTAC TGGTGACGAA
     ATGATTGCAG ACCTTTCTGC TGTTTTGAAA TCTAGCAATG CGATTGATAC TCCCAACAGA CACCGCAA TGTCCGCAAC ATCAAACATG ACCACTGCTT

1001 ACTCAGTGTC TAGCTAGAGT GGGGGTGGCT CTGGTTCCGG TGATTTTGAT TATGAAAAGA TGGCAAACGC TAATAAGGGG GCTATGACCG AAAATGCCGA
     TGAGTCACAG ATCGATCTCA CCGCCACCGA GACCAAGGCC ACTAAAACTA ATACTTTTCT ACCGTTTGCG ATTATTCCCC CGATACTGGC TTTTACGGCT
```

FIG. 24A

```
1101  TGAAAACGCG CTACAGTCTG ACGCTAAAGG CAAACTTGAT TCTGTGCTA CTGATTACGG TGCTGCTATC GATGGTTTCA TTGGTGACGT TTCCGGCCTT
      ACTTTTGCGC GATGTCAGAC TGCGATTTCC GTTTGAACTA AGACAGCGAT GACTAATGCC ACGACGATAG CTACCAAAGT AACCACTGCA AAGGCCGGAA

1201  GCTAATGGTA ATGGTGCTAC TGGTGATTTT GCTGGCTCTA ATTCCCAAAT GGCTCAAGTC GGTGACGGTG ATAATTCACC TTTAATGAAT AATTTCCGTC
      CGATTACCAT TACCACGATG ACCACTAAAA CGACCGAGAT TAAGGGTTTA CCGAGTTCAG CCACTGCCAC TATTAAGTGG AAATTACTTA TTAAGGCAG

1301  AATATTTACC TTCCCTCCCT CAATCGGTTG AATGTCGCCC TTTTGTCTTT AGCGCTGGTA AACCATATGA ATTTTCTATT GATTGTGACA AAATAAACTT
      TTATAAATGG AAGGGAGGGA GTTAGCCAAC TTACAGCGGG AAAACAGAAA TCGCGACCAT TTGGTATACT TAAAGATAA CTAACACTGT TTTATTTGAA

1401  ATTCCGTGGT GTCTTTGCGT TTCTTTTATA TGTTGCCACC TTTATGTATG GTTTGCTAAC ATACTGCGTA ATAAGGAGTC TTAATCATGC
      TAAGGCACCA CAGAACGCA AGAAAATAT ACAACGGTGG AAATACATAC ATAAAGATG CAAACGATTG TATGACGCAT TATTCCTCAG AATTAGTACG

3201  ACTCAAAGGC GGTAATACGG TTATCCACAG AAGAACATGT GAGCAAAAGG CCAGCAAAAG GCCAGGAACC GTAAAAAGGC
      TGAGTTTCCG CCATTATGCC AATAGGTGTC TTCTTGTACA CTCGTTTTCC GGTCGTTTTC CGGTCCTTGG CATTTTTCCG

3301  CGCGTTGCTG GCGTTTTTCC ATAGGCTCCG CCCCCCTGAC GAGCATCACA AAAATCGACG CTCAAGTCAG AGGTGGCGAA ACCCGACAGG ACTATAAAGA
      GCGCAACGAC CGCAAAAAGG TATCCGAGGC GGGGGGACTG CTCGTAGTGT TTTTAGCTGC GAGTTCAGTC TCCACCGCTT TGGGCTGTCC TGATATTTCT

3401  TACCAGGCGT TTCCCCCTGG AAGCTCCCTC GTGCGCTCTC CTGTTCCGAC CCTGCCGCTT ACCGGATACC TGTCCGCCTT TCTCCCTTCG GAAGCGTGG
      ATGTGGTCCA AAGGGGGACC TTCGAGGGAG CACGCGAGAG GACAAGGCTG GGACGGCGAA TGGCCTATGG ACAGGCGGAA AGAGGGAAGC CCTTCGCACC

3501  CGCTTTCTCA TAGCTCACGC TGTAGGTATC TCAGTTCGGT GTAGGTCGTT CGCTCCAAGC TGGGCTGTGT GCACGAACCC CCCGTTCAGC CCGACCGCTG
      GCGAAAGAGT ATCGAGTGCG ACATCCATAG AGTCAAGCCA CATCCAGCAA GCGAGGTTCG ACCGACACA CGTGCTTGGG GGGCAAGTCG GGCTGGCGAC

3601  CGCCTTATCC GGTAACTATC GTCTTGAGTC CAACCCGGTA TAGCGCCAT AGACACGACT TATCGCCACT GGCAGCAGCC ACTGGTAACA GGATTAGCAG AGCGAGGTAT
      GCGGAATAGG CCATTGATAG CAGAACTCAG GTTGGGCCAT ATCGCGGTA TCTGTGCTGA GCGAGGTGA CGTCGTCGG TGACCATTGT CCTAATCGTC TCGCTCCATA

3701  GTAGGCGGTG CTACAGAGTT CTTGAAGTGG TGGCCTAACT ACGGCTACAC TAGAAGGACA GTATTTGGTA TCTGCGCTCT GCTGAAGCCA GTTACCTTCG
      CATCCGCCAC GATGTCTCAA GAACTTCACC ACCGGATTGA TGCCGATGTG ATCTTCCTGT CATAAACCAT AGACGCGAGA CGACTTCGGT CAATGGAAGC

3801  GAAAAAGAGT TGGTAGCTCT TGATCCGGCA AACAAACCAC CGCTGGTAGC GGTGGTTTTT TTGTTTGCAA CCACCAAAAA GCAGCAGATT ACGCGCAGAA AAAAAGGATC
      CTTTTTCTCA ACCATCGAGA ACTAGGCCGT TTGTTTGGTG GCGACCATCG CCACCAAAAA AACAAACGTT CGTCGTCTAA CGCGCGTCTT TTTTCCTAG

3901  TCAAGAAGAT CCTTTGATCT TTTCTACGGG GTCTGACGCT CAGTGGAACG AAAACTCACG TTAAGGGATT TTGGTCATGA GATTATCAAA AAGGATCTTC
      AGTTCTTCTA GGAAACTAGA AAGATGCCC CAGACTGCGA GTCACCTTGC TTTTGAGTGC AATTCCCTAA AACCAGTACT CTAATAGTTT TTCCTAGAAG

4001  ACCTAGATCC TTTTAAATTA AAAATGAAGT TTTAAATCAA TCTAAAGTAT ATATGAGTAA ACTTGGTCTG ACAGTTACCA ATGCTTAATC AGTGAGGCAC
      TGGATCTAGG AAAATTTAAT TTTTACTTCA AAATTTAGTT AGATTTCATA TATACTCATT TGAACCAGAC TGTCAATGGT TACGAATTAG TCACTCCGTG
```

FIG. 24B

```
4101  CTATCTCAGC GATCTGTCTA TTTCGTTCAT CCATAGTTGC CTGACTCCCC GTCGTGTAGA TAACTACGAT ACGGGAGGGC TTACCATCTG GCCCCAGTGC
      GATAGAGTCG CTAGACAGAT AAAGCAAGTA GGTATCAACG GACTGAGGGG CAGCACATCT ATTGATGCTA TGCCCTCCCG AATGGTAGAC CGGGGTCACG

4201  TGCAATGATA CCGCGAGACC CACGCTCACC GGCTCCAGAT TTATCAGCAA TAAACCAGCC AGCCGAAGG  GCCGAGCGCA GAAGTGGTCC TGCAACTTTA
      ACGTTACTAT GGCGCTCTGG GTGCGAGTGG CCGAGGTCTA AATAGTCGTT ATTTGGTCGG TCGGCCTTCC CGGCTCGCGT CTTCACCAGG ACGTTGAAAT

4301  TCCGCCTCCA TCCAGTCTAT TAATTGTTGC CGGGAAGCTA GAGTAAGTAG TTCGCCAGTT AATAGTTGC  GCAACGTTGT TGCCATTGCT GCAGGCATCG
      AGGCGGAGGT AGTCAGATA  ATTAACACG  GCCCTTCGAT CTCATTCATC AAGCGGTCAA TTATCAAACG CGTTGCAACA ACGGTAACGA CGTCCGTAGC

4401  TGGTGTCACG CTCGTCGTTT GGTATGGCTT CATTCAGCTC CGGTTCCCAA CGATCAAGGC GAGTTACATG ATCCCCCATG TTGTGCAAAA AAGCGGTTAG
      ACCACAGTGC GAGCAGCAAA CCATACCGAA GTAAGTCGAG GCCAAGGGTT GCTAGTTCCG CTCAATGTAC TAGGGGGTAC AACACGTTTT TTCGCCAATC

4501  CTCCTTTCGT CCTCCGATCG TTGTCAGAAG TAAGTTGGCC GCAGTGTTAT CACTCATGGT TATGGCAGCA CTGCATAATT CTCTTACTGT CATGCCATCC
      GAGGAAGCCA GGAGGCTAGC AACAGTCTTC ATTCAACCGG CGTCACAATA GTGAGTACCA ATACCGTCGT GACGTATTAA GAGAATGACA GTACGGTAGG

4601  GTAAGATGCT TTTCTGTGAC TGGTGAGTAC TCAACCAAGT CATTCTGAGA ATAGTGTATG CGGCGACCGA GTTGCTCTTG CCCGGCGTCA ACACGGGATA
      CATTCTACGA AAAGACACTG ACCACTCATG AGTTGGTTCA GTAAGACTCT TATCACATAC GCCGCTGGCT CAACGAGAAC GGGCCGCAGT TGTGCCCTAT

4701  ATACCGCGCC ACATAGCAGA ACTTAAAAG  TGCTCATCAT TGGAAAACGT TCTTCGGGGC GAAAACTCTC AAGGATCTTA CCGCTGTTGA GATCCAGTTC
      TATGGCGCGG TGTATCGTCT TGAAATTTTC ACGAGTAGTA ACCTTTTGCA AGAAGCCCCG CTTTTGAGAG TTCCTAGAAT GGCGACAACT CTAGGTCAAG

4801  GATGTAACCC ACTCGTGCAC CCAACTGATC TTTACTTTCA CCAGCGTTTC TGGGTGAGCA AAAACAGGAA GGCAAAAATGC CGCAAAAAAG
      CTACATTGGG TGAGCACGTG GGTTGACTAG AAGTGAAAGT GGTCGCAAAG ACCCACTCGT TTTTGTCCTT CCGTTTTACG GCGTTTTTC

4901  GGAATAAGGG CGACACGGAA ATGTTGAATA CTCATACTCT TCCTTTTTCA ATATTATTGA AGCATTTATC AGGGTTATTG TCTCATGAGC GGATACATAT
      CCTTATTCCC GCTGTGCCTT TACAACTTAT GAGTATGAGA AGGAAAAAGT TATAATAACT TCGTAAATAG TCCCAATAAC AGAGTACTCG CCTATGTATA

5001  TTGAATGTAT TTAGAAAAAT AAACAAATAG GGGTTCCGCG CACATTTCCC CGAAAAGTGC CACCTGACGT CTAAGAAACC ATTATTATCA TGACATTAAC
      AACTTACATA AATCTTTTTA TTTGTTTATC CCCAAGGCGC GTGTAAAGGG GCTTTTCACG GTGGACTGCA GATTCTTTGG TAATAATAGT ACTGTAATTG

5101  CTATAAAAAT AGGCGTATCA CGAGGCCCTT TCGTCTTCAA
      GATATTTTTA TCCGCATAGT GCTCCGGGAA AGCAGAAGTT
```

FIG. 24C

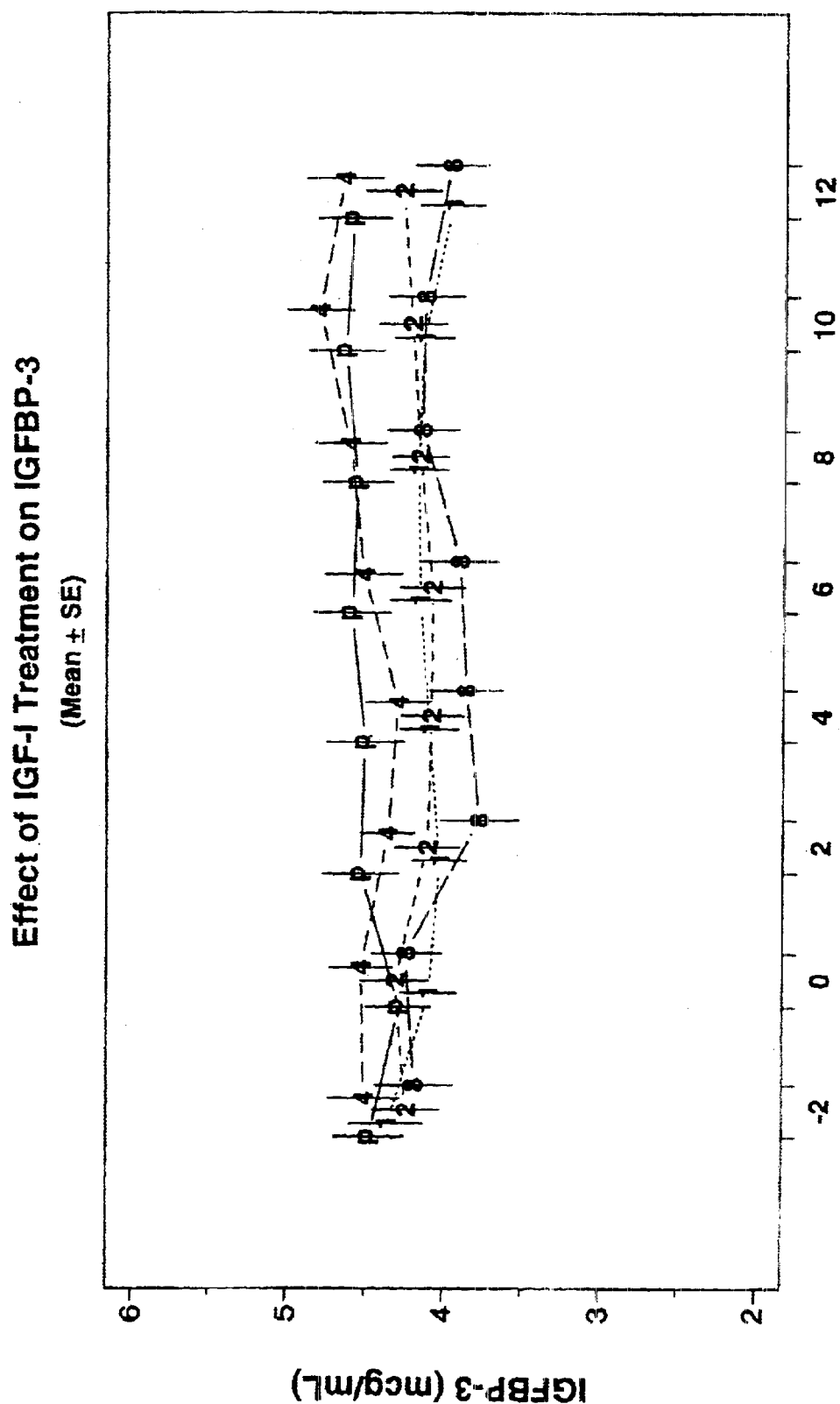

SEQUENCE LISTING (1) GENERAL INFORMATION:

(iii) NUMBER OF SEQUENCES: 109

(2) INFORMATION FOR SEQ ID NO: 1:

(i) SEQUENCE CHARACTERISTICS:
      (A) LENGTH: 21 amino acids
      (B) TYPE: Amino Acid
      (D) TOPOLOGY: Linear (xi) SEQUENCE DESCRIPTION: SEQ ID NO: 1:

```
Glu Leu Asp Gly Trp Val Cys Ile Lys Val Gly Glu Gln Asn Leu
 1               5                  10                  15
Cys Tyr Leu Ala Glu Gly
                20  21
```

(2) INFORMATION FOR SEQ ID NO: 2:

(i) SEQUENCE CHARACTERISTICS:
        (A) LENGTH: 21 amino acids
        (B) TYPE: Amino Acid
        (D) TOPOLOGY: Linear (xi) SEQUENCE DESCRIPTION: SEQ ID NO: 2:

```
Trp Phe Lys Thr Val Cys Tyr Glu Trp Glu Asp Glu Val Gln Cys
 1               5                  10                  15

Tyr Thr Leu Glu Glu Gly
                20  21
```

(2) INFORMATION FOR SEQ ID NO: 3:

(i) SEQUENCE CHARACTERISTICS:
        (A) LENGTH: 21 amino acids
        (B) TYPE: Amino Acid
        (D) TOPOLOGY: Linear (xi) SEQUENCE DESCRIPTION: SEQ ID NO: 3:

```
Arg Val Gly Ala Tyr Ile Ser Cys Ser Glu Thr Glu Cys Trp Val
 1               5                  10                  15

Glu Asp Leu Leu Asp Gly
                20  21
```

(2) INFORMATION FOR SEQ ID NO: 4:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 4:

```
Val Ala Trp Glu Val Cys Trp Asp Arg His Asp Gln Gly Tyr Ile
 1               5                  10                  15

Cys Thr Thr Asp Ser
                20
```

(2) INFORMATION FOR SEQ ID NO: 5:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 5:

```
Ala Trp Glu Val Cys Trp Asp Arg His Gln Gly Tyr Ile Cys Thr
 1               5                  10                  15

Thr Asp Ser
         18
```

(2) INFORMATION FOR SEQ ID NO: 6:

(i) SEQUENCE CHARACTERISTICS:
        (A) LENGTH: 15 amino acids
        (B) TYPE: Amino Acid
        (D) TOPOLOGY: Linear (xi) SEQUENCE DESCRIPTION: SEQ ID NO: 6:

```
Cys Trp Asp Arg His Asp Gln Gly Tyr Ile Cys Thr Thr Asp Ser
 1               5                  10                  15
```

(2) INFORMATION FOR SEQ ID NO: 7:

```
    (i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 7:

Glu Glu Ser Glu Cys Phe Glu Gly Pro Gly Tyr Val Ile Cys Gly
 1               5                  10                  15

Leu Val Gly
        18

(2) INFORMATION FOR SEQ ID NO: 8:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 8:

Asp Met Gly Val Cys Ala Asp Gly Pro Trp Met Tyr Val Cys Glu
 1               5                  10                  15

Trp Thr Glu
        18

(2) INFORMATION FOR SEQ ID NO: 9:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 9:

Ser Glu Glu Val Cys Trp Pro Val Ala Glu Trp Tyr Leu Cys Asn
 1               5                  10                  15

Met Trp Gly
        18

(2) INFORMATION FOR SEQ ID NO: 10:

(i) SEQUENCE CHARACTERISTICS:
        (A) LENGTH: 15 amino acids
        (B) TYPE: Amino Acid
        (D) TOPOLOGY: Linear (xi) SEQUENCE DESCRIPTION: SEQ ID NO: 10:

Ser Glu Glu Val Cys Trp Pro Val Ala Glu Trp Tyr Leu Cys Asn
 1               5                  10                  15

(2) INFORMATION FOR SEQ ID NO: 11:

(i) SEQUENCE CHARACTERISTICS:
        (A) LENGTH: 15 amino acids
        (B) TYPE: Amino Acid
        (D) TOPOLOGY: Linear (xi) SEQUENCE DESCRIPTION: SEQ ID NO: 11:

Val Cys Trp Pro Val Ala Glu Trp Tyr Leu Cys Asn Met Trp Gly
 1               5                  10                  15

(2) INFORMATION FOR SEQ ID NO: 12:

(i) SEQUENCE CHARACTERISTICS:
        (A) LENGTH: 12 amino acids
        (B) TYPE: Amino Acid
        (D) TOPOLOGY: Linear
```

(xi) SEQUENCE DESCRIPTION: SEQ ID NO: 12:

Val Cys Trp Pro Val Ala Glu Trp Tyr Leu Cys Asn
 1               5                  10      12

(2) INFORMATION FOR SEQ ID NO: 13:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 13:

Thr Gly Val Asp Cys Gln Cys Gly Pro Val His Cys Val Cys Met
 1               5                  10                  15

Asp Trp Ala
         18

(2) INFORMATION FOR SEQ ID NO: 14:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 14:

Thr Val Ala Asn Cys Asp Cys Tyr Met Pro Leu Cys Leu Cys Tyr
 1               5                  10                  15

Asp Ser Asp
         18

(2) INFORMATION FOR SEQ ID NO: 15:

(i) SEQUENCE CHARACTERISTICS:
        (A) LENGTH: 15 amino acids
        (B) TYPE: Amino Acid
        (D) TOPOLOGY: Linear (xi) SEQUENCE DESCRIPTION: SEQ ID NO: 15:

Cys Arg Ala Gly Pro Leu Gln Trp Leu Cys Glu Lys Tyr Phe Gly
 1               5                  10                  15

(2) INFORMATION FOR SEQ ID NO: 16:

(i) SEQUENCE CHARACTERISTICS:
        (A) LENGTH: 19 amino acids
        (B) TYPE: Amino Acid
        (D) TOPOLOGY: Linear (xi) SEQUENCE DESCRIPTION: SEQ ID NO: 16:

Ser Glu Val Gly Cys Arg Ala Gly Pro Leu Gln Trp Leu Cys Glu
 1               5                  10                  15

Lys Tyr Phe Gly
         19

(2) INFORMATION FOR SEQ ID NO: 17:

(i) SEQUENCE CHARACTERISTICS:
        (A) LENGTH: 400 base pairs
        (B) TYPE: Nucleic Acid
        (C) STRANDEDNESS: Double
        (D) TOPOLOGY: Linear (xi) SEQUENCE DESCRIPTION: SEQ ID NO: 17:

TCACGTAAAA AGGGTATCTA GAATTATGAT GATTACTCTG CGCAAACTTC            50

-continued

```
CTCTGGCGGT TGCCGTCGCA GCGGGCGTAA TGTCTGCTCA GGCCATGGCC         100

GGTCCCGAAA CTCTGTGCGG TGCTGAACTG GTTGACGCTC TGCAGTTCGT         150

ATGTGGTGAT CGAGGCTTCC TGTTCAACAA ACCGACTGGG GCTGGATCCT         200

CCTCTCGTCG TGCTCCCCAG ACTGGTATTG TTGACGAATG CTGCTTTCGT         250

TCTTGCGACC TGCGTCGTCT GGAAATGTAT TGCGCTCCCC TGAAACCCGC         300

TAAATCTGCT TAGAAGCTCC TAACGCTCGG TTGCCGCCGG GCGTTTTTTA         350

TTGTTAACTC ATGTTTGACA GCTTATCATC GATAAGCTTT AATGCGGTAG         400
```

(2) INFORMATION FOR SEQ ID NO: 18:

(i) SEQUENCE CHARACTERISTICS:
        (A) LENGTH: 95 amino acids
        (B) TYPE: Amino Acid
        (D) TOPOLOGY: Linear (xi) SEQUENCE DESCRIPTION: SEQ ID NO: 18:

```
Met Met Ile Thr Leu Arg Lys Leu Pro Leu Ala Val Ala Val Ala
 1               5                  10                  15

Ala Gly Val Met Ser Ala Gln Ala Met Ala Gly Pro Glu Thr Leu
                20                  25                  30

Cys Gly Ala Glu Leu Val Asp Ala Leu Gln Phe Val Cys Gly Asp
                35                  40                  45

Arg Gly Phe Leu Phe Asn Lys Pro Thr Gly Ala Gly Ser Ser Ser
                50                  55                  60

Arg Arg Ala Pro Gln Thr Gly Ile Val Asp Glu Cys Cys Phe Arg
                65                  70                  75

Ser Cys Asp Leu Arg Arg Leu Glu Met Tyr Cys Ala Pro Leu Lys
                80                  85                  90

Pro Ala Lys Ser Ala
                95
```

(2) INFORMATION FOR SEQ ID NO: 19:

(i) SEQUENCE CHARACTERISTICS:
        (A) LENGTH: 5115 base pairs
        (B) TYPE: Nucleic Acid
        (C) STRANDEDNESS: Double
        (D) TOPOLOGY: Linear (xi) SEQUENCE DESCRIPTION: SEQ ID NO: 19:

```
GAATTCAACT TCTCCATACT TTGGATAAGG AAATACAGAC ATGAAAAATC          50

TCATTGCTGA GTTGTTATTT AAGCTTGCCC AAAAAGAAGA AGAGTCGAAT         100

GAACTGTGTG CGCAGGTAGA AGCTTTGGAG ATTATCGTCA CTGCAATGCT         150

TCGCAATATG GCGCAAAATG ACCAACAGCG GTTGATTGAT CAGGTAGAGG         200

GGGCGCTGTA CGAGGTAAAG CCCGATGCCA GCATTCCTGA CGACGATACG         250

GAGCTGCTGC GCGATTACGT AAAGAAGTTA TTGAAGCATC CTCGTCAGTA         300

AAAAGTTAAT CTTTTCAACA GCTGTCATAA AGTTGTCACG GCCGAGACTT         350

ATAGTCGCTT TGTTTTTATT TTTTAATGTA TTTGTAACTA GTACGCAAGT         400

TCACGTAAAA AGGGTATCTA GAATTATGAT GATTACTCTG CGCAAACTTC         450

CTCTGGCGGT TGCCGTCGCA GCGGGCGTAA TGTCTGCTCA GGCCATGGCC         500

GGTCCCGAAA CTCTGTGCGG TGCTGAACTG GTTGACGCTC TGCAGTTCGT         550
```

```
ATGTGGTGAT CGAGGCTTCC TGTTCAACAA ACCGACTGGG GCTGGATCCT      600

CCTCTCGTCG TGCTCCCCAG ACTGGTATTG TTGACGAATG CTGCTTTCGT      650

TCTTGCGACC TGCGTCGTCT GGAAATGTAT TGCGCTCCCC TGAAACCCGC      700

TAAATCTGCT TAGAAGCTCC TAACGCTCGG TTGCCGCCGG GCGTTTTTTA      750

TTGTTAACTC ATGTTTGACA GCTTATCATC GATAAGCTTT AATGCGGTAG      800

TTTATCACAG TTAAATTGCT AACGCAGTCA GGCACCGTGT ATGAAATCTA      850

ACAATGCGCT CATCGTCATC CTCGGCACCG TCACCCTGGA TGCTGTAGGC      900

ATAGGCTTGG TTATGCCGGT ACTGCCGGGC CTCTTGCGGG ATATCGTCCA      950

TTCCGACAGC ATCGCCAGTC ACTATGGCGT GCTGCTAGCG CTATATGCGT     1000

TGATGCAATT TCTATGCGCA CCCGTTCTCG GAGCACTGTC CGACCGCTTT     1050

GGCCGCCGCC CAGTCCTGCT CGCTTCGCTA CTTGGAGCCA CTATCGACTA     1100

CGCGATCATG GCGACCACAC CCGTCCTGTG GATCCTCTAC GCCGGACGCA     1150

TCGTGGCCGG CATCACCGGC GCCACAGGTG CGGTTGCTGG CGCCTATATC     1200

GCCGACATCA CCGATGGGGA AGATCGGGCT CGCCACTTCG GGCTCATGAG     1250

CGCTTGTTTC GGCGTGGGTA TGGTGGCAGG CCCCGTGGCC GGGGGACTGT     1300

TGGGCGCCAT CTCCTTGCAT GCACCATTCC TTGCGGCGGC GGTGCTCAAC     1350

GGCCTCAACC TACTACTGGG CTGCTTCCTA ATGCAGGAGT CGCATAAGGG     1400

AGAGCGTCGA CCGATGCCCT TGAGAGCCTT CAACCCAGTC AGCTCCTTCC     1450

GGTGGGCGCG GGGCATGACT ATCGTCGCCG CACTTATGAC TGTCTTCTTT     1500

ATCATGCAAC TCGTAGGACA GGTGCCGGCA GCGCTCTGGG TCATTTTCGG     1550

CGAGGACCGC TTTCGCTGGA GCGCGACGAT GATCGGCCTG TCGCTTGCGG     1600

TATTCGGAAT CTTGCACGCC CTCGCTCAAG CCTTCGTCAC TGGTCCCGCC     1650

ACCAAACGTT TCGGCGAGAA GCAGGCCATT ATCGCCGGCA TGGCGGCCGA     1700

CGCGCTGGGC TACGTCTTGC TGGCGTTCGC GACGCGAGGC TGGATGGCCT     1750

TCCCCATTAT GATTCTTCTC GCTTCCGGCG GCATCGGGAT GCCCGCGTTG     1800

CAGGCCATGC TGTCCAGGCA GGTAGATGAC GACCATCAGG GACAGCTTCA     1850

AGGATCGCTC GCGGCTCTTA CCAGCCTAAC TTCGATCACT GGACCGCTGA     1900

TCGTCACGGC GATTTATGCC GCCTCGGCGA GCACATGGAA CGGGTTGGCA     1950

TGGATTGTAG GCGCCGCCCT ATACCTTGTC TGCCTCCCCG CGTTGCGTCG     2000

CGGTGCATGG AGCCGGGCCA CCTCGACCTG AATGGAAGCC GGCGGCACCT     2050

CGCTAACGGA TTCACCACTC CAAGAATTGG AGCCAATCAA TTCTTGCGGA     2100

GAACTGTGAA TGCGCAAACC AACCCTTGGC AGAACATATC CATCGCGTCC     2150

GCCATCTCCA GCAGCCGCAC GCGGCGCATC TCGGGCAGCG TTGGGTCCTG     2200

GCCACGGGTG CGCATGATCG TGCTCCTGTC GTTGAGGACC CGGCTAGGCT     2250

GGCGGGGTTG CCTTACTGGT TAGCAGAATG AATCACCGAT ACGCGAGCGA     2300

ACGTGAAGCG ACTGCTGCTG CAAAACGTCT GCGACCTGAG CAACAACATG     2350

AATGGTCTTC GGTTTCCGTG TTTCGTAAAG TCTGGAAACG CGGAAGTCAG     2400

CGCCCTGCAC CATTATGTTC CGGATCTGCA TCGCAGGATG CTGCTGGCTA     2450

CCCTGTGGAA CACCTACATC TGTATTAACG AAGCGCTGGC ATTGACCCTG     2500

AGTGATTTTT CTCTGGTCCC GCCGCATCCA TACCGCCAGT TGTTTACCCT     2550
```

-continued

| | |
|---|---|
| CACAACGTTC CAGTAACCGG GCATGTTCAT CATCAGTAAC CCGTATCGTG | 2600 |
| AGCATCCTCT CTCGTTTCAT CGGTATCATT ACCCCCATGA ACAGAAATTC | 2650 |
| CCCCTTACAC GGAGGCATCA AGTGACCAAA CAGGAAAAAA CCGCCCTTAA | 2700 |
| CATGGCCCGC TTTATCAGAA GCCAGACATT AACGCTTCTG GAGAAACTCA | 2750 |
| ACGAGCTGGA CGCGGATGAA CAGGCAGACA TCTGTGAATC GCTTCACGAC | 2800 |
| CACGCTGATG AGCTTTACCG CAGCTGCCTC GCGCGTTTCG GTGATGACGG | 2850 |
| TGAAAACCTC TGACACATGC AGCTCCCGGA GACGGTCACA GCTTGTCTGT | 2900 |
| AAGCGGATGC CGGGAGCAGA CAAGCCCGTC AGGGCGCGTC AGCGGGTGTT | 2950 |
| GGCGGGTGTC GGGGCGCAGC CATGACCCAG TCACGTAGCG ATAGCGGAGT | 3000 |
| GTATACTGGC TTAACTATGC GGCATCAGAG CAGATTGTAC TGAGAGTGCA | 3050 |
| CCATATGCGG TGTGAAATAC CGCACAGATG CGTAAGGAGA AAATACCGCA | 3100 |
| TCAGGCGCTC TTCCGCTTCC TCGCTCACTG ACTCGCTGCG CTCGGTCGTT | 3150 |
| CGGCTGCGGC GAGCGGTATC AGCTCACTCA AAGGCGGTAA TACGGTTATC | 3200 |
| CACAGAATCA GGGGATAACG CAGGAAAGAA CATGTGAGCA AAAGGCCAGC | 3250 |
| AAAAGGCCAG GAACCGTAAA AAGGCCGCGT TGCTGGCGTT TTTCCATAGG | 3300 |
| CTCCGCCCCC CTGACGAGCA TCACAAAAAT CGACGCTCAA GTCAGAGGTG | 3350 |
| GCGAAACCCG ACAGGACTAT AAAGATACCA GGCGTTTCCC CCTGGAAGCT | 3400 |
| CCCTCGTGCG CTCTCCTGTT CCGACCCTGC CGCTTACCGG ATACCTGTCC | 3450 |
| GCCTTTCTCC CTTCGGGAAG CGTGGCGCTT TCTCATAGCT CACGCTGTAG | 3500 |
| GTATCTCAGT TCGGTGTAGG TCGTTCGCTC CAAGCTGGGC TGTGTGCACG | 3550 |
| AACCCCCCGT TCAGCCCGAC CGCTGCGCCT TATCCGGTAA CTATCGTCTT | 3600 |
| GAGTCCAACC CGGTAAGACA CGACTTATCG CCACTGGCAG CAGCCACTGG | 3650 |
| TAACAGGATT AGCAGAGCGA GGTATGTAGG CGGTGCTACA GAGTTCTTGA | 3700 |
| AGTGGTGGCC TAACTACGGC TACACTAGAA GGACAGTATT TGGTATCTGC | 3750 |
| GCTCTGCTGA AGCCAGTTAC CTTCGGAAAA AGAGTTGGTA GCTCTTGATC | 3800 |
| CGGCAAACAA ACCACCGCTG GTAGCGGTGG TTTTTTTGTT TGCAAGCAGC | 3850 |
| AGATTACGCG CAGAAAAAAA GGATCTCAAG AAGATCCTTT GATCTTTTCT | 3900 |
| ACGGGGTCTG ACGCTCAGTG GAACGAAAAC TCACGTTAAG GGATTTTGGT | 3950 |
| CATGAGATTA TCAAAAAGGA TCTTCACCTA GATCCTTTTA AATTAAAAAT | 4000 |
| GAAGTTTTAA ATCAATCTAA AGTATATATG AGTAAACTTG GTCTGACAGT | 4050 |
| TACCAATGCT TAATCAGTGA GGCACCTATC TCAGCGATCT GTCTATTTCG | 4100 |
| TTCATCCATA GTTGCCTGAC TCCCCGTCGT GTAGATAACT ACGATACGGG | 4150 |
| AGGGCTTACC ATCTGGCCCC AGTGCTGCAA TGATACCGCG AGACCCACGC | 4200 |
| TCACCGGCTC CAGATTTATC AGCAATAAAC CAGCCAGCCG GAAGGGCCGA | 4250 |
| GCGCAGAAGT GGTCCTGCAA CTTTATCCGC CTCCATCCAG TCTATTAATT | 4300 |
| GTTGCCGGGA AGCTAGAGTA AGTAGTTCGC CAGTTAATAG TTTGCGCAAC | 4350 |
| GTTGTTGCCA TTGCTGCAGG CATCGTGGTG TCACGCTCGT CGTTTGGTAT | 4400 |
| GGCTTCATTC AGCTCCGGTT CCCAACGATC AAGGCGAGTT ACATGATCCC | 4450 |
| CCATGTTGTG CAAAAAAGCG GTTAGCTCCT TCGGTCCTCC GATCGTTGTC | 4500 |

```
AGAAGTAAGT TGGCCGCAGT GTTATCACTC ATGGTTATGG CAGCACTGCA         4550

TAATTCTCTT ACTGTCATGC CATCCGTAAG ATGCTTTTCT GTGACTGGTG         4600

AGTACTCAAC CAAGTCATTC TGAGAATAGT GTATGCGGCG ACCGAGTTGC         4650

TCTTGCCCGG CGTCAACACG GGATAATACC GCGCCACATA GCAGAACTTT         4700

AAAAGTGCTC ATCATTGGAA AACGTTCTTC GGGGCGAAAA CTCTCAAGGA         4750

TCTTACCGCT GTTGAGATCC AGTTCGATGT AACCCACTCG TGCACCCAAC         4800

TGATCTTCAG CATCTTTTAC TTTCACCAGC GTTTCTGGGT GAGCAAAAAC         4850

AGGAAGGCAA AATGCCGCAA AAAAGGGAAT AAGGGCGACA CGGAAATGTT         4900

GAATACTCAT ACTCTTCCTT TTTCAATATT ATTGAAGCAT TTATCAGGGT         4950

TATTGTCTCA TGAGCGGATA CATATTTGAA TGTATTTAGA AAAATAAACA         5000

AATAGGGGTT CCGCGCACAT TTCCCCGAAA AGTGCCACCT GACGTCTAAG         5050

AAACCATTAT TATCATGACA TTAACCTATA AAAATAGGCG TATCACGAGG         5100

CCCTTTCGTC TTCAA                                               5115

(2) INFORMATION FOR SEQ ID NO: 20:

(i) SEQUENCE CHARACTERISTICS:
        (A) LENGTH: 5140 base pairs
        (B) TYPE: Nucleic Acid
        (C) STRANDEDNESS: Single
        (D) TOPOLOGY: Linear (xi) SEQUENCE DESCRIPTION: SEQ ID NO: 20:

GAATTCAACT TCTCCATACT TTGGATAAGG AAATACAGAC ATGAAAAATC           50

TCATTGCTGA GTTGTTATTT AAGCTTGCCC AAAAAGAAGA AGAGTCGAAT          100

GAACTGTGTG CGCAGGTAGA AGCTTTGGAG ATTATCGTCA CTGCAATGCT          150

TCGCAATATG GCGCAAAATG ACCAACAGCG GTTGATTGAT CAGGTAGAGG          200

GGGCGCTGTA CGAGGTAAAG CCCGATGCCA GCATTCCTGA CGACGATACG          250

GAGCTGCTGC GCGATTACGT AAAGAAGTTA TTGAAGCATC CTCGTCAGTA          300

AAAAGTTAAT CTTTTCAACA GCTGTCATAA AGTTGTCACG GCCGAGACTT          350

ATAGTCGCTT TGTTTTTATT TTTTAATGTA TTTGTAACTA GTACGCAAGT          400

TCACGTAAAA AGGGTATCTA GAGGTTGAGG TGATTTTATG AAAAAGAATA          450

TCGCATTTCT TCTTGCATCT ATGTTCGTTT TTTCTATTGC TACAAATGCC          500

TATGCATCTG GTACCGCCAT GGCTGATCCG AACCGTTTCC GCGGTAAAGA          550

TCTGGCAGGT TCACCAGGTG GAGGATCCGG AGGAGGCGCC GAGGGTGACG          600

ATCCCGCAAA AGCGGCCTTT AACTCCCTGC AAGCCTCAGC GACCGAATAT          650

ATCGGTTATG CGTGGGCGAT GGTTGTTGTC ATTGTCGGCG CAACTATCGG          700

TATCAAGCTG TTTAAGAAAT TCACCTCGAA AGCAAGCTGA TAAACCGATA          750

CAATTAAAGG CTCCTTTTGG AGCCTTTTTT TTTGGAGATT TCAACGTGA           800

AAAAATTATT ATTCGCAATT CCTTTAGTTG TTCCTTTCTA TTCTCACTCC          850

GCTGAAACTG TTGAAAGTTG TTTAGCAAAA CCCCATACAG AAAATTCATT          900

TACTAACGTC TGGAAAGACG ACAAAACTTT AGATCGTTAC GCTAACTATG          950

AGGGTTGTCT GTGAATGCT ACAGGCGTTG TAGTTTGTAC TGGTGACGAA          1000

ACTCAGTGTC TAGCTAGAGT GGCGGTGGCT CTGGTTCCGG TGATTTTGAT         1050
```

```
TATGAAAAGA TGGCAAACGC TAATAAGGGG GCTATGACCG AAAATGCCGA        1100

TGAAAACGCG CTACAGTCTG ACGCTAAAGG CAAACTTGAT TCTGTCGCTA        1150

CTGATTACGG TGCTGCTATC GATGGTTTCA TTGGTGACGT TTCCGGCCTT        1200

GCTAATGGTA ATGGTGCTAC TGGTGATTTT GCTGGCTCTA ATTCCCAAAT        1250

GGCTCAAGTC GGTGACGGTG ATAATTCACC TTTAATGAAT AATTTCCGTC        1300

AATATTTACC TTCCCTCCCT CAATCGGTTG AATGTCGCCC TTTTGTCTTT        1350

AGCGCTGGTA AACCATATGA ATTTTCTATT GATTGTGACA AAATAAACTT        1400

ATTCCGTGGT GTCTTTGCGT TTCTTTTATA TGTTGCCACC TTTATGTATG        1450

TATTTTCTAC GTTTGCTAAC ATACTGCGTA ATAAGGAGTC TTAATCATGC        1500

CAGTTCTTTT GGCTAGCGCC GCCCTATACC TTGTCTGCCT CCCCGCGTTG        1550

CGTCGCGGTG CATGGAGCCG GGCCACCTCG ACCTGAATGG AAGCCGGCGG        1600

CACCTCGCTA ACGGATTCAC CACTCCAAGA ATTGGAGCCA ATCAATTCTT        1650

GCGGAGAACT GTGAATGCGC AAACCAACCC TTGGCAGAAC ATATCCATCG        1700

CGTCCGCCAT CTCCAGCAGC CGCACGCGGC GCATCTCGGG CAGCGTTGGG        1750

TCCTGGCCAC GGGTGCGCAT GATCGTGCTC CTGTCGTTGA GGACCCGGCT        1800

AGGCTGGCGG GGTTGCCTTA CTGGTTAGCA GAATGAATCA CCGATACGCG        1850

AGCGAACGTG AAGCGACTGC TGCTGCAAAA CGTCTGCGAC CTGAGCAACA        1900

ACATGAATGG TCTTCGGTTT CCGTGTTTCG TAAAGTCTGG AAACGCGGAA        1950

GTCAGCGCCC TGCACCATTA TGTTCCGGAT CTGCATCGCA GGATGCTGCT        2000

GGCTACCCTG TGGAACACCT ACATCTGTAT TAACGAAGCG CTGGCATTGA        2050

CCCTGAGTGA TTTTTCTCTG GTCCCGCCGC ATCCATACCG CCAGTTGTTT        2100

ACCCTCACAA CGTTCCAGTA ACCGGGCATG TTCATCATCA GTAACCCGTA        2150

TCGTGAGCAT CCTCTCTCGT TTCATCGGTA TCATTACCCC CATGAACAGA        2200

AATTCCCCCT TACACGGAGG CATCAAGTGA CCAAACAGGA AAAAACCGCC        2250

CTTAACATGG CCCGCTTTAT CAGAAGCCAG ACATTAACGC TTCTGGAGAA        2300

ACTCAACGAG CTGGACGCGG ATGAACAGGA AGACATCTGT GAATCGCTTC        2350

ACGACCACGC TGATGAGCTT TACCGCAGGA TCCGGAAATT GTAAACGTTA        2400

ATATTTTGTT AAAATTCGCG TTAAATTTTT GTTAAATCAG CTCATTTTTT        2450

AACCAATAGG CCGAAATCGG CAAAATCCCT TATAAATCAA AGAATAGAC        2500

CGAGATAGGG TTGAGTGTTG TTCCAGTTTG AACAAGAGT CCACTATTAA        2550

AGAACGTGGA CTCCAACGTC AAAGGGCGAA AAACCGTCTA TCAGGGCTAT        2600

GGCCCACTAC GTGAACCATC ACCCTAATCA AGTTTTTTGG GGTCGAGGTG        2650

CCGTAAAGCA CTAAATCGGA ACCCTAAAGG GAGCCCCCGA TTTAGAGCTT        2700

GACGGGGAAA GCCGGCGAAC GTGGCGAGAA AGGAAGGGAA GAAAGCGAAA        2750

GGAGCGGGCG CTAGGGCGCT GGCAAGTGTA GCGGTCACGC TGCGCGTAAC        2800

CACCACACCC GCCGCGCTTA ATGCGCCGCT ACAGGGCGCG TCCGGATCCT        2850

GCCTCGCGCG TTTCGGTGAT GACGGTGAAA ACCTCTGACA CATGCAGCTC        2900

CCGGAGACGG TCACAGCTTG TCTGTAAGCG GATGCCGGGA GCAGACAAGC        2950

CCGTCAGGGC GCGTCAGCGG GTGTTGGCGG GTGTCGGGGC GCAGCCATGA        3000

CCCAGTCACG TAGCGATAGC GGAGTGTATA CTGGCTTAAC TATGCGGCAT        3050
```

```
CAGAGCAGAT TGTACTGAGA GTGCACCATA TGCGGTGTGA AATACCGCAC      3100

AGATGCGTAA GGAGAAAATA CCGCATCAGG CGCTCTTCCG CTTCCTCGCT      3150

CACTGACTCG CTGCGCTCGG TCGTTCGGCT GCGGCGAGCG GTATCAGCTC      3200

ACTCAAAGGC GGTAATACGG TTATCCACAG AATCAGGGGA TAACGCAGGA      3250

AAGAACATGT GAGCAAAAGG CCAGCAAAAG GCCAGGAACC GTAAAAAGGC      3300

CGCGTTGCTG GCGTTTTTCC ATAGGCTCCG CCCCCCTGAC GAGCATCACA      3350

AAAATCGACG CTCAAGTCAG AGGTGGCGAA ACCCGACAGG ACTATAAAGA      3400

TACCAGGCGT TTCCCCCTGG AAGCTCCCTC GTGCGCTCTC CTGTTCCGAC      3450

CCTGCCGCTT ACCGGATACC TGTCCGCCTT TCTCCCTTCG GGAAGCGTGG      3500

CGCTTTCTCA TAGCTCACGC TGTAGGTATC TCAGTTCGGT GTAGGTCGTT      3550

CGCTCCAAGC TGGGCTGTGT GCACGAACCC CCCGTTCAGC CCGACCGCTG      3600

CGCCTTATCC GGTAACTATC GTCTTGAGTC CAACCCGGTA AGACACGACT      3650

TATCGCCACT GGCAGCAGCC ACTGGTAACA GGATTAGCAG AGCGAGGTAT      3700

GTAGGCGGTG CTACAGAGTT CTTGAAGTGG TGGCCTAACT ACGGCTACAC      3750

TAGAAGGACA GTATTTGGTA TCTGCGCTCT GCTGAAGCCA GTTACCTTCG      3800

GAAAAAGAGT TGGTAGCTCT TGATCCGGCA ACAAACCAC CGCTGGTAGC       3850

GGTGGTTTTT TTGTTTGCAA GCAGCAGATT ACGCGCAGAA AAAAGGATC       3900

TCAAGAAGAT CCTTTGATCT TTTCTACGGG GTCTGACGCT CAGTGGAACG      3950

AAAACTCACG TTAAGGGATT TTGGTCATGA GATTATCAAA AAGGATCTTC      4000

ACCTAGATCC TTTTAAATTA AAAATGAAGT TTTAAATCAA TCTAAAGTAT      4050

ATATGAGTAA ACTTGGTCTG ACAGTTACCA ATGCTTAATC AGTGAGGCAC      4100

CTATCTCAGC GATCTGTCTA TTTCGTTCAT CCATAGTTGC CTGACTCCCC      4150

GTCGTGTAGA TAACTACGAT ACGGGAGGGC TTACCATCTG GCCCCAGTGC      4200

TGCAATGATA CCGCGAGACC CACGCTCACC GGCTCCAGAT TTATCAGCAA      4250

TAAACCAGCC AGCCGGAAGG GCCGAGCGCA GAAGTGGTCC TGCAACTTTA      4300

TCCGCCTCCA TCCAGTCTAT TAATTGTTGC CGGGAAGCTA GAGTAAGTAG      4350

TTCGCCAGTT AATAGTTTGC GCAACGTTGT TGCCATTGCT GCAGGCATCG      4400

TGGTGTCACG CTCGTCGTTT GGTATGGCTT CATTCAGCTC CGGTTCCCAA      4450

CGATCAAGGC GAGTTACATG ATCCCCCATG TTGTGCAAAA AAGCGGTTAG      4500

CTCCTTCGGT CCTCCGATCG TTGTCAGAAG TAAGTTGGCC GCAGTGTTAT      4550

CACTCATGGT TATGGCAGCA CTGCATAATT CTCTTACTGT CATGCCATCC      4600

GTAAGATGCT TTTCTGTGAC TGGTGAGTAC TCAACCAAGT CATTCTGAGA      4650

ATAGTGTATG CGGCGACCGA GTTGCTCTTG CCCGGCGTCA ACACGGGATA      4700

ATACCGCGCC ACATAGCAGA ACTTTAAAAG TGCTCATCAT TGGAAAACGT      4750

TCTTCGGGGC GAAAACTCTC AAGGATCTTA CCGCTGTTGA GATCCAGTTC      4800

GATGTAACCC ACTCGTGCAC CCAACTGATC TTCAGCATCT TTTACTTTCA      4850

CCAGCGTTTC TGGGTGAGCA AAAACAGGAA GGCAAAATGC CGCAAAAAAG      4900

GGAATAAGGG CGACACGGAA ATGTTGAATA CTCATACTCT TCCTTTTTCA      4950

ATATTATTGA AGCATTTATC AGGGTTATTG TCTCATGAGC GGATACATAT      5000
```

```
TTGAATGTAT TTAGAAAAAT AAACAAATAG GGGTTCCGCG CACATTTCCC            5050

CGAAAAGTGC CACCTGACGT CTAAGAAACC ATTATTATCA TGACATTAAC            5100

CTATAAAAAT AGGCGTATCA CGAGGCCCTT TCGTCTTCAA                       5140
```

(2) INFORMATION FOR SEQ ID NO: 21:

(i) SEQUENCE CHARACTERISTICS:
        (A) LENGTH: 77 amino acids
        (B) TYPE: Amino Acid
        (D) TOPOLOGY: Linear (xi) SEQUENCE DESCRIPTION: SEQ ID NO: 21:

```
Ser Gly Thr Ala Met Ala Asp Pro Asn Arg Phe Arg Gly Lys Asp
 1               5                  10                  15

Leu Ala Gly Ser Pro Gly Gly Ser Gly Gly Gly Ala Glu Gly
                20              25                  30

Asp Asp Pro Ala Lys Ala Ala Phe Asn Ser Leu Gln Ala Ser Ala
                35                  40                  45

Thr Glu Tyr Ile Gly Tyr Ala Trp Ala Met Val Val Val Ile Val
                50                  55                  60

Gly Ala Thr Ile Gly Ile Lys Leu Phe Lys Lys Phe Thr Ser Lys
                65                  70                  75

Ala Ser
    77
```

(2) INFORMATION FOR SEQ ID NO: 22:

(i) SEQUENCE CHARACTERISTICS:
        (A) LENGTH: 50 base pairs
        (B) TYPE: Nucleic Acid
        (C) STRANDEDNESS: Single
        (D) TOPOLOGY: Linear (xi) SEQUENCE DESCRIPTION: SEQ ID NO: 22:

```
GTTCGTATGT GGTGATCGAG GCTTCCTGTT CAACAAACCG ACTGGGGCTG              50
```

(2) INFORMATION FOR SEQ ID NO: 23:

(i) SEQUENCE CHARACTERISTICS:
        (A) LENGTH: 58 base pairs
        (B) TYPE: Nucleic Acid
        (C) STRANDEDNESS: Single
        (D) TOPOLOGY: Linear (ii) MOLECULE TYPE: Nucleic Acid (xi) SEQUENCE DESCRIPTION: SEQ ID NO: 23:

```
GATCCAGCCC CAGTCGGTTT GTTGAACAGG AAGCCTCGAT CACCACATAC              50

GAACTGCA                                                            58
```

(2) INFORMATION FOR SEQ ID NO: 24:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 24:

```
Ser Gly Thr Ala Cys Xaa Xaa Gly Pro Xaa Xaa Xaa Xaa Cys Ser
 1               5                  10                  15

Leu Ala Gly Ser Pro
                20
```

(2) INFORMATION FOR SEQ ID NO: 25:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 25:

Xaa Xaa Xaa Xaa Cys Xaa Xaa Gly Pro Xaa Xaa Xaa Xaa Cys Xaa
1                5                    10                  15

Xaa Xaa Xaa
        18

(2) INFORMATION FOR SEQ ID NO: 26:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 26:

Xaa Xaa Xaa Xaa Xaa Xaa Xaa Xaa Xaa Xaa Xaa Xaa Xaa Xaa Xaa
1                5                    10                  15

Xaa Xaa Xaa Xaa Xaa
        20

(2) INFORMATION FOR SEQ ID NO: 27:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 27:

Xaa Xaa Xaa Xaa Xaa Xaa Xaa Cys Xaa Xaa Xaa Xaa Cys Xaa Xaa
1                5                    10                  15

Xaa Xaa Xaa Xaa Xaa
        20

(2) INFORMATION FOR SEQ ID NO: 28:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 28:

Xaa Xaa Xaa Xaa Xaa Xaa Xaa Cys Xaa Xaa Xaa Xaa Xaa Cys Xaa
1                5                    10                  15

Xaa Xaa Xaa Xaa Xaa
        20

(2) INFORMATION FOR SEQ ID NO: 29:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 29:

Xaa Xaa Xaa Xaa Xaa Xaa Cys Xaa Xaa Xaa Xaa Xaa Xaa Cys Xaa
1                5                    10                  15

Xaa Xaa Xaa Xaa Xaa

20

(2) INFORMATION FOR SEQ ID NO: 30:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 30:

Xaa Xaa Xaa Xaa Xaa Xaa Cys Xaa Xaa Xaa Xaa Xaa Xaa Xaa Cys
1            5                   10                 15

Xaa Xaa Xaa Xaa Xaa
           20

(2) INFORMATION FOR SEQ ID NO: 31:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 31:

Xaa Xaa Xaa Xaa Xaa Cys Xaa Xaa Xaa Xaa Xaa Xaa Xaa Xaa Cys
1            5                   10                 15

Xaa Xaa Xaa Xaa Xaa
           20

(2) INFORMATION FOR SEQ ID NO: 32:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 32:

Xaa Xaa Xaa Xaa Xaa Cys Xaa Xaa Xaa Xaa Xaa Xaa Xaa Xaa Xaa
1            5                   10                 15

Cys Xaa Xaa Xaa Xaa
           20

(2) INFORMATION FOR SEQ ID NO: 33:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 33:

Xaa Xaa Xaa Xaa Cys Xaa Xaa Xaa Xaa Xaa Xaa Xaa Xaa Xaa Xaa
1            5                   10                 15

Cys Xaa Xaa Xaa Xaa
           20

(2) INFORMATION FOR SEQ ID NO: 34:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 34:

Gly Gly Thr Tyr Ser Cys His Phe Gly Pro Leu Thr Trp Val Cys
1            5                   10                 15

```
Lys Pro Gln Gly Gly
            20

(2) INFORMATION FOR SEQ ID NO: 35:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 35:

Cys Xaa Xaa Gly Pro Xaa Xaa Xaa Xaa Cys
 1           5                      10

(2) INFORMATION FOR SEQ ID NO: 36:

(i) SEQUENCE CHARACTERISTICS:
        (A) LENGTH: 70 base pairs
        (B) TYPE: Nucleic Acid
        (C) STRANDEDNESS: Single
        (D) TOPOLOGY: Linear (xi) SEQUENCE DESCRIPTION: SEQ ID NO: 36:

GCCTATGCAT CTGGTACCGC CTGCNNSNNS GGTCCTNNSN NSNNSNNSTG            50

TTCTCTGGCA GGTTCACCAG                                             70

(2) INFORMATION FOR SEQ ID NO: 37:

(i) SEQUENCE CHARACTERISTICS:
        (A) LENGTH: 91 base pairs
        (B) TYPE: Nucleic Acid
        (C) STRANDEDNESS: Single
        (D) TOPOLOGY: Linear (ii) MOLECULE TYPE: Nucleic Acid (xi) SEQUENCE DESCRIPTION: SEQ ID NO: 37:

GCTACAAATG CCTATGCANN SNNSNNSNNS TGCNNSNNSG GTCCTNNSNN            50

SNNSNNSTGT NNSNNSNNSN NSGGTGGAGG ATCCGGAGGA G                     91

(2) INFORMATION FOR SEQ ID NO: 38:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 38:

GCTACAAATG CCTATGCANN SNNSNNSNNS NNSNNSNNST GCNNSNNSNN            50

SNNSTGCNNS NNSNNSNNSN NSNNSNNSGG TGGAGGATCC GGAGGAG               97

(2) INFORMATION FOR SEQ ID NO: 39:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 39:

GCTACAAATG CCTATGCANN SNNSNNSNNS NNSNNSNNST GCNNSNNSNN            50

SNNSNNSTGC NNSNNSNNSN NSNNSNNSGG TGGAGGATCC GGAGGAG               97
```

(2) INFORMATION FOR SEQ ID NO: 40:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 40:

```
GCTACAAATG CCTATGCANN SNNSNNSNNS NNSNNSTGCN NSNNSNNSNN         50

SNNSNNSTGC NNSNNSNNSN NSNNSNNSGG TGGAGGATCC GGAGGAG            97
```

(2) INFORMATION FOR SEQ ID NO: 41:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 41:

```
GCTACAAATG CCTATGCANN SNNSNNSNNS NNSNNSTGCN NSNNSNNSNN         50

SNNSNNSNNS TGCNNSNNSN NSNNSNNSGG TGGAGGATCC GGAGGAG            97
```

(2) INFORMATION FOR SEQ ID NO: 42:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 42:

```
GCTACAAATG CCTATGCANN SNNSNNSNNS NNSTGCNNSN NSNNSNNSNN         50

SNNSNNSNNS TGCNNSNNSN NSNNSNNSGG TGGAGGATCC GGAGGAG            97
```

(2) INFORMATION FOR SEQ ID NO: 43:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 43:

```
GCTACAAATG CCTATGCANN SNNSNNSNNS NNSTGCNNSN NSNNSNNSNN         50

SNNSNNSNNS NNSTGCNNSN NSNNSNNSGG TGGAGGATCC GGAGGAG            97
```

(2) INFORMATION FOR SEQ ID NO: 44:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 44:

```
GCTACAAATG CCTATGCANN SNNSNNSNNS TGCNNSNNSN NSNNSNNSNN         50

SNNSNNSNNS NNSTGCNNSN NSNNSNNSGG TGGAGGATCC GGAGGAG            97
```

(2) INFORMATION FOR SEQ ID NO: 45:

(i) SEQUENCE CHARACTERISTICS:
        (A) LENGTH: 20 amino acids (B) TYPE: Amino Acid
        (D) TOPOLOGY: Linear (xi) SEQUENCE DESCRIPTION: SEQ ID NO: 45:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

(2) INFORMATION FOR SEQ ID NO: 46:

(i) SEQUENCE CHARACTERISTICS:
        (A) LENGTH: 97 base pairs
        (B) TYPE: Nucleic Acid
        (C) STRANDEDNESS: Single
        (D) TOPOLOGY: Linear (xi) SEQUENCE DESCRIPTION: SEQ ID NO: 46:

GCTACAAATG CCTATGCANN SNNSNNSNNS NNSNNSNNSN NSNNSNNSNN          50

SNNSNNSNNS NNSNNSNNSN NSNNSNNSGG TGGAGGATCC GGAGGAG             97

(2) INFORMATION FOR SEQ ID NO: 47:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 47:

Ser Gly Thr Ala Cys Tyr Gly Gly Pro Glu Trp Trp Cys Cys Ser
1               5                   10                  15

Leu Ala Gly Ser Pro
            20

(2) INFORMATION FOR SEQ ID NO: 48:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 48:

Asp Leu Ala Ile Cys Ala Glu Gly Pro Glu Ile Trp Val Cys Glu
1               5                   10                  15

Glu Thr Ser
        18

(2) INFORMATION FOR SEQ ID NO: 49:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 49:

Asp Phe Trp Ile Cys Leu Ser Gly Pro Gly Trp Glu Glu Cys Leu
1               5                   10                  15

Glu Trp Trp
        18

(2) INFORMATION FOR SEQ ID NO: 50:

(i) SEQUENCE CHARACTERISTICS:
        (A) LENGTH: 20 amino acids (B) TYPE: Amino Acid
            (D) TOPOLOGY: Linear (xi) SEQUENCE DESCRIPTION: SEQ ID NO: 50:

Gly Ser Ala Gly Gln Gly Met Thr Glu Glu Trp Ala Trp Ile Trp
1               5                   10                  15

Glu Trp Trp Lys Glu
                20

(2) INFORMATION FOR SEQ ID NO: 51:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 51:

Glu Leu Asp Gly Trp Val Cys Ile Lys Val Gly Glu Gln Asn Leu
1               5                   10                  15

Cys Tyr Leu Ala Glu
                20

(2) INFORMATION FOR SEQ ID NO: 52:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 52:

Ala Ile Gly Gly Trp Cys Phe Ile Glu Leu Asp Ser Leu Trp Cys
1               5                   10                  15

Glu Glu Gln Ile Gly
                20

(2) INFORMATION FOR SEQ ID NO: 53:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 53:

Ser Glu Asp Val Glu Cys Trp Gln Val Trp Glu Asn Leu Val Cys
1               5                   10                  15

Ser Val Glu His Arg
                20

(2) INFORMATION FOR SEQ ID NO: 54:

(i) SEQUENCE CHARACTERISTICS:
        (A) LENGTH: 19 amino acids
        (B) TYPE: Amino Acid
        (D) TOPOLOGY: Linear (xi) SEQUENCE DESCRIPTION: SEQ ID NO: 54:

Ser Glu Glu Val Cys Trp Pro Val Ala Glu Trp Tyr Leu Cys Asn
1               5                   10                  15

Met Trp Gly Arg
                19

(2) INFORMATION FOR SEQ ID NO: 55:

(i) SEQUENCE CHARACTERISTICS:

```
          (A) LENGTH: 20 amino acids
          (B) TYPE: Amino Acid
          (D) TOPOLOGY: Linear (xi) SEQUENCE DESCRIPTION: SEQ ID NO: 55:

Arg Val Gly Ala Tyr Ile Ser Cys Ser Glu Thr Glu Cys Trp Val
1               5                   10                  15

Glu Asp Leu Leu Asp
            20

(2) INFORMATION FOR SEQ ID NO: 56:

(i) SEQUENCE CHARACTERISTICS:
          (A) LENGTH: 20 amino acids
          (B) TYPE: Amino Acid
          (D) TOPOLOGY: Linear (xi) SEQUENCE DESCRIPTION: SEQ ID NO: 56:

Trp Phe Lys Thr Val Cys Tyr Glu Trp Glu Asp Glu Val Gln Cys
1               5                   10                  15

Tyr Thr Leu Glu Glu
            20

(2) INFORMATION FOR SEQ ID NO: 57:

(i) SEQUENCE CHARACTERISTICS:
          (A) LENGTH: 20 amino acids
          (B) TYPE: Amino Acid
          (D) TOPOLOGY: Linear (xi) SEQUENCE DESCRIPTION: SEQ ID NO: 57:

Arg Leu Glu Glu Gln Cys Val Glu Val Asn Tyr Glu Pro Ser Cys
1               5                   10                  15

Ser Phe Thr Ala Asn
            20

(2) INFORMATION FOR SEQ ID NO: 58:

(i) SEQUENCE CHARACTERISTICS:
          (A) LENGTH: 19 amino acids
          (B) TYPE: Amino Acid
          (D) TOPOLOGY: Linear (xi) SEQUENCE DESCRIPTION: SEQ ID NO: 58:

Ser Glu Glu Val Cys Trp Pro Val Ala Glu Trp Tyr Leu Cys Asn
1               5                   10                  15

Ile Leu Gly Pro
            19

(2) INFORMATION FOR SEQ ID NO: 59:

(i) SEQUENCE CHARACTERISTICS:
          (A) LENGTH: 20 amino acids
          (B) TYPE: Amino Acid
          (D) TOPOLOGY: Linear (xi) SEQUENCE DESCRIPTION: SEQ ID NO: 59:

Glu Thr Val Ala Asn Cys Asp Cys Tyr Met Asp Leu Cys Leu Cys
1               5                   10                  15

Tyr Gly Ser Asp Arg
            20

(2) INFORMATION FOR SEQ ID NO: 60:
```

```
        (i) SEQUENCE CHARACTERISTICS:
            (A) LENGTH: 20 amino acids
            (B) TYPE: Amino Acid
            (D) TOPOLOGY: Linear (xi) SEQUENCE DESCRIPTION: SEQ ID NO: 60:

Tyr His Pro Ile Ser Cys Met Asp His Tyr Tyr Leu Ile Ile Cys
 1               5                  10                  15

Asp Glu Thr Val Asn
                 20

(2) INFORMATION FOR SEQ ID NO: 61:

(i) SEQUENCE CHARACTERISTICS:
            (A) LENGTH: 20 amino acids
            (B) TYPE: Amino Acid
            (D) TOPOLOGY: Linear (xi) SEQUENCE DESCRIPTION: SEQ ID NO: 61:

Ala Glu Trp Ala Glu Cys Trp Ile Ala Gly Asp Gln Leu Leu Cys
 1               5                  10                  15

Val Gly Lys Asp Asn
                 20

(2) INFORMATION FOR SEQ ID NO: 62:

(i) SEQUENCE CHARACTERISTICS:
            (A) LENGTH: 20 amino acids
            (B) TYPE: Amino Acid
            (D) TOPOLOGY: Linear (xi) SEQUENCE DESCRIPTION: SEQ ID NO: 62:

Glu Pro Trp Leu Cys Gln Tyr Tyr Glu Ala Ala Met Leu Tyr Leu
 1               5                  10                  15

Cys Trp Glu Glu Gly
                 20

(2) INFORMATION FOR SEQ ID NO: 63:

(i) SEQUENCE CHARACTERISTICS:
            (A) LENGTH: 20 amino acids
            (B) TYPE: Amino Acid
            (D) TOPOLOGY: Linear (xi) SEQUENCE DESCRIPTION: SEQ ID NO: 63:

Ala Glu Glu Gly Met Val Trp Gly Trp Thr Gly Gly Trp Tyr Asn
 1               5                  10                  15

Leu Asp Glu Leu Cys
                 20

(2) INFORMATION FOR SEQ ID NO: 64:

(i) SEQUENCE CHARACTERISTICS:
            (A) LENGTH: 20 amino acids
            (B) TYPE: Amino Acid
            (D) TOPOLOGY: Linear (xi) SEQUENCE DESCRIPTION: SEQ ID NO: 64:

Ser Gly Gly Ala Ile Tyr Trp Pro Val Glu Gln Phe Ile Ala Phe
 1               5                  10                  15

Met Ala Val Gly Lys
                 20

(2) INFORMATION FOR SEQ ID NO: 65:
```

(i) SEQUENCE CHARACTERISTICS:
            (A) LENGTH: 20 amino acids
            (B) TYPE: Amino Acid
            (D) TOPOLOGY: Linear (xi) SEQUENCE DESCRIPTION: SEQ ID NO: 65:

Ser Gly Gly Ala Ile Tyr Met Pro Val Glu Gln Phe Ile Ala Phe
 1               5                  10                  15

Met Ala Val Gly Lys
                20

(2) INFORMATION FOR SEQ ID NO: 66:

(i) SEQUENCE CHARACTERISTICS:
            (A) LENGTH: 18 amino acids
            (B) TYPE: Amino Acid
            (D) TOPOLOGY: Linear (xi) SEQUENCE DESCRIPTION: SEQ ID NO: 66:

Glu Val Leu Leu Cys Ser Asp Gly Pro Gln Leu Tyr Leu Cys Glu
 1               5                  10                  15

Leu Tyr Ala
        18

(2) INFORMATION FOR SEQ ID NO: 67:

(i) SEQUENCE CHARACTERISTICS:
            (A) LENGTH: 18 amino acids
            (B) TYPE: Amino Acid
            (D) TOPOLOGY: Linear (xi) SEQUENCE DESCRIPTION: SEQ ID NO: 67:

Ser Gly Val Glu Cys Val Trp Gly Pro Gln Trp Gly Phe Cys Val
 1               5                  10                  15

Glu Glu Tyr
        18

(2) INFORMATION FOR SEQ ID NO: 68:

(i) SEQUENCE CHARACTERISTICS:
            (A) LENGTH: 18 amino acids
            (B) TYPE: Amino Acid
            (D) TOPOLOGY: Linear (xi) SEQUENCE DESCRIPTION: SEQ ID NO: 68:

Asp Lys Glu Val Cys Tyr Leu Gly Pro Glu Thr Trp Leu Cys Phe
 1               5                  10                  15

Trp Trp Pro
        18

(2) INFORMATION FOR SEQ ID NO: 69:

(i) SEQUENCE CHARACTERISTICS:
            (A) LENGTH: 18 amino acids
            (B) TYPE: Amino Acid
            (D) TOPOLOGY: Linear (xi) SEQUENCE DESCRIPTION: SEQ ID NO: 69:

Gly Asp Val Glu Cys Ile Glu Gly Pro Trp Gly Glu Leu Cys Val
 1               5                  10                  15

Trp Ala Asp
        18

(2) INFORMATION FOR SEQ ID NO: 70:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 70:

```
Phe Gly Gly Trp Ser Cys Gln Pro Thr Trp Val Asp Val Tyr Val
 1               5                  10                  15
Cys Asn Phe Glu Glu
                 20
```

(2) INFORMATION FOR SEQ ID NO: 71:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 71:

```
Ala Met Trp Val Cys Val Ser Asp Trp Glu Thr Val Glu Glu Cys
 1               5                  10                  15
Ile Gln Tyr Met Tyr
                 20
```

(2) INFORMATION FOR SEQ ID NO: 72:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 72:

```
Thr Asn Trp Phe Phe Val Cys Glu Ser Gly His Gln Asp Ile Cys
 1               5                  10                  15
Trp Leu Ala Glu Glu
                 20
```

(2) INFORMATION FOR SEQ ID NO: 73:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 73:

```
Ser Glu Val Gly Cys Arg Ala Gly Pro Leu Gln Trp Leu Cys Glu
 1               5                  10                  15
Lys Tyr Phe
         18
```

(2) INFORMATION FOR SEQ ID NO: 74:

(i) SEQUENCE CHARACTERISTICS:
        (A) LENGTH: 19 amino acids
        (B) TYPE: Amino Acid
        (D) TOPOLOGY: Linear (xi) SEQUENCE DESCRIPTION: SEQ ID NO: 74:

```
Lys Asp Pro Val Cys Gly Glu Gly Pro Leu Met Arg Ile Cys Glu
 1               5                  10                  15
Arg Leu Phe Gly
                 19
```

(2) INFORMATION FOR SEQ ID NO: 75:

(i) SEQUENCE CHARACTERISTICS:
        (A) LENGTH: 21 amino acids
        (B) TYPE: Amino Acid
        (D) TOPOLOGY: Linear (xi) SEQUENCE DESCRIPTION: SEQ ID NO: 75:

```
Glu Val Asp Gly Arg Trp Trp Ile Val Glu Thr Phe Leu Ala Lys
 1               5                  10                  15
Trp Asp His Met Ala Gly
            20  21
```

(2) INFORMATION FOR SEQ ID NO: 76:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 76:

```
Trp Val Met Glu Cys Gly Ala Gly Pro Trp Pro Glu Gly Cys Thr
 1               5                  10                  15
Phe Met Leu
        18
```

(2) INFORMATION FOR SEQ ID NO: 77:

(i) SEQUENCE CHARACTERISTICS:
        (A) LENGTH: 19 amino acids
        (B) TYPE: Amino Acid
        (D) TOPOLOGY: Linear (xi) SEQUENCE DESCRIPTION: SEQ ID NO: 77:

```
Arg Lys Thr Ser Gln Gly Arg Gly Gln Glu Met Cys Trp Glu Thr
 1               5                  10                  15
Gly Gly Cys Ser
            19
```

(2) INFORMATION FOR SEQ ID NO: 78:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 78:

```
Ser Trp Glu Arg Gly Glu Leu Thr Tyr Met Lys Leu Cys Glu Tyr
 1               5                  10                  15
Met Arg Leu Gln Gln
            20
```

(2) INFORMATION FOR SEQ ID NO: 79:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 79:

```
Glu His Gly Arg Ala Asn Cys Leu Ile Thr Pro Glu Ala Gly Lys
 1               5                  10                  15
Leu Ala Arg Val Thr
            20
```

(2) INFORMATION FOR SEQ ID NO: 80:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 80:

```
Val Glu Asp Glu Cys Trp Met Gly Pro Asp Trp Ala Val Cys Trp
 1               5                  10                  15
Thr Trp Gly
         18
```

(2) INFORMATION FOR SEQ ID NO: 81:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 81:

```
Cys Arg Ala Gly Pro Leu Gln Trp Leu Cys Glu
 1               5                  10  11
```

(2) INFORMATION FOR SEQ ID NO: 82:

(i) SEQUENCE CHARACTERISTICS:
        (A) LENGTH: 12 amino acids
        (B) TYPE: Amino Acid
        (D) TOPOLOGY: Linear (xi) SEQUENCE DESCRIPTION: SEQ ID NO: 82:

```
Cys Arg Ala Gly Pro Leu Gln Trp Leu Cys Glu Lys
 1               5                  10      12
```

(2) INFORMATION FOR SEQ ID NO: 83:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 83:

```
Cys Arg Ala Gly Pro Leu Gln Trp Leu Cys Glu Lys Ala Ala
 1               5                  10                  14
```

(2) INFORMATION FOR SEQ ID NO: 84:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 84:

```
Cys Arg Lys Gly Pro Leu Gln Trp Leu Cys Glu Leu Tyr Phe
 1               5                  10                  14
```

(2) INFORMATION FOR SEQ ID NO: 85:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 85:

```
Cys Arg Lys Gly Pro Leu Gln Trp Leu Cys Glu Lys Tyr Phe
 1               5                  10                  14
```

(2) INFORMATION FOR SEQ ID NO: 86:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 86:

```
Cys Lys Glu Gly Pro Leu Gln Trp Leu Cys Glu Lys Tyr Phe
 1               5                  10                  14
```

(2) INFORMATION FOR SEQ ID NO: 87:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 87:

```
Cys Lys Glu Gly Pro Leu Leu Trp Leu Cys Glu Lys Tyr Phe
 1               5                  10                  14
```

(2) INFORMATION FOR SEQ ID NO: 88:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 88:

```
Ser Glu Val Gly Cys Arg Glu Gly Pro Leu Gln Trp Leu Cys Glu
 1               5                  10                      15

Lys Tyr Phe
         18
```

(2) INFORMATION FOR SEQ ID NO: 89:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 89:

```
Cys Ala Ala Gly Pro Leu Gln Trp Leu Cys Glu Lys Tyr Phe
 1               5                  10                  14
```

(2) INFORMATION FOR SEQ ID NO: 90:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 90:

```
Cys Arg Ala Gly Pro Leu Gln Trp Leu Cys Glu Arg Tyr Phe
 1               5                  10                  14
```

(2) INFORMATION FOR SEQ ID NO: 91:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 91:

Cys Arg Ala Gly Pro Leu Gln Trp Leu Cys Glu Lys Phe Phe
1               5                   10              14

(2) INFORMATION FOR SEQ ID NO: 92:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 92:

Cys Lys Ala Gly Pro Leu Leu Trp Leu Cys Glu Arg Phe Phe
1               5                   10              14

(2) INFORMATION FOR SEQ ID NO: 93:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 93:

Cys Arg Ala Gly Pro Leu Gln Trp Leu Cys Glu Arg Phe Phe
1               5                   10              14

(2) INFORMATION FOR SEQ ID NO: 94:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 94:

Cys Arg Glu Gly Pro Leu Gln Trp Leu Cys Glu Arg Phe Phe
1               5                   10              14

(2) INFORMATION FOR SEQ ID NO: 95:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 95:

Cys Lys Glu Gly Pro Leu Leu Trp Leu Cys Glu Arg Phe Phe
1               5                   10              14

(2) INFORMATION FOR SEQ ID NO: 96:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 96:

Cys Arg Ala Gly Pro Leu Gln Trp Leu Cys Glu Lys Tyr Phe
1               5                   10              14

(2) INFORMATION FOR SEQ ID NO: 97:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 97:

```
Ser Glu Met Val Cys Arg Ala Gly Pro Leu Gln Trp Leu Cys Glu
 1               5                  10                  15

Ile Tyr Phe
         18

(2) INFORMATION FOR SEQ ID NO: 98:

(i) SEQUENCE CHARACTERISTICS:
        (A) LENGTH: 18 amino acids
        (B) TYPE: Amino Acid
        (D) TOPOLOGY: Linear (xi) SEQUENCE DESCRIPTION: SEQ ID NO: 98:

Glu Ala Arg Val Cys Arg Ala Gly Pro Leu Gln Trp Leu Cys Glu
 1               5                  10                  15

Lys Tyr Phe
         18

(2) INFORMATION FOR SEQ ID NO: 99:

(i) SEQUENCE CHARACTERISTICS:
        (A) LENGTH: 21 amino acids
        (B) TYPE: Amino Acid
        (D) TOPOLOGY: Linear (xi) SEQUENCE DESCRIPTION: SEQ ID NO: 99:

Ser Glu Val Gly Cys Arg Ala Gly Pro Leu Gln Trp Leu Cys Glu
 1               5                  10                  15

Lys Tyr Phe Ser Thr Tyr
                 20  21

(2) INFORMATION FOR SEQ ID NO: 100:

(i) SEQUENCE CHARACTERISTICS:
        (A) LENGTH: 17 amino acids
        (B) TYPE: Amino Acid
        (D) TOPOLOGY: Linear (xi) SEQUENCE DESCRIPTION: SEQ ID NO: 100:

Cys Arg Ala Gly Pro Leu Gln Trp Leu Cys Glu Lys Tyr Phe Ser
 1               5                  10                  15

Thr Tyr
     17

(2) INFORMATION FOR SEQ ID NO: 101:

(i) SEQUENCE CHARACTERISTICS:
        (A) LENGTH: 20 amino acids
        (B) TYPE: Amino Acid
        (D) TOPOLOGY: Linear (xi) SEQUENCE DESCRIPTION: SEQ ID NO: 101:

Ala Ser Glu Glu Val Cys Trp Pro Val Ala Glu Trp Tyr Leu Cys
 1               5                  10                  15

Asn Met Trp Gly Arg
                 20

(2) INFORMATION FOR SEQ ID NO: 102:

(i) SEQUENCE CHARACTERISTICS:
        (A) LENGTH: 16 amino acids
        (B) TYPE: Amino Acid
        (D) TOPOLOGY: Linear
```

(xi) SEQUENCE DESCRIPTION: SEQ ID NO: 102:

Ala Ser Glu Glu Val Cys Trp Pro Val Ala Glu Trp Tyr Leu Cys
 1               5                  10                  15

Asn
16

(2) INFORMATION FOR SEQ ID NO: 103:

(i) SEQUENCE CHARACTERISTICS:
        (A) LENGTH: 15 amino acids
        (B) TYPE: Amino Acid
        (D) TOPOLOGY: Linear (xi) SEQUENCE DESCRIPTION: SEQ ID NO: 103:

Gly Pro Glu Thr Cys Trp Pro Val Ala Glu Trp Tyr Leu Cys Asn
 1               5                  10                  15

(2) INFORMATION FOR SEQ ID NO: 104:

(i) SEQUENCE CHARACTERISTICS:
        (A) LENGTH: 14 amino acids
        (B) TYPE: Amino Acid
        (D) TOPOLOGY: Linear (xi) SEQUENCE DESCRIPTION: SEQ ID NO: 104:

Glu Glu Val Cys Trp Pro Val Ala Glu Trp Tyr Leu Cys Asn
 1           5                  10              14

(2) INFORMATION FOR SEQ ID NO: 105:

(i) SEQUENCE CHARACTERISTICS:
        (A) LENGTH: 13 amino acids
        (B) TYPE: Amino Acid
        (D) TOPOLOGY: Linear (xi) SEQUENCE DESCRIPTION: SEQ ID NO: 105:

Glu Val Cys Trp Pro Val Ala Glu Trp Tyr Leu Cys Asn
 1           5                  10          13

(2) INFORMATION FOR SEQ ID NO: 106:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 106:

Cys Trp Pro Val Ala Glu Trp Tyr Leu Cys Asn
 1           5                  10  11

(2) INFORMATION FOR SEQ ID NO: 107:

(i) SEQUENCE CHARACTERISTICS:
        (A) LENGTH: 10 amino acids
        (B) TYPE: Amino Acid
        (D) TOPOLOGY: Linear (xi) SEQUENCE DESCRIPTION: SEQ ID NO: 107:

Trp Pro Val Ala Glu Trp Tyr Leu Cys Asn
 1           5                  10

(2) INFORMATION FOR SEQ ID NO: 108:

(i) SEQUENCE CHARACTERISTICS:
        (A) LENGTH: 12 amino acids
        (B) TYPE: Amino Acid

```
        (D) TOPOLOGY: Linear (xi) SEQUENCE DESCRIPTION: SEQ ID NO: 108:

Cys Gln Leu Val Arg Pro Asp Leu Leu Leu Cys Gln
 1               5                  10      12

(2) INFORMATION FOR SEQ ID NO: 109:

(i) SEQUENCE CHARACTERISTICS:
        (A) LENGTH: 11 amino acids
        (B) TYPE: Amino Acid
        (D) TOPOLOGY: Linear (xi) SEQUENCE DESCRIPTION: SEQ ID NO: 109:

Ile Pro Val Ser Pro Asp Trp Phe Val Cys Gln
 1               5                  10  11
```

INSULIN-LIKE GROWTH FACTOR AGONIST MOLECULES

BACKGROUND OF THE INVENTION

This is a divisional of application(s) Ser. No. 09/052,888 filed on Mar. 31, 1998, which is a C-I-P of application Ser. No. 08/825,852, filed on Apr. 4, 1997, which issued as U.S. Pat. No. 6,121,416, which applications are incorporated herein by reference and to which application(s) priority is claimed under 35 USC §120.

FIELD OF INVENTION

This invention relates to molecules useful as agonists of the insulin-like growth factors (IGFs). More particularly, these molecules inhibit the interaction of an IGF with one or more of its IGF binding proteins. Such molecules can be used, for example, in any methods where the IGFs are used, for example, in treating hyperglycemic, obesity-related, neurological, cardiac, renal, immunologic, and anabolic disorders.

DESCRIPTION OF BACKGROUND AND RELATED ART

There is a large body of literature on the actions and activities of IGFs (IGF-I, IGF-II, and IGF variants). Human IGF-I is a 7649-dalton polypeptide with a pI of 8.4 (Rinderknecht and Humbel, *Proc. Natl. Acad. Sci. USA*, 73: 2365 (1976); Rinderknecht and Humbel, *J. Biol. Chem.*, 253: 2769 (1978)) belonging to a family of somatomedins with insulin-like and mitogenic biological activities that modulate the action of growth hormone (GH). Van Wyk et al., *Recent Prog. Horm. Res.*, 30: 259 (1974); Binoux, *Ann. Endocrinol.*, 41: 157 (1980); Clemmons and Van Wyk, *Handbook Exp. Pharmacol.*, 57: 161 (1981); Baxter, *Adv. Clin. Chem.*, 25: 49 (1986); U.S. Pat. No. 4,988,675; WO 91/03253; WO 93/23071.

Like GH, IGF-I is a potent anabolic protein. See Tanner et al., *Acta Endocrinol.*, 84: 681–696 (1977); Uthne et al., *J. Clin. Endocrinol. Metab.*, 39: 548–554 (1974). See also Ross et al., *Intensive Care Med.*, 19 Suppl. 2: S54–57 (1993), which is a review of the role of insulin, GH, and IGF-I as anabolic agents in the critically ill. IGF-I has hypoglycemic effects similar to those of insulin, but also promotes positive nitrogen balance. Underwood et al., *Hormone Res.*, 24: 166 (1986); Guler et al., *N. Engl. J. Med.*, 317: 137 (1987). Due to this range of activities, IGF-I is being tested in humans for such widely disparate uses as wound healing, treatment of diabetes, reversal of whole body catabolic states, treatment of heart conditions such as congestive heart failure, and treatment of neurological disorders. Guler et al., *Proc. Natl. Acad. Sci. USA*, 85: 4889–4893 (1988); Duerr et al., *J. Clin. Invest.*, 95: 619–627 (1995); and *Science*, 264: 772–774 (1994).

U.S. Pat. Nos. 5,273,961; 5,466,670; 5,126,324; 5,187,151; 5,202,119; 5,374,620; 5,106,832; 4,988,675; 5,106,832; 5,068,224; 5,093,317; 5,569,648; and 4,876,242; WO 92/11865; WO 96/01124; WO 91/03253; WO 93/25219; WO 93/08826; and WO 94/16722 disclose various methods of treating mammals, especially human patients, using IGF-I. In addition, clinical uses of IGF-I are described, for example, in Bondy, *Ann Intern. Med.*, 120: 593–601 (1994).

As one specific use, IGF-I has been found to exert a variety of actions in the kidney. Hammerman and Miller, *Am. J. Physiol.*, 265: F1–F14 (1993). It has been recognized for decades that the increase in kidney size observed in patients with acromegaly is accompanied by a significant enhancement of glomerular filtration rate. O'Shea and Layish, *J. Am. Soc. Nephrol.*, 3: 157–161 (1992). U.S. Pat. No. 5,273,961 discloses a method for prophylactic treatment of mammals at risk for acute renal failure. In humans IGF-I has been shown to preserve renal function post-operatively. Franklin et al., *Am. J. Physiol.*, 272: F257–F259 (1997). Infusion of the peptide in humans with normal renal function increases glomerular filtration rate and renal plasma flow. Guler et al., *Acta Endocrinol.*, 121: 101–106 (1989); Guler et al., *Proc. Natl. Acad. Sci. USA*, 86: 2868–2872 (1989); Hirschberg et al., *Kidney Int.*, 43: 387–397 (1993); U.S. Pat. No. 5,106,832. Further, humans with moderately reduced renal function respond to short-term (four days) IGF-I administration by increasing their rates of glomerular filtration and renal plasma flow. Hence, IGF-I is a potential therapeutic agent in the setting of chronic renal failure. O'Shea et al., *Am. J. Physiol.*, 264: F917–F922 (1993). Despite the fact that IGF-I can enhance renal function for those experiencing end-stage chronic renal failure, the enhancements of the glomerular filtration rate and renal plasma flow induced by IGF-I short-term do not persist during long-term administration and incidence of side-effects is high. Miller et al., *Kidney International*, 46: 201–207 (1994).

For complete reviews of the effect of IGF-I on the kidney, see, e.g., Hammerman and Miller, *Am. J. Physiol.*, 265: F1–F14 (1993) and Hammerman and Miller, *J. Am. Soc. Nephrol.*, 5: 1–11 (1994).

As to anabolic indications for IGF-I, in HIV-infected patients treated consecutively with IGF-I, the IGF-I promoted anabolism, but tachyphylaxis developed rapidly in the patients. Lieberman et al., *U.S. Endocrine Meeting*, June 1993 (Abst. 1664); Lieberman et al., *J. Clin. Endo. Metab.*, 78: 404–410 (1994). In patients with severe head injuries, a condition associated with profound hypercatabolism and nitrogen loss, infusion of IGF-I produced only a transient positive nitrogen balance. In the first week the patients experienced a positive nitrogen balance, but during the second week, a negative nitrogen balance developed. Chen et al., *U.S. Endocrine Meeting*, June 1993 (Abst. 1596).

IGF-I has hypoglycemic effects in humans similar to those of insulin when administered by intravenous bolus injection. Underwood et al., *Hormone Research*, 24: 166 (1986). IGF-I is known to exert glucose-lowering effects in both normal (Guler et al., *N. Engl. J. Med.*, supra) and diabetic individuals (Schoenle et al., *Diabetologia*, 34: 675–679 (1991); Zenobi et al., *J. Clin. Invest.*, 90: 2234–2241 (1992); Sherwin et al., *Hormone Research*, 41 (Suppl. 2): 97–101 (1994); Takano et al., *Endocrinol. Japan*, 37: 309–317 (1990); Guler et al., *Acta Paediatr. Scand.* (*Suppl.*), 367: 52–54 (1990)), with a time course described as resembling regular insulin. See also Kerr et al., "Effect of Insulin-like Growth Factor 1 on the responses to and recognition of hypoglycemia," American Diabetes Association (ADA), 52nd Annual Meeting, San Antonio, Tex., Jun. 20–23, 1992, which reported an increased hypoglycemia awareness following recombinant human IGF-I (rhIGF-I) administration. In addition, single administration of rhIGF-I reduces overnight GH levels and insulin requirements in adolescents with IDDM. Cheetham et al., *Clin. Endocrinol*, 40: 515–555 (1994); Cheetham et al., *Diabetologia*, 36: 678–681 (1993).

The administration of rhIGF-I to Type II diabetics, as reported by Schalch et al., *J. Clin. Metab.*, 77: 1563–1568 (1993), demonstrated a fall in both serum insulin as well as a paralleled decrease in C peptide levels. This indicated a reduction in pancreatic insulin secretion after five days of IGF-I treatment. This effect has been independently confirmed by Froesch et al., *Horm. Res.*, 42: 66–71 (1994). In vivo studies in normal rats also illustrate that IGF-I infusion inhibits pancreatic insulin release. Fursinn et al., *Endocrinology*, 135: 2144–2149 (1994). In addition, in pancreas perfusion preparations, IGF-I also suppressed insulin secretion. Leahy et al., *Endocrinology*, 126: 1593–1598 (1990). Despite these clear in vivo inhibitory effects of IGF-I on insulin secretion in humans and animals, in vitro studies have not yielded such uniform results.

RhIGF-I has the ability to improve insulin sensitivity. For example, rhIGF-I (70 μg/kg bid) improved insulin sensitivity in non-diabetic, insulin-resistant patients with myotonic dystrophy. Vlachopapadopoulou et al., *J. Clin. Endo. Metab.*, 12: 3715–3723 (1995). Saad et al., *Diabetologia*, 37: Abstract 40 (1994) reported dose-dependent improvements in insulin sensitivity in adults with obesity and impaired glucose tolerance following 15 days of rhIGF-I treatment (25 μg and 100 μg/kg bid). RhIGF-I also improved insulin sensitivity and glycemic control in some patients with severe type A insulin resistance (Schoenle et al., *Diabetologia*, 34: 675–679 (1991); Morrow et al., *Diabetes*, 42 (Suppl.): 269 (1993) (abstract); Kuzuya et al., *Diabetes*, 42: 696–705 (1993)) and in other patients with non-insulin dependent diabetes mellitus. Schalch et al., "Short-term metabolic effects of recombinant human insulin-like growth factor I (rhIGF-I) in type II diabetes mellitus", in: Spencer E M, ed., *Modern Concepts of Insulin-like Growth Factors* (New York: Elsevier: 1991) pp. 705–715; Zenobi et al., *J. Clin. Invest.*, 90: 2234–2241 (1993).

A general scheme for the etiology of some clinical phenotypes that give rise to insulin resistance and the possible effects of administration of IGF-I on selected representative subjects is given in several references. See, e.g., Elahi et al., "Hemodynamic and metabolic responses to human insulin-like growth factor-1 (IGF-I) in men," in: *Modern Concepts of Insulin-Like Growth Factors*, (Spencer, E M, ed.), Elsevier, New York, pp. 219–224 (1991); Quinn et al., *New Engl. J. Med.*, 323: 1425–1426 (1990); Schalch et al., "Short-term metabolic effects of recombinant human insulin-like growth factor 1 (rhIGF-I) in type 11 diabetes mellitus," in: *Modern Concepts of Insulin-Like Growth Factors*, (Spencer, E M, ed.), Elsevier, New York, pp. 705–714 (1991); Schoenle et al., *Diabetologia*, 34: 675–679 (1991); Usala et al., *N. Eng. J. Med.*, 327: 853–857 (1992); Lieberman et al. *J. Clin. Endo. Metab.*, 75: 30–36 (1992); Zenobi et al., *J. Clin. Invest.*, 90: 2234–2241 (1992); Zenobi et al., *J. Clin. Invest.*, 89: 1908–1913 (1992); Kerr et al., *J. Clin. Invest.*, 91: 141–147 (1993). When IGF-I was used to treat Type II diabetic patients in the clinic at a dose of 120–160 μg/kg twice daily, the side effects outweighed the benefit of the treatment. Jabri et al., *Diabetes*, 43: 369–374 (1994). See also Wilton, *Acta Paediatr.*, 383: 137–141 (1992) regarding side effects observed upon treatment of patients with IGF-I.

The IGF binding proteins (IGFBPs) are a family of at least six proteins (Jones and Clemmons, *Endocr. Rev.*, 16: 3–34 (1995); Bach and Rechler, *Diabetes Reviews*, 3: 38–61 (1995)), with other related proteins also possibly binding the IGFs. The IGFBPs bind IGF-I and IGF-II with varying affinities and specificities. Jones and Clemmons, supra; Bach and Rechler, supra. For example, IGFBP-3 binds IGF-I and IGF-II with a similar affinity, whereas IGFBP-2 and IGFBP-6 bind IGF-II with a much higher affinity than they bind IGF-I. Bach and Rechler, supra; Oh et al., *Endocrinology*, 132, 1337–1344 (1993).

Unlike most other growth factors, the IGFs are present in high concentrations in the circulation, but only a small fraction of the IGFs is not protein bound. For example, it is generally known that in humans or rodents, less than 1% of the IGFs in blood is in a "free" or unbound form. Juul et al., *Clin. Endocrinol.*, 44: 515–523 (1996); Hizuka et al., *Growth Regulation*, 1: 51–55 (1991); Hasegawa et al., *J. Clin. Endocrinol. Metab.*, 80: 3284–3286 (1995). The overwhelming majority of the IGFs in blood circulate as part of a non-covalently associated ternary complex composed of IGF-I or IGF-II, IGFBP-3, and a large protein termed the acid-labile subunit (ALS). This complex is composed of equimolar amounts of each of the three components. The ternary complex of an IGF, IGFBP-3, and ALS has a molecular weight of approximately 150,000 daltons, and it has been suggested that the function of this complex in the circulation may be to serve as a reservoir and buffer for IGF-I and IGF-II, preventing rapid changes in free IGF-I or IGF-II.

IGF-I naturally occurs in human body fluids, for example, blood and human cerebral spinal fluid. Although IGF-I is produced in many tissues, most circulating IGF-I is believed to be synthesized in the liver. The IGFBPs are believed to modulate the biological activity of IGF-I (Jones and Clemmons, supra), with IGFBP-1 (Lee et al., *Proc. Soc. Exp. Biol. & Med.*, 204: 4–29 (1993)) being implicated as the primary binding protein involved in glucose metabolism. Baxter, "Physiological roles of IGF binding proteins", in: Spencer (Ed.), *Modern Concepts of Insulin-like Growth Factors* (Elsevier, New York, 1991), pp. 371–380. IGFBP-1 production by the liver is regulated by nutritional status, with insulin directly suppressing its production. Suikkari et al., *J. Clin. Endocrinol. Metab.*, 66: 266–272 (1988).

The function of IGFBP-1 in vivo is poorly understood. The administration of purified human IGFBP-1 to rats has been shown to cause an acute, but small, increase in blood glucose. Lewitt et al., *Endocrinology*, 129: 2254–2256 (1991). The regulation of IGFBP-1 is somewhat better understood. It has been proposed (Lewitt and Baxter, *Mol. Cell Endocrinology*, 79: 147–152 (1991)) that when blood glucose rises and insulin is secreted, IGFBP-1 is suppressed, allowing a slow increase in "free" IGF-I levels that might assist insulin action on glucose transport. Such a scenario places the function of IGFBP-1 as a direct regulator of blood glucose.

The IGF system is also composed of membrane-bound receptors for IGF-I, IGF-II, and insulin. The Type 1 IGF receptor is closely related to the insulin receptor in structure and shares some of its signaling pathways. Jones and Clemmons, supra. The IGF-II receptor is a clearance receptor that appears not to transmit an intracellular signal. Jones and Clemmons, supra. Since IGF-I and IGF-II bind to the Type 1 IGF-I receptor with a much higher affinity than to the insulin receptor, it is most likely that most of the effects of IGF-I and IGF-II are mediated by the Type 1 IGF receptor. Ballard et al., "Does IGF-I ever act through the insulin receptor?", in Baxter et al. (Eds.), *The Insulin-Like Growth Factors and Their Regulatory Proteins*, (Amsterdam: Elsevier, 1994), pp. 131–138.

There has been much work identifying the domains on IGF-I and IGF-II that bind to the IGFBPs. Bayne et al., *J. Biol. Chem.*, 265: 15648–15652 (1990); U.S. Pat. Nos. 5,077,276; 5,164,370; 5,470,828. For example, it has been discovered that the N-terminal region of IGF-I and IGF-II is critical for binding to the IGFBPs. U.S. Pat. Nos. 5,077,276; 5,164,370; 5,470,828. Thus, the natural IGF-I variant, designated des(1-3)IGF-I, binds poorly to IGFBPs.

A similar amount of research has been devoted to identifying the domains on IGF-I and IGF-II that bind to the Type 1 IGF receptor. Bayne et al., supra; Oh et al., supra. It was found that the tyrosine residues in IGF-I at positions 24, 31, and 60 are crucial to the binding of IGF-I to the Type 1 IGF receptor. Bayne et al., supra. Mutant IGF-I molecules where one or more of these tyrosine residues are substituted showed progressively reduced binding to Type 1 IGF receptors. Bayne et al., supra, also investigated whether such mutants of IGF-I could bind to the Type 1 IGF receptor and to the IGFBPs. They found that quite different residues on IGF-I and IGF-II are used to bind to the IGFBPs from those used to bind to the Type 1 IGF receptor. It is therefore possible to produce IGF variants that show reduced binding to the IGFBPs, but, because they bind well to the Type 1 IGF receptor, show maintained activity in in vitro activity assays.

Also reported was an IGF variant that binds to IGFBPs but not to IGF receptors and therefore shows reduced activity in in vitro activity assays. Bar et al., *Endocrinology*, 127: 3243–3245 (1990). In this variant, designated (1–27, gly$^4$,38–70)-hIGF-I, residues 28–37 of the C region of human IGF-I are replaced by a four-residue glycine bridge. Bar et al. studied the transport of the mutant IGF-I when it was perfused as a complex with IGFBP through the heart in terms of the localization of IGFBPs bound to the mutant IGF or to IGF itself. There were no data supplied by Bar et al. on the localization of the IGF mutant given alone, only data on the localization of the complex of the IGF mutant and IGFBP. Further, Bar et al. provided no data on any biological or efficacy response to the administration of the IGF mutant.

Other truncated IGF-I variants are disclosed. For example, in the patent literature, WO 96/33216 describes a truncated variant having residues 1–69 of authentic IGF-I. EP 742,228 discloses two-chain IGF-I superagonists which are derivatives of the naturally occurring single-chain IGF-I having an abbreviated C domain. The IGF-I analogs are of the formula:

$$BC^nA$$

wherein B is the B domain of IGF-I or a functional analog thereof, C is the C domain of IGF-I or a functional analog thereof, n is the number of amino acids in the C domain and is from about 6 to about 12, and A is the A domain of IGF-I or a functional analog thereof.

Additionally, Cascieri et al., *Biochemistry*, 27: 3229–3233 (1988) discloses four mutants of IGF-I, three of which have reduced affinity to the Type 1 IGF receptor. These mutants are: (Phe$^{23}$,Phe$^{24}$,Tyr$^{25}$)IGF-I (which is equipotent to human IGF-I in its affinity to the Types 1 and 2 IGF and insulin receptors), (Leu$^{24}$)IGF-I and (Ser$^{24}$)IGF-I (which have a lower affinity than IGF-I to the human placental Type 1 IGF receptor, the placental insulin receptor, and the Type 1 IGF receptor of rat and mouse cells), and desoctapeptide (Leu$^{24}$)IGF-I (in which the loss of aromaticity at position 24 is combined with the deletion of the carboxyl-terminal D region of hIGF-I, which has lower affinity than (Leu$^{24}$)IGF-I for the Type 1 receptor and higher affinity for the insulin receptor). These four mutants have normal affinities for human serum binding proteins.

Bayne et al., *J. Biol. Chem.*, 263: 6233–6239 (1988) discloses four structural analogs of human IGF-I: a B-chain mutant in which the first 16 amino acids of IGF-I were replaced with the first 17 amino acids of the B-chain of insulin, (Gln$^3$,Ala$^4$)IGF-I, (Tyr$^{15}$, Leu$^{16}$)IGF-I, and (Gln$^3$, Ala$^4$,Tyr$^{15}$,Leu$^{16}$)IGF-I. These studies identify some of the domains of IGF-I that are responsible for maintaining high-affinity binding with the serum binding protein and the Type 2 IGF receptor.

Bayne et al., *J. Biol. Chem.*, 264: 11004–11008 (1988) discloses three structural analogs of IGF-I: (1–62)IGF-I, which lacks the carboxyl-terminal 8-amino-acid D region of IGF-I; (1–27,Gly$^4$,38–70)IGF-I, in which residues 28–37 of the C region of IGF-I are replaced by a four-residue glycine bridge; and (1–27,Gly$^4$,38–62)IGF-I, with a C region glycine replacement and a D region deletion. Peterkofsky et al., *Endocrinology*, 128: 1769–1779 (1991) discloses data using the Gly$^4$ mutant of Bayne et al., supra (Vol. 264). U.S. Pat. No. 5,714,460 refers to using IGF-I or a compound that increases the active concentration of IGF-I to treat neural damage.

Cascieri et al., *J. Biol. Chem.*, 264: 2199–2202 (1989) discloses three IGF-I analogs in which specific residues in the A region of IGF-I are replaced with the corresponding residues in the A chain of insulin. The analogs are: (Ile$^{41}$, Glu$^{45}$,Gln$^{46}$,Thr$^{49}$,Ser$^{50}$,Ile$^{51}$,Ser$^{53}$,Tyr$^{55}$,Gln$^{56}$)IGF-I, an A chain mutant in which residue 41 is changed from threonine to isoleucine and residues 42–56 of the A region are replaced; (Thr$^{49}$,Ser$^{50}$,Ile$^{51}$)IGF-I; and (Tyr$^{55}$,Gln$^{56}$)IGF-I.

Clemmons et al., *J. Biol. Chem.*, 265: 12210–12216 (1990) discloses use of IGF-I analogs that have reduced binding affinity for either the Type 1 IGF receptor or binding proteins to study the ligand specificity of IGFBP-1 and the role of IGFBP-1 in modulating the biological activity of IGF-I.

WO 94/04569 discloses a specific binding molecule, other than a natural IGFBP, that is capable of binding to IGF-I and can enhance the biological activity of IGF-I.

U.S. Pat. Nos. 5,593,844 and 5,210,017 disclose a ligand-mediated immunofunctional binding protein assay method that can be used to quantitate the amount of GH binding protein or IGFBP in a liquid sample by the use of antibodies, where complex formation takes place between one of these binding proteins and the hormone ligand that binds to it.

The direction of research into IGF variants has mostly been to make IGF variants that do not bind to the IGFBPs but show maintained binding to the IGF receptor. The idea behind the study of such molecules is that the major actions of the IGFBPs are proposed to be an inhibition of the activity of the IGFs. Chief among these variants is the natural molecule, des(1-3)IGF-I, which shows selectively reduced affinity for some of the IGF binding proteins, yet a maintained affinity for the IGF receptor. U.S. Pat. Nos. 5,077,276; 5,164,370; 5,470,828, supra.

There is a need in the art for a molecule that acts as an IGF agonist, and also for a molecule that binds to IGF binding proteins with high affinity and specificity for therapeutic or diagnostic purposes.

SUMMARY OF THE INVENTION

This invention relates to a novel method for providing releasing factors which, as part of their actions, inhibit binding of an IGF to an IGFBP such as by binding to an IGFBP to agonize the action of IGF. Accordingly, the present invention provides a compound that inhibits the interaction of an IGF with any one of its IGFBPs and does not bind to a human IGF receptor, excluding (1–27,gly$^4$,38–70)-hIGF-I, excluding antibodies against an IGFBP that do not bind to a human IGF receptor, excluding antibodies that bind to an IGF, and excluding peptides having the native sequence of human IGF-I with the tyrosine residues at positions 24, 31, and/or 60 replaced or deleted.

Preferably, the compound herein binds to an IGFBP, preferably a serum IGFBP. Also, preferably, the compound reduces plasma insulin secretion, reduces plasma GH, and/or reduces blood glucose levels in a mammal.

In other preferred embodiments, the compound herein is a peptide, especially a peptide having about 10 to about 25 amino acid residues, and/or having a cysteine residue at position 5, 6, 7, or 8 numbered from its N-terminus or having a cysteine residue at position 5, 6, 7, or 8 numbered from its C-terminus, or both such cysteine residues, or a cysteine residue at position 2 numbered from its N-terminus.

In another embodiment, the invention provides a peptide comprising an amino acid sequence selected from the group consisting of the following peptides:

BP3-B23 ELDGWVCIKVGEQNLCYLAEG (SEQ ID NO: 1)
BP3-24 WFKTVCYEWEDEVQCYTLEEG (SEQ ID NO: 2)
BP3-25 RVGAYISCSETECWVEDLLDG (SEQ ID NO: 3)
BP3-4D3.11 (BP14) VAWEVCWDRHDQGYICTTDS (SEQ ID NO: 4)
BP3-4D3.11DEL AWEVCWDRHQGYICTTDS (SEQ ID NO: 5)
BP13 CWDRHDQGYICTTDS (SEQ ID NO: 6)
BP3-4B3.3 EESECFEGPGYVICGLVG (SEQ ID NO: 7)
BP3-02-ox DMGVCADGPWMYVCEWTE (SEQ ID NO: 8)
BP3-01-ox SEEVCWPVAEWYLCNMWG (SEQ ID NO: 9)
BP15 SEEVCWPVAEWYLCN (SEQ ID NO: 10)
BP16 VCWPVAEWYLCNMWG (SEQ ID NO: 11)
BP17 VCWPVAEWYLCN (SEQ ID NO: 12)
BP06 TGVDCQCGPVHCVCMDWA (SEQ ID NO: 13)
BP08 TVANCDCYMPLCLCYDSD (SEQ ID NO: 14)
bp1-01 CRAGPLQWLCEKYFG (SEQ ID NO: 15)
bp1-02 SEVGCRAGPLQWLCEKYFG (SEQ ID NO: 16)

In another embodiment, the peptide comprises an amino acid sequence that is SEQ ID NO:83. In another embodiment, the peptide comprises an amino acid sequence that is SEQ ID NO:84, SEQ ID NO:85, SEQ ID NO:86, SEQ ID NO:87, SEQ ID NO:89, SEQ ID NO:91, SEQ ID NO:92, SEQ ID NO:93, SEQ ID NO:94, or SEQ ID NO:95. In a still further embodiment, the peptide comprises an amino acid sequence that is SEQ ID NO:88, SEQ ID NO:96, SEQ ID NO:97, SEQ ID NO:98, SEQ ID NO:99, or SEQ ID NO:100. In a still further embodiment, the peptide comprises an amino acid sequence that is SEQ ID NO:101, SEQ ID NO:102, SEQ ID NO:103, SEQ ID NO:10, SEQ ID NO:10, SEQ ID NO:104, SEQ ID NO:105, SEQ ID NO:106, SEQ ID NO:108, or SEQ ID NO:109.

In yet another embodiment, the peptide comprises an amino acid sequence wherein SEQ ID NO:15 has a D-alanine substitution at position 2, 3, 4, or 6 or an alpha-aminoisobutyrate substitution at position 7, 8, 9, 11, 12, 13, or 14, or any combination of the above. Preferably, this peptide has a D-alanine substitution at position 2, 3, or 6 or an alpha-aminoisobutyrate substitution at position 7, 8, 9, 11, 12, 13, or 14, or any combination of the above. More preferably, this peptide has a D-alanine substitution at position 6 or an alpha-aminoisobutyrate substitution at position 8, 9, or 13. In a still more preferred embodiment, these latter sets of peptides have a C-terminus of SEQ ID NO:15 that is AA rather than YFG.

Also provided herein is a composition comprising one of the compounds or peptides described above in a pharmaceutically acceptable carrier. Preferably, this composition is sterile.

Uses of these compounds and peptides include all uses that liberate or enhance at least one biological activity of exogenous or endogenous IGFs. They can be used in treating, inhibiting, or preventing conditions in which an IGF such as IGF-I is useful, as described below.

Additionally provided herein is a method for increasing serum and tissue levels of biologically active IGF in a mammal comprising administering to the mammal an effective amount of a compound that inhibits the interaction of an IGF with any one of its IGFBPs and does not bind a human IGF receptor. Preferably, this compound also reduces plasma insulin secretion, plasma GH secretion, or blood glucose levels in a mammal, and does not directly stimulate the secretion or release of endogenous GH from any species. In other preferred embodiments, this compound binds to an IGFBP, such as IGFBP-1 and/or to IGFBP-3, and/or does not bind to a human Type 1 IGF-I receptor. In addition, the mammal is preferably human and the compound is preferably a peptide, more preferably one having about 10 to about 25 amino acid residues. Also preferred is where administering the compound, preferably in an amount effective to produce body weight gain, causes an increase in anabolism in the mammal. Additionally preferred is that glycemic control is effected in the mammal after the compound is administered.

Isolated nucleic acid encoding the compound herein, if it is a peptide, is also provided, and may be used for in vivo or ex vivo gene therapy.

The compound herein can be administered alone or together with another agent such as GH, a GH releasing peptide (GHRP), a GH releasing factor (GHRF), a GH releasing hormone (GHRH), a GH secretagogue, an IGF, an IGF in combination with an IGFBP, an IGFBP, GH in combination with a GH binding protein (GHBP), insulin, or a hypoglycemic agent (which includes in the definition below an insulin-sensitizing agent such as thiazolidinedione).

In yet another aspect of the invention, a method is provided for effecting glycemic control in a mammal comprising administering to the mammal an effective amount of a compound that inhibits the interaction of an IGF with any one of its IGFBPs and does not bind a human IGF receptor. Preferably, the compound also reduces plasma insulin secretion and blood glucose levels in a mammal and binds an IGFBP. Also preferably, the mammal has a hyperglycemic disorder such as diabetes. This method can additionally comprise administering to the mammal an effective amount of a hypoglycemic agent or insulin.

Also provided is a method for increasing serum and tissue levels of biologically active IGF in a mammal, or a method for increasing anabolism in a mammal, or a method for controlling glycemia in a mammal comprising administering to the mammal an effective amount of the composition containing the compound herein.

In another embodiment, a method is provided for determining appropriate dosing of a compound that inhibits the interaction of an IGF with any one of its IGFBPs and does not bind to a human IGF receptor comprising:

(a) measuring the level of an IGF in a body fluid;
(b) contacting the fluid with the compound herein using single or multiple doses; and
(c) re-measuring the level of an IGF in the fluid, wherein if the fluid IGF level has fallen by an amount sufficient to produce the desired efficacy for which the compound is to be administered, then the dose of the compound is adjustable or adjusted to produce maximal efficacy.

In yet another embodiment, a method is provided for determining the amount of a particular IGFBP or the amount of the compound bound to a particular IGFBP in a biological fluid so that dosing of the compound can be adjusted appropriately. This method involves:

(a) contacting the fluid with 1) a first antibody attached to a solid-phase carrier, wherein the first antibody is specific for epitopes on the IGFBP such that in the presence of antibody the IGF binding sites remain available on the IGFBP for binding to the compound, thereby forming a complex between the first antibody and the IGFBP; and 2) the above-identified compound for a period of time sufficient to saturate all available IGF binding sites on the is IGFBP, thereby forming a saturated complex;

(b) contacting the saturated complex with a detectably labeled second antibody which is specific for epitopes on the compound which are available for binding when the compound is bound to the IGFBP; and (c) quantitatively analyzing the amount of the labeled second antibody bound as a measure of the IGFBP in the biological fluid, and therefore as a measure of the amount of the compound bound.

Also contemplated herein is a kit comprising a container containing a pharmaceutical composition containing the compound herein and instructions directing the user to utilize the composition. This kit may optionally further comprise a container containing a GH, a GHRP, a GHRF, a GHRH, a GH secretagogue, an IGF, an IGF complexed to an IGFBP, an IGFBP, a GH complexed with a GHBP, insulin, or a hypoglycemic agent.

Also included herein is a method for predicting the relative affinity for binding to a ligand of a peptide that competes with a polypeptide for binding to the ligand, which peptide is derived from a phage-displayed library, which method comprises incubating a phagemid clone corresponding to the peptide with the polypeptide in the presence of the ligand, serially diluting the phage, and measuring the degree to which binding of the phagemid clone to the ligand is inhibited by the peptide, wherein a phagemid clone that is inhibited only at low phage concentrations has a higher affinity for the ligand than a phagemid clone that is inhibited at both high and low phage concentrations.

In another embodiment herein, a method for directing endogenous IGF either away from, or towards, a particular site in a mammal comprising administering to the mammal an effective amount of the compound herein that is specific for an IGFBP that is either prevalent at, or absent from, the site.

A further embodiment is a method for detecting endogenous or exogenous IGF bound to an IGF binding protein or the amount of a compound that binds to an IGF binding protein and does not bind to a human IGF receptor bound to an IGF binding protein or detecting the level of unbound IGF in a biological fluid comprising:

(a) contacting the fluid with 1) a means for detecting the compound attached to a solid-phase carrier, wherein the means is specific for the compound such that in the presence of the compound the IGF binding sites remain available on the compound for binding to the IGF binding protein, thereby forming a complex between the means and the IGF binding protein; and 2) the compound for a period of time sufficient to saturate all available IGF binding sites on the IGF binding protein, thereby forming a saturated complex;

(b) contacting the saturated complex with a detectably labeled second means which is specific for the IGF binding protein which are available for binding when the compound is bound to the IGF binding protein; and (c) quantitatively analyzing the amount of the labeled means bound as a measure of the IGFBP in the biological fluid, and therefore as a measure of the amount of bound compound and IGF binding protein, bound IGF and IGF binding protein, or active IGF present in the fluid.

There has been much debate as to the role of the IGFBPs in the action of an IGF. The activity of the IGFs in various situations has been shown to be either inhibited, enhanced, or unaffected by the presence of the IGFBPs. Jones and Clemmons, supra; Bach and Rechler, supra. It has been unclear if the presence of IGFBPs is obligatory for some actions of the IGFs. For some actions it was thought possible that it was necessary for the IGFs to be bound to the IGFBPs, or that it was necessary for the IGFBPs to be present if IGF-I were to be fully active. Before the present studies it was therefore unclear as to what would be the net biological effect in vivo of administering molecules that inhibit the interaction of an IGF with any one of its IGFBPs.

The compounds herein are superior to IGF mutants such as des(1-3)IGF-I, since the latter have short half-lives and effects, whereas the compounds herein have longer half lives and effects, and, if they bind to IGFBPs, this binding avoids normal renal filtration which would otherwise eliminate short peptides and other small molecules rapidly. Further, administering the compound herein together with exogenous GH or GH secretagogues would have the advantage of minimizing diabetogenic effects of such GH and secretagogues. Yet another advantage of the compounds herein is that there is a ceiling of the effects of the IGF agonist compound herein. That is, it cannot exert more effects than the maximum capacity of IGFBPs to carry IGFs, unlike IGF-I, which can have unwanted side effects if used in large concentrations over its maximum efficacy.

BRIEF DESCRIPTION OF THE DRAWINGS

FIG. 1 depicts the nucleotide sequence (SEQ ID NO:17) and translated amino acid sequence (SEQ ID NO:18) of the lamB signal connected at the 5' end of DNA encoding an IGF-I mutant designated herein as Y24L, Y31A, or (Leu$^{24}$, Ala$^{31}$)hIGF, or IGF-M, where the Tyr at position 24 is changed to Leu and the Tyr at position 31 is changed to Ala.

FIG. 3 depicts the full nucleotide sequence of pIGFMI (SEQ ID NO:19).

FIG. 24 depicts the DNA sequence (SEQ ID NO: 20) of plasmid pt4.g8 used as a template to construct a phage library. Also shown is the amino acid sequence (SEQ ID NO:21) of an antibody-recognizable (gD-tag) peptide fused to g8p of bacteriophage M13.

FIG. 37 depicts KIRA assays of IGF-I activity using three peptides (bp1-01: squares, bp1-02: circles, and bp03-ox:

triangles).

FIG. 44 shows the concentrations of IGFBP-3 in the blood of the patients treated as described for FIG. 42.

DESCRIPTION OF THE PREFERRED EMBODIMENTS

A. Definitions

Figure 2:
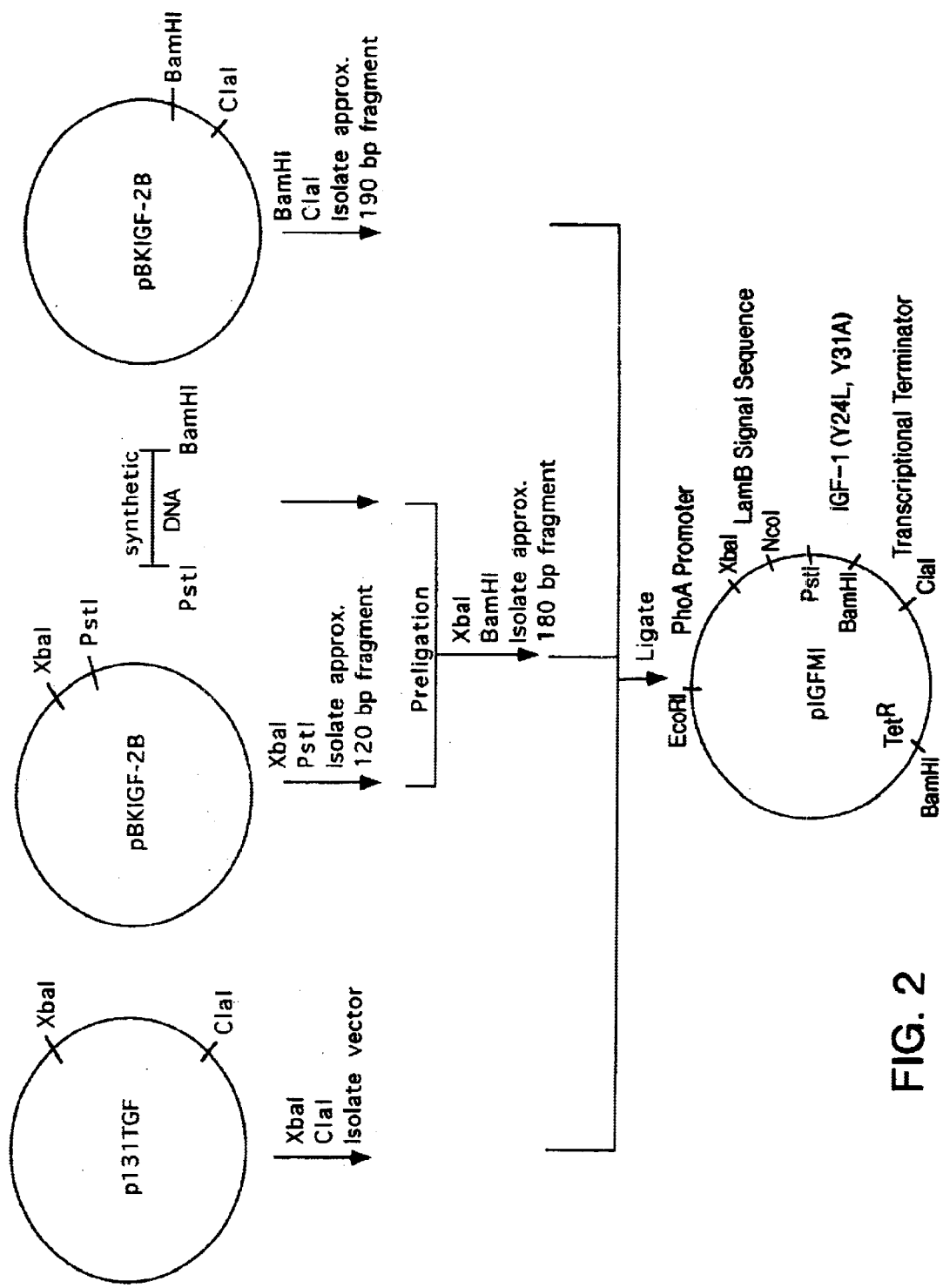
FIG. 2 depicts the construction of the plasmid pIGFMI from the vector fragment of p131TGF, from a 120-bp and a 190-bp fragment of pBKIGF-2B, and from a synthetic piece of DNA.

As used herein, "mammal" for purposes of treatment refers to any animal classified as a mammal, including humans, domestic, and farm animals, and zoo, sports, or pet animals, such as dogs, horses, cats, sheep, pigs, cows, etc. The preferred mammal herein is a human. The term "non-adult" refers to mammals that are from perinatal age (such as low-birth-weight infants) up to the age of puberty, the latter being those that have not yet reached full growth potential.

As used herein, "IGF" refers to native insulin-like growth factor-I and native insulin-like growth factor-II as well as natural variants thereof such as brain IGF, otherwise known as des(1-3)IGF-I.

As used herein, "IGF-I" refers to insulin-like growth factor-I from any species, including bovine, ovine, porcine, equine, and human, preferably human, and, if referring to exogenous administration, from any source, whether natural, synthetic, or recombinant. Human native-sequence, mature IGF-I, more preferably without a N-terminal methionine is prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

As used herein, "IGF-II" refers to insulin-like growth factor-II from any species, including bovine, ovine, porcine, equine, and human, preferably human, and, if referring to exogenous administration, from any source, whether natural, synthetic, or recombinant. It may be prepared by the method described in, e.g., EP 128,733, supra.

An "IGFBP" or an "IGF binding protein" refers to a protein or polypeptide normally associated with or bound or complexed to IGF-I or IGF-II, whether or not it is circulatory (i.e., in serum or tissue). Such binding proteins do not include receptors. This definition includes IGFBP-1, IGFBP-2, IGFBP-3, IGFBP-4, IGFBP-5, IGFBP-6, Mac 25 (IGFBP-7) and prostacyclin-stimulating factor (PSF) or endothelial cell-specific molecule (ESM-1), as well as other proteins with high homology to IGFBPs. Mac 25 is described, for example, in Swisshelm et al., *Proc. Natl. Acad. Sci. USA*, 92: 4472–4476 (1995) and Oh et al., *J. Biol. Chem.*, 271: 30322–30325 (1996). PSF is described in Yamauchi et al., *Biochemical Journal*, 303: 591–598 (1994). ESM-1 is described in Lassalle et al., *J. Biol. Chem.*, 271: 20458–20464 (1996). For other identified IGFBPs, see, e.g., EP 375,438 published Jun. 27, 1990; EP 369,943 published May 23, 1990; WO 89/09268 published Oct. 5, 1989; Wood et al., *Molecular Endocrinology*, 2: 1176–1185 (1988); Brinkman et al., *The EMBO J.*, 7: 2417–2423 (1988); Lee et al., *Mol. Endocrinol.*, 2: 404–411 (1988); Brewer et al., *BBRC*, 152: 1289–1297 (1988); EP 294,021 published Dec. 7, 1988; Baxter et al., *BBRC*, 147: 408–415 (1987); Leung et al., *Nature*, 330: 537–543 (1987); Martin et al., *J. Biol. Chem.*, 261: 8754–8760 (1986); Baxter et al., *Comp. Biochem. Physiol.*, 91B: 229–235 (1988); WO 89/08667 published Sep. 21, 1989; WO 89/09792 published Oct. 19, 1989; and Binkert et al., *EMBO J.*, 8: 2497–2502 (1989).

The term "body fluid" refers to a biological sample of liquid from a mammal, preferably from a human. Such fluids include aqueous fluids such as serum, plasma, lymph fluid, synovial fluid, follicular fluid, seminal fluid, amiotic fluid, milk, whole blood, urine, cerebrospinal fluid, saliva, sputum, tears, perspiration, mucus, tissue culture medium, tissue extracts, and cellular extracts.

As used herein, "human IGF receptor" refers to any receptor for an IGF found in humans and includes the Type 1 and Type 2 IGF receptors in humans to which both human IGF-I and IGF-II bind, such as the placental Type 1 IGF-I receptor, etc.

A compound that "inhibits" or "prevents" the interaction of an IGF with any one of its IGFBPs" refers to a molecule that increases serum and tissue levels of biologically active IGF, no matter how this increase occurs. For instance, the compound may partially or completely displace active IGF from a complex in which the IGF is bound to one or more of its IGFBPs. The compound under this definition may bind to an IGFBP, and possibly thereby act to displace an endogenous IGF formerly bound to the IGFBP, or it may bind to an IGF itself at a site remote from that involved in receptor interactions so as to inhibit or prevent the interaction of the IGF with one or more of its IGFBPs, but not inhibit or prevent the interaction of the IGF with any of its receptors. Further, while the compound will occupy the IGFBPs, the effect on the ternary complex will depend on whether the binary complexes can form ternary ones. IGF agonist compounds that can form complexes with ALS will replace IGFs but not affect the concentration of IGFBP-3 or of ternary complexes. IGF agonist compounds that cannot form complexes with ALS will occupy IGFBP-3, and the amount of ALS/IGFBP-3/IGF complex will be reduced. This may differ between full-length IGF mutants which may form ternary complexes and small peptides, which might not. With respect to the structure of one exemplary peptide herein and its interaction with an IGFBP, see Example 9 below.

A compound that "binds to IGF binding protein" refers to a compound that binds an IGFBP to at least some degree, whether with high affinity or not.

A compound that "does not bind to a human IGF receptor" does not bind at all to any such receptor, or binds to such receptor with an affinity more than about 200-fold less than wild-type human IGF-I (hIGF-I) or wild-type human IGF-II (hIGF-II) binds to such receptor. Preferably, the compound binds to such receptor with an affinity of more than about 250-fold less than wild-type hIGF-I or hIGF-II binds to the same receptor or does not bind at all. Such a compound is additionally defined as one that does not phosphorylate the human Type 1 IGF receptor and does not stimulate the mouse IGF-I receptor as measured by thymidine uptake into mouse 3T3 cells using the KIRA and mouse 3T3 assays of Example 1, i.e, the compound acts like $(Leu^{24}, Ala^{31})hIGF-I$ or binds the receptor even less than this mutant in these assays. Further, IGF-II could be construed as an IGF-I agonist, and IGF-I could be construed as an IGF-II agonist. However, both IGF-I and IGF-II bind to the Type 1 IGF receptor, and thus are both receptor-active molecules and not within the scope of the compounds as defined herein.

A "disorder" is any condition that would benefit from treatment with an IGF, including but not limited to, for example, lung diseases, hyperglycemic disorders as set forth below, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-insufficiency, Turner's syndrome, Laron's syndrome, short stature, undesirable symptoms associated with aging such as obesity and increased fat mass-to-lean ratios, immunological disorders such as immunodeficiencies including decreased CD4 counts and decreased immune tolerance or chemotherapy-induced tissue damage, bone marrow transplantation, diseases or insufficiencies of cardiac structure or function such as heart disfunctions and congestive heart failure, neuronal, neurological, or neuromuscular disorders, e.g., peripheral neuropathy, multiple sclerosis, muscular dystrophy, or myotonic dystrophy, and catabolic states associated with wasting caused by any condition, including, e.g., trauma or wounding or infection such as with a bacterium or human virus such as HIV, wounds, skin disorders, gut structure and function that need restoration, and so forth. The disorder being treated may be a combination of two or more of the above disorders. The preferred disorders targeted for treatment herein are diabetes and obesity, heart disfunctions, kidney disorders, neurological disorders, whole body growth disorders, and immunological disorders.

As used herein, the term "hyperglycemic disorders" refers to all forms of diabetes and disorders resulting from insulin resistance, such as Type I and Type II diabetes, as well as severe insulin resistance, hyperinsulinemia, and hyperlipidemia, e.g., obese subjects, and insulin-resistant diabetes, such as Mendenhall's Syndrome, Werner Syndrome, leprechaunism, lipoatrophic diabetes, and other lipoatrophies. The preferred hyperglycemic disorder is diabetes, especially Type 1 and Type II diabetes. "Diabetes" itself refers to a progressive disease of carbohydrate metabolism involving inadequate production or utilization of insulin and is characterized by hyperglycemia and glycosuria.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. The treatment regime herein can be either consecutive or intermittent.

As used herein, the term "hypoglycemic agent" refers to compounds that are useful for regulating glucose metabolism, preferably oral agents. More preferred herein for human use are insulin and the sulfonylurea class of oral hypoglycemic agents, which cause the secretion of insulin by the pancreas. Examples include glyburide, glipizide, and gliclazide. In addition, agents that enhance insulin sensitivity or are insulin sensitizing, such as biguanides (including metformin and phenformin) and thiazolidenediones such as REZULIN™ (troglitazone) brand insulin-sensitizing agent, and other compounds that bind to the PPARgamma nuclear receptor, are within this definition, and also are preferred.

As used herein, "insulin" refers to any form of insulin from any species, and whether natively or synthetically or recombinantly derived. Preferably it is NPH insulin.

As used herein, "active" or "biologically active" IGF in the context of changing serum and tissue levels of endogenous IGF refers to IGF that binds to its receptor or otherwise causes a biological activity to occur, such as those biological activities of endogenous or exogenous IGF referred to above.

A "molecule" or "compound" that inhibits interaction of an IGF with any one of its IGFBPs and does not bind a human IGF receptor includes molecules with high oral bioavailability, exemplified by GH secretagogues, organic chemical molecules modeled after the 3-dimensional model given herein, and peptides as defined below. Such compounds are also referred to herein as "IGF agonists" or "IGF agonist compounds".

"Peptides" include molecules having at least two amino acids and include polypeptides having at least about 50 amino acids. Preferably, the peptides have about 10 to about 25 amino acids, more preferably about 12–25, and most preferably about 15–25 amino acids. The definition includes peptide derivatives, their salts, or optical isomers.

"Growth hormone releasing peptides or factors" ("GHRP" or "GHRF") are described below, as are secretagogues. A "growth hormone releasing hormone" ("GHRH") can be any hormone that releases GH from the cells or tissue. "Growth hormone in combination with a growth hormone binding protein" ("GH" plus "GHBP") means a GH complexed with or otherwise associated with one of its binding proteins. Similarly, "IGF in combination with an IGF binding protein" ("IGF" plus "IGFBP") refers to an IGF complexed with or otherwise associated with one of its IGFBPs.

B. Modes for Carrying Out the Invention

The invention herein relates to a compound or molecule that inhibits interaction of an IGF with one or more of its IGFBPs and does not bind to a human IGF receptor, excluding (1–27,gly$^4$,38–70)-hIGF-I, excluding antibodies against (that bind to) an IGFBP, excluding antibodies against (that bind to) an IGF, and excluding peptides having the native sequence of human IGF-I with the tyrosine residues at positions 24, 31, and/or 60 replaced or deleted. Preferably, the compound binds to an IGFBP and/or to an IGF, especially to IGFBP-1, or to IGFBP-3, or to both IGFBP-1 and IGFBP-2, or to IGF-I, or to IGF-II, or to both IGF-I and IGF-II, or to IGFBP-1 or -3 and IGF-I or -II. Also preferably, the compound is a peptide. More preferably, it is a peptide that binds to an IGFBP, more preferably to a serum IGFBP. Also, preferably, the compound reduces plasma insulin secretion, reduces plasma GH, or reduces blood glucose levels in a mammal. More preferably, the peptide has about 10 to about 25 amino acid residues and/or has a cysteine residue at position 5, 6, 7, or 8 numbered from its N-terminus or a cysteine residue at position 5, 6, 7, or 8 numbered from its C-terminus, or both such cysteine residues, or a cysteine residue at position 2 numbered from its N-terminus. Preferably, the peptide described above has about 12 to 25, more preferably 15 to 25, amino acid residues. More preferably, the peptide has a tryptophan residue at position 1, 2, 3, 4, or 5 numbered from its N-terminus. Still more preferably, the peptide additionally has a valine, serine, or glutamine residue N-terminal to the N-terminal cysteine residue. Even more preferably, the peptide is such that the residue N-terminal to the N-terminal cysteine residue is a valine residue. Still more preferably, the peptide has a glycine-proline or valine-alanine sequence of residues beginning at a position that is three residues C-terminal to the N-terminal cysteine. This peptide further preferably has a tryptophan residue within three residues C-terminal to the glycine-proline or valine-alanine sequence of residues. This peptide more preferably has a leucine or valine residue within two residues N-terminal to the C-terminal cysteine residue. This peptide even more preferably has a tryptophan residue at position 2 or 3 numbered from its C-terminus.

Also preferred is a peptide comprising an amino acid sequence selected from the group consisting of SEQ ID NOS:1–16.

Preferably, this peptide comprises an amino acid sequence selected from the group consisting of SEQ ID NO:4, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16. More preferably, this peptide comprises an amino acid sequence that is SEQ ID NO:4, SEQ ID NO:9, SEQ ID NO:10, SEQ ID NO:12, SEQ ID NO:13, SEQ ID NO:15, or SEQ ID NO:16. Still more preferably, this peptide comprises an amino acid sequence that is SEQ ID NO:9, SEQ ID NO:10, SEQ ID NO:15, or SEQ ID NO:16. Most preferably, this peptide comprises an amino acid sequence that is SEQ ID NO:10, SEQ ID NO:15, or SEQ ID NO:16.

Alternatively, this peptide comprises an amino acid sequence that is SEQ ID NO:83, or this peptide comprises an amino acid sequence that is SEQ ID NO:84, SEQ ID NO:85, SEQ ID NO:86, SEQ ID NO:87, SEQ ID NO:89, SEQ ID NO:91, SEQ ID NO:92, SEQ ID NO:93, SEQ ID NO:94, or SEQ ID NO:95, or this peptide comprises an amino acid sequence that is SEQ ID NO:88, SEQ ID NO:96, SEQ ID NO:97, SEQ ID NO:98, SEQ ID NO:99, or SEQ ID NO:100, or this peptide comprises an amino acid sequence that is SEQ ID NO:101, SEQ ID NO:102, SEQ ID NO:103, SEQ ID NO:10, SEQ ID NO:10, SEQ ID NO:104, SEQ ID NO:105, SEQ ID NO:106, SEQ, ID NO:108, or SEQ ID NO:109.

In another preferred embodiment, the peptide comprises an amino acid sequence wherein SEQ ID NO:15 has a D-alanine substitution at position 2, 3, 4, or 6 or an alpha-aminoisobutyrate substitution at position 7, 8, 9, 11, 12, 13, or 14, or any combination of the above. More preferably, this peptide has a D-alanine substitution at position 2, 3, or 6 or an alpha-aminoisobutyrate substitution at position 7, 8, 9, 11, 12, 13, or 14, or any combination of the above. Still more preferably, this peptide has a D-alanine substitution at position 6 or an alpha-aminoisobutyrate substitution at position 8, 9, or 13. Any of these latter peptides preferably has a C-terminus of SEQ ID NO:15 that is AA rather than YFG.

The compound preferably excludes any IGF-I analogs of the formula:

$$BC_nA$$

wherein B is the B domain of IGF-I or a functional analog thereof, C is the C domain of IGF-I or a functional analog thereof, n is the number of amino acids in the C domain and is from about 6 to about 12, and A is the A domain of IGF-I or a functional analog thereof. The compounds herein specifically exclude (Leu$^{24}$)IGF-I and (Ser$^{24}$)IGF-I. The compounds also exclude a B-chain human IGF-I mutant in which the first 16 amino acids of IGF-I are replaced with the first 17 amino acids of the B-chain of insulin;

(Gln$^3$,Ala$^4$)IGF-I; (Tyr$^{15}$,Leu$^{16}$)IGF-I; (Gln$^3$,Ala$^4$,Tyr$^{15}$, Leu$^{16}$)IGF-I; (1–62)IGF-I, which lacks the carboxyl-terminal 8-amino-acid D region of IGF-I; (1–27,Gly$^4$, 38–62)IGF-I, with a C region glycine replacement and a D region,deletion;

(Ile$^{41}$Glu$^{45}$,Gln$^{46}$,Thr$^{49}$,Ser$^{50}$,Ile$^{51}$,Ser$^{53}$,Tyr$^{55}$,Gln$^{56}$) IGF-I, an A chain mutant in which residue 41 is changed from threonine to isoleucine and residues 42–56 of the A region are replaced;

(Thr$^{49}$,Ser$^{50}$,Ile$^{51}$)IGF-I; and (Tyr$^{55}$,Gln$^{56}$)IGF-I.

The compounds herein that are not peptides may be made by chemical synthesis or other appropriate methods in the art for making non-peptidyl molecules with high oral bioavailability (such as GH secretagogues) and other orally active organic molecules.

The peptides of this invention can be made by chemical synthesis or by employing recombinant technology. These methods are known in the art. Chemical synthesis, especially solid phase synthesis, is preferred for short (e.g., less than 50 residues) peptides or those containing unnatural or unusual amino acids such as D-Tyr, Ornithine, amino adipic acid, and the like. Recombinant procedures are preferred for longer polypeptides. When recombinant procedures are selected, a synthetic gene may be constructed de novo or a natural gene may be mutated by, for example, cassette mutagenesis. Set forth below are exemplary general recombinant procedures.

From a purified IGF and its amino acid sequence, for example, an IGF agonist that is a peptidyl mutant of an IGF may be produced using recombinant DNA techniques. These techniques contemplate, in simplified form, taking the gene, either natural or synthetic, encoding the peptide; inserting it into an appropriate vector; inserting the vector into an appropriate host cell; culturing the host cell to cause expression of the gene; and recovering or isolating the peptide produced thereby. Preferably, the recovered peptide is then purified to a suitable degree.

Somewhat more particularly, the DNA sequence encoding a peptidyl IGF agonist is cloned and manipulated so that it may be expressed in a convenient host. DNA encoding parent polypeptides can be obtained from a genomic library, from cDNA derived from mRNA from cells expressing the peptide, or by synthetically constructing the DNA sequence (Sambrook et al., *Molecular Cloning: A Laboratory Manual* (2d ed.), Cold Spring Harbor Laboratory, N.Y., 1989).

The parent DNA is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode proteins or peptides that are capable of providing phenotypic selection in transformed cells.

For example, *E. coli* may be transformed using pBR322, a plasmid derived from an *E. coli* species. Mandel et al., *J. Mol. Biol.* 53: 154 (1970). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

A preferred vector is pB0475. This vector contains origins of replication for phage and *E. coli* that allow it to be shuttled between such hosts, thereby facilitating both mutagenesis and expression. Cunningham et al., *Science*, 243: 1330–1336 (1989); U.S. Pat. No. 5,580,723. Other preferred vectors are pR1T5 and pR1T2T (Pharmacia Biotechnology). These vectors contain appropriate promoters followed by the Z domain of protein A, allowing genes inserted into the vectors to be expressed as fusion proteins.

Other preferred vectors can be constructed using standard techniques by combining the relevant traits of the vectors described above. Relevant traits include the promoter, the ribosome binding site, the decorsin or ornatin gene or gene fusion (the Z domain of protein A and decorsin or ornatin and its linker), the antibiotic resistance markers, and the appropriate origins of replication.

The host cell may be prokaryotic or eukaryotic. Prokaryotes are preferred for cloning and expressing DNA sequences to produce parent IGF-I polypeptide, segment-substituted peptides, residue-substituted peptides, and peptide variants. For example, *E. coli* K12 strain 294 (ATCC No. 31446) may be used as well as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella typhimurium* or *Serratia marcesans*, and various Pseudomonas species. The preferred prokaryote is *E. coli* W3110 (ATCC 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure. *Tissue Culture*, Academic Press, Kruse and Patterson, editors (1973). Examples of such useful host cell lines are VERO and HeLa cells, Chinese Hamster Ovary (CHO) cell lines, W138, 293, BHK, COS-7 and MDCK cell lines.

A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide which can be secreted by the cell, making it possible to isolate and purify the desired peptide from the culture medium and eliminating the necessity of destroying the host cells which arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in *E. coli* as well as the subsequent purification of those gene products. Harris, in *Genetic Engineering*, Williamson, R., Ed. (Academic Press, London, Vol. 4, 1983), p. 127; Ljungquist et al., *Eur. J. Biochem.*, 186: 557–561 (1989) and Ljungquist et al., *Eur. J. Biochem.*, 186: 563–569 (1989). Protein A fusions are often used because the binding of protein A, or more specifically the Z domain of protein A, to IgG provides an "affinity handle" for the purification of the fused protein. It has also been shown that many heterologous proteins are degraded when expressed directly in *E. coli*, but are stable when expressed as fusion proteins. Marston, *Biochem J.*, 240: 1 (1986).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein. Carter, in *Protein Purification: From Molecular Mechanisms to Large-Scale Processes*, Ladisch et al., eds. (American Chemical Society Symposium Series No. 427, 1990), Ch 13, pages 181–193.

Proteases such as Factor Xa, thrombin, and subtilisin or its mutants, and a number of others have been successfully used to cleave fusion proteins. Typically, a peptide linker that is amenable to cleavage by the protease used is inserted between the "other" protein (e.g., the Z domain of protein A) and the desired peptide. Using recombinant DNA methodology, the nucleotide base pairs encoding the linker, are inserted between the genes or gene fragments coding for the other proteins. Proteolytic cleavage of the partially purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

When peptides are not prepared using recombinant DNA technology, they are preferably prepared using solid-phase synthesis, such as that generally described by Merrifield, *J. Am. Chem. Soc.*, 85: 2149 (1963), although other equivalent chemical syntheses known in the art are employable. Solid-phase synthesis is initiated from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind. (London)*, 38: 1597–1598 (1966). Chloromethylated resins are commercially available from BioRad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropylcarbodiimide. Other appropriate coupling agents, apparent to those skilled in the art, are disclosed in E. Gross & J. Meienhofer, *The Peptides: Analysis, Structure, Biology*, Vol. I: Major Methods of Peptide Bond Formation (Academic Press, New York, 1979).

It should be recognized that the α-amino group of each amino acid employed in the peptide synthesis must be protected during the coupling reaction to prevent side reactions involving their active α-amino function. It should also be recognized that certain amino acids contain reactive side-chain functional groups (e.g., sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in Gross and Meienhofer, *The Peptides: Analysis, Structure, Biology*, Vol.3: "Protection of Functional Groups in Peptide Synthesis" (Academic Press, New York, 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl, adamantyloxycarbonyl, and p-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl) isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection may be by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl or 2,3,6-trimethyl-4-methoxyphenylsulfonyl, or BOC.

(4) for the hydroxyl group of Ser, Thr, or Tyr, protection may be, for example, by C1–C4 alkyl, such as t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, or 2,6-dichlorobenzyl is suitably employed. The preferred protecting group is 2,6-dichlorobenzyl.

(8) for the side chain amino group of Asn or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately selected protecting group, in the case of Lys, BOC. The BOC-Lys-OH can be first coupled to the benzyhydrylamine or chloromethylated resin according to the procedure set forth in Horiki et al., *Chemistry Letters*, 165–168 1978) or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific a-amino protecting groups are described in the literature.

After removal of the α-amino protecting group, the remaining α-amino and side-chain protected amino acids are coupled stepwise within the desired order. As an alternative to adding each amino acid separately in the synthesis, some may be coupled to one another prior to addition to the solid-phase synthesizer. The selection of an appropriate coupling reagent is within the skill of the art. Particularly suitable as a coupling reagent is N,N'-dicyclohexylcarbodiimide or diisopropylcarbodiimide.

Each protected amino acid or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem*, 34: 595 (1970). The coupling reactions can be performed automatically using well known methods, for example, a BIOSEARCH 9500™ peptide synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloromethylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix.

One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used, hydrogen fluoride treatment results in the formation of the free peptide acids. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides, Proc. Fifth Amer. Pept. Symp.*, M. Goodman and J. Meienhofer, Eds., (John Wiley, N.Y., 1977), p. 518–521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the polypeptides of the invention is typically achieved using conventional procedures such as preparative HPLC (including reversed phase HPLC) or other known chromatographic techniques such as gel permeation, ion exchange, partition chromatography, affinity chromatography (including monoclonal antibody columns) or countercurrent distribution.

The peptides of this invention may be stabilized by polymerization. This may be accomplished by crosslinking monomer chains with polyfunctional crosslinking agents, either directly or indirectly, through multi-functional polymers. Ordinarily, two substantially identical polypeptides are crosslinked at their C- or N-termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the alpha amino of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of the reactive side chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side chains of internal residues of the peptides or residues introduced into flanking sequences. Crosslinking through externally added crosslinking agents is suitably achieved, e.g., using any of a number of reagents familiar to those skilled in the art, for example, via carbodiimide treatment of the polypeptide. Other examples of suitable multi functional (ordinarily bifunctional) crosslinking agents are found in the literature.

The peptides of this invention also may be conformationally stabilized by cyclization. The peptides ordinarily are cyclized by covalently bonding the N- and C-terminal domains of one peptide to the corresponding domain of another peptide of this invention so as to form cyclo-oligomers containing two or more iterated peptide sequences, each internal peptide having substantially the same sequence. Further, cyclized peptides (whether cyclo-oligomers or cyclo-monomers) are crosslinked to form 1–3 cyclic structures having from 2 to 6 peptides comprised therein. The peptides preferably are not covalently bonded through α-amino and main chain carboxyl groups (head to tail), but rather are crosslinked through the side chains of residues located in the N- and C-terminal domains. The linking sites thus generally will be between the side chains of the residues.

Many suitable methods per se are known for preparing mono- or poly-cyclized peptides as contemplated herein. Lys/Asp cyclization has been accomplished using Nα-Boc-amino acids on solid-phase support with Fmbo/9-fluorenylmethyl (OFm) side-chain protection for Lys/Asp; the process is completed by piperidine treatment followed by cyclization.

Glu and Lys side chains also have been crosslinked in preparing cyclic or bicyclic peptides: the peptide is synthesized by solid phase chemistry on a p-methylbenzhydrylamine resin. The peptide is cleaved from the resin and deprotected. The cyclic peptide is formed using diphenylphosphorylazide in diluted methylformamide. For an alternative procedure, see Schiller et al., *Peptide Protein Res.*, 25: 171–177 (1985). See also U.S. Pat. No. 4,547,489.

Disulfide crosslinked or cyclized peptides are generated by conventional methods. The method of Pelton et al. (*J. Med. Chem.*, 29: 2370–2375 (1986)) is suitable, except that a greater proportion of cyclo-oligomers are produced by conducting the reaction in more concentrated solutions than the dilute reaction mixture described by Pelton et al., for the production of cyclo-monomers. The same chemistry is useful for synthesis of dimers or cyclo-oligomers or cyclo-monomers. Also useful are thiomethylene bridges. Lebl and Hruby, *Tetrahedron Letters*, 25: 2067–2068 (1984). See also Cody et al., *J. Med. Chem.*, 28: 583 (1985).

The desired cyclic or polymeric peptides are purified by gel filtration followed by reversed-phase high pressure liquid chromatography or other conventional procedures. The peptides are sterile filtered and formulated into conventional pharmacologically acceptable vehicles.

The starting materials required for the processes described herein are known in the literature or can be prepared using known methods and known starting materials.

If in the peptides being created carbon atoms bonded to four nonidentical substituents are asymmetric, then the compounds may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present, may be in one of two configurations (R or S) and both are within the scope of the present invention.

The compounds described in this invention may be isolated as the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric and the like. Non-toxic and physiologically compatible salts are particularly useful, although other less desirable salts may have use in the processes of isolation and purification.

A number of methods are useful for the preparation of the salts described above and are known to those skilled in the art. Examples include reaction of the free acid or free base form of the peptide with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion-exchange resin to form the desired salt or one salt form of the product may be converted to another using the same general process.

Certain specific schemes that may be appropriate for chemical synthesis of the peptide's herein are shown in WO 96/15148 published May 23, 1996, the disclosure of which is incorporated herein by reference.

The compounds of this invention are shown to inhibit the interaction of an IGF with one or more of its binding proteins and thereby agonize IGF action. It is known to those skilled in the art that there are many uses for IGFs. Therefore, administration of the compounds of this invention for purposes of agonizing an IGF action can have the same effects or uses as administration of an exogenous IGF itself. These uses of IGF include the following, which may be additional to or the same as the disorders as defined above: increasing whole body, bone, and muscle growth rate in normal and hypopituitary animals; protection of body weight and nitrogen loss during catabolic states (such as fasting, nitrogen restriction, elevated corticosteroid levels, and/or diabetes); kidney regeneration; treating peripheral and central nervous system (CNS) degenerative disorders and promoting neuroprotection or repair following CNS damage or injury; treating hypoxia; promotion of wound healing; cardiac regeneration; reversal of cancer cachexia; inhibition of angiogenesis; regeneration of the gastrointestinal tract; stimulation of mammary function; counteracting IGF-I-dependent actions of GH such as metabolic stress, age-related decreases in GH activity, and adult GH deficiency; treating maturity-onset diabetes; and/or treating a specific IGF deficiency.

Additional and specific disorders for which the compounds herein are useful include growth disorders such as GH-resistant short stature, GH-insensitivity syndrome, osteoporosis, and catabolic states; disorders where treatment requires regeneration of tissues or cells, for example, peripheral nerves and supporting cells, central nervous system cells including nerves and glia, and other cells such as oligodendrocytes, muscle, skin, and bone; heart disorders, e.g., heart ischemia, cardiac myopathy, and congestive heart disorders; hyperglycemic disorders such as insulin-dependent and non-insulin-dependent diabetes mellitus and extreme insulin resistance; and renal disorders such as renal failure. These also include stimulation of an anabolic response in elderly humans, prevention of catabolic side effects of glucocorticoids, treatment of osteoporosis, stimulation of the immune system, reduction of obesity, acceleration of wound healing, acceleration of bond fracture repair, treatment of growth retardation, treatment of renal failure or insufficiency resulting in growth retardation, treatment of physiological short stature, including growth-hormone-deficient children, treating short stature associated with chronic illness, treatment of obesity and growth retardation associated with obesity, treatment of growth retardation associated with Prader-Willi syndrome and Turner's syndrome, acceleration of the recovery and reduction in the hospitalization of burn patients, treatment of interuterine growth retardation, skeletal dysplasia, hypercortisolism, and Cushings syndrome, induction of pulsatile growth hormone release, replacement of growth hormone in stressed patients, treatment of osteochondrodysplasias, Noonans syndrome, schizophrenia, depression, peripheral neuropathy, ALS, depression, Alzheimer's disease, diseases of demyelination, multiple sclerosis, and delayed wound healing, stimulation of the immune system, treatment of physcosocia depravation, treatment of pulmonary dysfunction and ventilator dependency, attenuation of protein catabolic response after a major operation, reduction of cachexia and protein loss due to chronic illness such as cancer or AIDS, treatment of hyperinsulinemia including. Type II and Type I diabetes, adjuvant treatment for ovulation: induction, stimulation of thymic development and prevention of the age-related decline of thymic function, treatment of immunosuppressed patients, treatment of bone marrow transplanted patients, improvement in muscle strength, mobility, diseases of muscle function, muscular dystrophy, maintenance of skin thickness, and metabolic homeostasis, enhancement of renal function and homeostasis including acute and chronic renal failure, stimulation of osteoblasts, bone remodeling, and cartilage growth, stimulation of the immune system, and growth promotion in livestock. Various IGF-I uses are found, for example, in WO 94/04569; WO 96/33216; and Bondy, *Ann Intern. Med.*, 120: 593–601 (1994). All these are included in the definition of "disorder."

In one example, the compounds can be administered to commercially important mammals such as swine, cattle, sheep, and the like to accelerate and increase their rate and extent of growth and the efficiency of their conversion of feed into body tissue. The compounds can be administered in vivo to adults and children to stimulate IGF action.

The compounds of this invention may be administered to the mammal by any suitable technique, including oral, parenteral (e.g., intramuscular, intraperitoneal, intravenous, or subcutaneous injection or infusion, or implant), nasal, pulmonary, vaginal, rectal, sublingual, or topical routes of administration, and can be formulated in dosage forms appropriate for each route of administration. The specific route of administration will depend, e.g., on the medical history of the patient, including any perceived or anticipated side effects using the compound, the type of compound being administered, and the particular disorder to be corrected. Most preferably, the administration is orally or by continuous infusion (using, e.g., slow-release devices or minipumps such as osmotic pumps or skin patches), or by injection (using, e.g., intravenous or subcutaneous means).

The compound to be used in the therapy will be formulated and dosed in a fashion consistent with good medical practice, taking into account the clinical condition of the individual patient (especially the side effects of treatment with the compound), the site of delivery, the method of administration, the scheduling of administration, and other factors known to practitioners. The "effective amounts" of the compound for purposes herein are thus determined by such considerations and must be amounts that result in bioavailability of the drugs to the mammal and the desired effect.

If a small molecule antagonist is used as an IGF agonist, it may have cyclical effects and require, for efficacy, an administration regimen appropriate thereto, the variable concentration of IGFBP-1 in blood being an example. Jones and Clemmons, supra. For a peptide, a preferred administration is a chronic administration of about two times per day for 4–8 weeks to reproduce the effects of IGF-I. Although injection is preferred, chronic infusion may also be employed using an infusion device for continuous subcutaneous (SC) infusions. A small peptide may be administered orally. An intravenous bag solution may also be employed. The key factor in selecting an appropriate dose for diabetes is the result obtained, as measured by decreases in blood glucose so as to approximate the normal range, or by other criteria for measuring treatment of diabetes as are deemed appropriate by the medical practitioner.

As a general proposition, the total pharmaceutically effective amount of the IGF agonist compound administered parenterally per dose will be in a range that can be measured by a dose-response curve. For example, IGFs bound to IGFBPs or in the blood can be measured in body fluids of the mammal to be treated to determine the dosing. Alternatively, one can administer increasing amounts of the IGF agonist compound to the patient and check the serum levels of the patient for IGF-I and IGF-II. The amount of IGF agonist to be employed can be calculated on a molar basis based on these serum levels of IGF-I and IGF-II. See the examples below on displacement of IGF-I tracer from IGFBPs present in human serum.

Specifically, one method for determining appropriate dosing of the compound entails measuring IGF levels in a biological fluid such as a body or blood fluid. Measuring such levels can be done by any means, including RIA and ELISA. After measuring IGF levels, the fluid is contacted with the compound using single or multiple doses. After this contacting step, the IGF levels are re-measured in the fluid. If the fluid IGF levels have fallen by an amount sufficient to produce the desired efficacy for which the molecule is to be administered, then the dose of the molecule can be adjusted to produce maximal efficacy. This method may be carried out in vitro or in vivo. Preferably, this method is carried out in vivo, i.e., after the fluid is extracted from a mammal and the IGF levels measured, the compound herein is administered to the mammal using single or multiple doses (that is, the contacting step is achieved by administration to a mammal) and then the IGF levels are remeasured from fluid extracted from the mammal.

Another method for determining the amount of a particular IGFBP or the amount of the compound bound to a particular IGFBP in a biological fluid so that dosing of the compound can be adjusted appropriately involves:

(a) contacting the fluid with 1) a first antibody attached to a solid-phase carrier, wherein the first antibody is specific for epitopes on the IGFBP such that in the presence of antibody the IGF binding sites remain available on the IGFBP for binding to the compound, thereby forming a complex between the first antibody and the IGFBP; and 2) the compound for a period of time sufficient to saturate all available IGF binding sites on the IGFBP, thereby forming a saturated complex;

(b) contacting the saturated complex with a detectably labeled second antibody which is specific for epitopes on the compound which are available for binding when the compound is bound to the IGFBP; and (c) quantitatively analyzing the amount of the labeled second antibody bound as a measure of the IGFBP in the biological fluid, and therefore as a measure of the amount of the compound bound. This technique can be expanded to include a diagnostic use whereby the compound is administered to a mammal to displace an IGF from a specific IGFBP for which the compound has affinity, such as IGFBP-1 or IGFBP-3, and measuring the amount that is displaced.

The quantitative technique mentioned above using antibodies, called the ligand-mediated immunofunctional method (LIFA), is described for determining the amount of IGFBP by contact with IGF in U.S. Pat. No. 5,593,844, and for determining the amount of GHBP by contact with GH in U.S. Pat. No. 5,210,017. The disclosures of these patents are incorporated herein by reference regarding antibodies and other materials and conditions that can be used in the assay.

Another method for determining dosing is to use antibodies to the IGF agonist or another detection method for the IGF agonist in the LIFA format. This would allow detection of endogenous or exogenous IGFs bound to IGFBP and the amount of IGF agonist bound to the IGFBP.

Another method for determining dosing would be to measure the level of "free" or active IGF in blood. For some uses the level of "free" IGF would be a suitable marker of efficacy and effective doses or dosing.

For example, one method is described for detecting endogenous or exogenous IGF bound to an IGF binding protein or the amount of a compound that binds to an IGF binding protein and does not bind to a human IGF receptor bound to an IGF binding protein or detecting the level of unbound IGF in a biological fluid. This method comprises:

(a) contacting the fluid with 1) a means for detecting the compound that is specific for the compound (such as a first antibody specific for epitopes on the compound) attached to a solid-phase carrier, such that in the presence of the compound the IGF binding sites remain available on the compound for binding to the IGF binding protein, thereby forming a complex between the means and the IGF binding protein; and 2) the compound for a period of time sufficient to saturate all available IGF binding sites on the IGF binding protein, thereby forming a saturated complex;

(b) contacting the saturated complex with a detectably labeled second means which is specific for the IGF binding protein (such as a second antibody specific for epitopes on the IGFBP) which are available for binding when the compound is bound to the IGF binding protein; and (c) quantitatively analyzing the amount of the labeled means bound as a measure of the IGFBP in the biological fluid, and therefore as a measure of the amount of bound compound and IGF binding protein, bound IGF and IGF binding protein, or active IGF present in the fluid.

Given the above methods for determining dosages, and assuming dosing shares at least some of the characteristics demonstrated in Example 11 for IGF-I, in general, the amount of IGF agonist compound that may be employed can be estimated. An orally active small IGF agonist would have a molecular weight of approximately 500 daltons, compared to 7500 daltons for IGF-I and IGF-II. Assuming the IGF agonist is 16-fold less able to bind to IGFBPs than IGF-I or IGF-II, then equal weights of IGF-I or IGF-II and these molecules could be equally effective, so that doses from about 10 µg/kg/day to 200 µg/kg/day might be used, based on kg of patient body weight, although, as noted above, this will be subject to a great deal of therapeutic discretion.

A further method is provided to estimate the distribution of IGFs on specific IGFBPs, e.g., on IGFBP-1 or IGFBP-3 using the LIFA format.

The compound is suitably administered by a sustained-release system. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al., *Biopolymers*, 22, 547–556 (1983), poly(2-hydroxyethyl methacrylate) (Langer et al., *J. Biomed. Mater. Res.*, 15: 167–277 (1981), and Langer, *Chem. Tech.*, 12: 98–105 (1982), ethylene vinyl acetate (Langer et al., supra) or poly-D-(−)-3-hydroxybutyric acid (EP 133,988). Sustained-release compositions also include a liposomally entrapped compound. Liposomes containing the compound are prepared by methods known per se: DE 3,218,121; Epstein et al., *Proc. Natl. Acad. Sci. U.S.A.*, 82: 3688–3692 (1985); Hwang et al., *Proc. Natl. Acad. Sci. U.S.A.*, 77: 4030–4034 (1980); EP 52,322; EP 36,676; EP 88,046; EP 143,949; EP 142,641; Japanese Pat. Appln. 83–118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol. percent cholesterol, the selected proportion being adjusted for the most efficacious therapy.

PEGylated peptides having a longer life can also be employed, based on, e.g., the conjugate technology described in WO 95/32003 published Nov. 30, 1995.

For parenteral administration, in one embodiment, the compound is formulated generally by mixing each at the desired degree of purity, in a unit dosage injectable form (solution, suspension, or emulsion), with a pharmaceutically, or parenterally, acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the compound uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, a buffered solution, and dextrose solution. Non-aqueous vehicles such as fixed oils and ethyl oleate are also useful herein.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counterions such as sodium; non-ionic surfactants such as polysorbates, poloxamers, or polyethylene glycol (PEG); and/or neutral salts, e.g., NaCl, KCl, $MgCl_2$, $CaCl_2$, etc.

The compound typically formulated in such vehicles at a pH of from or about 4.5 to 8. It will be understood that use of certain of the foregoing excipients, carriers, or stabilizers will result in the formation of salts of the compound. The final preparation may be a stable liquid or lyophilized solid.

Typical formulations of the peptide or oral secretagogues as pharmaceutical compositions are discussed below. About 0.5 to 500 mg of the compound or mixture of compounds, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Typical adjuvants which may be incorporated into tablets, capsules, and the like are a binder such as acacia, corn starch or gelatin; an excipient such as microcrystalline cellulose; a disintegrating agent like corn starch or alginic acid; a lubricant such as magnesium stearate; a sweetening agent such as sucrose, or lactose; a flavoring agent such as peppermint, wintergreen or cherry. When the dosage form is a capsule, in addition to the above materials, it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The compound to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

The compound ordinarily will be stored in unit or multi-dose containers, for example, sealed ampules or vials, as an aqueous solution or as a lyophilized formulation for reconstitution. As an example of a lyophilized formulation, 10-mL vials are filled with 5 mL of sterile-filtered 1% (w/v) aqueous solution of compound, and the resulting mixture is lyophilized. The infusion solution is prepared by reconstituting the lyophilized compound using bacteriostatic Water-for-Injection.

Combination therapy with the IGF agonist compound herein and one or more other appropriate reagents that increase total IGF in the blood or enhance the effect of the IGF agonist is also part of this invention. These reagents generally allow the IGF agonist compound herein to release the generated IGF, and include growth-promoting agents.

Growth-promoting agents for this purpose include, but are not limited to, GH secretagogues that promote the release of endogenous GH in mammals to increase concentrations of the IGF in the blood. Examples include TRH, diethylstilbestrol, theophylline, enkephalins, E series prostaglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat. No. 5,206,235. See also, e.g., WO 96/15148 published May 23, 1996. Other growth-promoting agents include GHRPs, GHRFs, GH and their analogs. For example, GHRPs are described in WO 95/17422 and WO 95/17423 both published Jun. 29, 1995; Bowers, *J. Pediatr. Endocrinol.*, 6: 21–31 (1993); and Schoen et al., *Annual Reports in Medicinal Chemistry*, 28: 177–186 (1993). GHRFs and their analogs are described, for example, in WO 96/37514 published Nov. 28, 1996.

Additionally, GHRH, any of the IGFBPs, long-acting GH, GH plus GHBP, insulin, or a hypoglycemic agent can be employed in conjunction with the IGF agonist compound herein for this purpose. In addition, IGF-I or IGF-II or an IGF with an IGFBP such as IGF-I complexed to IGFBP-3 can also be employed with the IGF agonist compound herein. For example, pharmaceutical compositions containing IGF-I and IGFBP in a carrier as described in WO 94/16723 published Aug. 4, 1994 can be used in conjunction with the compound. The entities can be administered sequentially or simultaneously with the IGF agonist compound. In addition, other means of manipulating IGF status, such as regimens of diet or exercise, are also considered to be combination treatments as part of this invention.

If insulin is also administered, it can be any formulation of insulin, but is preferably NPH insulin, and the dose of NPH insulin is from or about 5 to 50 units/injection (i.e., from or about 0.2 to 2 mg) twice a day subcutaneously. For a combination of insulin and the compound, the ratio of NPH insulin to compound in this formulation by weight is generally from or about 10:1 to 1:50, preferably from or about 1:1 to 1:20, more preferably from or about 1:1 to 1:10, still more preferably, from or about 1:1 to 1:5, and most preferably from or about 1:1 to 1:3.

Furthermore, the formulation is suitably administered along with an effective amount of a hypoglycemic agent such as a sulfonylurea. The hypoglycemic agent is administered to the mammal by any suitable technique including parenterally, intranasally, orally, or by any other effective route. Most preferably, the administration is by the oral route. For example, MICRONASE™ tablets (glyburide) marketed by Upjohn in 1.25, 2.5, and 5 mg tablet concentrations are suitable for oral administration. The usual maintenance dose for Type II diabetics, placed on this therapy, is generally in the range of from or about 1.25 to 20 mg per day, which may be given as a single dose or divided throughout the day as deemed appropriate. *Physician's Desk Reference*, 2563–2565 (1995). Other examples of glyburide-based tablets available for prescription include GLYNASE™ brand drug (Upjohn) and DIABETA™ brand drug (Hoechst-Roussel). GLUCOTROL™ (Pratt) is the trademark for a glipizide(1-cyclohexyl-3-(p-(2-(5-methylpyrazine carboxamide)ethyl)phenyl)sulfonyl)urea) tablet available in both 5- and 10-mg strengths and is also prescribed to Type II diabetics who require hypoglycemic therapy following dietary control or in patients who have ceased to respond to other sulfonylureas. *Physician's Desk Reference*, 1902–1903 (1995). Other hypoglycemic agents than sulfonylureas, such as the biguanides (e.g., metformin and phenformin) or thiazolidinediones (e.g., troglitozone), or other drugs affecting insulin action may also be employed. If a thiazolidinedione is employed with the compound, it is used at the same level as currently used or at somewhat lower levels, which can be adjusted for effects seen with the compound alone or together with the dione. The typical dose of troglitazone (REZULIN™) employed by itself is about 100–1000 mg per day, more preferably 200–800 mg/day, and this range is applicable herein. See, for example, Ghazzi et al., *Diabetes*, 46: 433–439 (1997). Other thiazolidinediones that are stronger insulin-sensitizing agents than troglitazone would be employed in lower doses.

Another aspect of this invention is a composition comprising an IGF and a thiazolidinedione, or a combination of an IGF, a thiazolidinedione, and a compound of this invention. Additionally, a method for effecting glycemic control is provided by administering to a mammal in need thereof an effective amount of an IGF and a thiazolidinedione, or an effective amount of an IGF, a thiazolidinedione, and the compound of this invention. The active agents may be administered to the mammal sequentially or together, whether in the same formulation or concurrently. Effective amounts are determined by the practitioner as described above and would generally mean an amount the same or less than the amount of IGF that is used to treat the condition in question (for example, from about 10 to about 250 μg/kg/day of IGF-I for diabetes) and an amount of dione that is known to be useful to treat the condition in question, or if the three are used, the amount of compound using the dosages as determined above.

In addition, the invention contemplates using gene therapy for treating a mammal, using nucleic acid encoding the IGF agonist compound, if it is a peptide. Generally, gene therapy is used to increase (or overexpress) IGF levels in the mammal. Nucleic acids which encode the IGF agonist peptide can be used for this purpose. Once the amino acid sequence is known, one can generate several nucleic acid molecules using the degeneracy of the genetic code, and select which to use for gene therapy.

There are two major approaches to getting the nucleic acid (optionally contained in a vector) into the patient's cells for purposes of gene therapy: in vivo and ex vivo. For in vivo delivery, the nucleic acid is injected directly into the patient, usually at the site where the IGF agonist compound is required. For ex vivo treatment, the patient's cells are removed, the nucleic acid is introduced into these isolated cells and the modified cells are administered to the patient either directly or, for example, encapsulated within porous membranes which are implanted into the patient. See, e.g. U.S. Pat. Nos. 4,892,538 and 5,283,187.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.*, 262: 4429–4432 (1987); and Wagner et al., *Proc. Natl. Acad. Sci. USA*, 87: 3410–3414 (1990). For review of the currently known gene marking and gene therapy protocols, see Anderson et al., *Science*, 256: 808–813 (1992). See also WO 93/25673 and the references cited therein.

Kits are also contemplated for this invention. A typical kit would comprise a container, preferably a vial, for the IGF agonist compound formulation comprising IGF agonist compound in a pharmaceutically acceptable buffer and instructions, such as a product insert or label, directing the user to utilize the pharmaceutical formulation. The kit optionally includes a container, preferably a vial, for a GH, a GHRP, a GHRH, a GH secretagogue, an IGF, an IGF complexed to an IGFBP, an IGFBP, a GH complexed with a GHBP; insulin, or a hypoglycemic agent.

Also provided is a method for predicting the relative affinity for binding to a ligand of a peptide that competes with a polypeptide for binding to the ligand, which peptide is derived from a phage-displayed library, which method comprises incubating a phagemid clone corresponding to the peptide with the polypeptide in the presence of the ligand, serially diluting the phage, and measuring the degree to which binding of the phagemid clone to the ligand is inhibited by the peptide, wherein a phagemid clone that is inhibited only at low phage concentrations has a higher affinity for the ligand than a phagemid clone that is inhibited at both high and low phage concentrations. Details are provided in Example 7 below. Preferably, the ligand is an IGFBP such as IGFBP-1 or IGFBP-3 and the polypeptide is an IGF.

In another embodiment herein, a method is provided for directing endogenous IGF either away from, or towards, a particular site in a mammal comprising administering to the mammal an effective amount of the compound herein that is specific for an IGFBP that is either prevalent at, or absent from, the site. "Sites" for this purpose include specific tissues or organs such as the heart, or such as the brain via brain-specific IGFBPs. Prevalence at the site indicates that the IGFBP in question is located at the site and constitutes a substantial or biologically important portion of the IGFBP at the site. This indication follows from the specificity for IGFBP-1 versus IGFBP-3 of the compounds demonstrated herein.

The invention will be more fully understood by reference to the following examples. They should not, however, be construed as limiting the scope of the invention. All literature and patent citations mentioned herein are expressly incorporated by reference.

EXAMPLES

Figure 1:
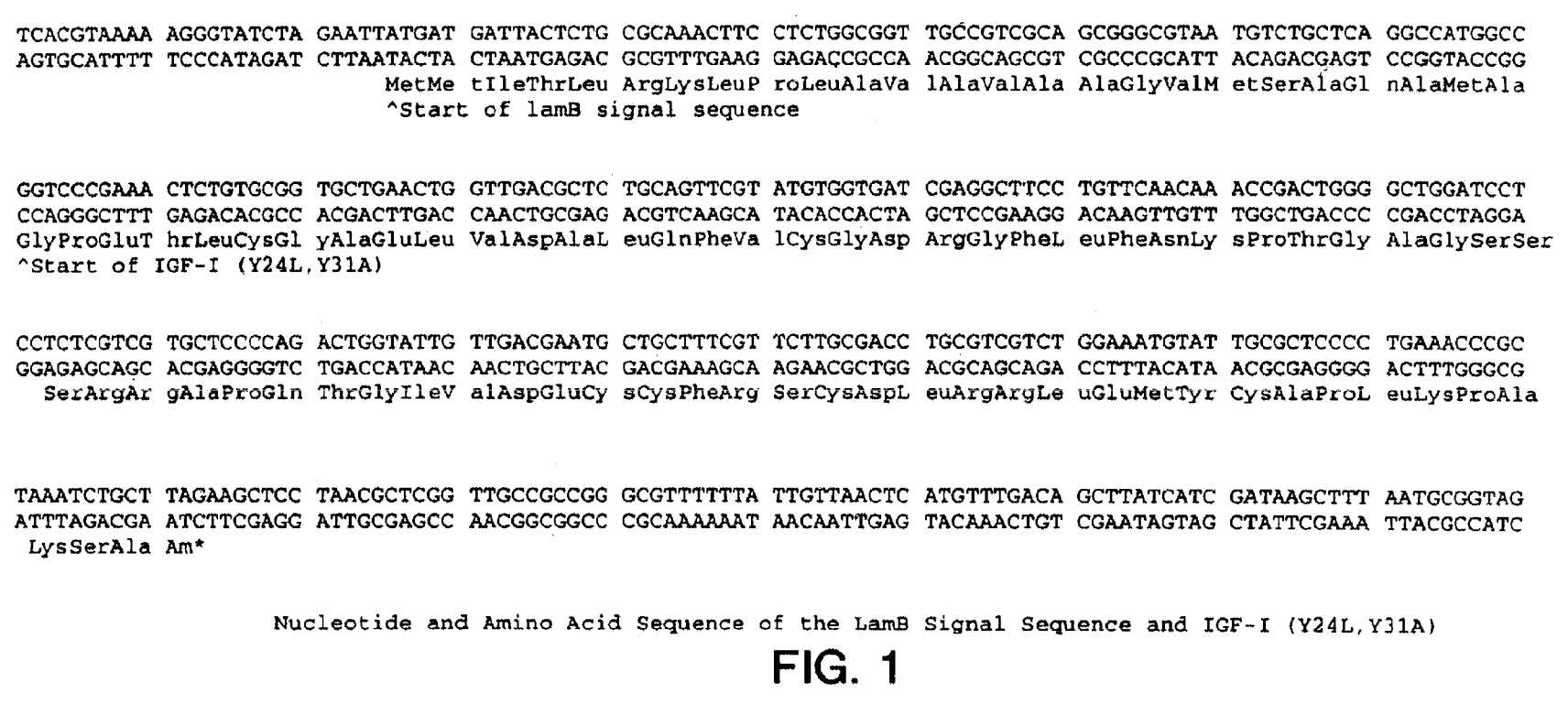

To discover the effect of molecules that bind to the IGFBPs but not to IGF receptors, a mutant human IGF-I described by Bayne et al., *J. Biol. Chem.*, supra, was produced by recombinant DNA technology in *E. coli*. Specifically, the plasmid pIGFMI was designed for the production of an IGF-I mutant with amino acid changes at residues 24 and 31 (Y24L,Y31A), also designated (Leu$^{24}$, Ala$^{31}$)hIGF-I or IGF-M in these examples. The plasmid was constructed from a basic backbone of pBR322 (Sutcliffe, *Cold Spring Harb. Symp. Quant. Biol.*, 43: 77–90 (1978)) as described for the construction of phGH1. Chang et al., *Gene*, 55: 189–196 (1987). The transcriptional and translational sequences required for the expression of the gene were provided by the alkaline phosphatase promoter and the trp Shine-Dalgarno sequence. Chang et al., supra. Additionally, the lambda transcriptional termination sequence is located downstream of the gene. Scholtissek and Grosse, *Nucleic Acids Res.*, 15: 3185 (1987). Secretion of the protein from the cytoplasm to the periplasmic space is directed by the lamB signal sequence. Clement and Hofnung, *Cell*, 27: 507–514 (1981). The nucleotide and amino acid sequences for the lamB signal sequence and the IGF-I mutant (Y24L, Y31A) are given in FIG. 1.

The vector fragment for the construction of pIGFMI was isolated by digestion of p131TGF with XbaI and ClaI. The vector p131TGF contains the sequences for the alkaline phosphatase promoter, the ampicillin and tetracycline resistance markers, and the trp Shine-Dalgarno sequence. The LamB signal sequence and amino acids 1–15 of IGF-I were provided by digestion of pBKIGF-IIB (U.S. Pat. No. 5,487,980) with XbaI and PstI. This fragment of approximately 120 bp was isolated and pre-ligated to the following strands of synthetic DNA encoding the amino acid changes Y24L and Y31A (codons underlined):

5'-G TTC GTA TGT GGT GAT CGA GGC TTC CTG TTC MC AAA CCG ACT GGG GCT G
3'-ACGT C MG CAT ACA CCA CTA GCT CCG MG GAC MG TTG TTT GGC TGA CCC CGA CCTAG
(SEQ ID NOS:22 and 23, respectively)

The remaining IGF-I coding sequence and the lambda transcriptional terminator were provided by isolating the approximately 190 bp BamHI to ClaI fragment of pBKIGF-IIB. These fragments were then ligated together to construct pIGFMI as illustrated in FIG. 2. The full nucleotide sequence of pIGFMI is shown in FIG. 3.

Bayne et al., *J. Biol. Chem.*, supra, described the properties of IGF-I mutants in terms of their binding to IGF binding proteins or to IGF or insulin receptors. This work showed that the tyrosine residues at positions 24, 31, and 60 on human IGF-I are important for binding to the Type 1 IGF-I receptor. The mutant (Leu$^{24}$,Ala$^{31}$)hIGF-I, where two of these tyrosine residues are mutated, has a half maximal inhibition of ligand binding of 2,000 nM compared to the affinity of wild-type hIGF-I of 8.7 nM. This indicates a relative reduction in affinity for the Type 1 IGF receptor (derived from placental membranes) by about 250-fold (Leu$^{24}$,Ala$^{31}$)hIGF-I compared to wild-type hIGF-I.

The functional effect of mutations in IGF-I on activity in vitro was also studied by Bayne et al., *J. Biol. Chem.*, supra. The assay system used, the incorporation of $^3$H thymidine into L7 murine fibroblasts, shows a good correlation between the ability of IGF mutants to bind to the Type 1 receptor and their ability to stimulate DNA synthesis. This is reflected in the reduction in activity of (Leu$^{24}$,Ala$^{31}$)hIGF-I by more than 200-fold in this in vitro activity assay. However, the binding of (Leu$^{24}$,Ala$^{31}$)hIGF-I to human serum IGFBPs is similar to that seen for wild-type IGF-I. Bayne et al., *J. Biol. Chem.*, supra. Therefore, in the following examples, (Leu$^{24}$,Ala$^{31}$)hIGF-I was chosen to be tested in animals. This molecule was chosen because the mutant contains only two mutations, because Type 1 IGF receptor binding is reduced more than 200-fold, and because binding to the IGFBPs is largely maintained.

Example 1

In Vitro Activity of (Leu$^{24}$,Ala$^{31}$)hIGF-I

To test the direct activity of the IGF-I mutant on the IGF receptor, two different assays were employed. A third assay was used to determine if the mutant could displace IGF from IGFBPs in a competitive environment.

Assay 1: KIRA for Phosphorylation of the Human Type 1 Receptor

This assay is a direct activity assay for the human Type 1 receptor. When a receptor in the tyrosine kinase family, such as the Type 1 IGF receptor, is activated, it is phosphorylated on tyrosine residues. In this assay cells containing the Type 1 IGF receptor are activated in vitro, then disrupted, and antibodies against the receptor are used to precipitate the IGF receptor. Next, an anti-phosphotyrosine antibody is used to assay the amount of Type 1 IGF receptor that is phosphorylated. If a fixed number of cells is used, then the amount of receptor that is phosphorylated is a direct measure of the activity of a molecule on the Type 1 IGF receptor.

Figure 4:
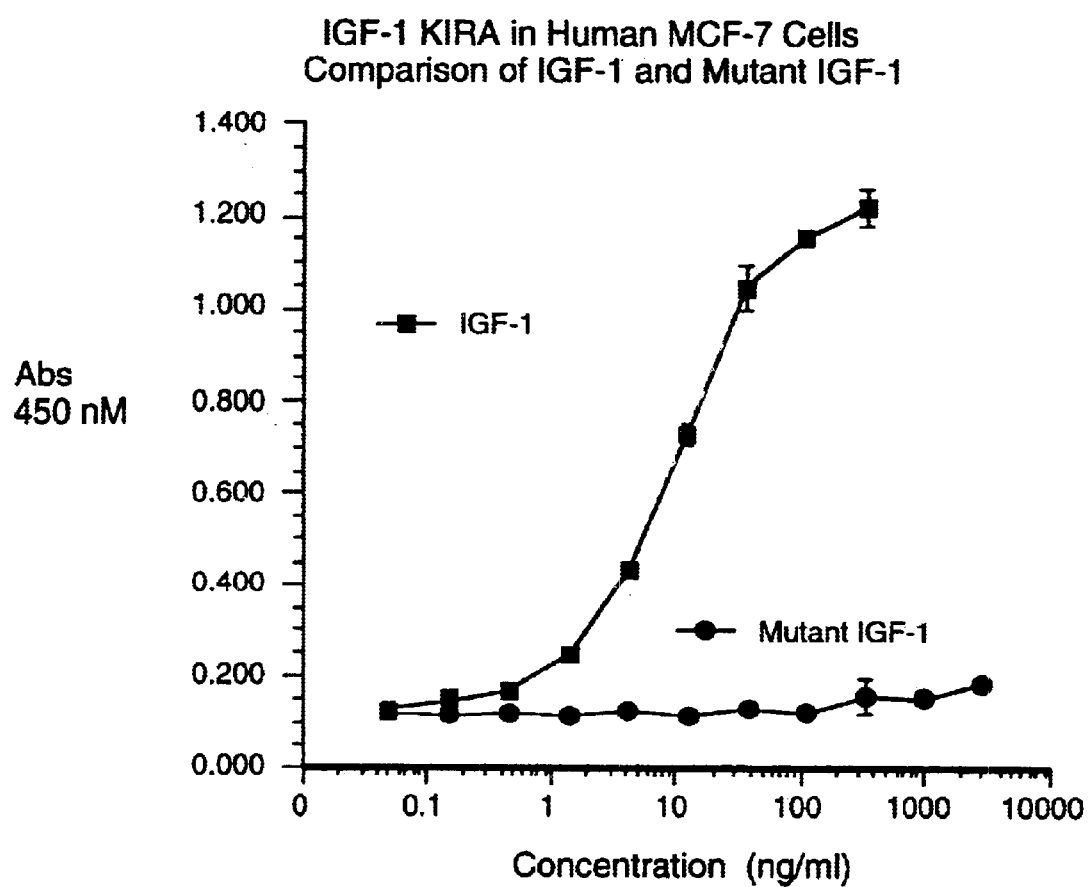
FIG. 4 is a standard curve for receptor phosphorylation when IGF-I (squares) or (Leu$^{24}$,Ala$^{31}$)hIGF-I (circles) is added to MCF-7 cell in a KIRA phosphorylation assay.

A KIRA for the human Type 1 IGF-I receptor was developed using human MCF-7 cells. This cell line was derived originally from a human breast cancer tumor and is available from the ATCC. The growth of these cells is known to respond to the addition of IGF-I. When IGF-I is added to these cells, a dose-related increase in the phosphorylation of the IGF-I receptor occurs (FIG. 4). The addition of the IGF mutant did not cause any change in receptor phosphorylation (FIG. 4). There was no indication of phosphorylation even at very high concentrations of the mutant IGF.

Specifically, the assay is as follows:

Cells

MCF-7, an adherent cell line isolated from a human breast adenocarcinoma, was purchased from American Type Culture Collection (ATCC-HTB 22; American Type Culture Collection, Rockville, Md.). MCF-7 cells have been shown to express measurable levels of surface IGF-IR by FACS analysis. For culture passage, the cells were cultured in 150 cm$^2$ tissue culture flasks (Corning Inc, Corning, N.Y.), 1.5×10$^6$/flask for 4–7 days. For the assay, cells were detached from the tissue culture flasks with PBS/5 mM EDTA, quantified, and cultured in flat-bottom microtiter plates (Falcon 3072, Becton Dickinson Labware, Lincoln Park, N.J.), 2×10$^5$ per well, overnight at 37° C. in 5% CO$_2$.

Media

Cells were grown in F12/DMEM 50:50 prepared in the media facility of Genentech, Inc. (obtained from Gibco as a custom formulation, Gibco/BRL, Life Technologies, Grand Island, N.Y.). The medium was supplemented with 10% FBS (HyClone, Logan, Utah), 25 mM HEPES (Gibco), and 2 mM L-glutamine (Gibco).

KIRA-ELISA

MCF7 cells (2×10$^5$) in 100 µl medium were added to each well in a flat-bottom, 96-well culture plate and cultured overnight at 37° C. in 5% CO$_2$. The following morning the well supernatants were decanted, and the plates were lightly blotted on a paper towel. Stimulation media (F12/DMEM 50:50 with 25 mM HEPES and 2.0% BSA) containing either experimental samples or the recombinant hIGF-I standards were then added to each well. The cells were stimulated at 37° C. for 30 min., the well supernatants were decanted, and the plates were once again lightly blotted on a paper towel. To lyse the cells and solubilize the receptors, 100 µl of lysis buffer were added to each well. Lysis buffer consisted of 150 mM NaCl containing 50 mM HEPES (Gibco), 0.5% Triton-X 100 (Gibco), 0.01% thimerosol, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), and 2 mM sodium orthovanadate. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the polyclonal anti-IGF-IR (antibodies to human Type 1 IGF-I receptor, catalogue 3B7, Santa Cruz Biotech, 5.0 µg/ml in PBS, 100 µl/well) was decanted, blotted on a paper towel and blocked with 150 µl/well of Block Buffer (PBS containing 0.5% BSA (Intergen Company, Purchase, N.Y.) and 0.01% thimerosol) for 60 min. at room temperature with gentle agitation. After 60 minutes, the anti-IGF-IR coated plate was washed six times with wash buffer (PBS containing 0.05% Tween-20 and 0.01% thimerosol) using an automated plate washer (ScanWasher 300, Skatron Instruments, Inc, Sterling, Va.).

The lysate containing solubilized IGF-IR from the cell-culture microtiter well was transferred (85 µl/well) to anti-IGF-IR-coated and -blocked ELISA wells and incubated for 2 h at room temperature with gentle agitation. The unbound receptor was removed by washing with wash buffer, and 100 µl of biotinylated antibody 4G10 (anti-phosphotyrosine) diluted to 0.1 µg/ml in dilution buffer (PBS containing 0.5% BSA, 0.05% Tween-20, 5 mM EDTA, and 0.01% thimerosol) was added to each well. After incubation for 2 h at room temperature the plate was washed and 100 µl of HRP-conjugated Dextran-streptavidin (Amdex Laboratories) diluted 1:50,000 in dilution buffer was added to each well. The plate was incubated for 30 minutes at room temperature with gentle agitation. The free avidip-conjugate was washed away and 100 µl of freshly prepared substrate solution (tetramethyl benzidine; TMB, 2-component substrate kit; Kirkegard and Perry, Gaithersburg, Md.) was added to each well. The reaction was allowed to proceed for 10 minutes, after which the color development was stopped by the addition of 100 µl/well of 1.0 M $H_3PO_4$. The absorbance at 450 nm was read with a reference wavelength of 650 nm ($Abs_{450}$), using a vmax plate reader (Molecular Devices, Palo Alto, Calif.) controlled with a MACINTOSH CENTRIS 650™ computer (Apple Computers, Cupertino, Calif.) and SOFTMAX™ software (Molecular Devices).

The standard curve (FIG. 4) was generated by stimulating MCF7 cells with 300, 100, 33.3, 11.1, 3.7, 1.2, 0.4, or 0 ng/ml IGF-I as a reference standard (Genentech, Inc., lot 1189-2 or equivalent). Sample concentrations were obtained by interpolation of their absorbance on the standard curve and are expressed in terms of IGF-I ng/ml activity. The mutant did not phosphorylate the receptor in this assay.

Assay 2: Increase in Cell Number of Mouse 3T3 Cells

Figure 5:
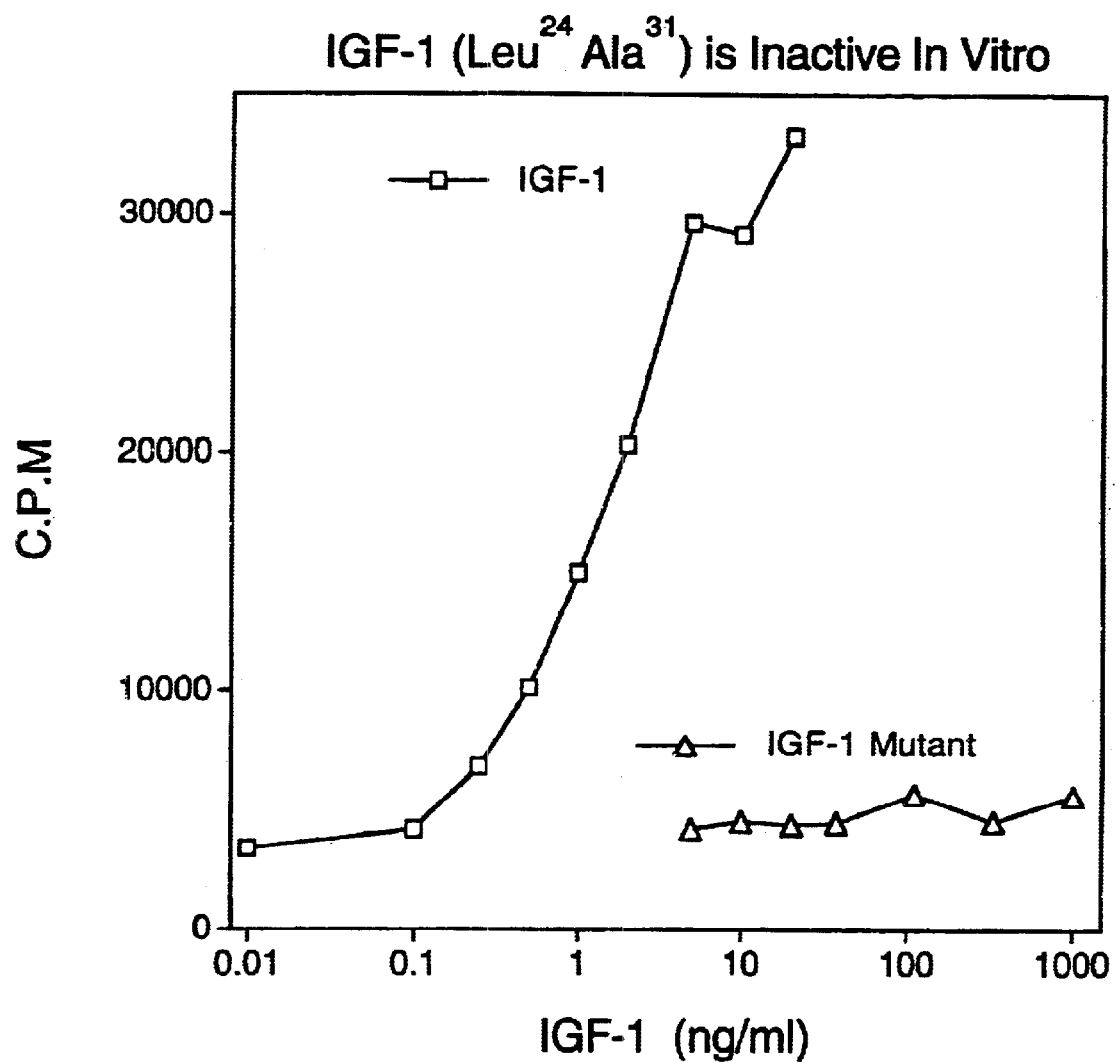
FIG. 5 shows thymidine incorporation into mouse 3T3 cells using IGF-I or (Leu$^{24}$,Ala$^{3}$)hIGF-I.

The activity of the IGF mutant was also measured in a bioassay for the activity of IGF-I on DNA synthesis and cell replication. In this assay mouse 3T3 cells are cultured, and the IGF mutant or IGF-I is added, followed by tritiated 3H-thymidine. The amount of $^3$H-thymidine incorporated is a measure of the replication of DNA and thus of cell replication. IGF-I increased thymidine incorporation in a dose-related manner (FIG. 5). The IGF mutant showed no activity in this assay even when added at very high concentrations.

Assay 3: In Vitro Binding of $(Leu^{24},Ala^{31})hIGF-I$ to IGFBPs

Figure 6:
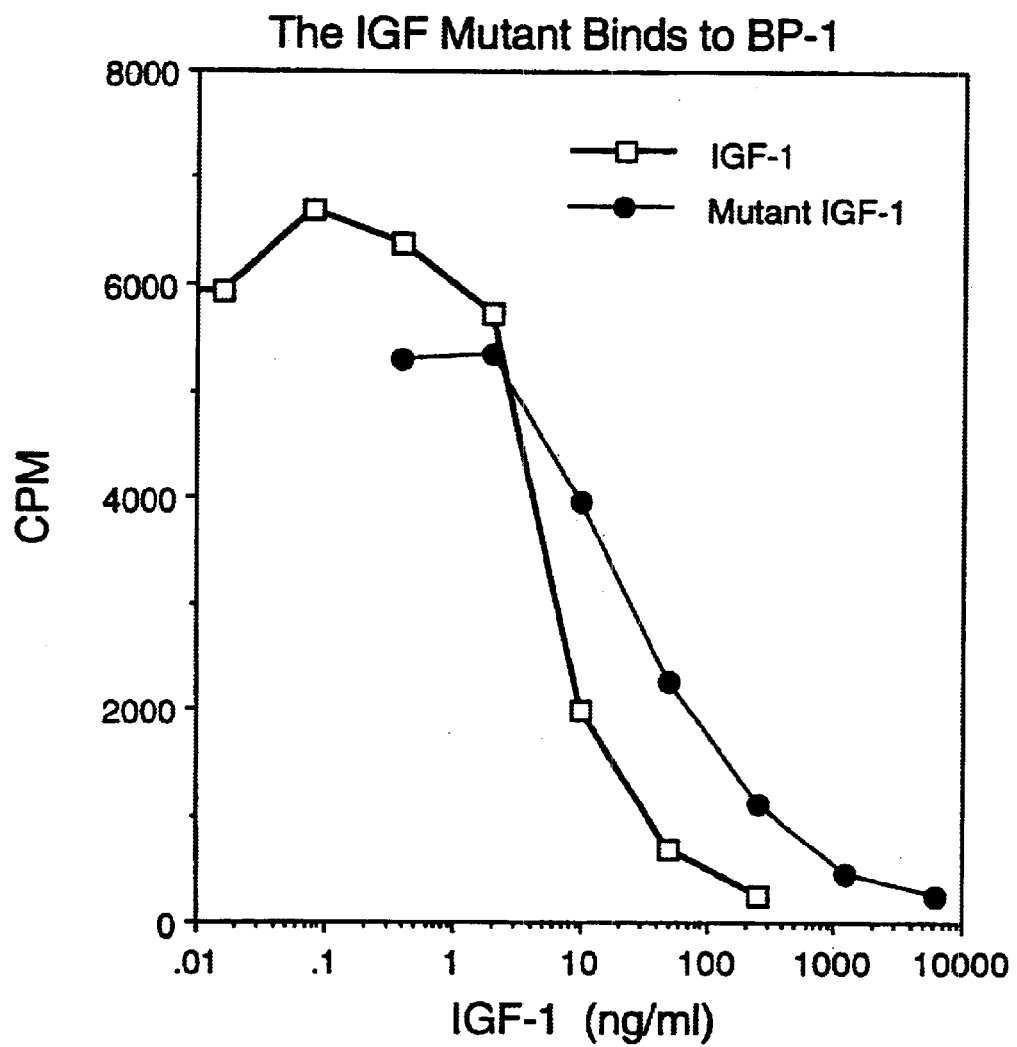
FIG. 6 shows the binding affinity of (Leu$^{24}$,Ala$^{31}$)hIGF-I to IGFBP-1.
Figure 7:
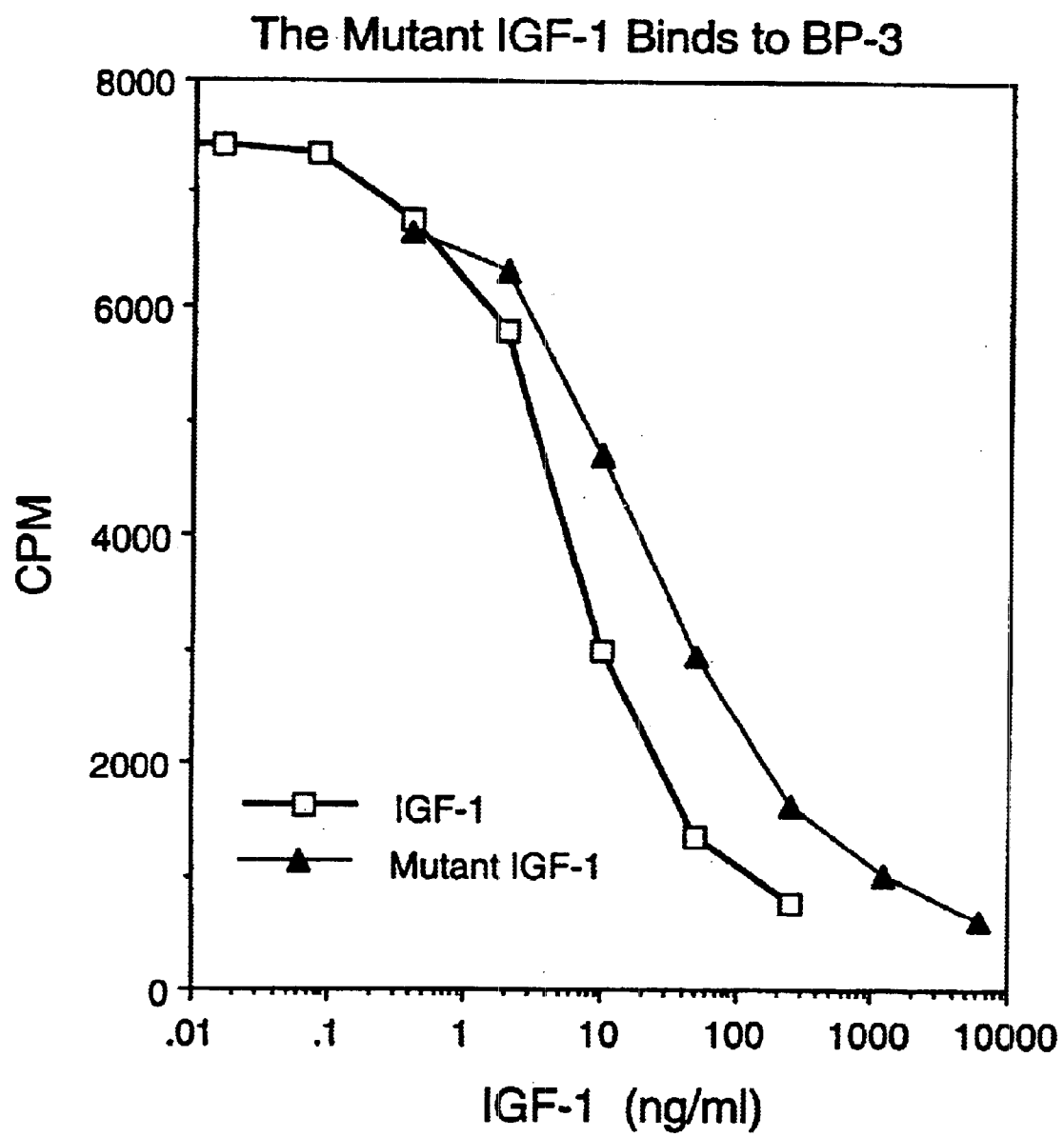
FIG. 7 shows the binding affinity of (Leu$^{24}$,Ala$^{31}$)hIGF-I to IGFBP-3.

The mutant $(Leu^{24},Ala^{31})hIGF-I$ was also tested for its ability to displace radio-labeled rhIGF-I off the IGFBPs in a competitive binding assay. This assay involves coating recombinant human (rh) IGFBP-1 or rhIGFBP-3 (160 ng/ml) onto 96-well plates overnight, blocking the plates for one hour with 0.5% BSA, adding rhIGF-I (250–0.08 ng/ml) or $(Leu^{24},Ala^{31})hIGF-I$ for 1 hour, then adding 20,000 cpm of $^{125}$I-IGF-I and incubating for 2 hours before washing and counting. FIG. 6 shows that the mutant $(Leu^{24},Ala^{31})hIGF-I$ binds to recombinant IGFBP-1 with an affinity only several fold different from that of wild-type hIGF-I. FIG. 7 shows that the mutant $(Leu^{24},Ala^{31})hIGF-I$ also binds to recombinant IGFBP-3 with an affinity only several fold different from that of wild-type hIGF-I.

Conclusion

In two in vitro assays the mutant $(Leu^{24},Ala^{31})hIGF-I$ showed little or no direct activity on the Type 1 IGF-receptor. Firstly, it did not activate the human IGF-I receptor, as measured by the phosphorylation of the receptor in the KIRA assay. Secondly, it did not stimulate the mouse IGF-I receptor directly, as measured by thymidine uptake into 3T3 cells. Therefore, on the basis of the lack of its activation of the IGF receptor, the IGF mutant would also be expected to be inactive in vivo. However, the mutant $(Leu^{24},Ala^{31})hIGF-I$ did show significant binding to IGFBP-1 and IGFBP-3 in vitro. This in vitro data provided the basis for testing the mutant $(Leu^{24},Ala^{31})hIGF-I$ in vivo.

Example 2

In Vivo Activity of $(Leu^{24}{}_1,Ala^{31})hIGF-I$

Introduction

The mutant $(Leu^{24},Ala^{31})hIGF-I$ tested in Example 1 in vitro was tested in vivo. Even though the mutant $(Leu^{24},Ala^{31})hIGF-I$ was inactive in vitro, it was hypothesized that molecules of this class (molecules that are inactive directly on receptors, but capable of binding to IGFBPs) would show some activity in vivo. In the first studies $(Leu^{24},Ala^{31})hIGF-I$ was given by IV injection to conscious rats and effects on glycemic control were determined.

Methods

Seven week old male Wistar rats (240–250 g, Charles Rivers Laboratories, Hollister, Calif.) were anesthetized with KETAMINE/XYLAZINE™ anesthesia and the right jugular vein was cannulated with a silicone rubber cannula that was developed for chronic blood sampling. Clark et al., J. Endocrinol., 111: 27–35 (1986). Following a two- to three-day recovery period, two basal blood samples were taken at –10 and –5 minutes, the test substances administered to the rats by IV injection, and then blood samples collected after 5, 10, 20, 30, 45, 60, and 120 minutes, and the plasma was immediately separated by centrifugation. The glucose and insulin concentrations were subsequently determined either by a coupled hexokinase procedure using a Chem 1A serum chemistry analyzer or, in the later case, a rat insulin RIA kit (Linco Research, Inc., St. Charles, Mo.).

Statistical comparisons were made by an analysis of variance (ANOVA) with a Duncan's Multiple Range test. A p value of <0.05 was considered as being statistically significant. All data are represented as the mean±SEM.

Results

Study One

Two treatment groups, with five rats per group, were dosed IV with either $(Leu^{24},Ala^{31})hIGF-I$ (100 µg) or PBS.

Figure 8A:
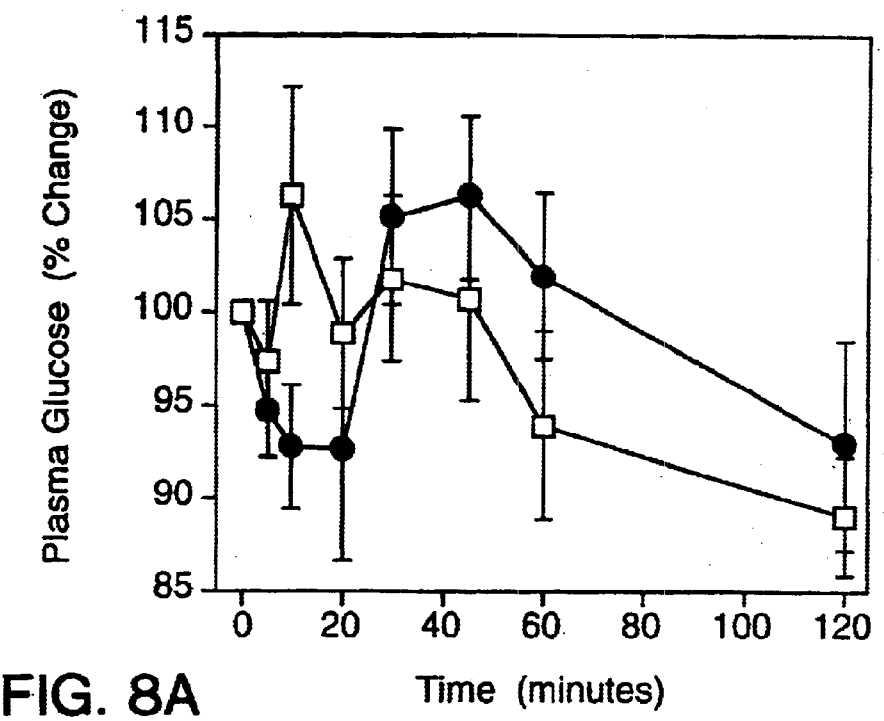
FIGS. 8A and 8B depict the-responses in-plasma glucose (FIG. 8A) and plasma insulin (FIG. 8B) of normal rats treated, in a first study, with (Leu$^{24}$,Ala$^{31}$)hIGF-I (solid circles) or a control (PBS) (open squares), expressed as a percentage of the values in the pre-treatment blood samples which were averaged and set at 100%.
Figure 8B:
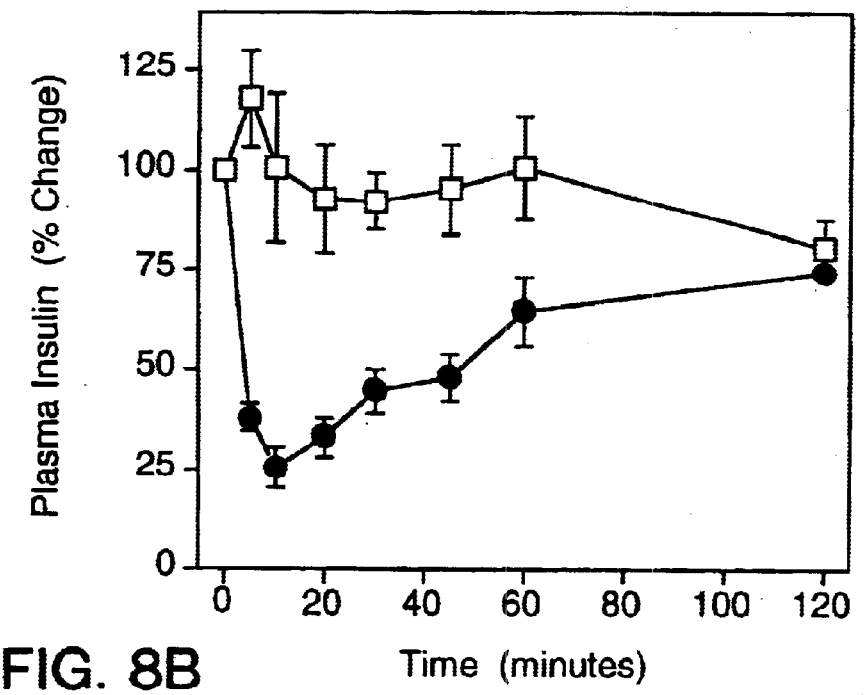

The responses of plasma glucose and plasma insulin to the treatments are shown in FIGS. 8A and 8B, respectively. The data are expressed as a percentage of the values in the pre-treatment blood samples which were averaged and set at 100%. One IV injection of $(Leu^{24},Ala^{31})hIGF-I$ (100 µg) caused plasma insulin levels to be immediately (after 5 minutes), dramatically, and significantly (after 10 mins, P<0.001 vs. control) decreased to 25% of that of the control group, and remained depressed for 60 minutes. This fall in plasma insulin was accompanied by a brief but statistically significant (after 10 mins, P<0.05 vs. control) fall in blood glucose.

Study Two

The rats in three treatment groups, with 4–5 rats per group, were dosed IV with either $(Leu^{24},Ala^{31})hIGF-I$ (100 µg) or rhIGF-I (100 µg) and a control group was given PBS.

Figure 9A:
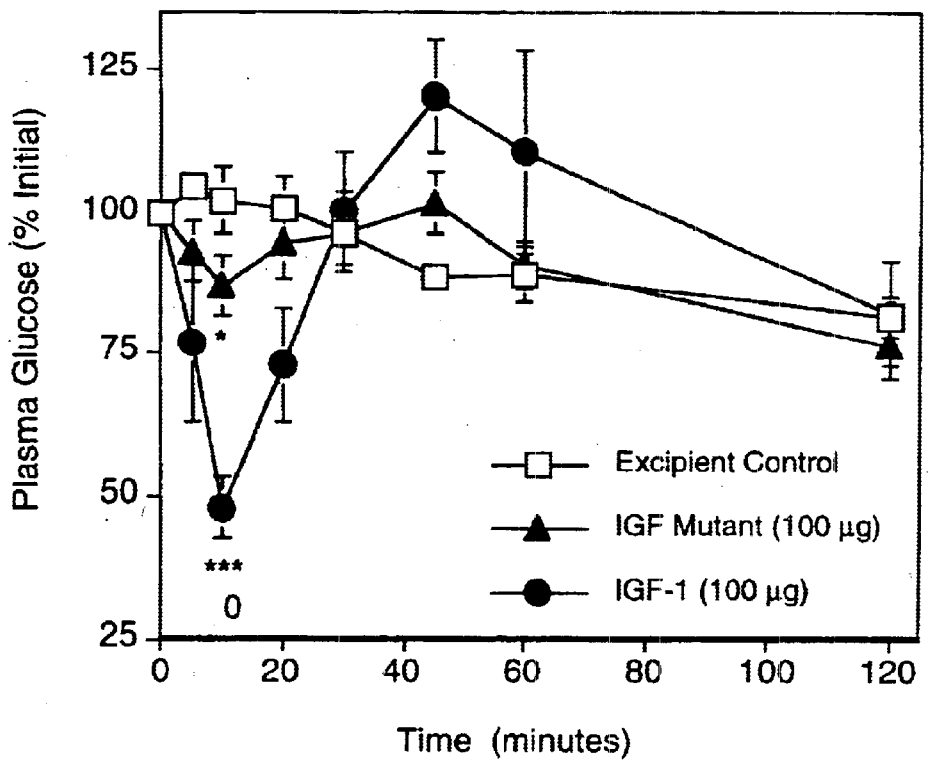
FIGS. 9A and 9B depict the responses in plasma glucose (FIG. 9A) and plasma insulin (FIG. 9B) of normal rats treated, in a second study, with (Leu$^{24}$,Ala$^{31}$)hIGF-I (solid triangles), or IGF-I (solid circles), or a control (open squares), expressed as a percentage of the values in the pre-treatment blood samples which were averaged and set at 100%.
Figure 9B:
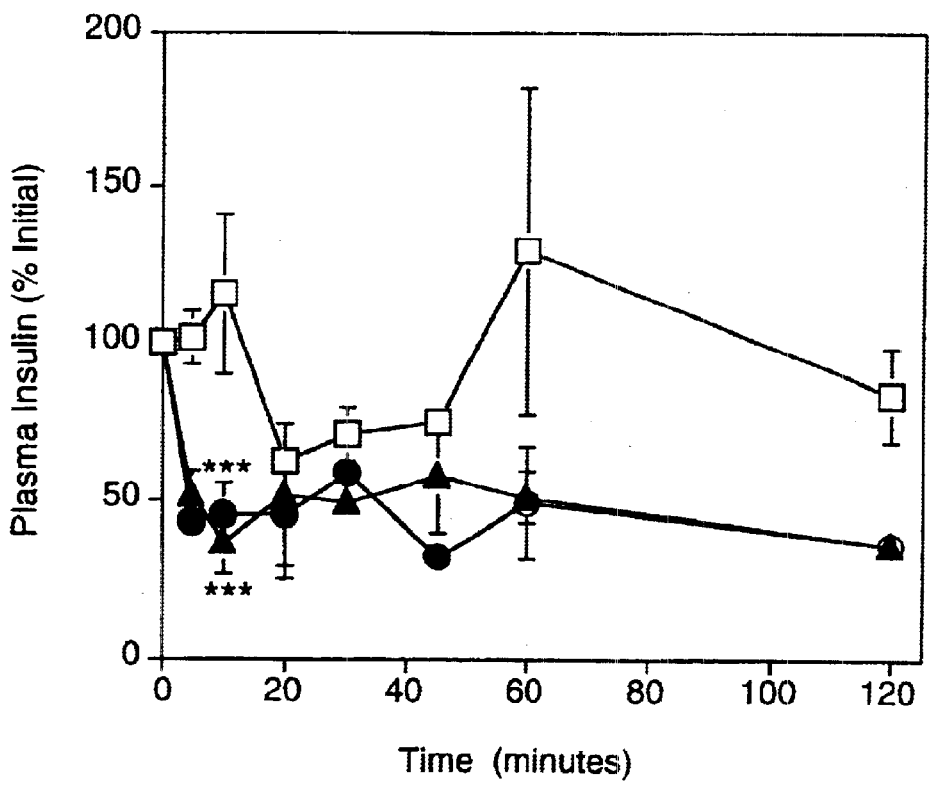

FIGS. 9A and 9B show the responses of plasma glucose (FIG. 9A) and plasma insulin (FIG. 9B) expressed as a percentage of the values in the pre-treatment blood samples which were averaged and set at 100%. Plasma insulin levels decreased significantly (after 10 mins, p<0.001 vs. control), and remained depressed for 120 minutes in response to the IV injection of rhIGF-I. In addition, there was a brief but statistically significant fall in blood glucose (after 10 mins, p<0.01 vs. control). These are the expected responses to the injection of rhIGF-I. When (Leu$^{24}$,Ala$^{31}$)hIGF-I was injected, there was a fall in insulin concentrations of a similar magnitude and degree of statistical significance (after 10 mins, p<0.001 vs. control) to the fall in insulin in the rats given wild-type rhIGF-I. The insulin levels after (Leu$^{24}$,Ala$^{31}$)hIGF-I administration remained significantly suppressed to the end of the study (after 120 min., p<0.05 vs. control). There was also a small but statistically significant fall in blood glucose (after 10 min., p<0.05 vs. control).

Conclusion

In two separate experiments, (Leu$^{24}$,Ala$^{31}$)hIGF-I, a molecule that binds to IGFBPs with high affinity but binds poorly to IGF receptors, shows IGF-like activity on glycemic response variables when given by IV injection in a normal rat. This activity could not have been predicted from data in the literature. The IGF mutant showed suppressive effects on insulin secretion that were of a similar magnitude to the effect of wild-type rhIGF-I. The size of this effect, and its similarity to that seen following administering rhIGF-I itself, were surprising. The fall in glucose levels was not as large as that seen following the administration of rhIGF-I. This order of responses, a larger effect on insulin secretion than on blood glucose levels, follows from the sensitivity of these responses to rhIGF-I. A suppression of insulin secretion is seen at much lower doses of rhIGF-I than are needed to lower blood glucose levels. Furnsinn et al., *Endocrinology*, 135: 2144–2149 (1994).

Example 3

Injections of (Leu$^{24}$,Ala$^{31}$)hIGF-I Into Diabetic Rats

Introduction

In Example 2 the IGF-I mutant reduced insulin secretion and lowered blood glucose in normal non-diabetic rats. It was unclear if, in the diabetic state, manipulating the endogenous IGF system would lead to similar changes in glycemic control. Therefore, an animal model of Type II diabetes was also chosen to test the glycemic activity of the IGF-I mutant. The animal chosen, the Zucker Rat, is a well known model of obesity associated with diabetes in the rat. Stern et al., *Proc. Soc. Exp. Biol. Med.*, 139: 66–69 (1972). A substrain of these rats, the Zucker Diabetic Fatty strain (ZDF), is a good model of Type II diabetes, since they become obese and insulin resistant at an early age, with progressive b-cell failure and then frank diabetes. Johnson et al., *Science*, 250: 546–549. (1990). It has been previously shown in ZDF rats that IGF-I administration can in the long term slow the onset and severity of Type II diabetes (WO 96/15148 published May 23, 1996). Therefore, the ZDF rat provides a relevant and sensitive animal model of Type II diabetes to examine the effects of IGF agonist compounds on glycemic control.

In the present example intravenous bolus injections of the IGF mutant were given and effects on the blood glucose and insulin concentrations were studied.

Methods

Eighteen 7-week-old male Zucker Diabetic Fatty rats (250–300 g, Genetic Models Inc.) were anesthetized using KETAMINE™ (62.5 mg/kg)/ROMPUN XYLAZINE™ (12.5 mg/kg) anesthesia. The right jugular vein was cannulated using a silicone rubber catheter and the rats were allowed to recover.

Study One

Two days after surgery the rats (5–6/group) were divided into three treatment groups and given IV via the jugular catheter 200 µl of:

1) The PBS vehicle;
2) IGF mutant (100 µg); or
3) rhIGF-I (100 µg)

The dose of rhIGF-I was chosen as a dose that might cause a small fall in blood glucose levels and in blood insulin levels. The same dose of IGF mutant was given for comparison.

Study Two

Three days later, using the same rats the study was repeated. The rats that were dosed with IGF-I in the initial study received the IGF mutant in the repeat study and vice versa. Control animals received PBS in both experiments.

Measurements

Two blood samples were collected from each rat via the jugular cannula prior to IV dosing with the hormones and then blood samples were collected after 10, 30, 60, and 120 minutes. The plasma was immediately separated by centrifugation. The glucose concentration was measured by a coupled hexokinase procedure using a Chem 1A serum chemistry analyzer. Insulin concentration was measured using a rat insulin RIA kit (Linco Research, Inc., St. Charles, Mo.).

Statistical comparisons for each time point were made by an ANOVA with a Duncan's Multiple Range test. A p value of <0.05 was considered as being statistically significant. All data are represented as the mean±SEM, with five or six animals per treatment group.

Results

Figure 10A:
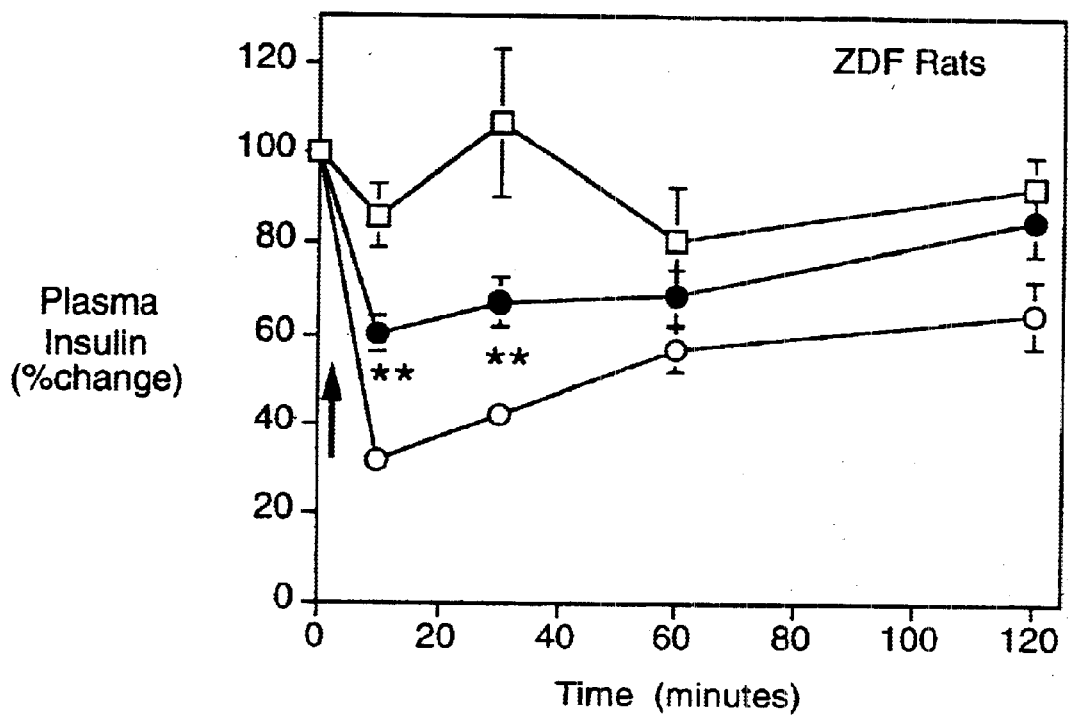
FIGS. 10A and 10B show the percentage change in plasma insulin from baseline (set as 100%) (FIG. 10A) and the percentage change in plasma glucose from baseline (set as 100%) (FIG. 10B) of diabetic rats treated with (Leu$^{24}$, Ala$^{31}$)hIGF-I, IGF-I, or a control.
Figure 10B:
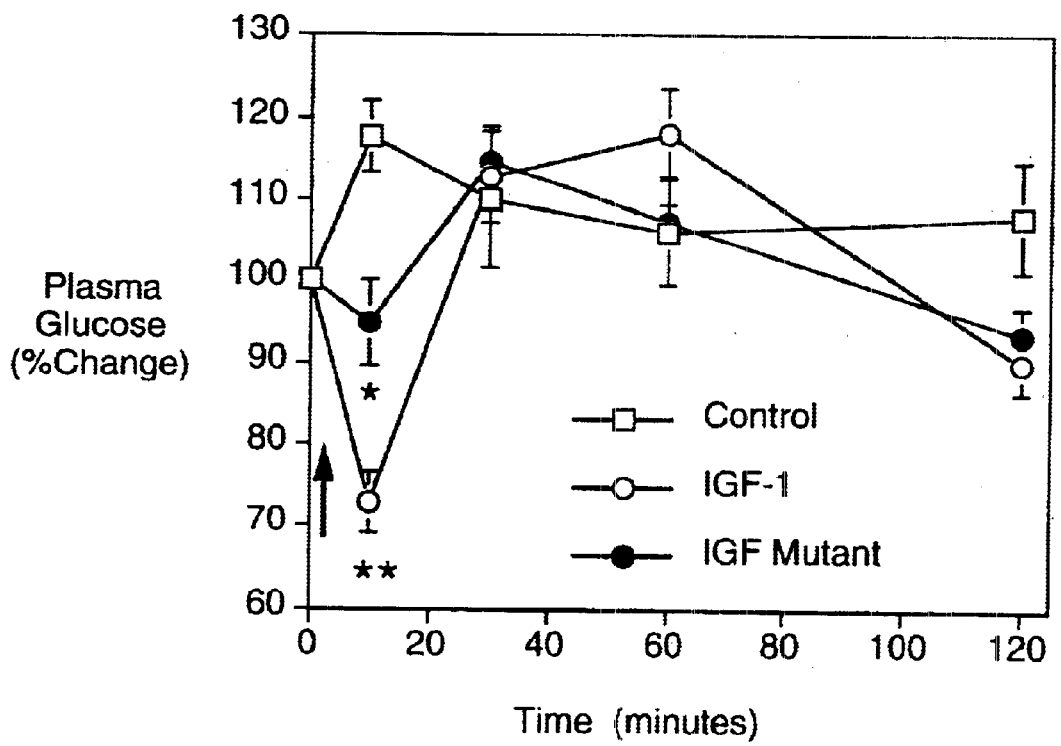
Figure 11A:
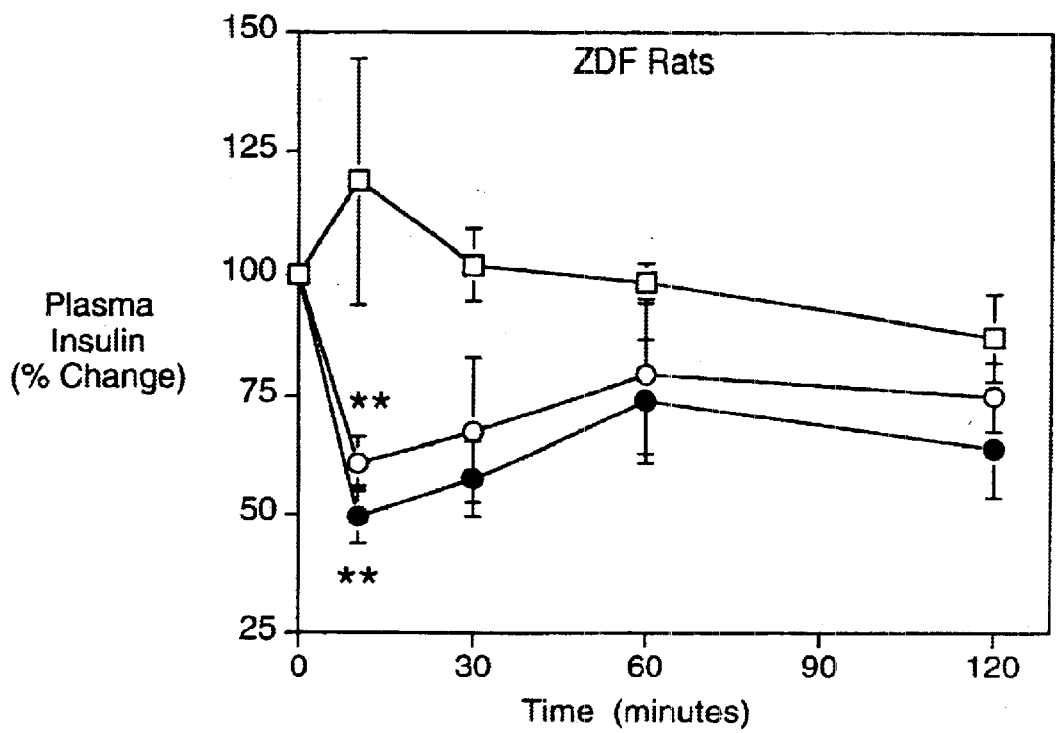
FIGS. 11A and 11B show the percentage change in plasma insulin from baseline (set as 100%) (FIG. 11A) and the percentage change in plasma glucose from baseline (set as 100%) (FIG. 11B) of diabetic (ZDF) rats treated, in a second study, with (Leu$^{24}$,Ala$^{31}$)hIGF-I, IGF-I, or a control.
Figure 11B:
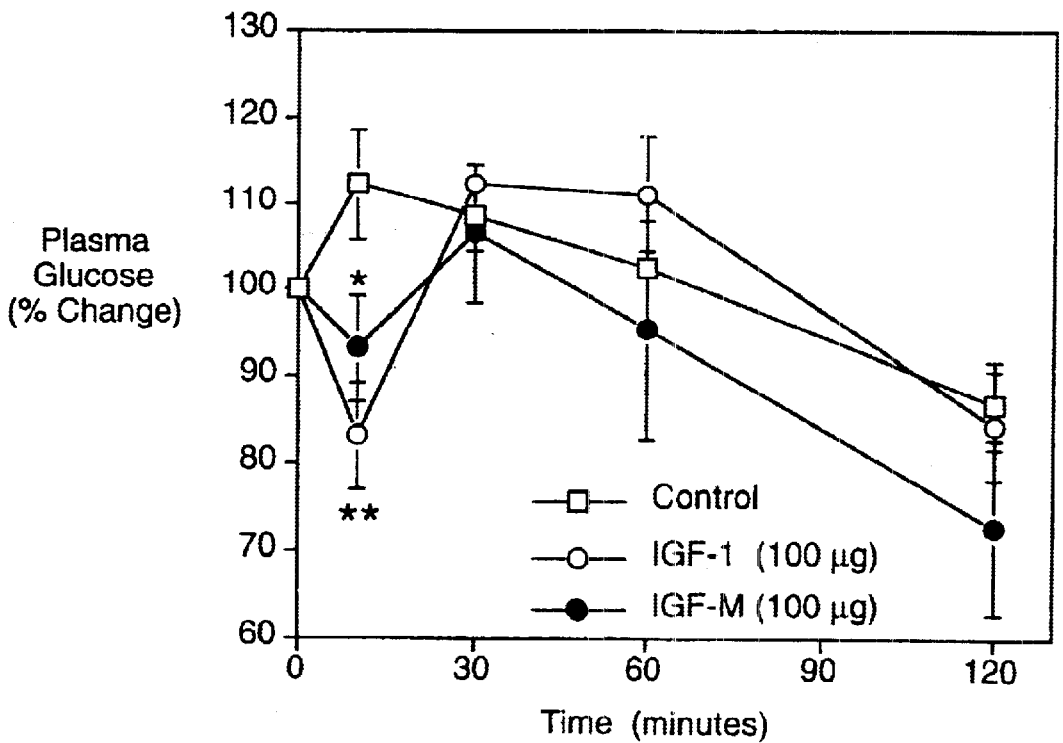

The results from Study One are shown in FIGS. 10A and 10B and from Study Two in FIGS. 11A and 11B. In each Figure the top panel (A) shows the percentage change in plasma insulin from baseline (set as 100%) and the bottom panel (B) the percentage change in plasma glucose from baseline (set as 100%).

In Study One the IV injection of rhIGF-I caused an immediate, moderate, and statistically significant (p<0.01 vs. control, excipient-treated rats) fall in blood glucose (FIG. 10B). In comparison, there was a small rise in blood glucose in the excipient-treated rats. Blood glucose then rebounded to the level in control animals. A smaller, but statistically significant (P<0.05 vs. control, excipient-treated rats) fall in blood glucose was also seen after 10 minutes in animals treated with the IGF mutant. Blood glucose then rebounded to control levels. After 120 minutes blood glucose drifted to lower levels in the animals treated with both rhIGF-I and the IGF mutant. This is suggestive of a long-term effect of the IGF mutant on blood glucose.

These changes in blood glucose were accompanied by changes in the concentrations of insulin in the blood. In the control rats blood insulin levels were high and the levels were maintained throughout the two hours of sampling. The injection of rhIGF-I caused a statistically significant (P<0.01 vs. control, excipient-treated rats), large, and maintained fall in plasma insulin. Injection of the IGF mutant also significantly (P<0.01, vs. control, excipient-treated rats) suppressed blood insulin concentrations. In this group insulin slowly returned to control levels two hours after the injection.

In Study Two (FIGS. 11A and 11B) similar results were obtained to those found in Study One and shown in FIGS.

10A and 10B. In Study Two an IV injection of rhIGF-I caused an immediate, moderate, and statistically significant (p<0.01 vs. control, excipient-treated rats) fall in blood glucose after 10 minutes. Blood glucose then rebounded to the level in control animals after minutes. In this study a similar and statistically significant (P<0.05 vs. control, excipient-treated rats) fall in blood glucose was seen after 10 minutes in animals treated with the IGF mutant. Blood glucose then rebounded to control levels, then drifted to lower levels. Once again, this is suggestive of a long-term effect of the IGF mutant on blood glucose.

The changes in blood glucose were accompanied by changes in the insulin concentrations in the blood. In the controls blood insulin levels were high and were maintained throughout the two hours of sampling. The injection of rhIGF-I caused a statistically significant (P<0.01 vs. control excipient-treated rats), large, and maintained fall in plasma insulin. Injection of the IGF mutant caused a similar and significant fall in blood insulin concentrations (P<0.01, vs. control, excipient-treated rats). In both groups insulin slowly returned toward control levels, but after two hours did not appear to have fully returned to pre-injection levels or the levels in control rats.

These experiments show that the acute administration of an IGF agonist 1) reduces insulin levels and 2) reduces blood glucose levels. In the present study only one injection was given, and the delivery was intravenous. Since one injection of the IGF mutant showed efficacy on glycemic parameters, it would be most likely that multiple injections would show similar acute glycemic effects leading to beneficial long-term cumulative effects. It would also be expected that injections given subcutaneously would have a similar effect to the intravenous injections used here, but may show a different time course, due to their slower absorption from the subcutaneous injection site.

In humans, infusions of rhIGF-I inhibit insulin release at much lower doses than those needed to reduce blood glucose (Hartman et al., *J. Clin. Invest.*, 91: 2453–2462 (1993)), and such low-dose euglycemic infusions of rhIGF-I also rapidly suppress fasting-enhanced pulsatile GH secretion. Therefore, a fall in insulin is expected to be a sensitive marker of the release of IGF-I after the administration of a molecule that inhibits the interaction of an IGF with one of its IGFBPs, assuming that the IGF agonist increases the bioavailability of IGF-I, causing endogenous active IGF-I levels to rise.

In the examples shown herein, using normal animals and diabetic animals, it can be deduced that sufficient IGF-I is activated to induce significant falls in blood insulin and blood glucose concentrations.

Example 4

Long-term Administration of (Leu$^{24}$,Ala$^{31}$)hIGF-I to Hypox Rats

Introduction

The previous set of studies addressed the acute effect of administering molecules that preferentially bind to the IGFBPs rather than to IGF receptors. The short-term effect of the administration of these molecules is now shown to cause an IGF-like agonist effect, as shown by a fall in blood glucose and insulin levels.

An important issue that then arises is the longer-term effects of administration of the IGF agonist. If the mechanism of these activities is a simple displacement of IGF, then it is possible that with time, with long-term exposure, with continual exposure, or with high-dose exposure, the response to the IGF agonist will show tachyphylaxis and the acute response will diminish. If the mechanism of action is other than simple displacement of IGF, then the long-term effect in animals of an IGF agonist is even less certain. In addition, the short-term studies on glucose regulation do not show the longer-term effects of IGF-I, for example, the anabolic effects, the differentiative effects, the mitotic effects, and the effects on organ function. It was therefore important to administer an IGF agonist long term to animals.

The first model chosen was the hypophysectomized rat. The hypophysectomized rat is very sensitive to the effects of both GH and IGF-I. Guler et al., *Proc. Natl. Acad. Sci. USA*, (1988), supra; Clark et al., *Endocrine*, 3: 297–304 (1995). However, as endogenous IGF-I levels are very low in hypophysectomized rats (perhaps only 10% of normal), it was possible that the IGF mutant might not show activity by itself. Therefore, a group of hypophysectomized rats were also given recombinant human GH. GH treatment in hypophysectomized rats raises the levels of IGF-I in blood (Guler et al., *Proc. Natl. Acad. Sci. USA*, (1988), supra; Clark et al., *Endocrine*, supra), and it was reasonable to assume that this increased blood level of IGF-I might be activated by the co-administration of the IGF mutant.

Methods

Young female SD rats were hypophysectomized at Taconic Laboratories and delivered several days later. The rats were then weighed frequently and those whose weight increased or decreased by more than 7 grams between 2 and 3 weeks following hypophysectomy were excluded from the study. Twenty-five rats were grouped randomly into five groups based on their body weight, and then randomly assigned to cages, with four rats per cage. The animals were allowed ad libitum access to food and water and housed in a room controlled for temperature and lighting.

Experimental Groups

1) Excipient pump, excipient injections;

2) (Leu$^{24}$,Ala$^{31}$)hIGF-I (10 μg/day, by SC minipump), excipient injections;

3) (Leu$^{24}$,Ala$^{31}$)hIGF-I (50 μg/day, by SC minipump), excipient injections;

4) Recombinant human GH (NUTROPIN™ brand from Genentech, Inc., 20 μg/day, by SC injection, two injections each of 10 μg/day), excipient minipump; or 5) (Leu$^{24}$,Ala$^{31}$)hIGF-I (50 μg/day, by SC minipump) plus recombinant human GH (20 μg/day, by SC injection, two injections each of 10 μg/day).

The rats were dosed for one week.

Hormones

The mutant (Leu$^{24}$,Ala$^{31}$)hIGF-I was administered by osmotic minipumps (ALZET 2001™, Alza, Palo Alto, Calif.), which were placed in a subcutaneous tunnel in the dorsal neck region of the rats while they were anesthetized with KETAMINE™/XYLAZINE™ anesthesia. The pumps were filled with solutions so that the calculated daily dose was 50 μg or 10 μg, assuming that 24 μl of solution was delivered each day for one week.

Recombinant human GH was administered for one week by twice daily SC injections of 10 μg in 100 μl volume.

Animals not receiving injections of rhGH received injections of vehicle and animals which were not administered IGF-I had a saline-filled pump implanted.

Measurements

Body weights were measured daily in the morning. At the end of the week of dosing the animals were anesthetized via $CO_2$ and exsanguinated via cardiac puncture. The remaining blood was allowed to clot and serum was separated and stored for further analysis.

Spleen, thymus, heart, liver, kidney, and perirenal fat were removed and weighed. The tibia was removed and fixed in neutral buffered formalin for histological measurement of epiphyseal plate width.

Serum chemistries were measured on an automated Chem I analyzer. Serum insulin concentration was measured using an RIA Kit supplied by Linco, Inc. To measure the IGF-I concentrations the serum was extracted using acid ethanol and the supernatant diluted to neutrality and assayed for IGF-I by RIA. The concentration of rat IGF-I in serum extract was measured by RIA using a kit from Diagnostic Systems Laboratories, Inc. This rat IGF-I assay does not measure human IGF-I. Human IGF-I concentration was measured by RIA at Genentech, Inc.

Tibia were sectioned longitudinally, stained with Toluene Blue, and mounted on microscope slides. The tibial epiphyseal plate width was measured using an ocular micrometer attached to a microscope.

Data were analyzed statistically by analysis of variance using one factor and two factor ANOVA.

Results and Discussion

Figure 12:
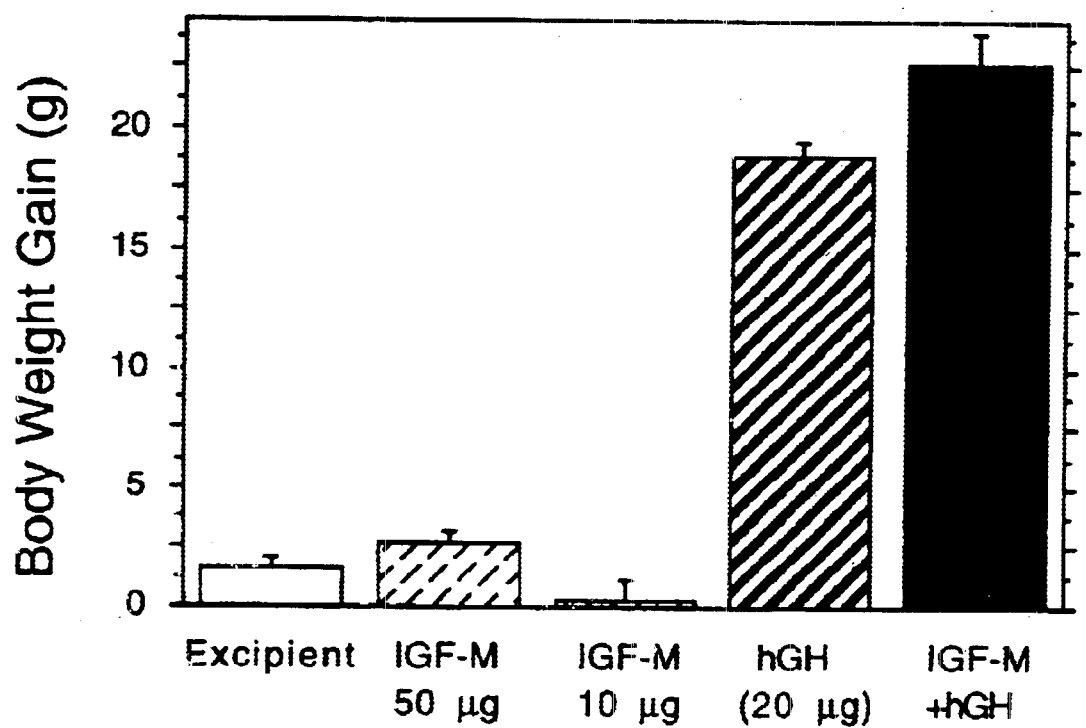
FIG. 12 shows the final body weights of rats treated with (Leu$^{24}$Ala$^{31}$)hIGF-I at two doses, with GH, with a combination of GH and (Leu$^{24}$,Ala$^{31}$)hIGF-I, or with a control over seven days.

Body Weight:

FIG. 12 shows the final body weight gains of the animals at the end of the study. There was a significant increase in body weight as a result of hGH injections. This is the expected response in these GH-deficient hypophysectomized rats, which, when treated with excipients, failed to gain weight. By itself, the IGF agonist showed only a small amount of activity at 50 $\mu$g per day. At 10 $\mu$g per day the IGF agonist group had a mean weight gain that was numerically smaller than that of the control group. However, when the IGF agonist was given along with hGH, the IGF agonist showed an enhancement of the activity of hGH on whole body growth. This is shown in the final body weights in FIG. 12.

Figure 13A:
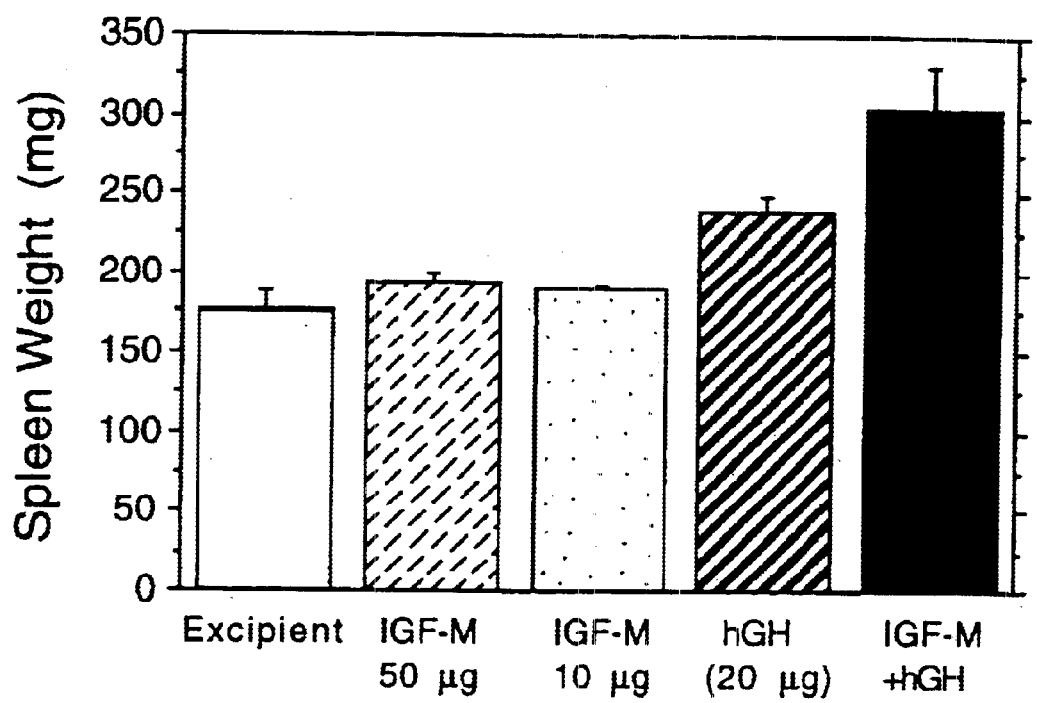
FIGS. 13A and 13B show the weight of the spleen in the study described above for FIG. 12, with FIG. 13A showing absolute spleen weight and FIG. 13B showing spleen weight expressed as a percentage of body weight.
Figure 13B:
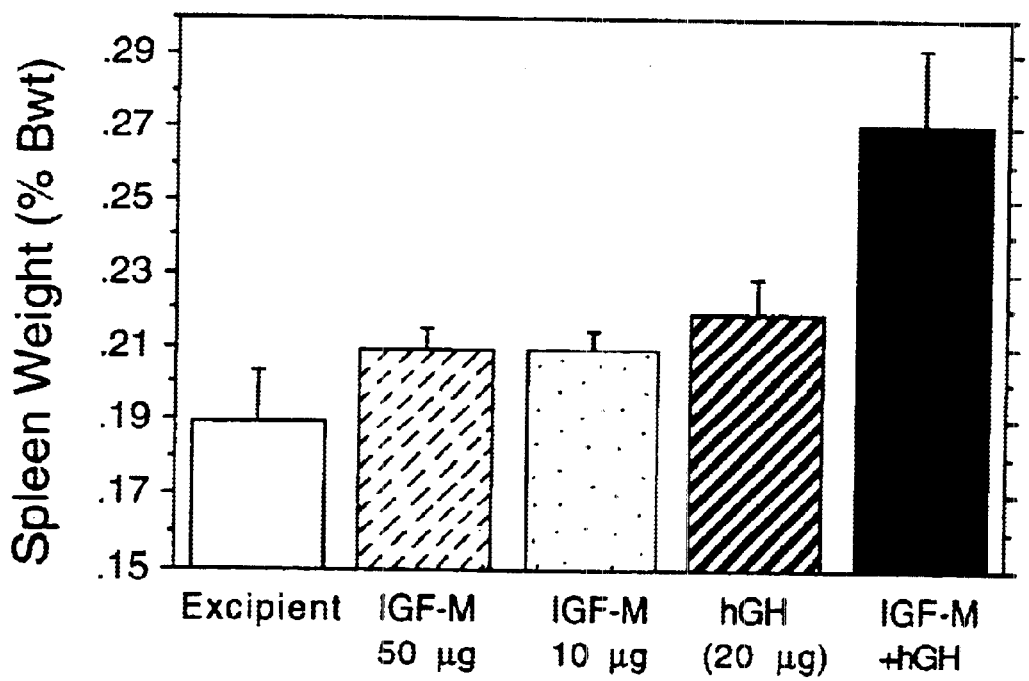
Figure 14A:
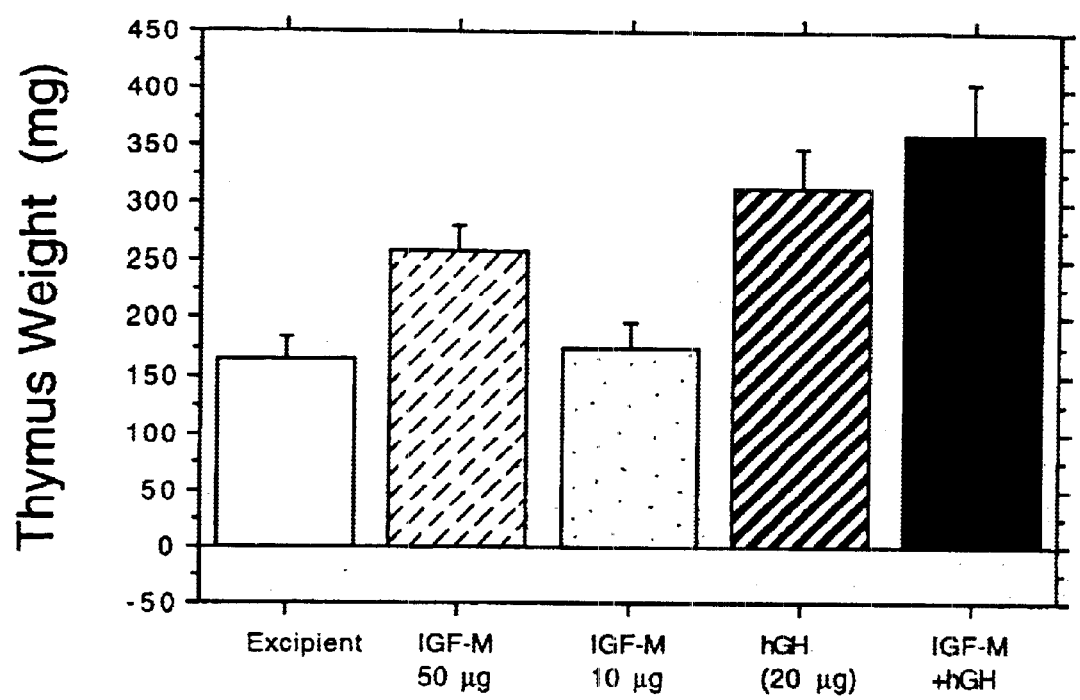
FIGS. 14A and 14B show the weight of the thymus in the study described above for FIG. 12, with FIG. 14A showing absolute thymus weight and FIG. 14B showing thymus weight expressed as a percentage of body weight.
Figure 14B:
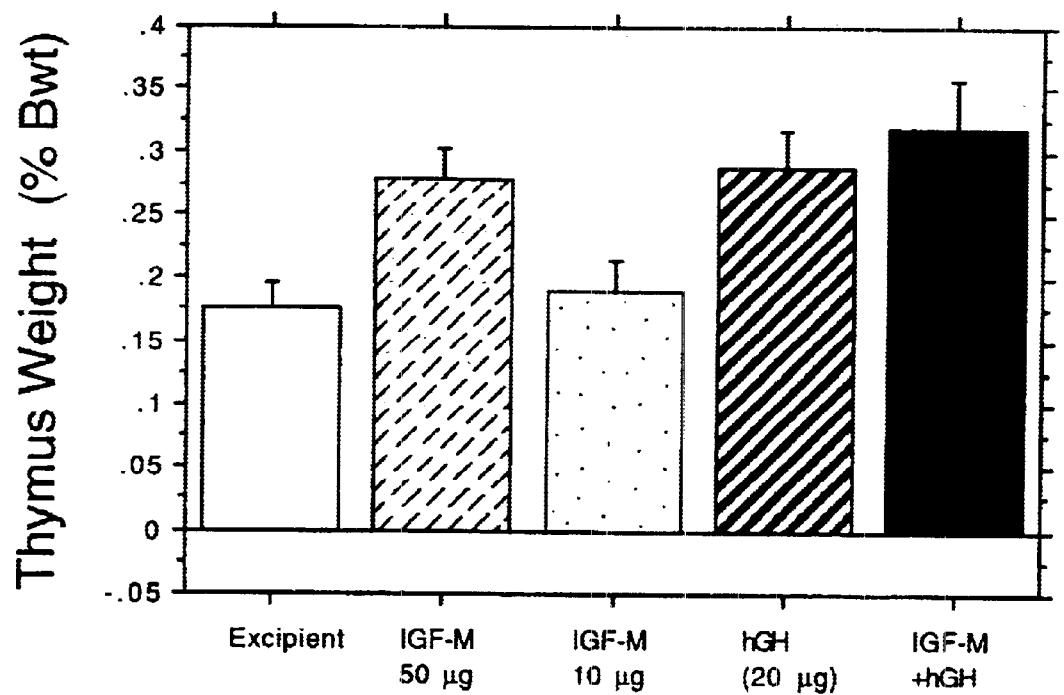
Figure 15A:
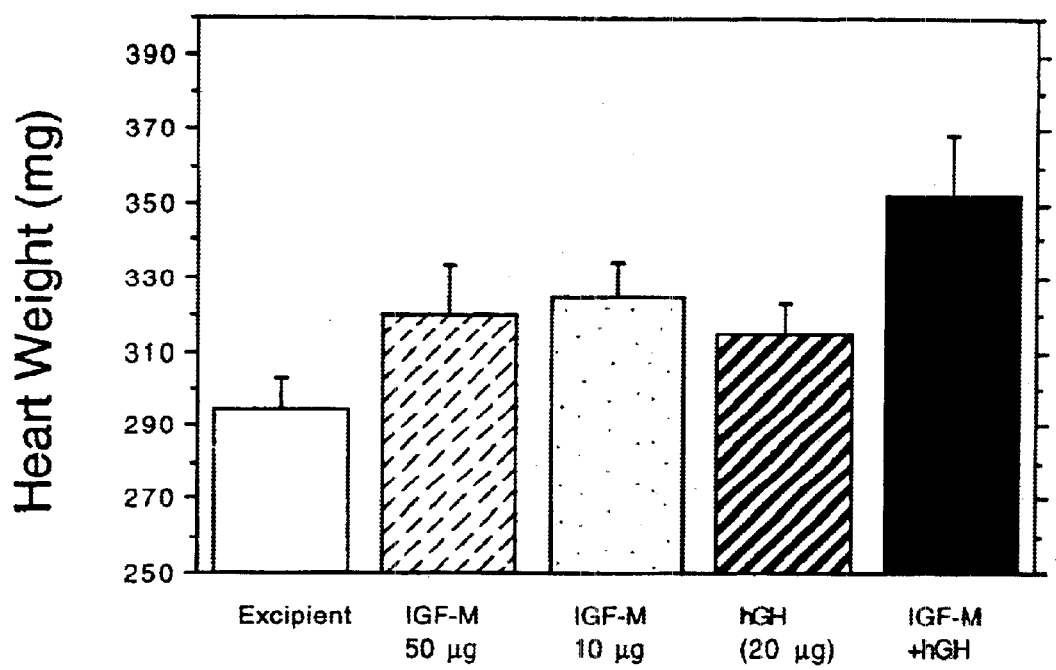
FIGS. 15A and 15B show the weight of the heart in the study described above for FIG. 12, with FIG. 15A showing absolute heart weight and FIG. 15B showing heart weight expressed as a percentage of body weight.
Figure 15B:
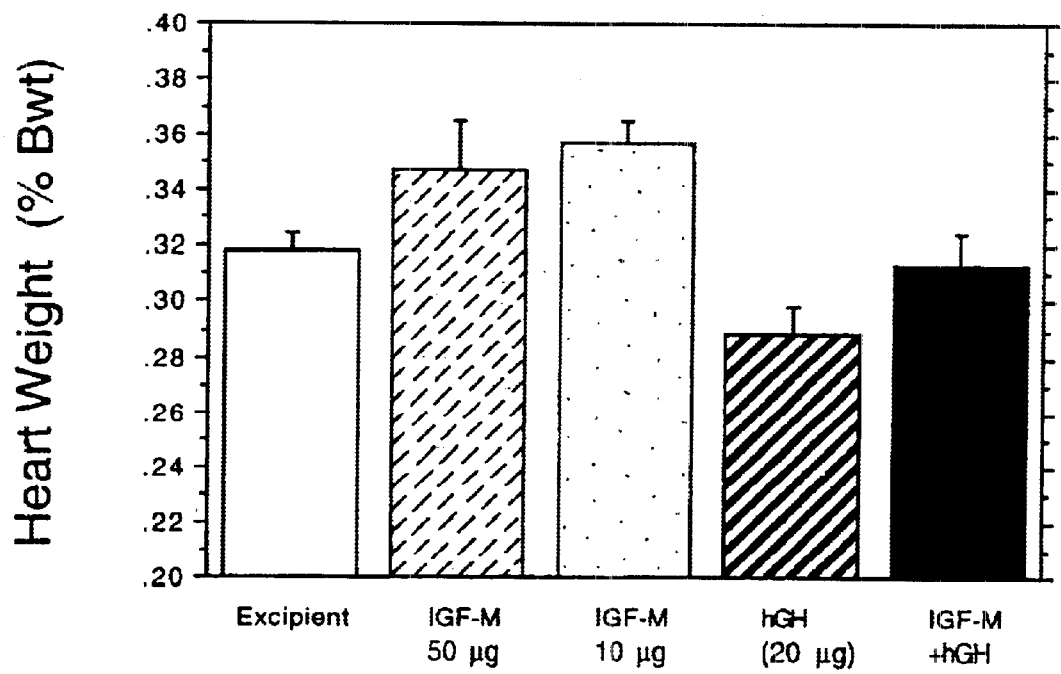

Organ Growth:

The organ weight data is illustrated for spleen (FIGS. 13A and 13B), thymus (FIGS. 14A and 14B), and heart (FIGS. 15A and 15B). In each Figure the absolute organ weight is shown in A, the top panel, and the organ weight expressed as a percentage of body weight is shown in B, the bottom panel.

Absolute spleen weight (FIG. 13A) was increased by both doses of the IGF mutant alone, as it was by hGH. The response to hGH was greater than that to the IGF agonist. However, the combination of hGH plus IGF agonist doubled spleen size with evidence of a synergistic effect. When the spleen size was corrected for the growth of the whole body (by expressing the data as a percent of whole body weight), the IGF agonist again showed evidence of activity when given alone. However, now the synergistic effect of the combination of hGH and IGF mutant was more obvious, as there was a very large response to combination treatment.

Absolute thymus weight (FIG. 14A) was also increased by the high-dose IGF agonist alone. The responses to hGH and to the IGF displacer were almost equal. The combination of hGH plus IGF agonist also increased thymus weight. When the thymus size was corrected for the growth of the whole body (by expressing the data as a percent of whole body weight), the IGF agonist again showed evidence of activity when given alone, with the response again being similar to that caused by hGH. The combination of hGH and IGF mutant also increased relative thymic weight.

In the present Example the IGF agonist at both 10- and 50-$\mu$g doses caused a significant increase in the absolute and the relative size of the heart (FIGS. 15A and 15B). In comparison, treatment with hGH slightly increased absolute heart weight and caused a fall in relative heart weight. Treatment with the IGF mutant in combination with hGH greatly increased the absolute weight of the heart and reversed the GH-induced decline in relative heart weight.

Figure 16:
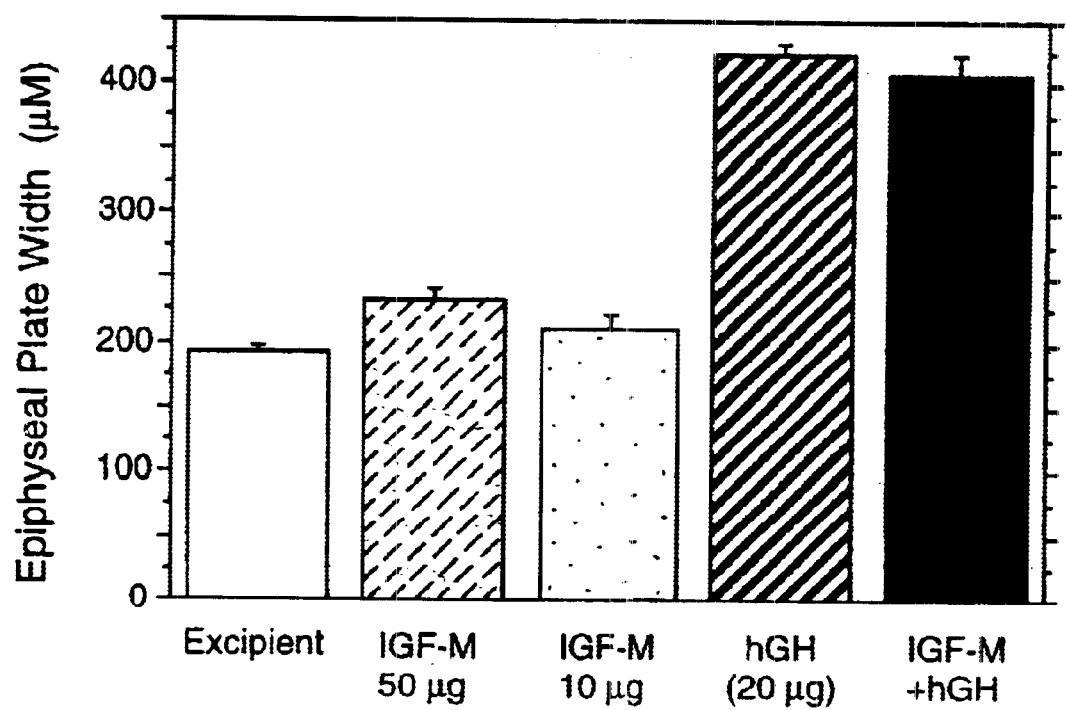
FIG. 16 shows the epiphyseal plate widths from the five treatment groups in the study described for FIG. 12.

Bone Growth:

The epiphyseal plate widths from the five treatment groups in this study are shown in FIG. 16. The width of the epiphysis in the control hypophysectomized rats (about 200 microns) is similar to that reported in the literature in similar rats. Clark et al., *Endocrine*, 3: 717–723 (1995). When given by itself, the (Leu$^{24}$,Ala$^{31}$)hIGF-I at 50 $\mu$g/day induced a significant increase in bone growth (P<0.01 vs. control). Low-dose (Leu$^{24}$₁Ala$^{31}$)hIGF-I did not increase bone growth. In comparison, the injections of rhGH induced a very large increase in bone growth, doubling plate width to around 400 $\mu$m. The combination of rhGH and (Leu$^{24}$,Ala$^{31}$) hIGF-I did not cause a further increase in bone growth. However, an epiphyseal plate width of 400 $\mu$m is near maximal, making it unlikely that a further increase could occur with combination dosing at the doses used. Since there was a growth response to (Leu$^{24}$,Ala$^{31}$)hIGF-I given alone, it would be expected that at lower doses of hGH a greater effect of the combination would be seen than for each agent given alone.

Figure 17A:
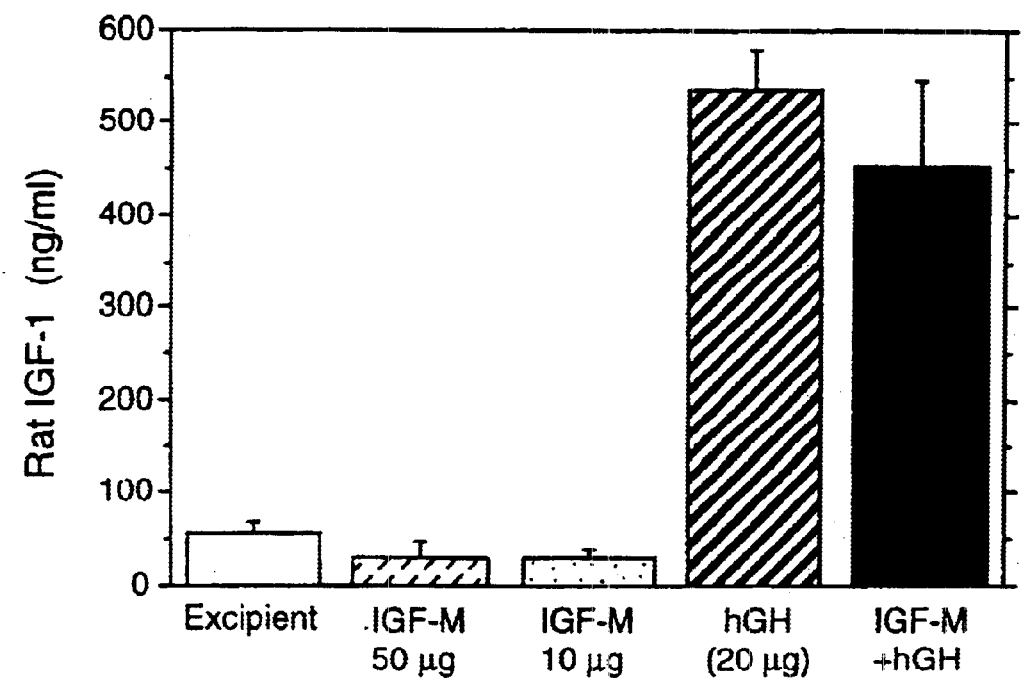
FIGS. 17A and 17B show the amount of rat IGF-I (FIG. 17A) and the amount of total IGF-I (FIG. 17B) in the blood in the five treatment groups in the study described for FIG. 12.
Figure 17B:
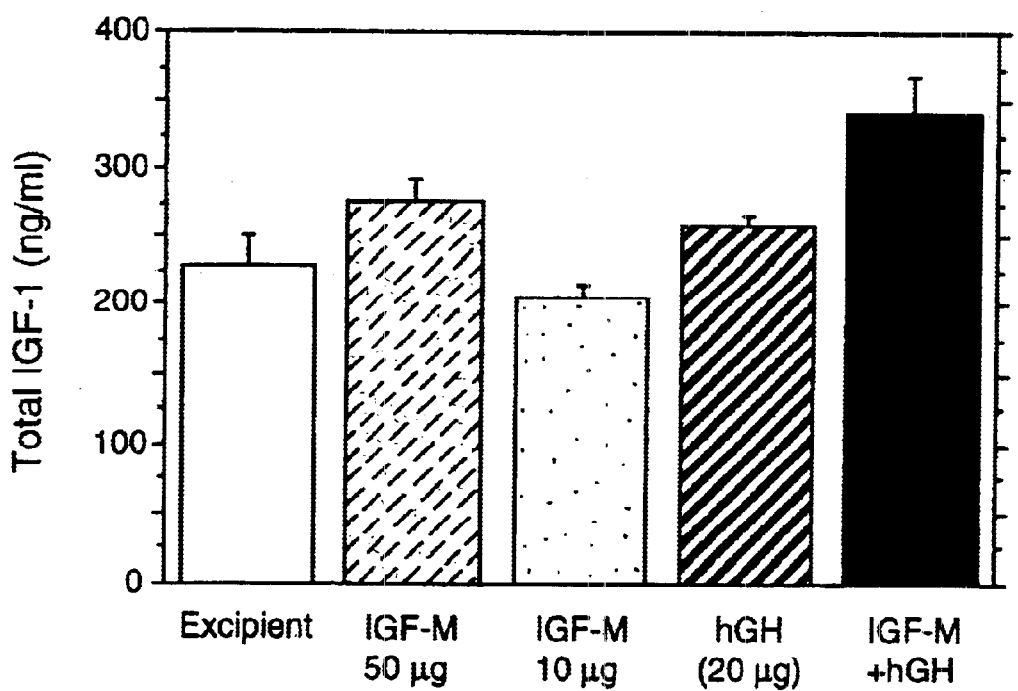

Serum IGF-I Levels:

The levels of IGF-I in the blood were measured in two assays: one assay measured the amount of rat IGF-I in the blood, another the amount of human IGF-I in the blood. FIG. 17 shows the amount of rat IGF-I (FIG. 17A) and the amount of total IGF-I (FIG. 17B) in the blood in the five treatment groups. A remarkable aspect of these data (FIG. 17A) is that the blood levels of receptor-active IGF-I (endogenous rat IGF-I) are lower in the animals given the IGF agonist, yet these lower blood IGF-I levels were associated with marked IGF-like responses in various organs and tissues. Clearly, it is counter-intuitive to observe evidence of increased activity of a hormone when the blood levels of the hormone are decreased.

The assay for total IGF-I (FIG. 17B) measures both rat and human IGF-I. In this assay there was a rise in total IGF-I in the rats given 50 $\mu$g of IGF-I agonist, probably due to the IGF-I agonist binding to binding proteins and therefore being present in the blood. At the lower dose of 10 $\mu$g of IGF agonist, there was not a rise in total IGF in the blood. The total IGF in the blood did rise (p<0.05 vs. hGH alone) in the rats given the combination of GH and the IGF agonist, in contrast to the level of rat IGF-I, which tended to fall in this treatment group. This indicates that when GH generates IGF-I and IGFBPs, there is spare binding capacity, and that this capacity has been in part filled by the IGF agonist.

Conclusion

It has been previously shown that the combination of GH and IGF-I, when administered together to animals, including humans (U.S. Pat. No. 5,126,324; Kupfer et al., *J. Clin. Invest.*, 91: 391–396 (1993)) shows greater activity than either agent alone. However, it was unclear if administering an IGF agonist would result in activation of the IGF axis and enhance the effect of GH administration. The present experiment shows that administering compounds that bind tightly to IGFBPs, but bind poorly to IGF receptors, can enhance the activity of GH.

It has also been reported that the administration of IGF-I to animals induces a different pattern of growth to that induced by GH. In particular, IGF-I administration causes the spleen, thymus, and kidney to show marked over growth. Guler et al., *Proc. Natl. Acad. Sci. USA*, 85: 4889–4893 (1988); Skottner et al., *Endocrinology*, 124: 2519–2526

(1989); Clark et al., *Endocrine*, 3: 297–304 (1995). However, since the whole body size of the rats treated with IGF mutant alone showed only a small response, it might be expected that there would also be little change in the size of the organs of the treated animals. This was not the case; it is shown in this Example that the IGF mutant has very large "IGF-like" effects on some of the organs known to be sensitive to IGF-I, the spleen and thymus.

A very surprising finding in this study was the effect of the treatments on the size of the heart. In previous studies in hypophysectomized or GH-deficient rats, it had been shown that the administration of IGF-I had a very small or no effect on cardiac size. Guler et al., *Proc. Natl. Acad. Sci. USA*, 85: 4889–4893 (1988); Skottner et al., *Endocrinology*, 124: 2519–2526 (1989); Clark et al., *Endocrine*, 3: 297–304 (1995).

In view of the efficacy of the IGF mutant as an agonist of IGF-I as shown above, the present invention is expected to have application in the treatment of a large group of disorders associated with, or characterized by, a lack of active IGF-I in the bloodstream. Representative of such disorders are diabetes, obesity, anabolic disorders, immunologic disorders, cardiac disorders, and renal disorders, as well as others noted above.

Example 5

Long-term Administration of (Leu$^{24}$,Ala$^{31}$)hIGF-I to Dwarf Rats

Introduction

The previous Example addressed the long-term effect in hypophysectomized rats of administering molecules that preferentially bind to the IGFBPs rather than to IGF-receptors, represented by (Leu$^{24}$,Ala$^{31}$)hIGF-I. Hypophysectomized rats have very low serum IGF-I levels and very low levels of IGFBPs because they lack pituitary hormones. Fielder et al., *Endocrinology*, 137: 1913–1920 (1996). However despite these low levels of endogenous proteins the IGF mutant showed remarkable activity. The next model chosen to test the activity of the IGF mutant was the GH-deficient dwarf (dw/dw) rat (Charlton et al., *J. Endocr.*, 119: 51–58 (1988)), which shows a growth response to both GH and IGF-I. Skottner et al., *Endocrinology*, 124: 2519–2526 (1989); Clark et al., Endocrine 3:717–727 (1995). The dw/dw rat is not totally GH-deficient, as is the hypophysectomized rat, and thus has higher levels of serum IGF-I and the IGFBPs. Therefore, the dose of the IGF mutant given to the dw/dw rats was increased, since the blood of the dw/dw rats was expected to contain more IGF binding capacity and more IGF.

In the hypophysectomized rat (Example 4) GH was given to produce greater amounts of IGF and IGFBP, and the IGF mutant tested in the presence of this exogenous hormone. In the present Example the addition of exogenous GH was repeated as was the addition of exogenous IGF-I, to discover the activity of the IGF mutant in the presence of these exogenously administered hormones. The aim of the study was to discover the effects of administering a molecule that binds well to the IGFBPs but binds poorly to IGF receptors.

Methods

Animals:

Young female dwarf rats (11–12 wk of age, 115–140 g) were bred by homozygous mating (Charles Rivers Laboratories) and delivered to the Genentech Animal House where they were housed five per cage on polystyrene chips and fed a standard animal chow and water ad libitum, and kept in a room of constant humidity and with controlled temperature and lighting. The animals were weighed, and based on uniformity of body weight, 37 of the animals were selected and randomized into treatment groups and cages to give six treatment groups of equal initial body weights (approximately 120 g).

Experimental Groups:

The study consisted of six groups of rats with six or seven rats per group.

| | | |
|---|---|---|
| 1) | Excipient control (Excipient pumps) | Excipient injections |
| 2) | IGF mutant (IGF-M) (120 µg/day by pump) | Excipient injections |
| 3) | IGF-I (120 µg/day by pump) | Excipient injections |
| 4) | IGF-M (120 µg/day) plus IGF-I (120 µg/day) | Excipient injections |
| 5) | Excipient pumps | hGH injections (50 µg/d) |
| 6) | IGF-M (120 µg/day by pump) | hGH injections (50 µg/d) |

The rats were dosed for eight days.

Hormones:

The mutant (Leu$^{24}$,Ala$^{31}$)hIGF-I and native sequence recombinant human IGF-I were administered by osmotic minipumps (ALZET 2001™, Alza, Palo Alto, Calif.) which were placed in a subcutaneous tunnel in the dorsal neck region while the rats were anesthetized with KETAMINE/XYLAZINE™ anesthesia. The pumps were filled with solutions so that the calculated daily dose was 120 µg per rat per day (1 mg/kg/day), assuming that the pump delivered as per the manufacturer's description (24 µl of solution per day).

Recombinant human GH (50 µg/day) was administered for eight days by twice daily sc injection, with each injection being of 25 µg in a volume of 100 µl.

Animals not receiving injections of rhGH received injections of vehicle and animals which were not administered IGF-M had a saline-filled pump implanted.

Measurements:

Body weights were measured daily in the morning. After 8 days the animals were anesthetized using $CO_2$ and exsanguinated by cardiac puncture. The remaining blood was allowed to clot and serum was separated and stored for further analysis.

Spleen, thymus, heart, liver, kidney, and perirenal fat were removed and weighed. The tibia was removed and fixed in neutral buffered formalin for histological measurement of epiphyseal plate width.

Serum chemistries were measured using a TECHNICON CHEM I PLUS™ analyzer. Serum insulin concentration was measured using an RIA kit supplied by Linco, Inc. To measure the IGF-I concentrations the serum was extracted using acid ethanol and the supernatant diluted to neutrality and assayed for IGF-I by RIA. The concentration of rat IGF-I in serum extract was measured by RIA using a kit from Diagnostic Systems Laboratories, Inc. Human IGF-I concentration was measured by RIA at Genentech, Inc.

Tibia were sectioned longitudinally, stained with TOLUENE BLUE™ stain and mounted on microscope slides. The tibial epiphyseal plate width was measured using an ocular micrometer attached to a microscope.

Data were analyzed statistically by analysis of variance using one-factor ANOVA followed by Duncan's Range Test.

Results and Discussion

Figure 18:
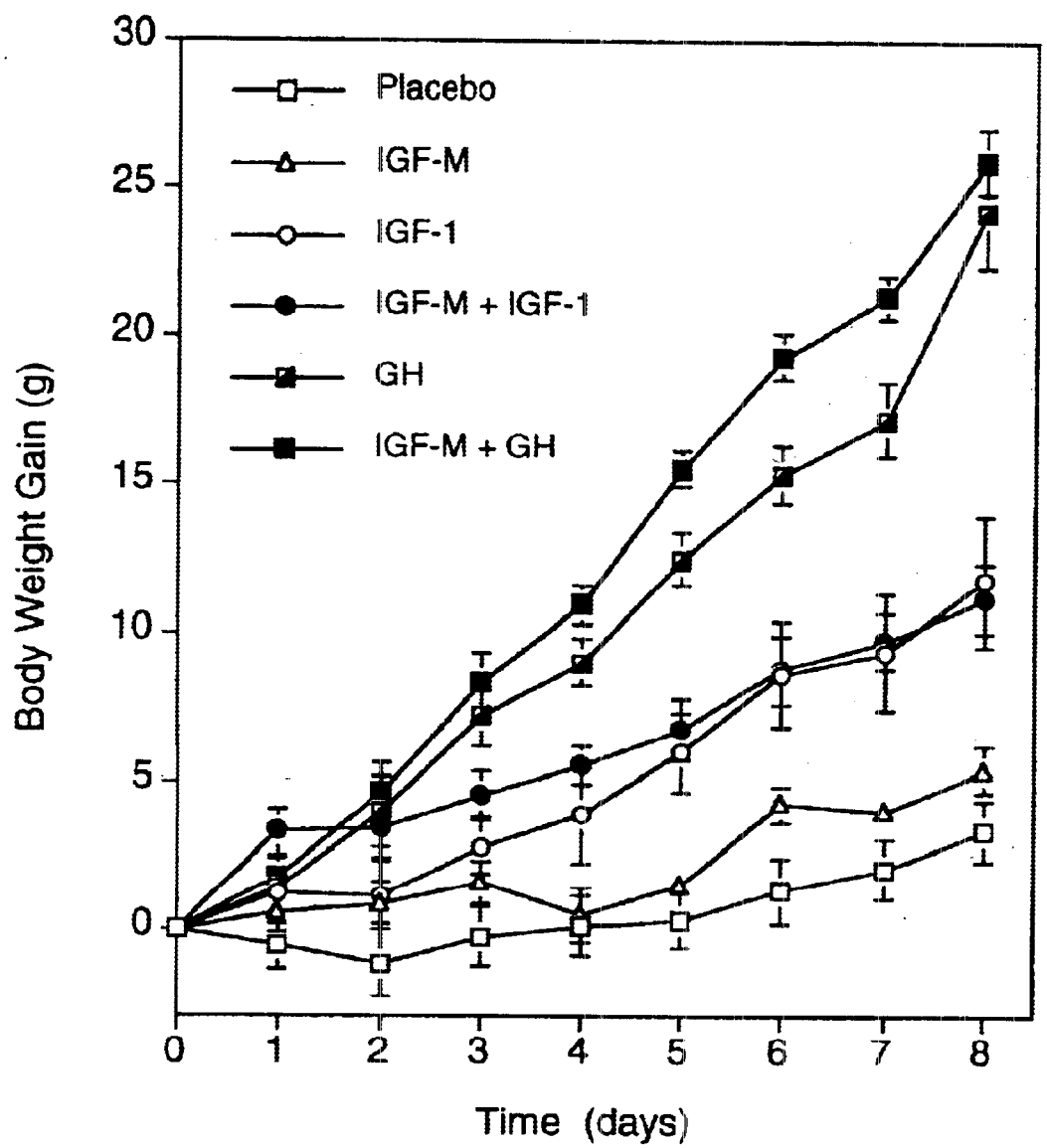
FIG. 18 depicts the final body weights over seven days of dwarf rats treated with placebo (open squares), (Leu$^{24}$, Ala$^{31}$)hIGF-I (open triangles), IGF-I (open circles), a combination of (Leu$^{24}$,Ala$^{31}$)hIGF-I and IGF-I (solid circles), GH (half open/half solid squares), and a combination of (Leu$^{24}$,Ala$^{31}$)hIGF-I and GH (solid squares).

Body Weight:

FIG. 18 shows the effect on body weight gain of the treatments over the 8 days of the study. On day 7 of the study it was decided to continue the study for one further day, and a new preparation of hGH was made and injected. The large weight gain between Days 7 and 8 suggests that this preparation of hGH was different from that used between Days 0 and 7. Therefore, it was believed that the weight gain data for the hGH groups on Day 7 are a better reflection of the overall experiment than those on Day 8. There were significant increases in body weight as a result of infusions of IGF-I or injections of hGH, the expected responses in these GH-deficient dwarf rats. By itself, the IGF agonist showed only a small amount of growth promoting activity, with the weight gain only approaching statistical significance at day 6 (excipient 1.3±1.1 g vs. IGF mutant 4.2±0.6 g, p<0.10). However, when the IGF mutant was given along with IGF-I there was initially clear weight gain (Day one excipient −0.6±0.8 g, IGF mutant 0.5±0.6 g, IGF-I 1.2±0.4 g, IGF mutant plus IGF-I 3.3±0.8 g, p<0.05 vs. IGF mutant alone and IGF-I alone), but this response waned with time. In contrast, the difference between hGH alone and hGH plus the IGF mutant increased with time, reaching statistical significance by Day 5 (hGH alone 12.4±0.9 g vs. hGH plus IGF mutant 15.5±0.6 g, p<0.05). Therefore, the IGF mutant enhanced the activity of hGH on whole body growth. These effects are shown in the growth curves and the final body weights (FIG. 18).

Organ Growth:

The organ weight data are illustrated for spleen (FIG. 19) and kidney (FIG. 20). In each Figure the absolute organ weight is shown in A (the top panel) and the organ weight expressed as a percentage of body weight is shown in B (the bottom panel).

Figure 19A:
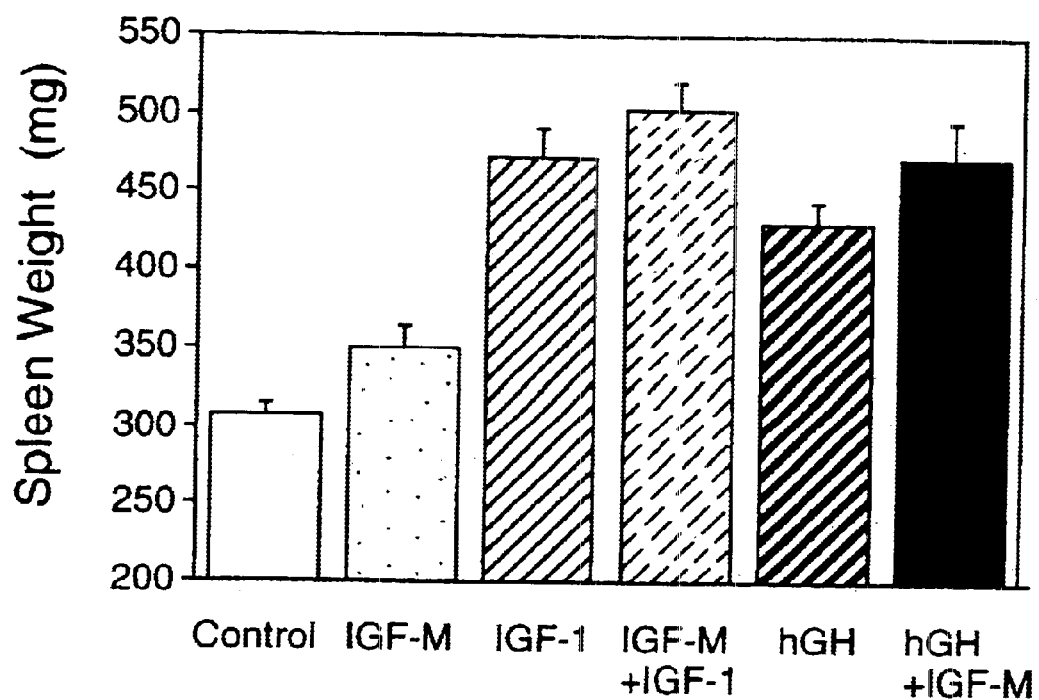
FIGS. 19A and 19B show the weight of the spleen in the study described above for FIG. 18, with FIG. 19A showing absolute spleen weight and FIG. 19B showing spleen weight expressed as a percentage of body weight.
Figure 19B:
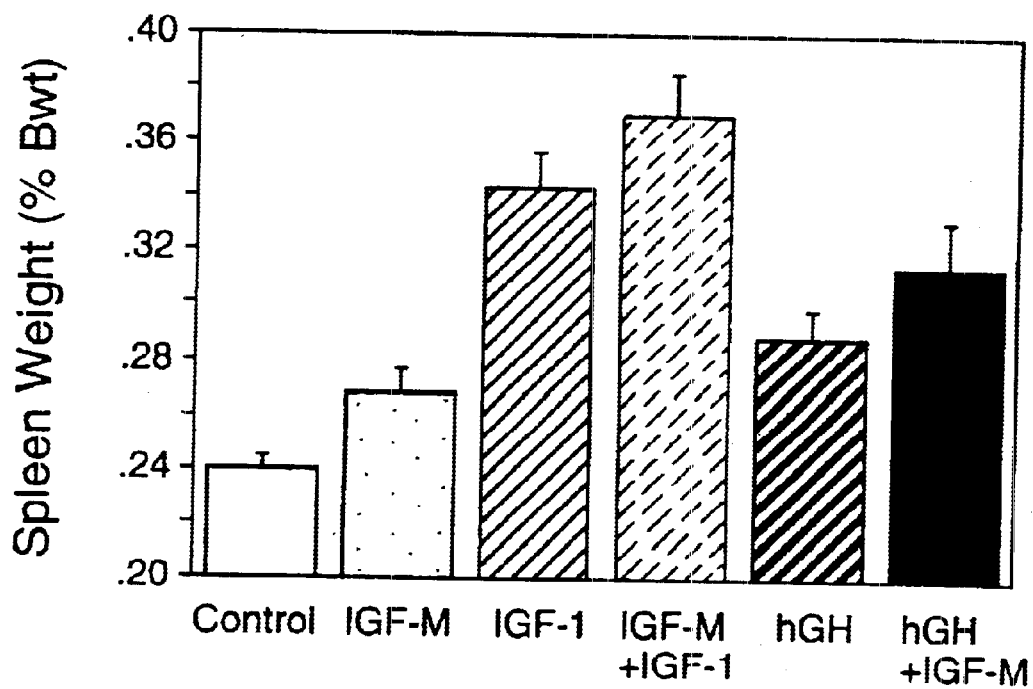

The absolute spleen weight (FIG. 19A) tended to increase in all groups treated with the IGF mutant. For example, the spleen weights in excipient control rats (308±6 mg) were increased by treatment with the IGF mutant alone to 350±14 mg (p<0.10 vs. excipient). Combining the IGF-M with either IGF-I or hGH treatments also tended to give larger spleens (FIG. 19A). When the spleen weights are expressed as a percentage of body weight, similar increases in spleen size caused by the IGF mutant were seen (FIG. 19B).

Figure 20A:
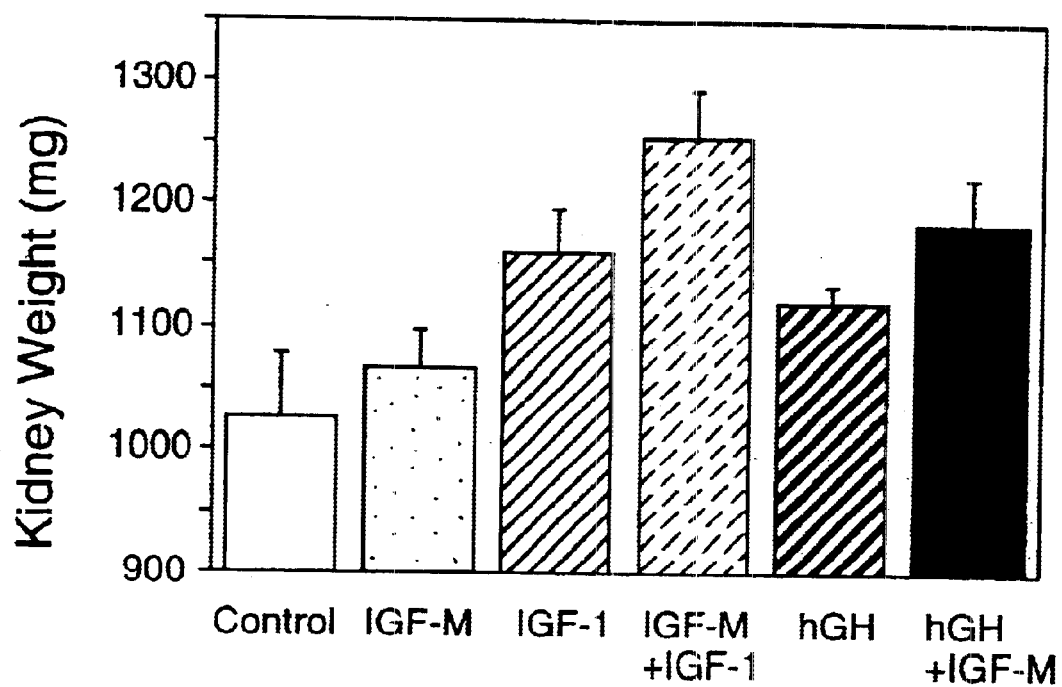
FIGS. 20A and 20B show the weight of the kidney in the study described above for FIG. 18, with FIG. 20A showing absolute kidney weight and FIG. 20B showing kidney weight expressed as a percentage of body weight.
Figure 20B:
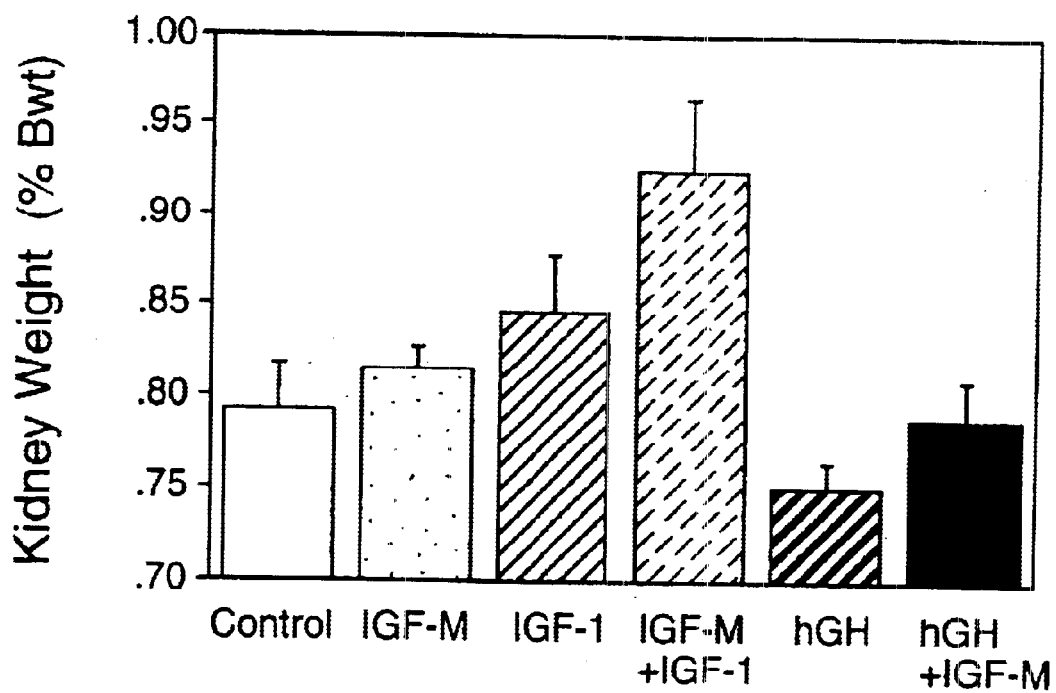

The absolute kidney weight and the relative kidney weight are shown in FIGS. 20A and 20B, respectively. The responses of the kidney to the IGF mutant were similar to those of the spleen. For example, relative kidney weight was increased by treatment with the IGF mutant, especially,when it was given in combination with IGF-I (IGF-I alone, 0.85±0.3% vs IGF-I plus IGF mutant 0.92±0.04%, p<0.05).

The retroperitoneal fat depot was removed from the rats at sacrifice and weighed. There was a tendency for the IGF mutant to decrease adipose tissue stores (placebo 0.56±0.09 g, IGF mutant 0.53±0.10 g, IGF-I 0.48±0.06 g, and IGF-I plus IGF mutant 0.43±0.05 g).

Serum Chemistries and Hormones:

Table I shows data collected from analyses of the sera collected at sacrifice. There was some effect of the various treatments on the blood glucose levels in the rats, but there were very significant effects on the insulin levels. The diabetogenic effect of GH was shown by the significantly (p<0.05) increased insulin concentrations in GH-treated rats compared to excipient-treated controls. If the rats were co-treated with the IGF mutant, this increase in serum insulin (diabetogenic effect of GH) was prevented (Table I), as the serum insulin level in the co-treatment group was no different from the insulin level in the excipient control group.

TABLE I

Serum Measurements in Dwarf Rats

| Group | Glucose (mg/dl) | Insulin (ng/ml) | BUN (mg/dl) | Creatinine (mg/dl) | AST (U/l) | CK (u/l) |
|---|---|---|---|---|---|---|
| Excipient | 198 ± 25 | 0.82 ± 0.04 | 19.3 ± 0.6 | 0.28 ± 0.02 | 137 ± 9 | 245 ± 47 |
| IGF-M | 174 ± 18 | 0.88 ± 0.09 | 17.8 ± 0.04 | 0.23 ± 0.03 | 143 ± 8 | 301 ± 44 |
| IGF-I | 190 ± 24 | 0.54 ± 0.06 | 16.0 ± 0.7 | 0.22 ± 0.05 | 128 ± 11 | 225 ± 18 |
| IGF M + IGF-I | 193 ± 19 | 0.69 ± 0.07 | 13.8 ± 0.8* | 0.18 ± 0.02* | 101 ± 2* | 138 ± 11* |
| hGH | 192 ± 10 | 1.48 ± 0.29* | 15.6 ± 0.7* | 0.33 ± 0.02 | 123 ± 13 | 184 ± 29 |
| hGH + IGF-M | 202 ± 27 | 1.03 ± 0.20 | 15.3 ± 0.6* | 0.25 ± 0.02 | 113 ± 9 | 229 ± 30 |

Data are Means ± SEM, *p <0.05 vs excipient control.

The IGF mutant (IGF-M) significantly increased kidney size. Two indications of serum measurements of renal function, the serum creatinine and the blood urea nitrogen (BUN) levels were reduced by the IGF mutant. Table I shows that the creatinine concentration in blood tended to be reduced by both IGF-I and the IGF mutant when they were given alone; however, these effects were not statistically significant. However, the combination of IGF-I plus IGF mutant significantly (p<0.05) reduced serum creatinine, indicative of an improvement in renal function. A second measure of renal function, the blood urea nitrogen, was also reduced by IGF-I and by IGF-I plus the IGF mutant, with the response to the combination being significantly greater than that to IGF-I alone (p<0.05)

The combination of IGF-I plus IGF mutant decreased the amounts of the enzyme AST (alanine serine transferase) and CK (creatinine kinase) in the blood compared to the excipient controls (p<0.05). AST is a measure of cardiac damage or function and CK is a measure of skeletal muscle function. These data could be interpreted as showing beneficial effects of the IGF mutant on skeletal and cardiac muscle.

Bone Growth:

The epiphyseal plate widths were significantly (p<0.05) increased by hGH and by IGF-I treatment, compared to excipient-treated controls. The IGF mutant in all cases increased the mean plate widths compared to the individual treatments, but these increases did not reach statistical significance.

Figure 21A:
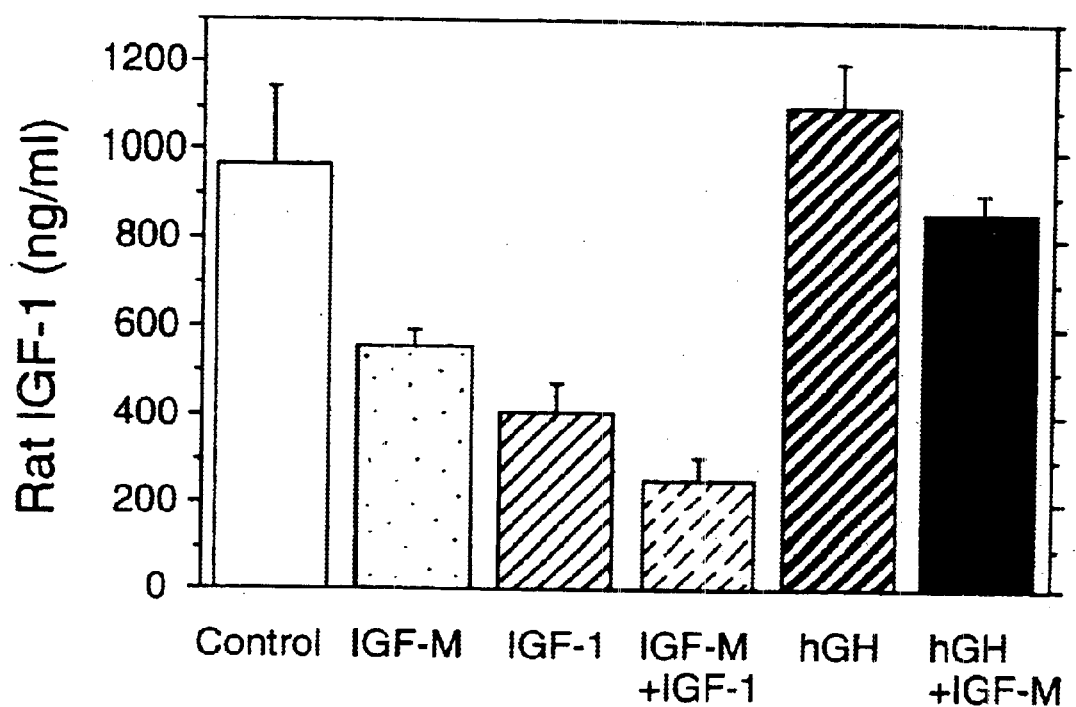
FIGS. 21A and 21B show the amount of rat IGF-I (FIG. 21A) and the amount of total IGF-I (FIG. 21B) in the blood in the six treatment groups in the study described for FIG. 18.
Figure 21B:
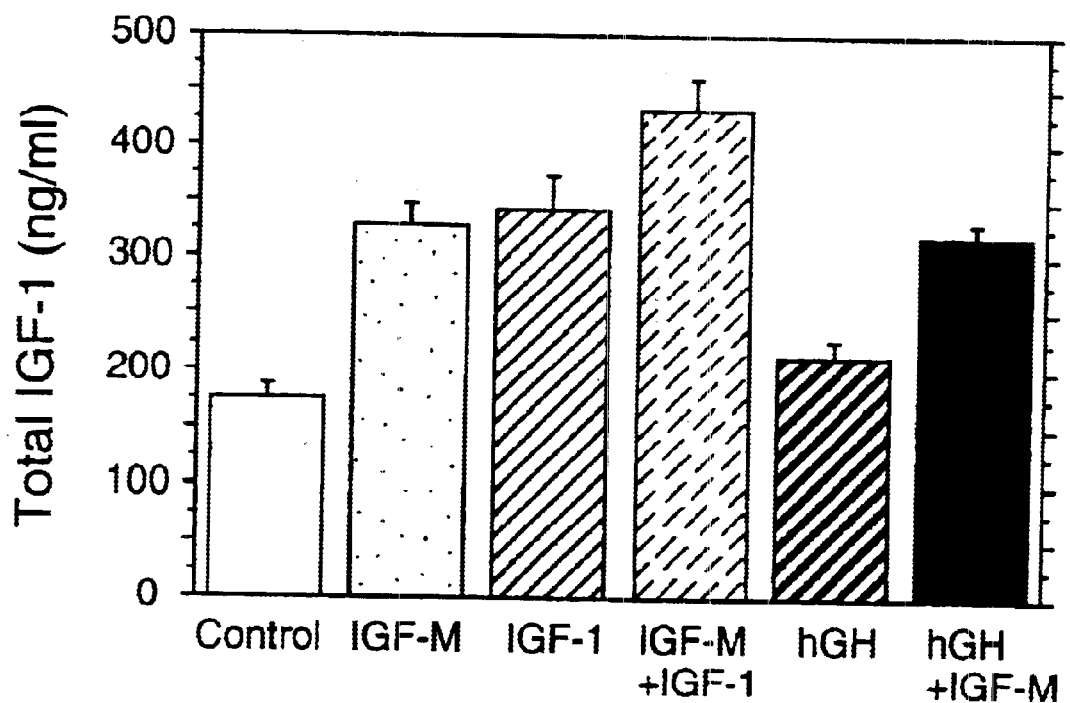

Serum IGF-I Levels:

The levels of IGF-I in the blood were measured in two assays (FIGS. 21A and 21B). One assay (FIG. 21A) measured the amount of rat IGF-I, and another assay (FIG. 21B) measured both human and rat IGF-I (total IGF-I) in the blood in the five treatment groups. A remarkable aspect of these data (FIG. 21A) is that the blood levels of receptor-active IGF-I (endogenous rat IGF-I) were lower in the animals given the mutant IGF, yet these lower blood IGF-I levels were associated with marked IGF-like responses in various organs and tissues. Clearly, it is counter-intuitive to observe evidence of increased activity of a hormone when the blood levels of the hormone are decreased.

The assay for total IGF-I (FIG. 21B) measures both rat and human IGF-I. In this assay there was a rise in total IGF-I in the rats given 150 µg of IGF-I agonist, probably due to the IGF-I agonist binding to binding proteins and therefore being present in the blood. The total IGF level in the blood did rise (p<0.05 vs. IGF-I alone or hGH alone) in the rats given the combination of either IGF-I or GH and the IGF agonist, in contrast to the level of rat IGF-I, which fell in these combination treatment groups. This indicates that when GH generates IGF and IGFBPs, there is spare binding capacity, and that this capacity has been in part filled by the IGF agonist.

Conclusion

These long-term data in the GH-deficient dwarf rat confirm and extend the long-term data collected in hypophysectomized rats; the IGF mutant produced anabolic and growth-promoting effects. In addition, this experiment confirms that the IGF mutant shows growth-promoting activity when administered with GH. Further, when the IGF mutant was given along with IGF-I to the dwarf rats, the IGF mutant could increase the activity of the administered IGF-I. Therefore, the present experiment shows that the long-term administration of compounds that bind tightly to IGFBPs, but bind poorly to IGF receptors, can enhance the activity of endogenous IGF-I, exogenously administered GH, and exogenously administered IGF-I.

In this Example several important findings were made which extend the discoveries made in the hypophysectomized rat.

Firstly, the increased size of the kidney in the rats treated with the IGF mutant was accompanied by a fall in the concentration of creatinine and blood urea nitrogen in the blood. These falls in blood metabolites are a hallmark of an increased functioning of the kidney. Additional evidence of a functional effect on cardiac and skeletal muscle was also obtained. Evidence of a decrease in fat mass was obtained using the IGF mutant. This indicates uses for IGF agonists in controlling body composition, especially obesity. See, for example, U.S. Pat. No. 5,597,797 on use of GH and IGF-I to prevent or treat obesity.

Secondly, the administration of GH significantly increased the blood concentrations of insulin, while the co-administration of the IGF mutant prevented this rise in insulin. Therefore, this well known diabetogenic effect of GH could be reversed by the co-administration of the IGF mutant.

Thirdly, these responses to the IGF mutant occurred in the presence of a fall in the blood concentrations of "active" rat IGF-I.

Therefore, long-term infusions of the IGF mutant showed multiple activities in 1) hypophysectomized rats, which have no detectable GH in their blood and very low IGF-I concentrations, and 2) in dwarf rats which have low GH and low IGF-I levels in their blood.

Example 6

Long-term Administration of $(Leu^{24}, Ala^{31})hIGF-I$ to Diabetic Rats

In this Example an animal model of diabetes was treated long-term with the IGF mutant. The animal chosen was a Type II diabetic rat (the Zucker Diabetic Fatty (ZDF) rat). This rat has relatively normal pituitary function (in terms of GH secretion) and relatively normal serum IGF-I concentrations. Therefore, this animal model differs from the two previous rat models, which have a complete lack of GH (hypophysectomized rat) or a clear deficiency of GH (the dw/dw rat) and are both IGF deficient. In addition, in this Example, the mode of administration of the IGF mutant was altered from infusions (used in the two previous Examples) to multiple injections. Furthermore, the dose of the IGF mutant was increased because, as explained above, the ZDF rats are not as IGF deficient as the hypophysectomized or dw/dw rats and therefore have a larger amount of active IGF to be released. The main endpoints used to measure efficacy in the previous Examples were measures of body growth, while in the present Example the major endpoints were blood glucose and insulin concentrations, measures of the diabetic state of the animals.

In the earlier Examples it was shown that the acute intravenous administration of one injection of an IGF agonist 1) reduced insulin levels and 2) reduced blood glucose levels. Since one injection of the IGF agonist showed efficacy on glycemic parameters and long-term infusions showed efficacy (without tachyphylaxis on growth parameters), it was hypothesized that multiple injections would each show acute glycemic effects leading to beneficial long-term cumulative glycemic effects. It was also hypothesized that injections given subcutaneously would show efficacy. Therefore, the long-term study in diabetic rats described below was initiated.

Methods and Experimental Groups

Animals:

Obese male Zucker Diabetic Fatty (ZDF) rats (6–7 weeks of age, 225–250 g, Genetic Models Inc., Indianapolis, Ind. 46268) were group housed (3/cage) in a room controlled for temperature and lighting and fed the pelleted rat diet specified by the breeders (Purina 5008, 6% fat breeder chow) and tap water ad libitum. After three days acclimation, a blood sample was obtained from the tail vein for measurement of blood glucose and insulin, which was measured by rat-specific RIA (Linco Research Inc., St. Charles, Mo.). Animals were randomized into four treatment groups and into cages to give groups balance so as to have equivalent initial blood glucose levels, insulin levels, and body weights.

The experiment consisted of four groups of rats with seven rats per group.

1) Excipient injections three times a day,
2) Injections of IGF mutant (IGF-M) (50 $\mu$g three times a day),
3) Injections of IGF-M (150 $\mu$g three times a day),
4) Injections of rhIGF-I (150 $\mu$g three times a day).

The injections were each of 100 $\mu$l given three times a day.

Hormones:

The mutant $(Leu^{24}, Ala^{31})hIGF-I$ was prepared at two concentrations (1.5 mg/ml, and 0.5 mg/ml) so that with three injections per day two doses were given (a total of 450 $\mu$g/d or 150 $\mu$g/d). rhIGF-I was prepared at one concentration (1.5 mg/ml) so that with three injections per day one dose was given (450 $\mu$g/d). A fourth group of rats were given the excipient. The injections, each of 100 $\mu$l volume, were given at 7 am, 1 pm, and 7 pm for 15 days without disrupting the controlled diurnal lighting of the vivarium room. Body weights were measured each day at 1 pm.

Blood Sampling:

Blood samples were collected from non-fasted rats on the evening before the first day of dosing and on days 3, 7, and 10. Blood samples (400 $\mu$l) on days 3, 7, and 10 were taken by bleeding from a tail vein one hour after the mid-day injection. The blood was allowed to clot, and serum was separated and stored before analysis.

A glucose tolerance test was performed on day 14 of the study. Rats received their regular morning injection and then their food was withdrawn. After a 3–5-hour fast a blood sample (400 $\mu$l) was taken via the tail vein. Rats then received 2 g/kg dextrose (50%) by intraperitoneal (ip) injection. A blood sample (200 $\mu$l) was taken via tail vein at 10, 60, and 120 minutes after dextrose administration. Blood was allowed to clot and serum was separated and stored for measurement of glucose and insulin concentrations. After the glucose tolerance test was completed, animals were re-fed.

On day 15, one hour after the morning injection, rats were asphyxiated with carbon dioxide and bled by cardiac puncture. Blood was allowed to clot and serum was separated and frozen. Spleen, thymus, heart, liver, kidney, and perirenal fat were removed, blotted dry, and immediately weighed.

Statistical Analysis:

Statistical comparisons for each time point were made by an analysis of variance with a Duncan's Multiple Range test. A p value of <0.05 was considered as being statistically significant. All data are represented as the mean±SEM, with seven animals per treatment group.

Results

Figure 22A:
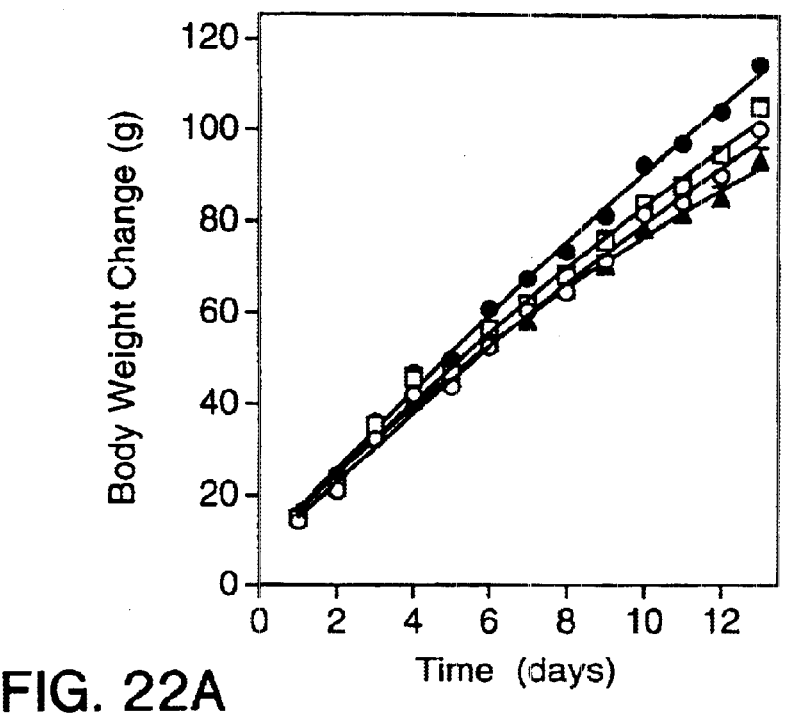
FIGS. 22A and 22B depict body weight gain (FIG. 22A) and percent increase in blood glucose levels (FIG. 22B) over a longer time period of diabetic rats treated with excipient control (solid triangles), with (Leu$^{24}$,Ala$^{31}$)hIGF-I at 150 μg, tid (three times daily) (open squares), with (Leu$^{24}$,Ala$^{31}$) hIGF-I at 50 μg, tid (open circles), and with IGF-I at 150 μg, tid (solid circles).

The body weight gains plotted against time are shown for the four different treatment groups in FIG. 22A. On day 13 the body weight gains were significantly increased vs. control (control, 93.3±2.9 g) for the IGF mutant at 50 µg (100±2.1 g, p<0.05 vs. control), for the IGF mutant at 150 µg (105.1±2.3 g, p<0.01 vs. control), and for IGF-I (114.5±1.6 g, p<0.0001 vs. control). The dose-related anabolic effect on body weight of the IGF mutant confirms the data in hypophysectomized and dwarf rats in the earlier examples.

Figure 22B:
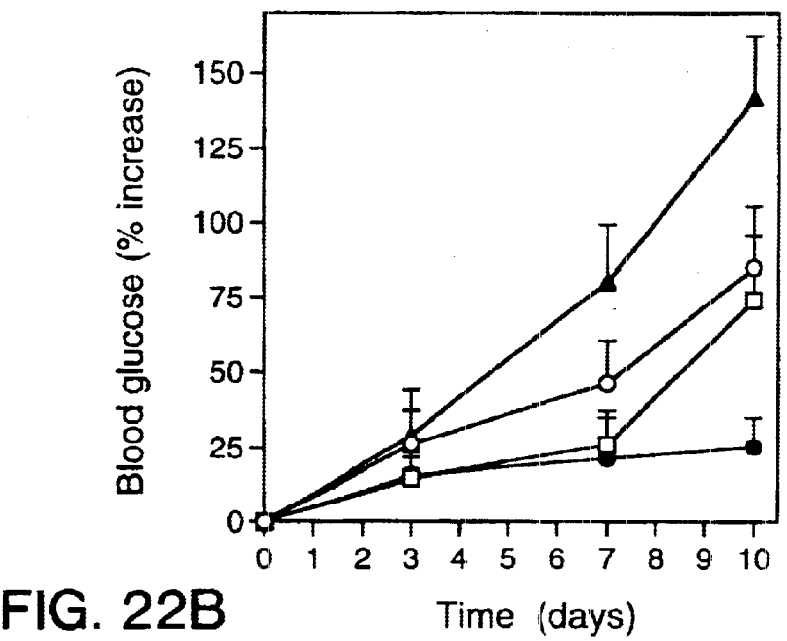

In these diabetic animals the reason for the gain in body weight could also be an indirect effect rather than an anabolic effect because the treatments improved the diabetic state of the animals. Carlsson et al., *J. Endocrinol.*, 122: 661 (1989). This interpretation of the data is supported by the illustration in FIG. 22B showing the changes in blood glucose with time in these same animals. Blood glucose was measured before the injections were commenced, and the Figure shows the percentage change from this basal level. FIG. 22B shows that the blood glucose rose steadily in the rats treated with repeated injections of excipient to reach 141±21% of basal at day 10, while at this time injections of IGF-I (150 µg three times a day) largely prevented (25±10%, p<0.001 vs control) this rise in blood glucose. Injections of the IGF mutant at 50 µg (84±20%, p<0.05 vs. control) and the IGF mutant at 150 µg (74±22%, p<0.05 vs. control) also slowed the rise of blood glucose in these diabetic rats at Day 10. At earlier time points, for example at day 7, the high-dose IGF mutant and IGF-I were equally effective at suppressing the rise in blood glucose.

Figure 23A:
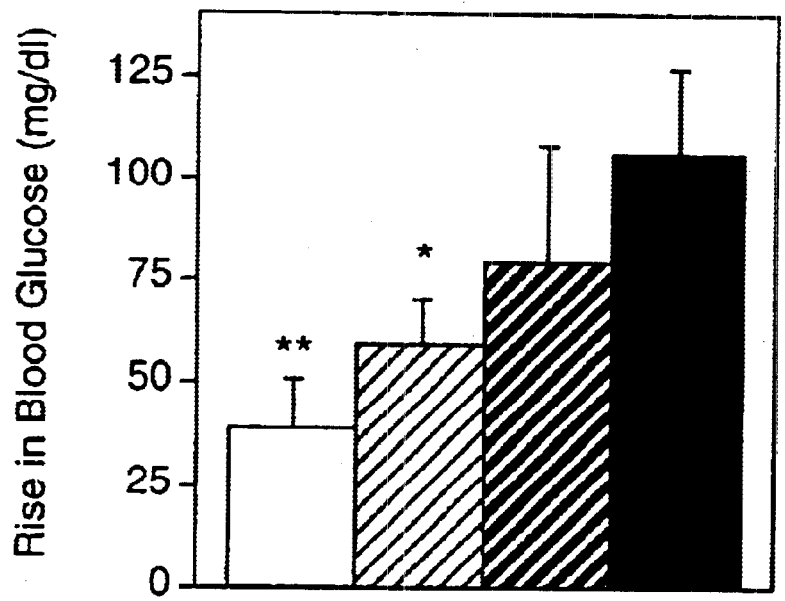
FIGS. 23A and 23B show the increase in blood glucose levels (FIG. 23A) and the changes in insulin levels (FIG. 23B) in the study described for FIG. 22. The control is indicated by black bars, the mutant at 150 μg by dark stippled bars, the mutant at 50 μg by light stippled bars, and the IGF-I by open bars.
Figure 23B:
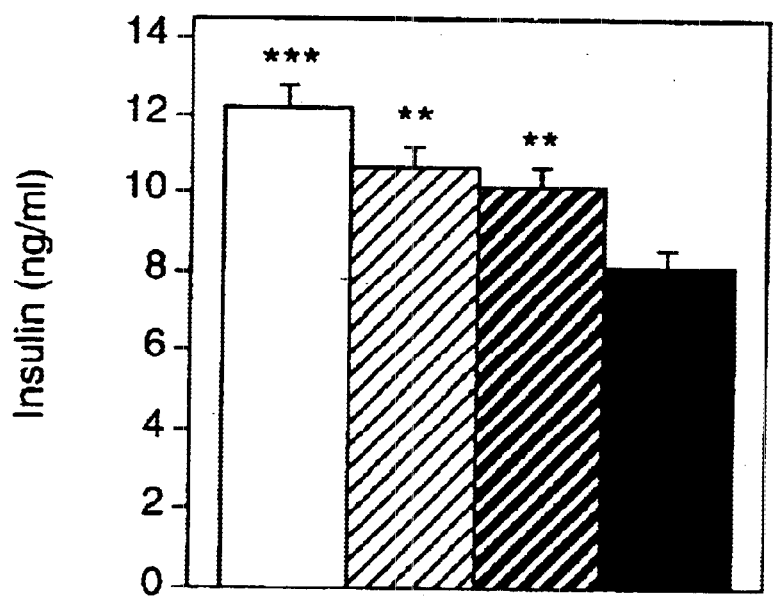

FIGS. 23A and 23B show the effect of a glucose tolerance test in these diabetic rats on blood glucose and on insulin concentrations. A glucose tolerance test can be viewed as a simulated meal. The rats were bled and then given an intraperitoneal injection of glucose at 2 g/kg of body weight and were then bled again following the injection. FIG. 23A shows the change in blood glucose two hours following the glucose challenge. In the diabetic rats treated with injections of excipient, blood glucose rose substantially (105±21 mg/dl). Treatment with IGF-I caused blood glucose to rise much less (39±12 mg/dl, P<0.05 vs control), while treatment with the IGF mutant (150 µg, tid) also blunted this rise (59±11 mg/dl, p<0. 1 vs. control).

A possible reason for these beneficial effects of treatment with IGF-1 or the IGF-mutant is provided by the insulin levels shown in FIG. 23B. In the rats treated with IGF-I more insulin secretion occurred in response to the glucose challenge (control, 8.1±0.6 ng/ml vs. IGF-1, 12.2±0.7 ng/ml, p<0.01) than it did in the rats treated with IGF mutant at 50 µg (10.2±0.7 ng/ml, p<0.05 vs. control) or 150 µg (10.6±0.6 ng/ml, p<0.05 vs. control). Therefore, long-term treatment with the IGF mutant allowed greater insulin secretion in response to a simulated meal which was associated with an improved ability to dispose of a glucose load.

Conclusions

This long-term study administering the IGF-mutant to diabetic rats shows that blood glucose can be controlled in the long term by manipulating the endogenous IGF system. The body weight gain, perhaps an indirect marker of improved glucose control in diabetic animals, and the direct measures of glucose control (blood glucose and insulin), show the surprising efficacy of this class of receptor-inactive molecules in improving the diabetic state. In the present example multiple subcutaneous daily injections were given for 15 days with no evidence of tachyphylaxis. In the previous examples infusions of this molecule produced maintained anabolic responses. It is therefore reasonable to assume that most routes and patterns of delivery would also show similar efficacy. For example, oral formulations of molecules with long half-lives would be expected to be efficacious as would shorter half-life molecules delivered by the oral or other routes.

Example 7

Phage-derived Peptides to Bind IGF-I and Binding Proteins

In the next set of examples, common α-amino acids may be described by the standard one- or three-letter amino acid code when referring to intermediates and final products. By common α-amino acids is meant those amino acids incorporated into proteins under mRNA direction. Standard abbreviations are listed in The Merck Index, 10th Edition, pp Misc-2–Misc-3. Unless otherwise designated the common α-amino acids have the natural or "L"-configuration at the alpha carbon atom. If the code is preceded by a "D" this signifies the opposite enantiomer of the common α-amino acid. Modified or unusual α-amino acids such as norleucine (Nle) and ornithine (Orn) are designated as described in U.S. Patent and Trademark Office Official Gazette 1114 TMOG, May 15, 1990.

Based upon the results of experiments using the IGF mutant described above, it is predicted that other molecules, such as peptides or small organic molecules, which inhibit the interaction of an IGF with an IGFBP, and bind poorly or not at all to the IGF-I receptor, should increase active IGF levels in a subject being treated. In addition, it is possible that another class of molecules, in particular peptidic or small molecules, might bind IGF-I itself at a site remote from that involved in receptor interactions in such a way as to inhibit or prevent the interaction of IGF-I with the IGFBPs, but not the interaction of IGF-I with its receptor.

It has been shown that peptides which bind specifically and with measurable affinity to target molecules, such as proteins, can be identified from an initial library of many binding and non-binding peptides through binding selections using bacteriophage coat-protein fusions. Smith, *Science*, 228: 1315 (1985); Scott and Smith, *Science*, 249: 386 (1990); Cwirla et al., *Proc. Natl. Acad. Sci. USA*, 8: 309 (1990); Devlin et al., *Science*, 249: 404 (1990); reviewed by Wells and Lowman, *Curr. Opin. Struct. Biol.*, 2: 597 (1992); U.S. Pat. No. 5,223,409. In addition, both proteins and peptides displayed on phage can be affinity-enhanced through iterative cycles of mutations, selection, and propagation.

Libraries of peptides differing in sequence at particular residue positions can be constructed using synthetic oligodeoxynucleotides. Peptides are displayed as fusion proteins with a phage coat protein (such as g3p or g8p) on bacteriophage particles, each of which contains a single-stranded DNA genome encoding the particular peptide variant. After cycles of affinity purification, using an immobilized target molecule, individual bacteriophage clones are isolated, and the amino acid sequence of their displayed peptides is deduced from their DNA sequences.

I. Construction of Peptide-phage Libraries

To identify a set of peptide molecules having the ability to bind to IGF-I or to an IGF binding protein, such as IGFBP-1 or IGFBP-3, several diverse phage libraries of peptides, of length ranging from 18 to 20 residues, were constructed. Peptides of this size were chosen in order to favor the selection of peptides capable of maintaining well-defined structures in solution.

Because natural-amino acid peptides of this size have a potential sequence diversity of $20^{18}$–$20^{20}$ (i.e., $2.6 \times 10^{23}$ to $1.0 \times 10^{26}$) variants, it is not practical to construct and test all such variants. Instead, certain residues were fixed or constant, which might be expected to allow or promote stable elements of peptide structure such as disulfide bonds or beta-turns, within each peptide.

Structural constraints or frameworks have previously been used for presentation of peptide libraries on phage and for subsequent, successive enhancement of binding affinities through mutation and selection. Such structured frameworks may favor stable binding conformations of peptide segments. By analogy, immunoglobulins provide a stable (and conserved) structural framework for presentation of a diversity of different peptide loops (CDR's, complementarity-determining regions) which can bind different antigens.

Used as a template for library constructions was a plasmid, pt4.g8 (complete DNA sequence shown in FIG. 24) expressing an antibody-recognizable (gD-tag) peptide fused to g8p of bacteriophage M13. This plasmid contains single-stranded and double-stranded origins of DNA replication. The phoA promoter and STII secretion-signal sequences are upstream of the gD peptide (underlined below), which is followed by a "linker" peptide (double underlined below), and then the g8p of bacteriophage M13:

SGTAMADPNRFRGKDLAGSP
GGGSGGGAEGDDPAKAAFNSLQASATEYI
GYAWAMVVVIVGATIGIKLFKKFTSKAS (SEQ ID NO:21)

Several random-sequence peptide libraries (Table II) were constructed using single-stranded template-directed mutagenesis (Kunkel et al., *Methods. Enzymol.*, 204:125 (1991)), with the oligonucleotides described below.

TABLE II

Large Naive Libraries for g8 Display

| Library | Oligo no. | Peptide motif | |
|---|---|---|---|
| A | HL-300 | SGTACX$_2$GPX$_4$CSLAGSP | SEQ ID NO: 24 |
| B | HL-301 | X$_4$CX$_2$GPX$_4$CX$_4$ | SEQ ID NO: 25 |
| C | HL-302 | X$_{20}$ | SEQ ID NO: 26 |
| D | HL-303 | X$_7$CX$_4$CX$_7$ | SEQ ID NO: 27 |
| D | HL-304 | X$_7$CX$_5$CX$_6$ | SEQ ID NO: 28 |
| D | HL-305 | X$_6$CX$_6$CX$_6$ | SEQ ID NO: 29 |
| D | HL-306 | X$_6$CX$_7$CX$_5$ | SEQ ID NO: 30 |
| D | HL-307 | X$_5$CX$_8$CX$_5$ | SEQ ID NO: 31 |
| D | HL-308 | X$_5$CX$_9$CX$_4$ | SEQ ID NO: 32 |
| D | HL-309 | X$_4$CX$_{10}$CX$_4$ | SEQ ID NO: 33 |

A. Beta-turn Sequence Motif

An example of a peptide of known three-dimensional structure is given by Wrighton et al., who selected a peptide agonist for the erythropoietin receptor (EPO-R) by phage display Wrighton et al., *Science*, 273: 458 (1996). The peptide GGTYSCHFGPLTWVCKPQGG (SEQ ID NO:34) (having a disulfide bond joining the two Cys residues) forms a dimer of two beta hairpins, in the crystallized complex with EPO-R. Livnah et al., *Science*, 273: 464 (1996). Although the structure of the unbound form of this peptide in solution has not been reported, the beta-turn structure formed by this peptide in complex with EPO-R suggested that similar structures might be formed by peptides of the form CX$_2$GPX$_4$C (SEQ ID NO:35).

As one type of structured peptide library, a portion of the gD peptide was replaced with the motif CX$_2$GPX$_4$C (SEQ ID NO:35), leaving the upstream and downstream ("flanking") residues unchanged from that of the starting plasmid. Thus, this library was designed to display on phage particles the peptide SGTACX$_2$GPX$_4$CSLAGSP (SEQ ID NO:24), where X represents any of the 20 natural L-amino acids, fused to the linker and g8p described above. This library was constructed using the oligonucleotide HL-300:

5'-GCC TAT GCA TCT GGT ACC GCC TGC NNS NNS GGT CCT NNS NNS NNS NNS TGT TCT CTG GCA GGT TCA CCA G-3' (SEQ ID NO:36), where N indicates a mixture of the nucleotides A, G, C, and T, and S represents a mixture of the nucleotides G and C.

An additional library was constructed to allow for further interactions within the peptide and/or with the target proteins by randomizing the flanking sequences as well. This library was constructed with the form, X$_4$CX$_2$GPX$_4$CX$_4$ (SEQ ID NO:25) by using oligonucleotide HL-301:

5'-GCT ACA AAT GCC TAT GCA NNS NNS NNS NNS TGC NNS NNS GGT CCT NNS NNS NNS NNS TGT NNS NNS NNS NNS GGT GGA GGA TCC GGA GGA G-3' (SEQ ID NO:37).

B. Disulfide-loop Motifs

Because many additional peptide conformations might be productive for binding to a given target protein, it was desirable to test other types of peptide sequence motifs in phage-displayed libraries. For example, a single disulfide bond within a small peptide may favor stable structures which allow for relatively higher-affinity binding than in unconstrained structures. Geysen et al., *Mol. Immunol.*, 23: 709 (1986); Wood et al., *Science*, 232: 633 (1986); Oldenburg et al., *Proc. Natl. Acad. Sci. USA*, 89: 5393 (1992); O'Neil et al., *Proteins*, 14: 509 (1992); McLafferty et al., *Gene*, 128: 29 (1993); Giebel et al., *Biochem.*, 34: 15430 (1995). Several peptide-phage libraries were therefore constructed, of the form X$_m$CX$_n$CX$_k$ (SEQ ID NO:33), where m=4, n=10, and k=4, or where m=5, n=8–9, and k=4–5, or m=6, n=6–7, and k=5–6, or m=7, n=4–5, and k=6–7 (SEQ ID NOS:27 to 33). In these peptides, a disulfide bond is predicted to form a stabilizing constraint for peptide conformation.

These peptide libraries (see Table II) were constructed as X$_7$CX$_4$CX$_7$ (SEQ ID NO:27), using oligonucleotide HL-303:

5'-GCT ACA AAT GCC TAT GCA NNS NNS NNS NNS NNS NNS NNS TGC NNS NNS NNS NNS TGC NNS NNS NNS NNS NNS NNS NNS GGT GGA GGA TCC GGA GGA G-3' (SEQ ID NO:38);

X$_7$CX$_5$CX$_6$ (SEQ ID NO:28), using oligonucleotide HL-304:

5'-GCT ACA AAT GCC TAT GCA NNS NNS NNS NNS NNS NNS NNS TGC NNS NNS NNS NNS NNS TGC NNS NNS NNS NNS NNS NNS GGT GGA GGA TCC GGA GGA G-3' (SEQ ID NO:39);

X$_6$CX$_6$CX$_6$ (SEQ ID NO:29), using oligonucleotide HL-305:

5'-GCT ACA AAT GCC TAT GCA NNS NNS NNS NNS NNS NNS TGC NNS NNS NNS NNS NNS NNS TGC NNS NNS NNS NNS NNS NNS GGT GGA GGA TCC GGA GGA G-3' (SEQ ID NO:40);

X$_6$CX$_7$CX$_5$ (SEQ ID NO:30), using oligonucleotide HL-306:

5'-GCT ACA AAT GCC TAT GCA NNS NNS NNS NNS NNS NNS TGC NNS NNS NNS NNS NNS NNS NNS TGC NNS NNS NNS NNS NNS GGT GGA GGA TCC GGA GGA G-3' (SEQ ID NO:41);

$X_5CX_8CX_5$ (SEQ ID NO:31), using oligonucleotide HL-307:

5'-GCT ACA AAT GCC TAT GCA NNS NNS NNS NNS NNS TGC NNS NNS NNS NNS NNS NNS NNS NNS TGC NNS NNS NNS NNS NNS GGT GGA GGA TCC GGA GGA G-3' (SEQ ID NO:42);

$X_5CX_9CX_4$ (SEQ ID NO:32), using oligonucleotide HL-308:

5'-GCT ACA AAT GCC TAT GCA NNS NNS NNS NNS NNS TGC NNS NNS NNS NNS NNS NNS NNS NNS NNS TGC NNS NNS NNS NNS GGT GGA GGA TCC GGA GGA G-3' (SEQ ID NO:43); and $X_4CX_{10}CX_4$ (SEQ ID NO:33), using oligonucleotide HL-309:

5'-GCT ACA AAT GCC TAT GCA NNS NNS NNS NNS TGC NNS NNS NNS NNS NNS NNS NNS NNS NNS NNS TGC NNS NNS NNS NNS GGT GGA GGA TCC GGA GGA G-3' (SEQ ID NO:44).

C. Unconstrained Peptides

Unconstrained libraries (i.e., having no fixed residues within the peptide) have also yielded specific binding molecules. Scott and Smith, *Science*, supra; Cwirla et al., *Proc. Natl. Acad. Sci. USA*, supra; Devlin et al., *Science*, supra; Kay et al., *Gene*, 128: 59 (1993). Such libraries may yield structured peptides, nevertheless, since noncovalent interactions may still induce structure in the bound and/or unbound forms. An unconstrained peptide library, of the form $X_{20}$ (SEQ ID NO:45), was constructed using oligonucleotide HL-302:

5'-GCT ACA AAT GCC TAT GCA NNS NNS NNS NNS NNS NNS NNS NNS NNS NNS NNS NNS NNS NNS NNS NNS NNS NNS NNS NNS GGT GGA GGA TCC GGA GGA G-3' (SEQ ID NO:46).

II. Polyvalent (g8) Phage Binding Selections

The products of random mutagenesis reactions were transformed into XL1-BLUE™ *E. coli* cells (Stratagene) by electroporation and amplified by growing 15–16 h with M13K07 (Vieira and Messing, *Methods Enzymol.*, 153: 3–11 (1987)) or VCSM13 helper phage (Stratagene Corp.). Based upon plating of the initial transformations, the number of transformants per library was approximately $1.8 \times 10^8$ for library HL-300, $7.9 \times 10^8$ for HL-301, $5.0 \times 10^8$ for HL-302, $5.3 \times 10^8$ for HL-303, $5.6 \times 10^8$ for HL-304, $5.0 \times 10^8$ for HL-305, $6.3 \times 10^8$ for HL-306, $4.5 \times 10^8$ for HL-307, $1.9 \times 10^8$ for HL-308, and $2.1 \times 10^8$ for HL-309.

IGFBP-1, IGFBP-3, and IGF-I were biotinylated with a 1.5:1 molar ratio of a cleavable biotin reagent, EZ-LINK™ NHS-SS-Biotin (Pierce), to protein, using the manufacturer's instructions.

The initial selection of peptides for binding to IGFBP-1, IGFBP-3, or IGF-I was carried out using phage pools of approximately $10^{10}$ phage/ml (100 µl total volume). MAXISORP™ 96-well plastic plates (Nunc) were coated with a solution of 2 µg/ml of NEUTRAVIDIN™ brand avidin (Pierce) in 50 mM sodium carbonate buffer, pH 9.6, overnight at 4° C. The NEUTRAVIDIN™ solution was then removed, and the plates were incubated with a blocking solution of 5 g/l of bovine serum albumin, or 5 g/l of ovalbumin, or 5 g/l of instant milk in 50 mM sodium carbonate buffer, for 1–2 h at room temperature. The blocking solution was then removed, and a solution of biotinylated target protein was added. After 1–2 h at room temperature, the target solution was removed, and the plates were washed ten times with PBS/TWEEN™ surfactant (0.05% TWEEN-20™ in PBS buffer).

Phage from the libraries described above were pooled as follows: pool A consisted of HL-300 phage, pool B of HL-301 phage, pool C of HL-302 phage, and pool D of phage from the HL-303, HL-304, HL-305, HL-306, HL-307, HL-308, and HL-309 libraries. Phage were added in PBS/TWEEN™/albumin/biotin (PBS/TWEEN™ buffer with 1 M biotin, 5 g/l bovine serum albumin, or ovalbumin) to wells coated with each target, and with control wells that were coated with NEUTRAVIDIN™ or with albumin, but not biotinylated target. The phage were allowed to bind 5–15 h at room temperature. The plates were then washed ten times with PBS/TWEEN™ buffer.

Phage remaining bound to the plates were eluted by incubating with 50 mM DTT for 1–2 h at room temperature. The eluted phage were transfected into *E. coli* cells and allowed to grow overnight at 37° C. to amplify the gpage.

The second and third cycles of binding selection were carried out as above, except that streptavidin (0.1 mg/mL) was included in the phage cocktails along with biotin. An aliquot was taken from each target-coated and control well incubated with each library, and serial dilutions of the diluted phage were performed to measure specific binding to target. The diluted phage were then transfected into *E. coli* cells and plated for colony counting.

Figure 25:
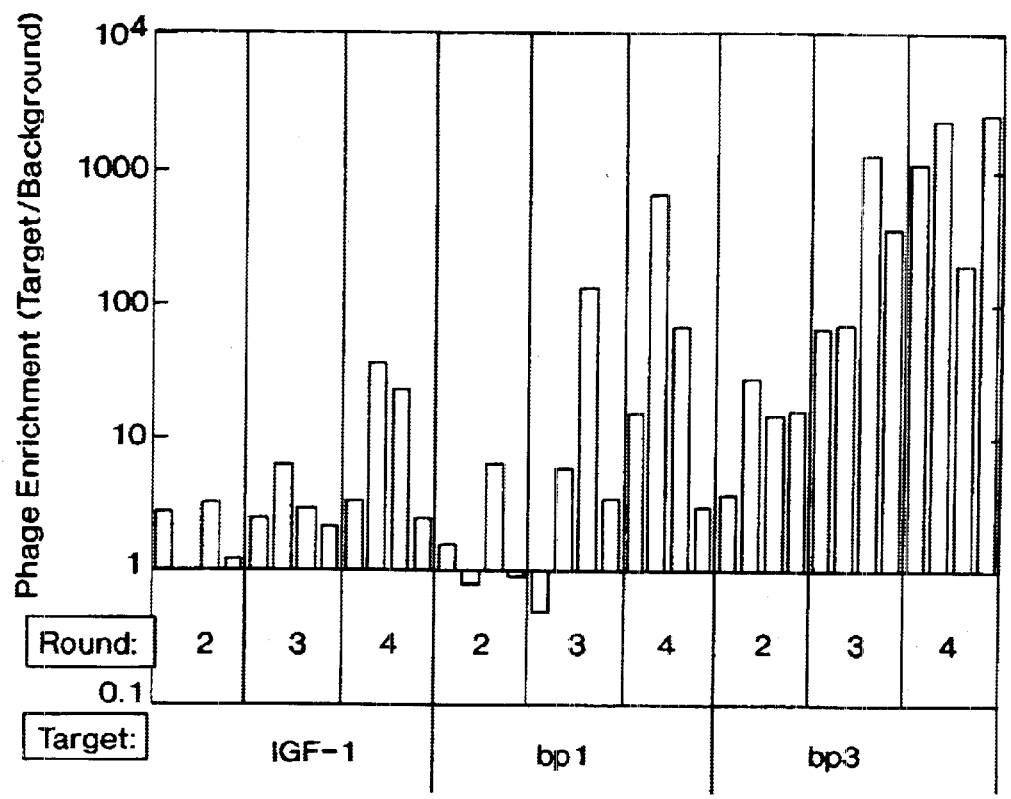
FIG. 25 shows gene-8 naive phage library enrichments with a selection using four library pools each and the targets IGF-I, IGFBP-1, and IGFBP-3.

The fourth round of binding selection was carried out on MAXISORP™ plates directly coated with 2 µg/ml of each target protein, or with albumin only. The results of phage-binding selections in cycles 2–4 are shown in FIG. 25.

The same initial phage libraries (A, B, C, D) were also used for binding selections to directly-coated IGFBP-3. In this case, MAXISORP™ 96-well plastic plates (Nunc) were coated with a solution of 2 µg/ml of IGFBP-3 in 50 mM sodium carbonate buffer, pH 9.6, overnight at 4° C. The target solution was then removed, and the plates were incubated with a blocking solution of 5 g/L of bovine serum albumin, for 1–2 h at room temperature. Phage were incubated with the plates as above, and non-binding phage washed away. The phage remaining bound were eluted by incubating with 20 mM HCl for 10 min at room temperature. Thereafter, the acid-eluted phage were neutralized with one-fifth volume of 1 M Tris-HCl, pH 8.0. Phage were transfected for colony counting as described above.

III. Screening of Polyvalent Phage Clones (IGF-blocking Phage Assay)

Peptide-phage clones were isolated by mixing phage pools with *E. coli* cells, and plating onto antibiotic-containing media. Colonies were isolated and grown with helper phage (as above) to obtain single-stranded DNA for sequencing. Peptide sequences selected for binding IGFBP-3, IGFBP-1, or IGF-I were deduced from the DNA sequences of phagemid clones. A number of such clones are represented by the peptide sequences in Tables III–V, respectively.

TABLE III

Peptide sequences from
g8 display, IGFBP-3 selection

| Name | Peptide sequence |
|---|---|
| 4A3.1 | SGTACYGGPEWWCCSLAGSP (SEQ ID NO: 47) |
| 4A3.3 | SGTACYGGPEWWCCSLAGSP (SEQ ID NO: 47) |
| 4A3.4 | SGTACYGGPEWWCCSLAGSP (SEQ ID NO: 47) |
| 4B3.1 | DLAICAEGPEIWVCEETS (SEQ ID NO: 48) |

TABLE III-continued

Peptide sequences from
g8 display, IGFBP-3 selection

| Name | Peptide sequence | |
|---|---|---|
| 4B3.2 | DFWICLSGPGWEECLEWW | (SEQ ID NO: 49) |
| 4B3.3 | EESECFEGPGYVICGLVG | (SEQ ID NO: 7) |
| 4B3.4 | DMGVCADGPWMYVCEWTE | (SEQ ID NO: 8) |
| 4B3.5 | DMGVCADGPWMYVCEWTE | (SEQ ID NO: 8) |
| 4C3.1 | GSAGQGMTEEWAWIWEWWKE | (SEQ ID NO: 50) |
| 4C3.2 | ELDGWVCIKVGEQNLCYLAE | (SEQ ID NO: 51) |
| 4C3.4 | ELDGWVCIKVGEQNLCYLAE | (SEQ ID NO: 51) |
| 4C3.4 | ELDGWVCIKVGEQNLCYLAE | (SEQ ID NO: 51) |
| 4C3.5 | ELDGWVCIKVGEQNLCYLAE | (SEQ ID NO: 51) |
| 4D3.1 | AIGGWCFIELDSLWCEEQIG | (SEQ ID NO: 52) |
| 4D3.2 | SEDVECWQVWENLVCSVEHR | (SEQ ID NO: 53) |
| 4D3.3 | SEEVCWPVAEWYLCNMWGR | (SEQ ID NO: 54) |
| 4D3.4 | RVGAYISCSETECWVEDLLD | (SEQ ID NO: 55) |
| 4D3.5 | WFKTVCYEWEDEVQCYTLEE | (SEQ ID NO: 56) |
| 4D3.6 | SEDVECWQVWENLVCSVEHR | (SEQ ID NO: 53) |
| 4D3.7 | RLEEQCVEVNYEPSCSFTAN | (SEQ ID NO: 57) |
| 4D3.8 | SEEVCWPVAEWYLCNILGP | (SEQ ID NO: 58) |
| 4D3.9 | ETVANCDCYMDLCLCYGSDR | (SEQ ID NO: 59) |
| 4D3.10 | YHPISCMDHYYLIICDETVN | (SEQ ID NO: 60) |
| 4D3.11 | VAWEVCWDRHDQGYICTTDS | (SEQ ID NO: 4) |
| 4D3.12 | AEWAECWIAGDQLLCVGKDN | (SEQ ID NO: 61) |
| 23A3.1 | EPWLCQYYEAAMLYLCWEEG | (SEQ ID NO: 62) |
| 23A3.2 | AEEGMVWGWTGGWYNLDELC | (SEQ ID NO: 63) |
| 23A3.3 | SGGAIYWPVEQFIAFMAVGK | (SEQ ID NO: 64) |
| 23A3.4 | EPWLCQYYEAAMLYLCWEEG | (SEQ ID NO: 62) |
| 23A3.5 | SGGAIYMPVEQFIAFMAVGK | (SEQ ID NO: 65) |
| 23B3.1 | TGVDCQCGPVHCVCMDWA | (SEQ ID NO: 13) |
| 23B3.2 | EVLLCSDGPQLYLCELYA | (SEQ ID NO: 66) |
| 23B3.4 | SGVECVWGPQWGFCVEEY | (SEQ ID NO: 67) |
| 23B3.5 | DKEVCYLGPETWLCFWWP | (SEQ ID NO: 68) |
| 23B3.6 | EVLLCSDGPQLYLCELYA | (SEQ ID NO: 66) |
| 23B3.7 | GDVECIEGPWGELCVWAD | (SEQ ID NO: 69) |
| 23D3.1 | FGGWSCQPTWVDVYVCNFEE | (SEQ ID NO: 70) |
| 23D3.2 | AMWVCVSDWETVEECIQYMY | (SEQ ID NO: 71) |
| 23D3.3 | AMWVCVSDWETVEECIQYMY | (SEQ ID NO: 71) |
| 23D3.4 | AMWVCVSDWETVEECIQYMY | (SEQ ID NO: 71) |
| 23D3.5 | AMWVCVSDWETVEECIQYMY | (SEQ ID NO: 71) |
| 23D3.6 | TNWFFVCESGHQDICWLAEE | (SEQ ID NO: 72) |

TABLE IV

Peptide sequences from
g8 display, IGFBP-1 selection

| Clone | Peptide sequence | Library | Frequency |
|---|---|---|---|
|  | SEVGCRAGPLQWLCEKYF (SEQ ID NO: 73) | A | 6/6 |
| HL-14 | SEVGCRAGPLQWLCEKYF (SEQ ID NO: 73) | B | 5/6 |
| HL-13 | KDPVCGEGPLMRICERLFG (SEQ ID NO: 74) | B | 1/6 |
| HL-31 | EVDGRWWIVETFLAKWDHMAG (SEQ ID NO: 75) | C | 6/6 |

TABLE V

Peptide sequences from g8
display, IGF-I selection

| Clone | Peptide sequence | Library | Frequency |
|---|---|---|---|
| HL-8 | WVMECGAGPWPEGCTFML (SEQ ID NO: 76) | B | 5/6 |
| HL-26 | RKTSQGRGQEMCWETGGCS (SEQ ID NO: 77) | C | 1/6 |
| HL-25 | SWERGELTYMKLCEYMRLQQ (SEQ ID NO: 78) | C | 4/6 |
| HL-30 | EHGRANCLITPEAGKLARVT (SEQ ID NO: 79) | C | 1/6 |

Such peptide-phage clones could represent specific target-binding peptides which either do or do not block ligand (IGF-I to IGFBP) binding, or any of a number of non-binding or background members of the selected pool. To distinguish among these possibilities, phage clones were tested for the ability to bind to IGFBP-1 or IGFBP-3 in the presence and absence of IGF-I. IGFBP-1 or IGFBP-3 was coated directly onto MAXISORP™ plates as above. Phage from clonal cultures were mixed with IGF-I (100 nM final concentration), and incubated with the immobilized IGFBP for 1 hour at room temperature. The plates were then washed ten times, as above, and a solution of rabbit anti-phage antibody mixed with a goat-anti-rabbitt conjugate of horse radish peroxidase was added. After an incubation of 1 hour at room temperature, the plates were developed with a chromogenic substrate, o-phenylenediamine (Sigma). The reaction was stopped with addition of 1/2 volume of 2.5 M $H_2O_4$. Optical density at 490 nm was measured on a spectrophotometric plate reader.

Figure 26:
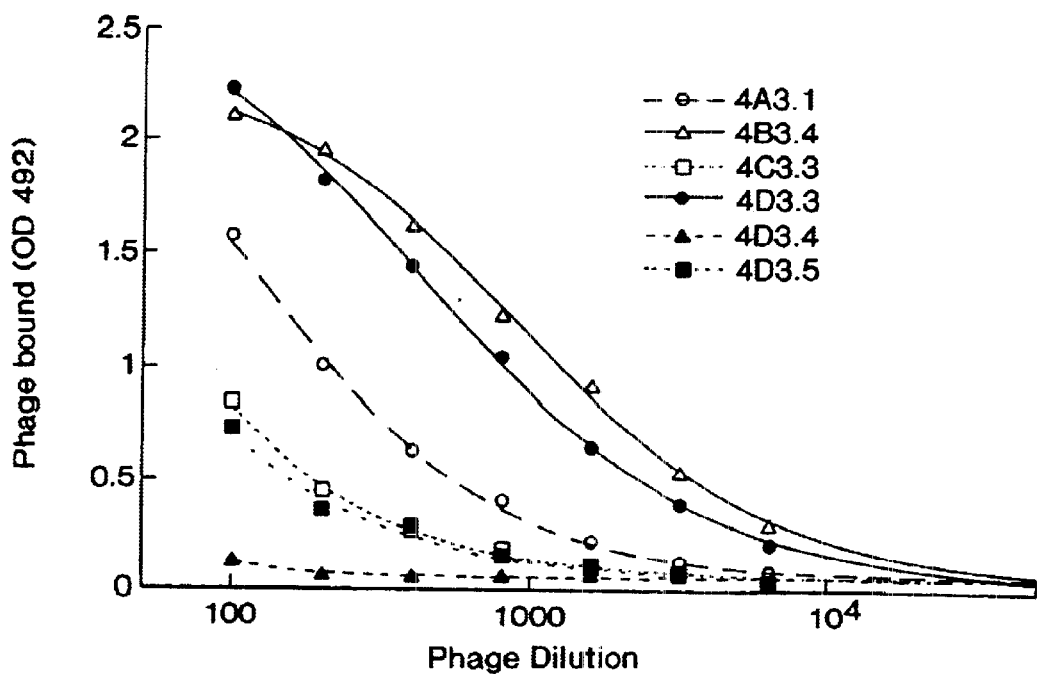
FIG. 26 shows an IGF-I blocking assay using g8-phage peptides from IGFBP-3 selections, where the phage titration is with 100 nM IGF-I. In the Figure, the open circles are peptide 4A3.1, the open triangles are peptide 4B3.4, the open squares are peptide 4C3.2, the solid circles are peptide 4D3.3, the solid triangles are peptide 4D3.4, and the solid squares are peptide 4D3.5.
Figure 27:
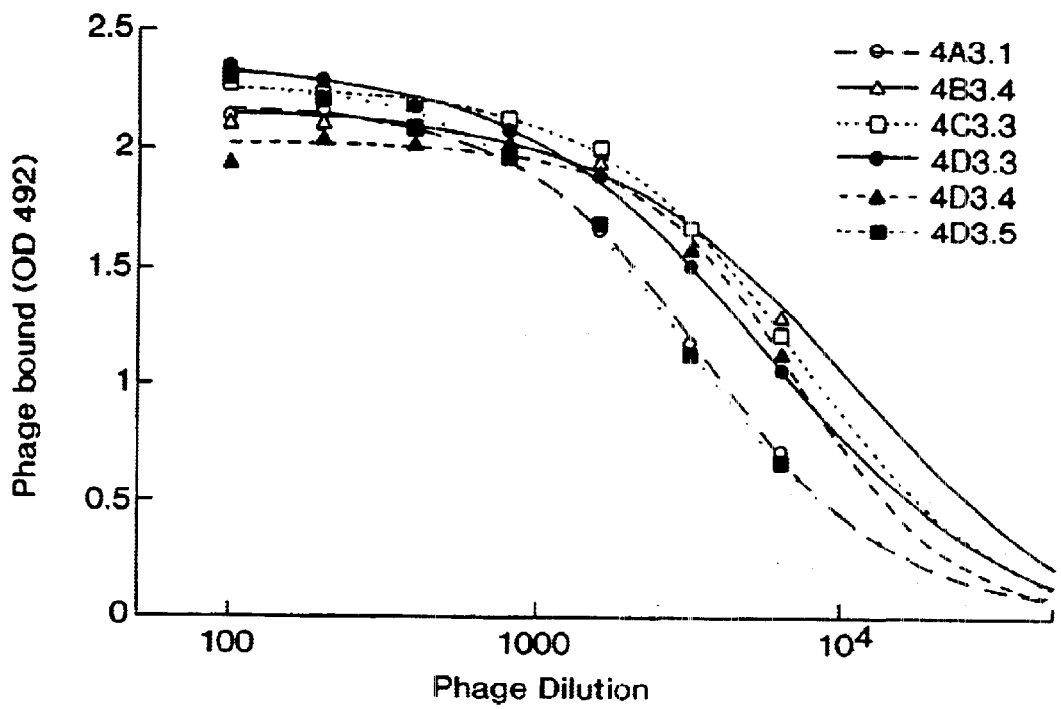
FIG. 27 shows an IGF-I blocking assay using g8-phage peptides from IGFBP-3 selections, where the phage titration is without IGF-I. The designations for the peptides are the same as those described above for FIG. 26.
Figure 28:
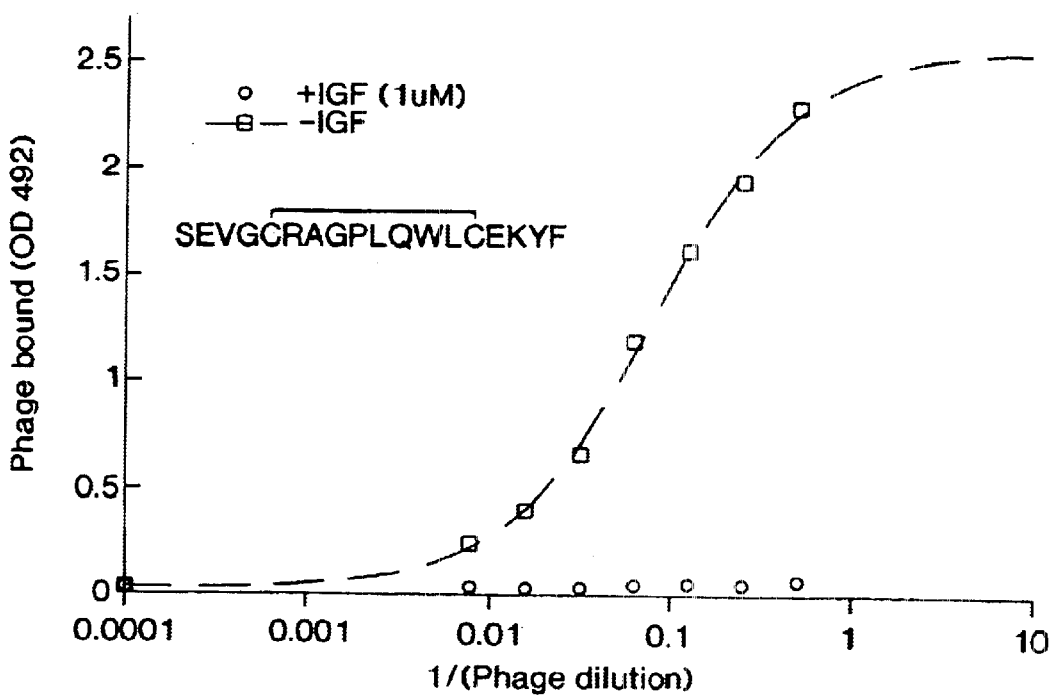
FIG. 28 shows an IGF-I blocking assay using a g8-phage peptide from an IGFBP-1 selection (peptide bp1-01), where the phage titration is with 1 μM IGF-I.

Titration of several IGFBP-3-selected peptide-phage clones showed all were inhibited by IGF-I for binding to IGFBP-3 at some phage concentration (FIGS. 26 and 27). These peptides are thus likely to occupy an overlapping site with the IGF-binding epitope on IGFBP-3. Titration of an IGFBP-1-selected peptide-phage clone HL-1 showed it was inhibited by IGF-I for binding to IGFBP-1 at some phage concentration (FIG. 28). Additional peptide-phage clones were screened similarly, at a low concentration of phage, with and without IGF-I.

Figure 29:
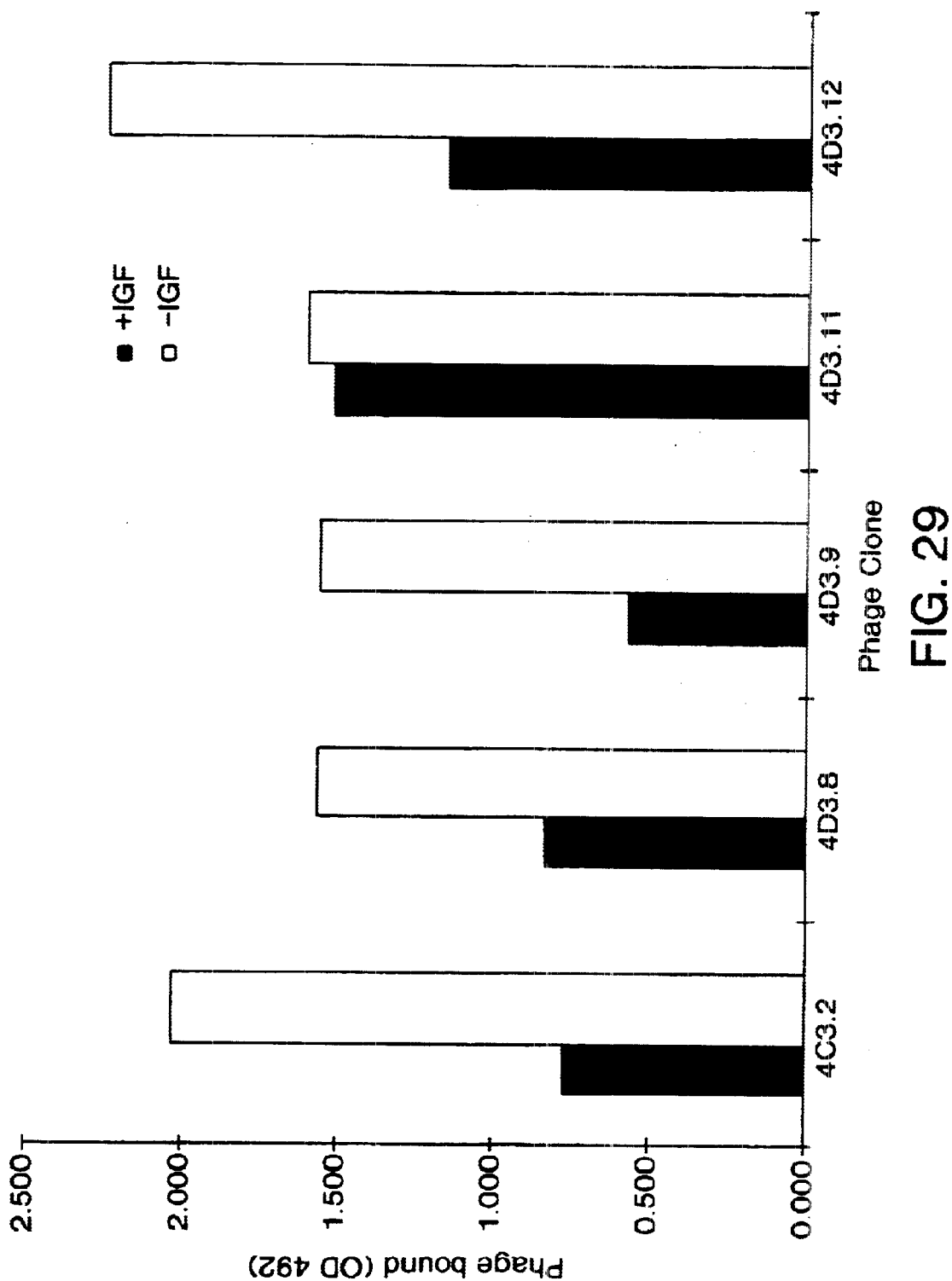
FIG. 29 shows an IGF-I blocking assay using g8-phage peptides from IGFBP-3 selections, where the peptides (4C3.2, 4D3.8, 4D3.9, 4D3.11, and 4D3.12) are from a NEUTRAVIDIN™/DTT selection. The solid bars are with 100 μM IGF-I and the open bars are without IGF-I.

FIG. 29 shows the results of a blocking assay of several phagemid clones derived from three rounds of DTT elution, followed by one round of HCl elution, as described above. In each case, the phagemid clone was grown from a single colony overnight at 37° C. in a culture volume of 5 ml. The phage particles were precipitated and resuspended in 0.5 ml of PBS buffer. A 50-fold dilution of each phage solution was made into PBS/TWEEN™ buffer, and the phage were incubated with or without 100 nM IGF-I on an IGFBP-3 coated MAXISORP™ plate. As shown in FIG. 29, most clones were >40% inhibited for binding to IGFBP-3 at these phage concentrations, although clone 4D3.11 was only 5% inhibited under these conditions.

Figure 30:
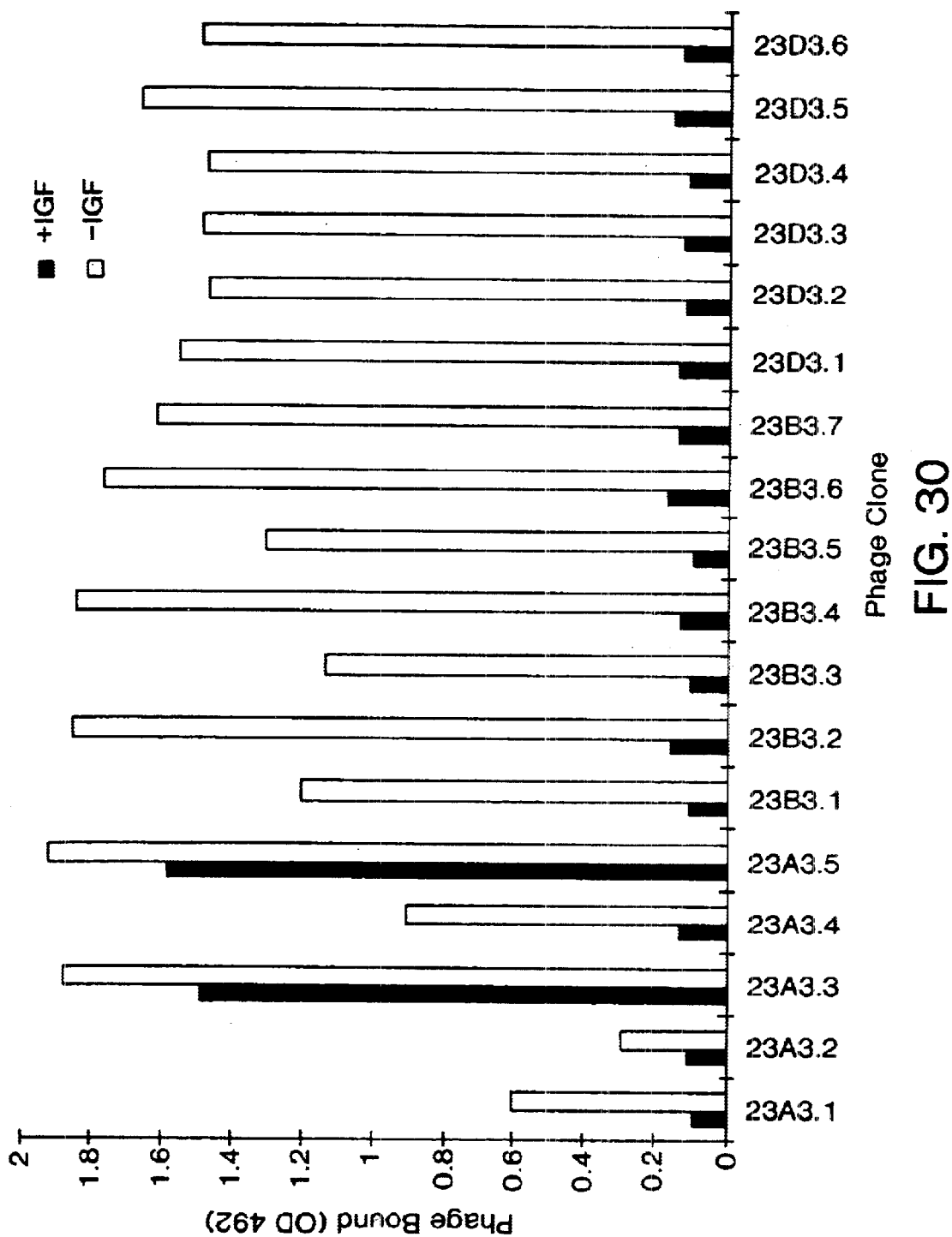
FIG. 30 shows an IGF-I blocking assay using g8-phage peptides from IGFBP-3 selections where the peptides (indicated on the x axis) are from direct-coat/HCl selection. The solid bars are with 100 μM IGF-I and the open bars are without IGF-I.

FIG. 30 shows the results of a blocking assay of several phagemid clones derived from three rounds of HCl elution, as described above. In each case, the phagemid clone was grown from a single colony overnight at 37° C. in a culture volume of 5 ml. The phage particles were prepared as described above. In this case, as shown in FIG. 30, most clones were >80% inhibited for binding to IGFBP-3 at these phage concentrations, although clones 23A3.3 and 23A3.5 were only about 20% inhibited under these conditions.

The variation in the degree to which phage binding is blocked by a constant concentration of IGF-I, as a function of phage dilution (FIGS. 26, 28), or as a function of peptide displayed (FIGS. 29–30) is of interest because, without being limited to any one theory, it may be predictive of (1) the degree of overlap between IGF-I- and peptide-binding epitopes on the IGFBP-3 molecule, and/or (2) the relative affinity of IGF-I versus phage-displayed peptide for binding to IGFBP-3. Since all peptide-phage clones tested here showed some degree of inhibition with IGF-I, it is likely that the epitope for peptide-binding on IGFBP-3 for each lies within an area occupied by bound IGF-I. Peptide assays (see below) support this conclusion (i.e., case 1). On the other hand, without being limited to any one theory, it is possible that some peptide epitopes could be simply within an area for which binding of the phage particle displaying such peptides is sterically excluded by bound IGF-I.

The dependence of inhibition upon phage concentration, and the differences among phage clones (FIG. 26) may reflect case 2. In particular, phage clones whose binding to an IGFBP-3 coated plate was inhibited only at low phage concentrations (e.g., 4D3.3, 4B3.4, corresponding to peptides BP3-01-ox and BP3-02-ox, respectively) appear to yield higher-affinity peptides (see below) for IGFBP-3 than do those phage clones whose binding to an IGFBP-3 coated plate was inhibited both at high and at low phage concentrations (e.g., 4C3.2, 4D3.5, corresponding to peptides BP3-23 and BP3-24, respectively).

Thus, this type of phage-titration blocking assay may be generally useful as a means to predict the relative affinities and inhibitory potencies of peptides derived from phage displayed libraries.

IV. Monovalent (g3) Display of IGFBP-3-binding Peptides

Affinity maturation of a peptide or protein sequence by successive rounds of random mutagenesis, selection, and propagation can be efficiently accomplished when the copy number of displayed peptides or proteins is limited. Bass et al., *Proteins*, 8: 309 (1990). Such an affinity maturation process is illustrated by the affinity maturation of hGH. U.S. Pat. No. 5,534,617. In this case, the copy number of displayed hGH was limited by fusing the displayed protein to g3, rather than to g8 of bacteriophage particles, restricting the expression level of hGH, and using a helper phage to supply wild-type g3p for phagemid packaging and propagation.

To select for higher affinity peptide variants from pools of phage displaying peptides on g8p, peptide cDNAs from two round 4 g8 library pools, 4B and 4D, were transferred to a g3 vector for monovalent phage display. Binding selections were carried out for three rounds, as described above, with acid elution of binding phage.

Peptide sequences obtained after three rounds of selections are shown in Table VI. Two clones, 4B3.3 and 4D3.11, dominated the selected pools, and were seen in the earlier, g8 phage selections. A third clone, 3Ai.2, represents a new peptide sequence that was not identified from g8 display. In phage-ELISA competition assays, the apparent affinity of the g3-4B3.3 and g3-4D3.11 clones was <100 nM; however, the corresponding peptides showed much weaker inhibition (see below).

TABLE VI

| | Peptide sequences from g3 display, IGFBP-3 selection | | |
|---|---|---|---|
| Clone | Peptide sequence | Library | Frequency |
| 3Ai.1 = 4B3.3 | EESECFEGPGYVICGLVG (SEQ ID NO: 7) | 4B | 6/10 |

TABLE VI-continued

| | Peptide sequences from g3 display, IGFBP-3 selection | | |
|---|---|---|---|
| Clone | Peptide sequence | Library | Frequency |
| 3Ai.2 | VEDECWMGPDWAVCWTWG (SEQ ID NO: 80) | 4B | 4/10 |
| 3Bi.1 = 4D3.11 | VAWEVCWDRHDQGYICTTDS (SEQ ID NO: 4) | 4D | 10/10 |

It is anticipated that affinity improvements can be obtained by iteratively mutating, selecting, and propagating peptide-phage libraries, as described for hGH. See, e.g., U.S. Pat. No. 5,534,617.

V. Peptide Assays

Peptides were synthesized corresponding to a number of phage-derived sequences. In cases where two Cys residues were found in the peptide sequence, the disulfide (oxidized or "ox" suffix) monomeric form of the peptide was prepared and purified. In cases where four Cys residues were found, the {1-4,2-3}disulfide form was prepared and purified.

The ability of these peptides to bind IGFBP-1 or IGFBP-3 and block IGF-I binding was tested in one or more of the following assays.

A. BIAcore™ Competition Assay (for IGFBP-3 Binders)

IGF-I was immobilized on a dextran chip for inhibition assays using a BIAcore™ 2000 surface-plasmon-resonance device (BIAcore, Inc., Piscataway, N.J.) to measure free binding protein. IGF-I was biotinylated as described above, and injected over a chip to which streptavidin had been coupled (BIAcore, Inc.) to give 400 to 800 RU (response units) of immobilized IGF-I. The IGF-I showed no detectable dissociation over the time course of each experiment. Serial dilutions of peptide were mixed with a constant concentration (40 nM) of IGFBP-3. After incubation for ≧1 hour at room temperature, an aliquot of 20 μL was injected at a flow rate of 20 μL/min over the IGF-I chip. Following the injection, a response reading was taken to measure the relative amount of IGFBP-3 bound to the IGF-I.

Figure 31:
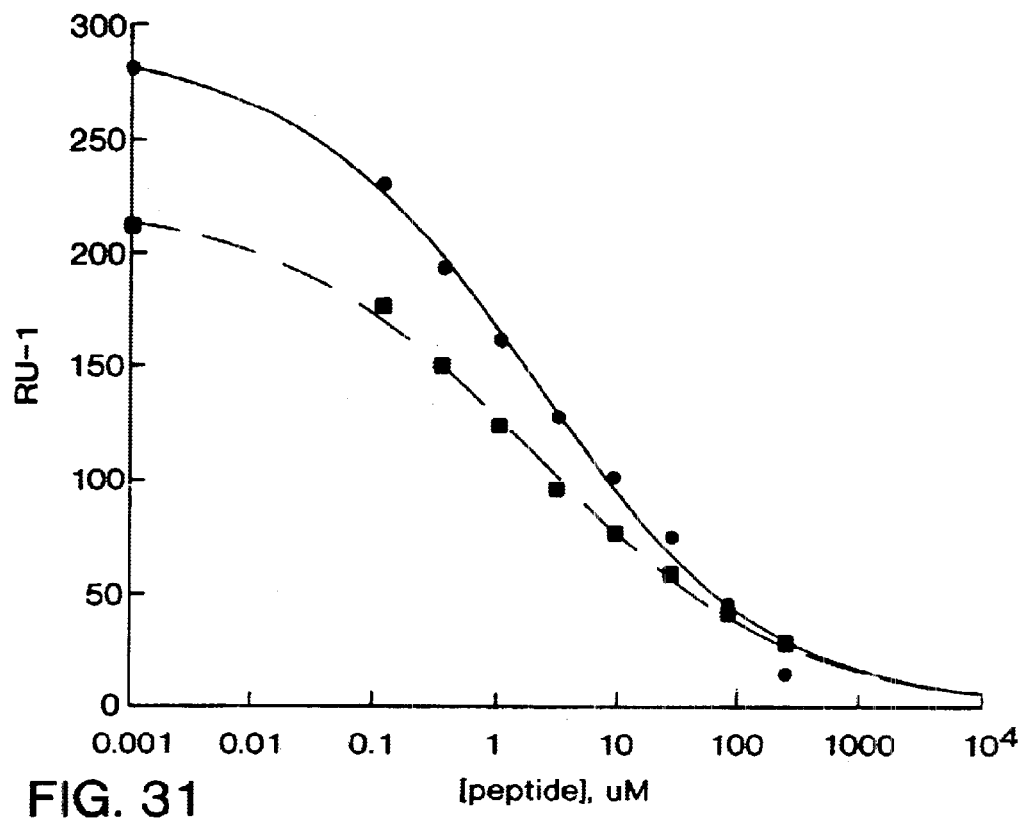
FIG. 31 depicts a competition assay of IGFBP-3 inhibition by a peptide binding to IGFBP-3 (designated BP3-01) using a BIAcore™ surface-plasmon-resonance device to measure free binding protein. The circles indicate 800 response units (RU) of IGF-I and the squares indicate 400 RU of immobilized IGF-I.
Figure 32:
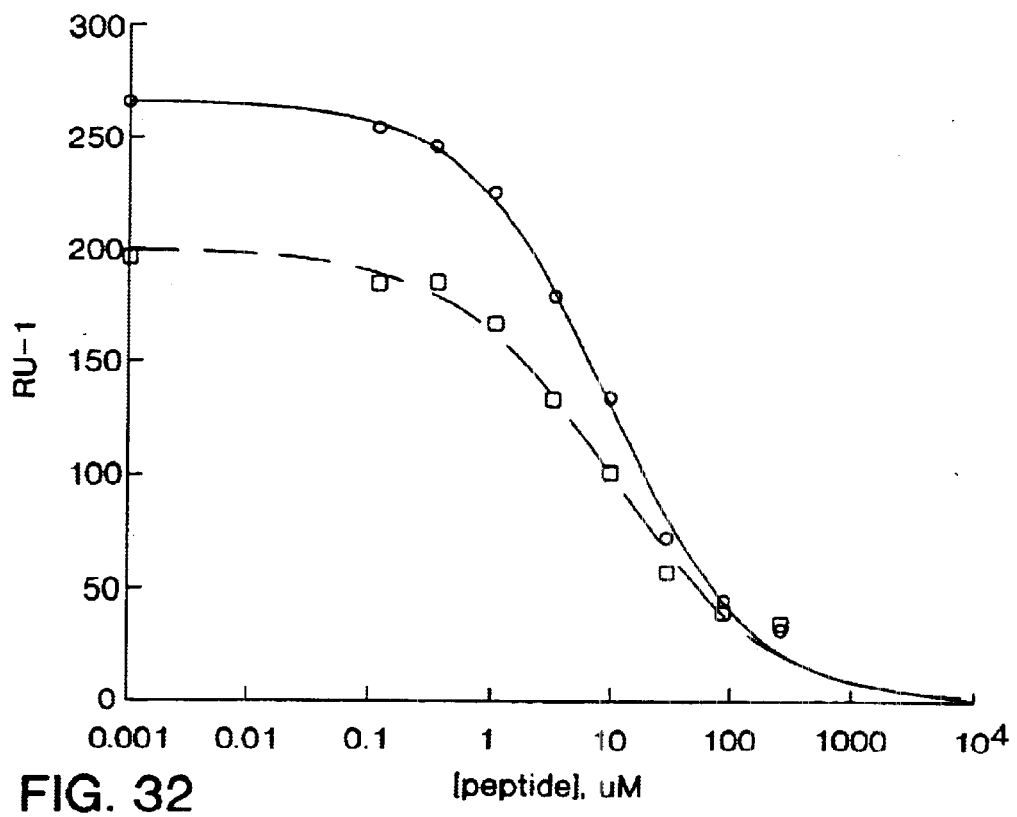
FIG. 32 depicts a competition assay of IGFBP-3 inhibition by a peptide binding to IGFBP-3 (designated BP3-02) using a BIAcore™ surface-plasmon-resonance device to measure free binding protein. The circles indicate 800 RU of IGF-I and the squares indicate 400 RU of immobilized IGF-I.

The results (FIGS. 31–32) show a dose-response curve for each peptide's inhibition of IGFBP-3 binding to the chip. In particular, the most effective inhibitors of IGFBP-3 binding tested were peptides BP3-01-ox (corresponding to phage clone 4D3.3), and a truncated form of this peptide, BP15 (see Table VII). In that table, a disulfide bond is formed between the two Cys residues of each 2-Cys containing peptide. For peptides containing four cysteines, the two Cys* residues form a disulfide and the remaining two form a second disulfide. These peptides showed IC50's of 2 μM and 0.75 μM, respectively. Other peptides such as BP3-4D3.11 (phage clone 4D3.11 from g8 display and 3Bi.1 from g3 display) showed inhibition with IC50's of <10 μM.

IGFBP-1 did not show binding to IGF-I immobilized in this manner.

TABLE VII

Inhibition of IGF-I binding to
IGFBP-3 by synthetic peptides

| Peptide | Sequence | BIAcore ™ Assay IC50 ($\mu$M) |
|---|---|---|
| BP3-23 | ELDGWVCIKVGEQNLCYLAEG-nh2 (SEQ ID NO: 1) | 220 |
| BP3-24 | WFKTVCYEWEDEVQCYTLEEG-nh2 (SEQ ID NO: 2) | 100–300 |
| BP3-25 | RVGAYISCSETECWVEDLLDG-nh2 (SEQ ID NO: 3) | >1000 |
| BP3-4D3.11 | VAWEVCWDRHDQGYICTTDS (SEQ ID NO: 4) | <10 |
| BP3-4D3.11DEL | AWEVCWDRHQGYICTTDS (SEQ ID NO: 5) | 80 |
| BP13 | CWDRHDQGYICTTDS (SEQ ID NO: 6) | >1000 |
| BP3-4B3.3 | EESECFEGPGYVICGLVG (SEQ ID NO: 7) | 80 |
| BP3-02-ox | DMGVCADGPWMYVCEWTE (SEQ ID NO: 8) | 12 |
| BP3-01-ox | SEEVCWPVAEWYLCNMWG (SEQ ID NO: 9) | 2 |
| BP15 | SEEVCWPVAEWYLCN (SEQ ID NO: 10) | 0.75 |
| BP16 | VCWPVAEWYLCNMWG (SEQ ID NO: 11) | 30 |
| BP17 | VCWPVAEWYLCN (SEQ ID NO: 12) | 9 |
| BP06 | TGVDCQC*GPVHC*VCMDWA (SEQ ID NO: 13) | 5 |
| BP08 | TVANCDC*YMPLC*LCYDSD (SEQ ID NO: 14) | 15 | where nh2 means that the peptide has been blocked with an amide and where the C* indicates a cysteine that has been linked to another cysteine in the peptide.

B. Plate Assays

1. Biotin-BP Assay (for IGFBP-1 Binders)

For inhibition of IGFBP-1 binding, IGFBP-1 (as well as IGFBP-3 as a control) were biotinylated as described above. MAXISORP™ plates were coated and blocked as described above, using 2 $\mu$g/mL IGF-I. In a separate plate, serial dilutions of peptide were premixed with a constant concentration (20 nM) of biotinylated IGFBP-1. After 20 min. at room temperature, the mixture was added to the IGF-I plate. The peptide/IGFBP mix was then removed and the plate was washed ten times with PBS buffer containing 0.05% TWEEN-20™ surfactant. Bound biotin-IGFBP-1 was then detected using streptavidin-conjugated horse radish peroxidase, and a chromogenic substrate.

Figure 33:
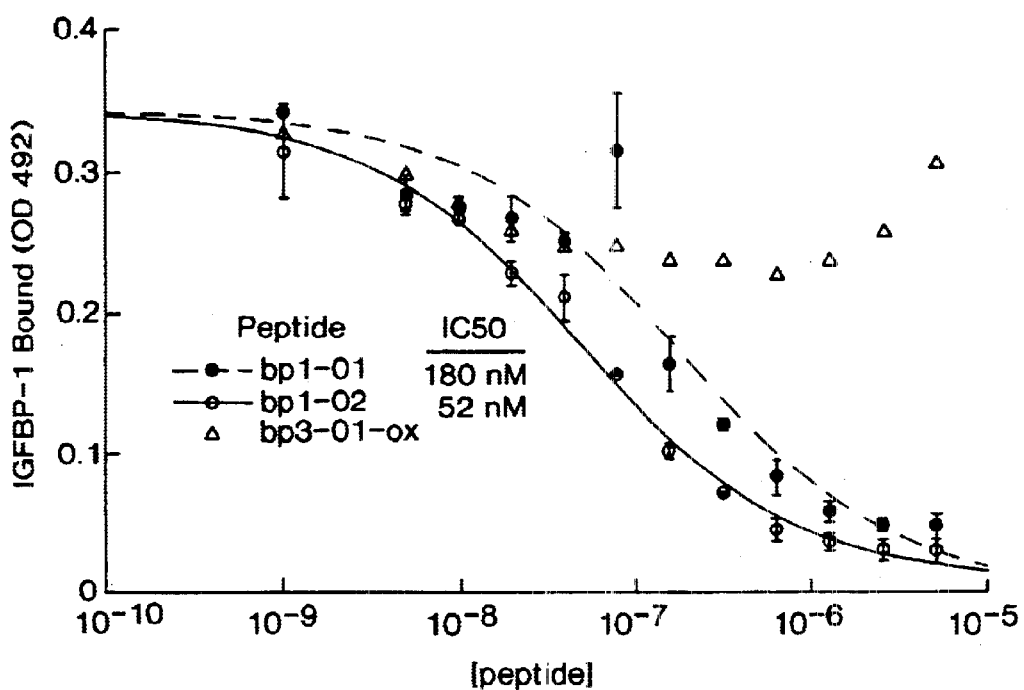
FIG. 33 shows inhibition of biotinylated IGFBP-1 binding to IGF-I on plates by three peptides that bind to IGFBP-1 or IGFBP-3 but do not bind to the Type 1 IGF receptor (bp1-01: solid circles, bp1-02: open circles, and bp3-01-ox: open triangles).
Figure 34:
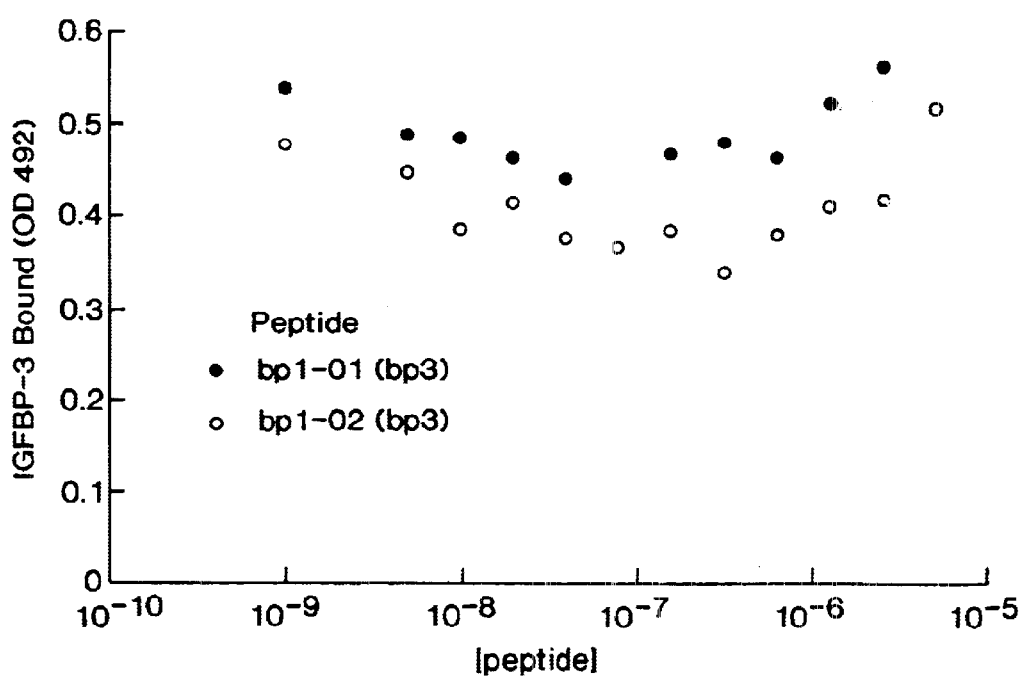
FIG. 34 shows inhibition of biotinylated IGFBP-3 binding to IGF-I on plates by two peptides that bind to IGFBP-1 but not to the Type 1 IGF receptor (bp1-01 (bp3): solid circles, and bp1-02 (bp3): open circles).

The results of assays of IGFBP-1 inhibition (FIGS. 33 and 34) show that peptides bp1-01 and bp1-02 (Table VIII) inhibited IGFBP-1 binding with IC50's of about 0.18 and 0.05 uM, respectively. In contrast, the IGFBP-3 selectant BP3-01-ox showed little or no inhibition of IGFBP-1 binding. Conversely, bp1-01 and bp1-02 showed no inhibition of biotinylated IGFBP-3 binding in this assay. A bp1-01 variant in which the Cys residues were changed to serine showed an IC50 of greater than 10 $\mu$M.

TABLE VIII

Inhibition of IGF-I binding to
IGFBP-1 by synthetic peptides

| Peptide | Sequence | ELISA IC50 ($\mu$M) |
|---|---|---|
| bp1-01 | CRAGPLQWLCEKYFG-nh2 (SEQ ID NO: 15) | 0.18 |
| bp1-02 | SEVGCRAGPLQWLCEKYFG-nh2 (SEQ ID NO: 16) | 0.05 |

2. Radiolabeled IGF Assay (for IGFBP-3 Binders)

As an additional assay of peptide activity, several peptides were tested in an assay using $^{125}$I-labeled IGF-I to measure inhibition of IGFBP binding, as described in Example 1 (Assay 3). Serial dilutions of peptide were added to an IGFBP-1 or an IGFBP-3 plate. Thereafter, $^{125}$I-labeled IGF-I was added and the plates were incubated for 2 hours. The plates were then washed and counted to determine the amount of bound IGF-I.

Figure 35:
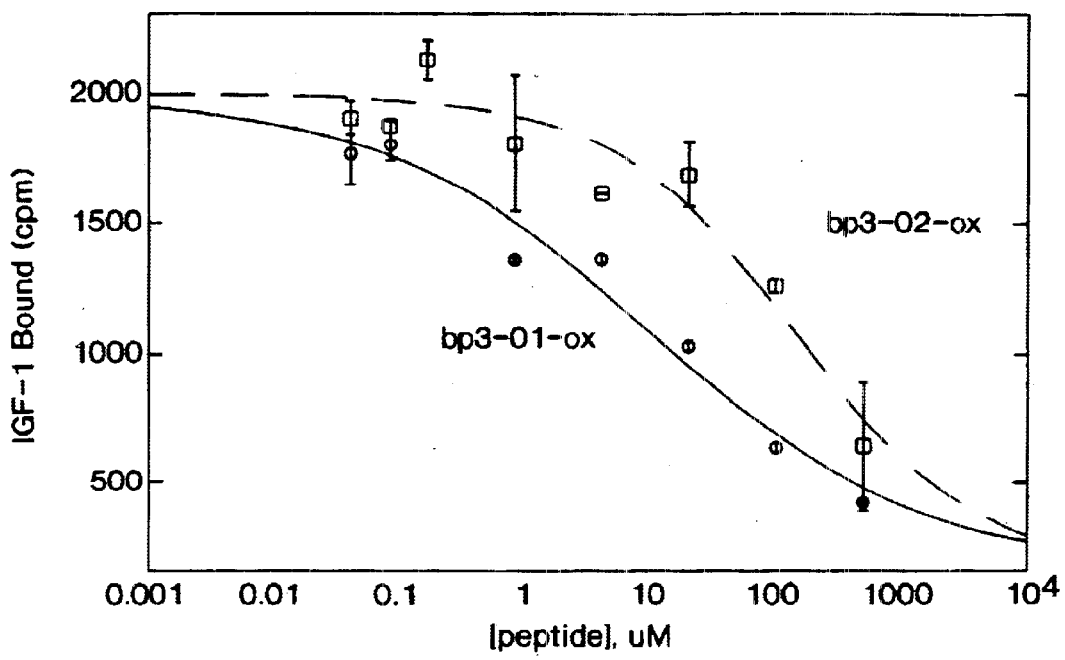
FIG. 35 shows a radiolabeled IGF-I plate assay of the ability of two peptides that bind to IGFBP-3 but not to the Type 1 IGF receptor (bp3-01-ox: circles, and bp3-02-ox: squares) to inhibit IGFBP-3.
Figure 36:
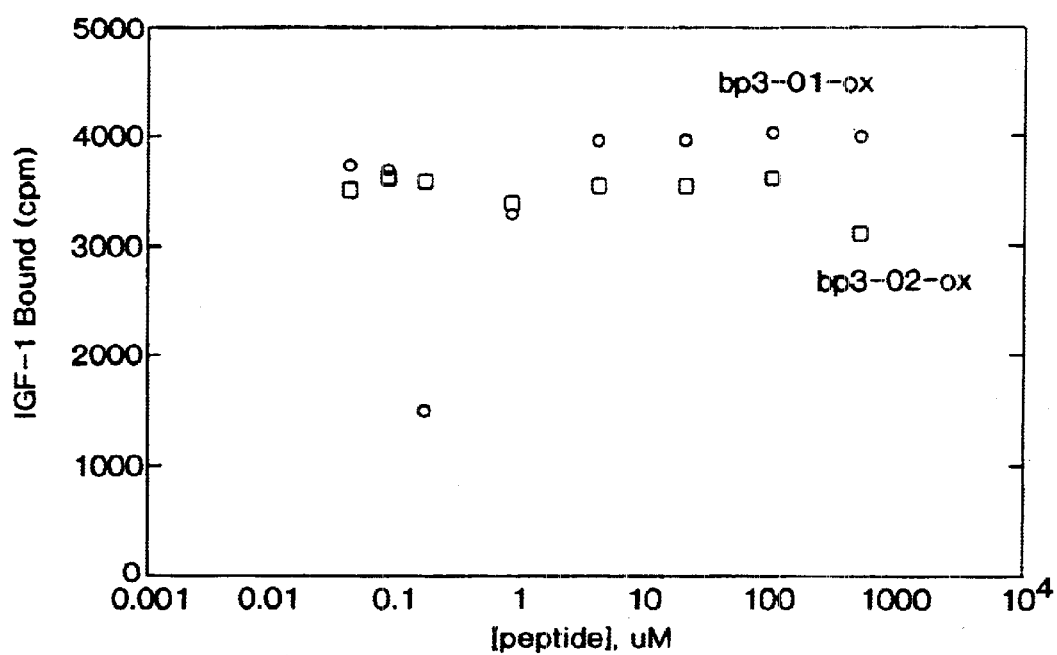
FIG. 36 shows a radiolabeled IGF-I plate assay of the ability of the two IGFBP-3 binding peptides described for FIG. 35 to inhibit IGFBP-1 (symbols are the same).
Figure 37A:
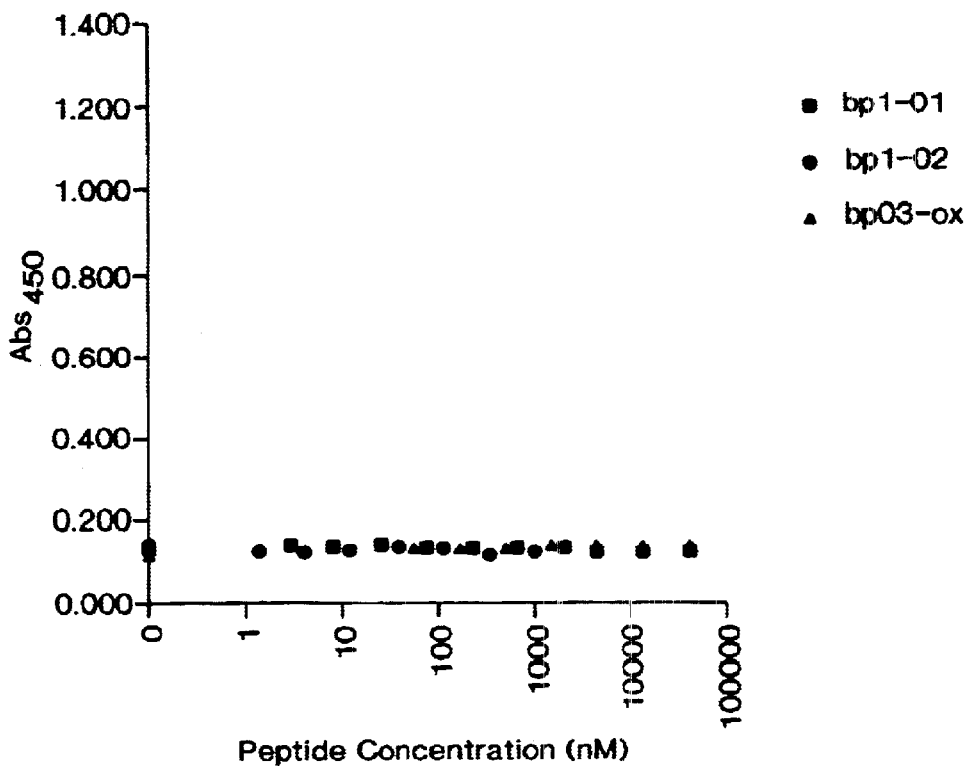
FIG. 37A depicts the peptides alone.
Figure 37B:
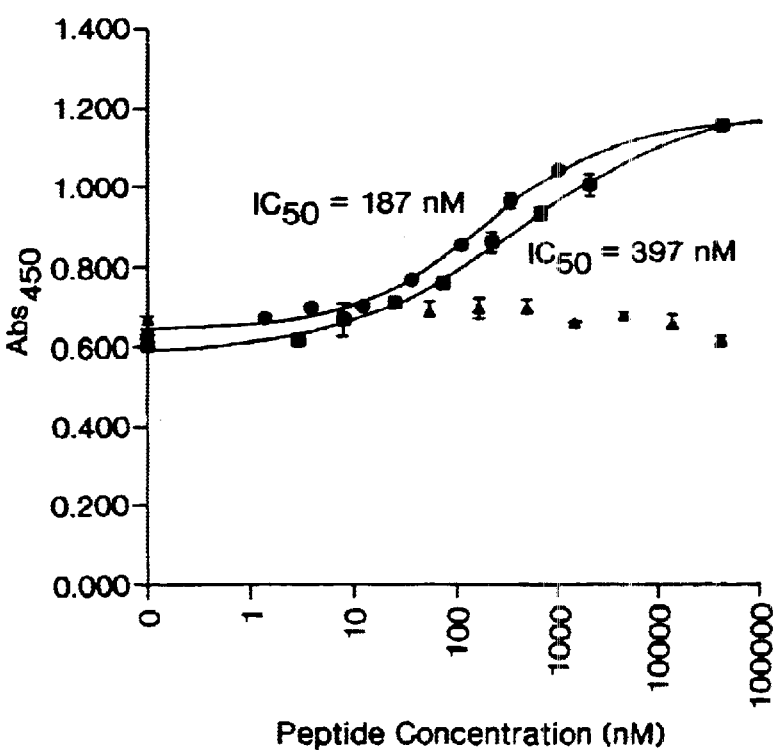
FIG. 37B depicts the peptides plus IGF-I plus IGFBP-1.
Figure 37C:
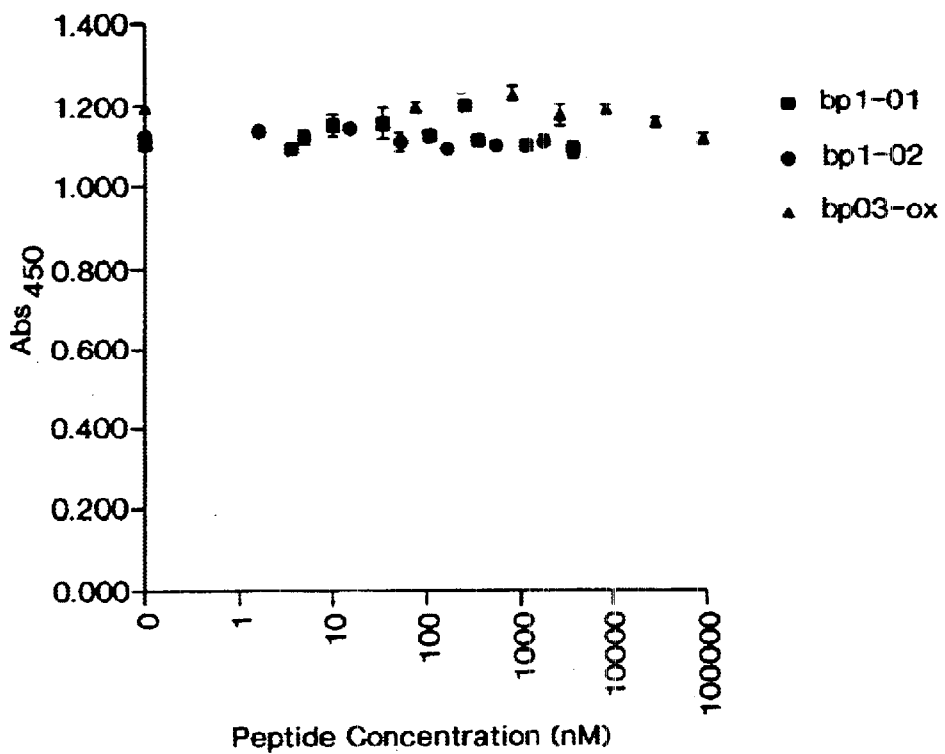
FIG. 37C depicts the peptides plus IGF-I.
Figure 37D:
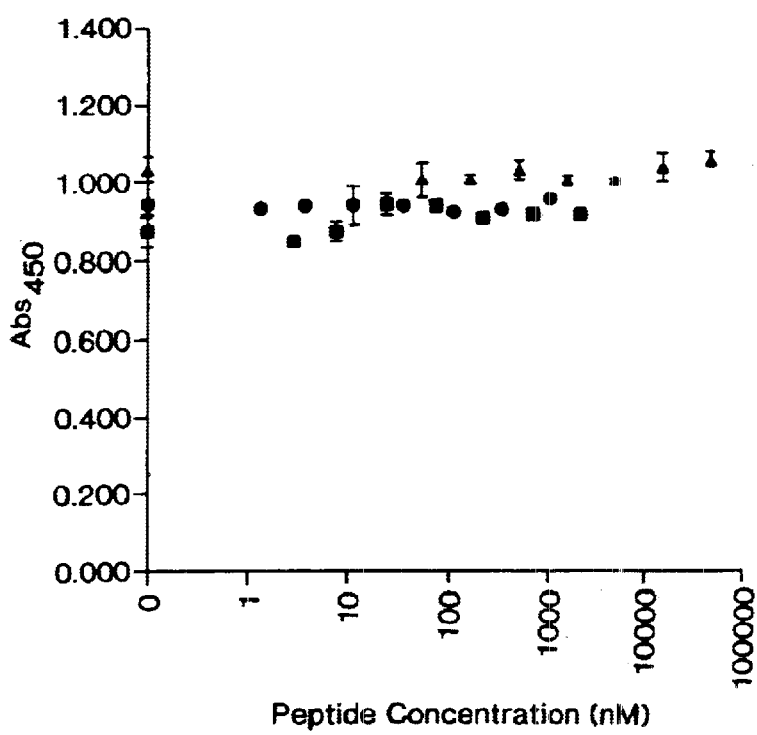
FIG. 37D depicts the peptides plus IGF-I plus IGFBP-3.

FIG. 35 shows the inhibition of two IGFBP-3-selected peptides, bp3-01-ox and bp3-02-ox, for IGF-I binding to an IGFBP-3 plate. In contrast, these peptides did not inhibit IGF-I binding to an IGFBP-1 coated plate (FIG. 36).

C. In Vitro Activation (KIRA)

The ability of several synthetic peptides to block IGF-I binding to IGFBPs and release functional IGF-I was tested in a KIRA assay of IGF-I activity, as described in Example 1. Cells were treated with IGF-I alone, peptide alone, peptide plus IGF-I, IGF-I plus binding protein (IGFBP-1 or IGFBP-3), or IGF-I plus binding protein (IGFBP-1 or IGFBP-3) and peptide.

The results (FIG. 37) show that the peptides alone had no activity. Furthermore, when mixed with IGF-I, the peptides did not significantly alter IGF-I activity. The peptide BP3-01-ox also showed no significant effect on IGF-I activity when mixed with IGF-I plus IGFBP-1 or IGFBP-3. However, both peptides bp1-01 and bp1-02 appeared to block the inhibition of IGF-I activity by IGFBP-1, with IC50's of 397 nM and 187 nM, respectively. Neither of these peptides showed activity with IGF-I and IGFBP-3.

In addition, the IGFBP-3 peptide BP15 incubated with IGFBP-3:IGF-1 (at a 3:1 ratio) caused an activation of the KIRA assay, where blocking of IGFBP-3 occurred with an IC50 of 95 $\mu$M for BP15. It is believed that this would drop to 30 uM with a 1:1 ratio.

D. BIAcore™ Competition Assay (for IGFBP-3 Binders)

IGF-II was immobilized on a dextran chip for inhibition assays using a BIAcore™ 2000 surface-plasmon-resonance device (BIAcore, Inc., Piscataway; N.J.) to measure free binding protein. IGF-II was biotinylated as described above, and injected over a chip to which streptavidin had been coupled (BIAcore, Inc.) to give approximately 1500 RU of immobilized IGF-II. The IGF-II showed no detectable dissociation over the time course of each experiment. Serial dilutions of peptide were mixed with a constant concentration (20 nM) of IGFBP-3. After incubation for ≧1 hour at room temperature, an aliquot of 20 $\mu$l was injected at a flow rate of 20 $\mu$l/min over the IGF-II chip. Following the injection, a response reading was taken to measure the relative amount of IGFBP-3 bound to the IGF-II.

Figure 38:
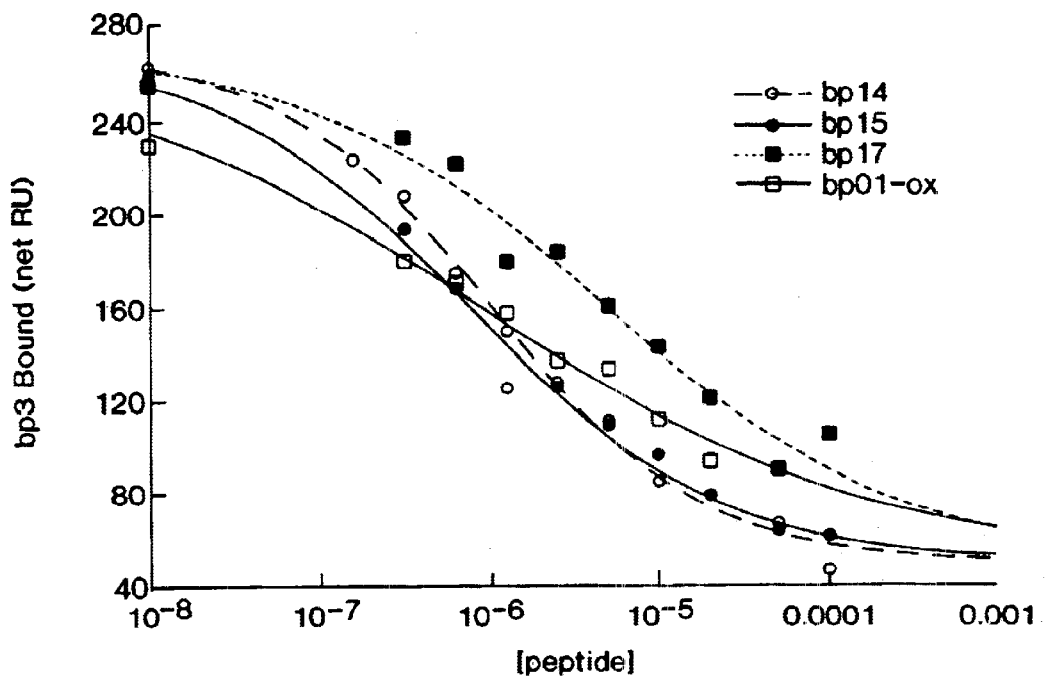
FIG. 38 depicts an IGF-II competition assay of IGFBP-3 inhibition by four peptides, designated bp3-01-ox (open squares), BP14 (open circles), BP15 (closed circles), and BP17 (closed squares), using a BIAcore™ surface-plasmon-resonance device to measure free binding protein. Each peptide was tested using 20 nM IGFBP-3 and approximately 1500 RU of immobilized IGF-II.

The results (e.g., see FIG. 38) show a dose-response curve for each peptide's inhibition of IGFBP-3 binding to IGF-II. Peptides bp3-01-ox, BP14, BP15, and BP17 showed IC50's of 0.92 $\mu$M, 1.0 $\mu$M, 0.78 $\mu$M, and 5.1 $\mu$M, respectively. Thus, these peptides inhibit the binding of IGFBP-3 both to IGF-I and to IGF-II.

Example 8

NMR Spectra of Peptide bp1-01

$^1$H NMR data were collected on peptide bp1-01 in H$_2$O solution at 30° C. and pH 5.2 at a concentration of 6.7 millimolar. For generation of the one-dimensional NMR spectrum of FIG. 39, a total of 5.0 mg of purified peptide was dissolved in 440 µl H$_2$O containing 7% (v/v) $^2$H$_2$O for the spectrometers field frequency lock. The pH of the sample was adjusted to 5.2 by the addition of 3 µl of 1N NaOH. The spectrum consisting of 32 transients was collected on a BRUKER AMX-500™ spectrometer ($^1$H frequency of 500.13 MHz) equipped with a 5-mm triple axis pulsed-field gradient probe. The chemical shift scale is in parts per million, referenced to the water resonance at 4.75 p.p.m. The water resonance was suppressed by the excitation sculpting method. Hwang and Shaka, *J. Magn. Reson.*, 112A: 275–279 (1995).

Figure 39:
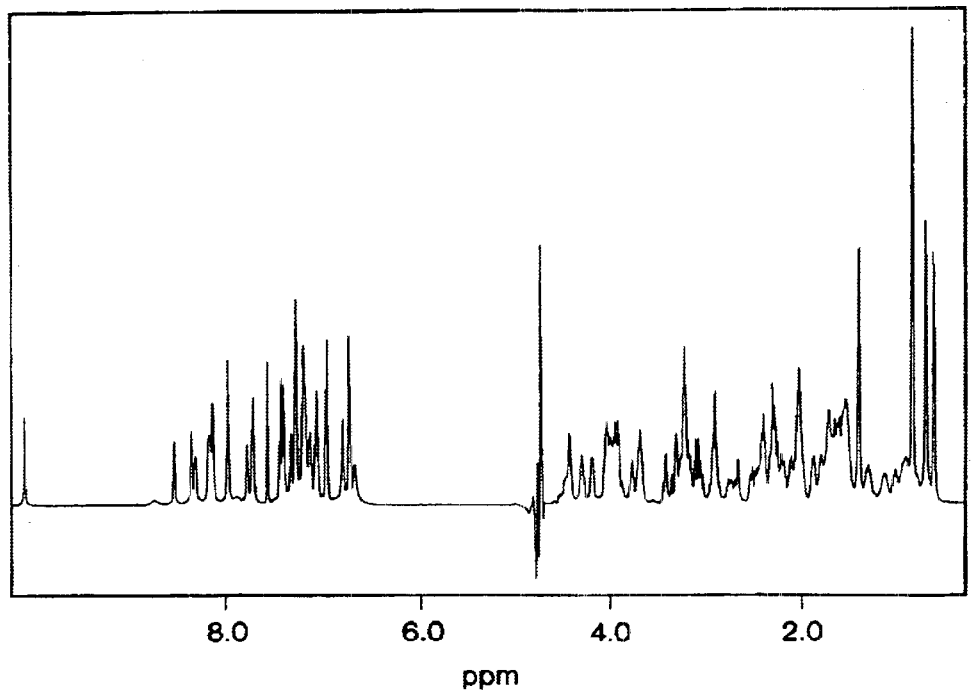
FIG. 39 depicts a one-dimensional $^1$H NMR spectrum of a peptide binding to IGFBP-1 (bp1-01) in $H_2O$ solution at 30° C.

In addition to the one-dimensional spectrum of FIG. 39, two-dimensional double-quantum-filtered correlation spectroscopy (2QF-COSY), total correlation spectra (TOCSY), and rotating-frame Overhauser effect spectra (ROESY) were collected. The experiments were recorded as described by Cavanagh et al. in "Protein NMR Spectroscopy, Principles and Practice" (Academic Press, San Diego: ISBN 0-12-164490-1, 1995), except that pulsed-field gradients were used for coherence selection in the 2QF-COSY (van Zijl et al., *J. Magn. Reson.*, 113A: 265–270 (1995)), and excitation sculpting was used to suppress the water resonance in the TOCSY and ROESY experiments (Hwang and Shaka, supra). After lyophilization and dissolution of the peptide in $^2$H$_2$O, a 2-D ROESY spectrum (Cavanagh et al., supra) and a COSY spectrum with a 35° C. mixing pulse (Cavanagh et al., supra) were acquired. Complete $^1$H resonance assignments were obtained from these data by standard methods. Wuethrich, in "NMR of proteins and nucleic acids", (John Wiley & Sons, New York: ISBN 0-471-82893-9, 1986).

Evidence of a well-defined three-dimensional structure for bp1-01 was obtained from the following:

1) The resonance positions in the one-dimensional spectrum (FIG. 39) are significantly different from those expected in an unstructured peptide. For example, the amide protons span a range of 8.73–6.64 p.p.m. (unstructured peptides are in the range 8.50–8.00 p.p.m.); the methyl groups are at lower chemical shift (0.82 p.p.m. for Leu6, and 0.66, 0.59 p.p.m. for Leu9) then for an unstructured molecule (0.90–0.85 p.p.m.).

2) Scalar coupling constants between amide and alpha protons (obtained from the 2QF-COSY spectrum) are distinct from the averaged values observed in unstructured peptides. The values less than 5.5 Hz for Gln7, Trp8, Cys10, Glu11, and Lys12 are indicative of a helix spanning these residues. The values greater than 8.0 Hz observed for Leu6, Tyr13, and Phe14 are indicative of an extended conformation in these regions. Scalar coupling constants were also measured between alpha and beta protons in the COSY-35 spectrum. These data indicate that the side chains of Cys1, Gln7, Trp8, Cys10, Tyr13, and Phe14 have fixed chi-1 angles, i.e., these side chains do not sample the range of chi-1 rotamers that are populated in unstructured peptides.

3) Peaks in the ROESY spectra indicate that there are many proton-proton contacts (<5 Å) between residues that are not adjacent in the primary sequence. These can only occur if the peptide folds up into a well defined structure. Contacts between residues at position i and i+3 in the primary sequence are prevalent between Leu6 and Tyr13, consistent with the presence of a helix in this region. Many contacts are observed between the three aromatic side chains (Trp8, Tyr13, and Phe14) and the leucine methyl groups (Leu6 and Leu9), indicating the presence of a mini-hydrophobic core along one face of the helix.

The NMR data were used to derive restraints that could be used to determine a three-dimensional model of the bp1-01 structure. Dihedral angle restraints were derived from the amide-alpha and alpha-beta scalar coupling constants via an appropriate Karplus relationship. Karplus, *J. Phys. Chem.*, 30: 11–15 (1959). Distance restraints were introduced between protons which exhibited a through-space interaction in the ROESY spectrum; the size of the upper bound, and corrections to the upper bound because of peak overlap or resonance degeneracy were as described by Skelton et al., *Biochemistry*, 33: 13581–92 (1994). These restraints were used to generate a family of structures using the program DGII (Havel, *Prog. Biophys. Mol. Biol.*, 56: 43–78 (1991)), which were subsequently refined by restrained molecular dynamics with the program Discover (MSI, San Diego) using the AMBER all atom force field. Weiner et al., *J. Comput. Chem.*, 7: 230–252 (1986). The resulting structures converged to a single global fold (mean root-mean-squared deviation from the mean structure of 0.37 Å for N, C-alpha, and carbonyl carbons of residues 4–14). The best 25 structures (least violation of the input restraints) agreed with the input data very well (no distance restraint violations greater than 0.1 Å and no dihedral angle violations greater than 1.4°), and had good covalent geometry as judged by the program PROCHECK™. Laskowski et al., *J. Appl. Cryst.*, 26: 283–291 (1993).

Figure 40A:
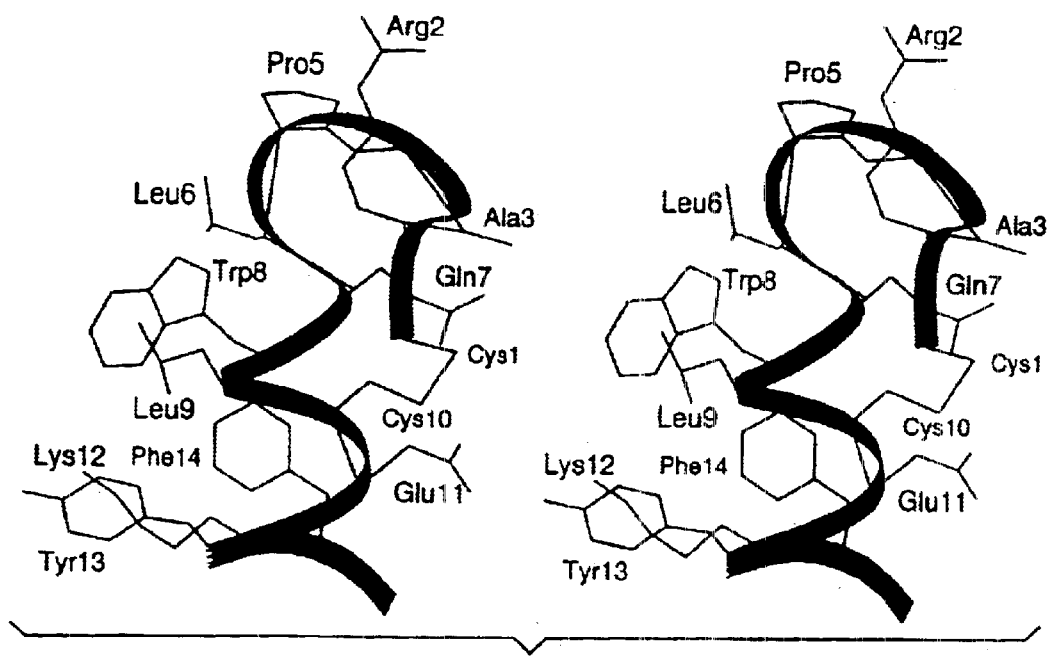
FIGS. 40A and 40B disclose a three-dimensional model of the structure of the peptide bp1-01 in solution. These are stereoviews of a representative structure of bp1-01 from the ensemble of structures calculated using restraints derived from NMR data. The backbone fold is depicted as a ribbon, and all side-chain heavy atoms are shown; each non-glycine residue is labeled. The two views differ by approximately 90°. The relatively flat hydrophobic surface (on the left in FIG. 40A, and towards the viewer in FIG. 40B) is involved in self association, and may also be involved in IGFBP-1 binding.
Figure 40B:
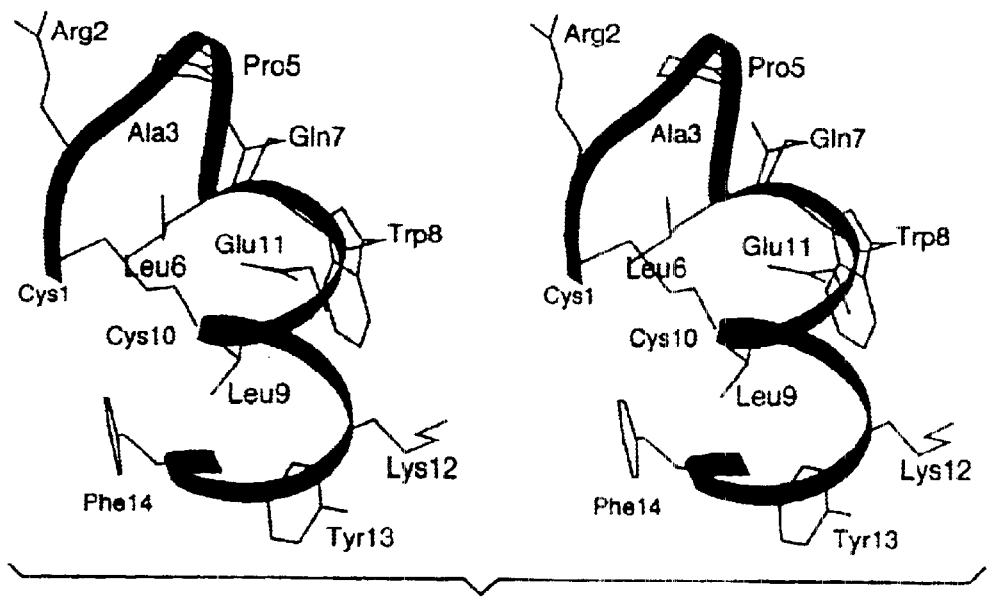

A representative member of the ensemble is shown in FIGS. 40A and 40B. According to the Kabsch and Sander secondary structure algorithm within the PROCHECK™ program, bp1-01 contains a reverse turn centered at Pro5-Leu6 (Type I) and an alpha helix from Gln7 to Lys12; Leu6 and Tyr13 are extensions of the main helix. The residues Cys1, Arg2, Ala3, and Gly15 are not well defined by the NMR restraints and may be more flexible in solution than residues Gly4 to Phe14. FIGS. 40A and 40B indicate that the aromatic rings of Trp8, Tyr13, and Phe13 pack onto the aliphatic portions of Leu6, Leu9, and Lys12 to form a relatively flat, hydrophobic face on one side of the peptide. This packing is accomplished by the periodicity of the helix (bringing Leu6, Leu9, and Tyr13 together), the chi-1 angle of Trp8 (the chi-1 of +60 degrees, relatively unusual for this amino acid, allows Trp8 to pack onto Leu9), and the extended nature of the peptide backbone of Phe14 (allowing the side chain of Phe14 to fold back on to Leu9).

Although bp1-01 is prone to self-association under some conditions, the three-dimensional structure observed for bp1-01 is not stabilized by such intermolecular interactions. The hydrophobic packing within the helix undoubtedly contributes to the stability of the fold. The disulfide bond between Cys1 and Cys10 is also important for structure and function. Peptides in which both cystine residues are replaced by serine have much reduced affinity for IGFBP-1 (see Example 7) and exhibit no evidence of helical or other stable structure in one- and two-dimensional NMR spectra, suggesting that the structure displayed by bp1-01 is important for its function. Without being limited to any one theory, one possibility is that the reverse turn (Pro5-Leu6) and disulfide bond help to initiate the first turn of helix (Gln7-Cys10), which is then propagated by the hydrophobic side chain-side chain contacts involving residues in the second turn of helix (Glu11-Phe14).

The structure of bp1-01 shown in FIG. 40 suggests several possibilities for the way in which the peptide is able to bind to IGFBP-1, thereby enhancing levels of active IGF-I.

1) The flat, hydrophobic surface formed by the side chains of Leu6, Leu9, Trp8, Tyr13, and Phe14 in the bp1-01 monomer may pack onto an exposed hydrophobic region of IGFBP-1; in this case the helix is the key structural feature recognized by IGFBP-1.

2) BP-1 may recognize some part of bp1-01 other than the hydrophobic face of the helix, e.g., the five N-terminal residues preceding the helix, or a combination of these residues and the face of the helix away from hydrophobic side chains. In this case, the helix may still be important as a scaffold to set up a geometry appropriate for IGFBP-1-binding elsewhere in the peptide.

3) bp1-01 may bind to IGFBP-1 in an aggregated form. Given the likelihood of self-association of bp1-01 via the hydrophobic face of the helix (Leu6, Trp8, Leu9, Tyr13, and Phe14), some other region of the peptide would be involved in IGFBP-1 contact. In this case the helices and the contacts between them would act as a scaffold to present the IGFBP-1-binding region.

Below are the coordinates for the representative structure that is shown in FIG. 39 (standard protein database format).

REMARK BP1-01 IGF-I-BINDING PROTEIN BINDING PEPTIDE
REMARK REPRESENTATIVE STRUCTURE FROM ENSEMBLE CALCULATED
REMARK WITH NMR-DERIVED RESTRAINTS

| ATOM | 1 | N | CYS | 1 | −5.022 | −1.559 | 0.892 | 1.00 | 0.00 |
|------|---|---|-----|---|--------|--------|-------|------|------|
| ATOM | 2 | CA | CYS | 1 | −4.328 | −1.133 | −0.335 | 1.00 | 0.00 |
| ATOM | 3 | C | CYS | 1 | −3.837 | 0.310 | −0.220 | 1.00 | 0.00 |
| ATOM | 4 | O | CYS | 1 | −2.646 | 0.544 | −0.024 | 1.00 | 0.00 |
| ATOM | 5 | CB | CYS | 1 | −5.220 | −1.340 | −1.567 | 1.00 | 0.00 |
| ATOM | 6 | SG | CYS | 1 | −4.498 | −0.877 | −3.166 | 1.00 | 0.00 |
| ATOM | 7 | 1H | CYS | 1 | −5.842 | −0.987 | 1.034 | 1.00 | 0.00 |
| ATOM | 8 | 2H | CYS | 1 | −5.296 | −2.527 | 0.807 | 1.00 | 0.00 |
| ATOM | 9 | 3H | CYS | 1 | −4.400 | −1.455 | 1.682 | 1.00 | 0.00 |
| ATOM | 10 | HA | CYS | 1 | −3.456 | −1.777 | −0.448 | 1.00 | 0.00 |
| ATOM | 11 | 1HB | CYS | 1 | −5.484 | −2.396 | −1.625 | 1.00 | 0.00 |
| ATOM | 12 | 2HB | CYS | 1 | −6.143 | −0.773 | −1.446 | 1.00 | 0.00 |
| ATOM | 13 | 1LG | CYS | 1 | −4.970 | −1.181 | −3.550 | 1.00 | 0.00 |
| ATOM | 14 | 2LG | CYS | 1 | −4.093 | −0.385 | −2.924 | 1.00 | 0.00 |
| ATOM | 15 | N | ARG | 2 | −4.756 | 1.275 | −0.336 | 1.00 | 0.00 |
| ATOM | 16 | CA | ARG | 2 | −4.410 | 2.685 | −0.348 | 1.00 | 0.00 |
| ATOM | 17 | C | ARG | 2 | −3.778 | 3.012 | −1.703 | 1.00 | 0.00 |
| ATOM | 18 | O | ARG | 2 | −2.559 | 3.112 | −1.836 | 1.00 | 0.00 |
| ATOM | 19 | CB | ARG | 2 | −3.519 | 2.999 | 0.862 | 1.00 | 0.00 |
| ATOM | 20 | CG | ARG | 2 | −3.052 | 4.460 | 0.950 | 1.00 | 0.00 |
| ATOM | 21 | CD | ARG | 2 | −4.211 | 5.459 | 0.892 | 1.00 | 0.00 |
| ATOM | 22 | NE | ARG | 2 | −3.742 | 6.823 | 1.164 | 1.00 | 0.00 |
| ATOM | 23 | CZ | ARG | 2 | −4.455 | 7.940 | 0.945 | 1.00 | 0.00 |
| ATOM | 24 | NH1 | ARG | 2 | −5.701 | 7.877 | 0.455 | 1.00 | 0.00 |
| ATOM | 25 | NH2 | ARG | 2 | −3.914 | 9.134 | 1.222 | 1.00 | 0.00 |
| ATOM | 26 | H | ARG | 2 | −5.723 | 1.024 | −0.475 | 1.00 | 0.00 |
| ATOM | 27 | HA | ARG | 2 | −5.340 | 3.246 | −0.248 | 1.00 | 0.00 |
| ATOM | 28 | 1HB | ARG | 2 | −4.084 | 2.770 | 1.767 | 1.00 | 0.00 |
| ATOM | 29 | 2HB | ARG | 2 | −2.647 | 2.346 | 0.839 | 1.00 | 0.00 |
| ATOM | 30 | 1HG | ARG | 2 | −2.523 | 4.585 | 1.896 | 1.00 | 0.00 |
| ATOM | 31 | 2HG | ARG | 2 | −2.356 | 4.680 | 0.142 | 1.00 | 0.00 |
| ATOM | 32 | 1HD | ARG | 2 | −4.657 | 5.430 | −0.103 | 1.00 | 0.00 |
| ATOM | 33 | 2HD | ARG | 2 | −4.962 | 5.189 | 1.635 | 1.00 | 0.00 |
| ATOM | 34 | HE | ARG | 2 | −2.813 | 6.913 | 1.550 | 1.00 | 0.00 |
| ATOM | 35 | 2HH1 | ARG | 2 | −6.227 | 8.724 | 0.294 | 1.00 | 0.00 |
| ATOM | 36 | 1HH1 | ARG | 2 | −6.122 | 6.981 | 0.254 | 1.00 | 0.00 |
| ATOM | 37 | 1HH2 | ARG | 2 | −2.979 | 9.192 | 1.599 | 1.00 | 0.00 |
| ATOM | 38 | 2HH2 | ARG | 2 | −4.442 | 9.979 | 1.061 | 1.00 | 0.00 |
| ATOM | 39 | N | ALA | 3 | −4.640 | 3.150 | −2.718 | 1.00 | 0.00 |
| ATOM | 40 | CA | ALA | 3 | −4.259 | 3.352 | −4.106 | 1.00 | 0.00 |
| ATOM | 41 | C | ALA | 3 | −3.843 | 4.805 | −4.352 | 1.00 | 0.00 |
| ATOM | 42 | O | ALA | 3 | −4.546 | 5.555 | −5.027 | 1.00 | 0.00 |
| ATOM | 43 | CB | ALA | 3 | −5.430 | 2.931 | −5.001 | 1.00 | 0.00 |
| ATOM | 44 | H | ALA | 3 | −5.626 | 3.058 | −2.522 | 1.00 | 0.00 |
| ATOM | 45 | HA | ALA | 3 | −3.412 | 2.706 | −4.345 | 1.00 | 0.00 |
| ATOM | 46 | 3HB | ALA | 3 | −5.643 | 1.872 | −4.851 | 1.00 | 0.00 |
| ATOM | 47 | 1HB | ALA | 3 | −6.320 | 3.511 | −4.753 | 1.00 | 0.00 |
| ATOM | 48 | 2HB | ALA | 3 | −5.182 | 3.096 | −6.049 | 1.00 | 0.00 |
| ATOM | 49 | N | GLY | 4 | −2.681 | 5.191 | −3.818 | 1.00 | 0.00 |
| ATOM | 50 | CA | GLY | 4 | −2.069 | 6.481 | −4.087 | 1.00 | 0.00 |
| ATOM | 51 | C | GLY | 4 | −0.636 | 6.488 | −3.558 | 1.00 | 0.00 |
| ATOM | 52 | O | GLY | 4 | 0.272 | 6.072 | −4.276 | 1.00 | 0.00 |
| ATOM | 53 | H | GLY | 4 | −2.169 | 4.528 | −3.249 | 1.00 | 0.00 |
| ATOM | 54 | 1HA | GLY | 4 | −2.035 | 6.637 | −5.166 | 1.00 | 0.00 |
| ATOM | 55 | 2HA | GLY | 4 | −2.666 | 7.280 | −3.648 | 1.00 | 0.00 |
| ATOM | 56 | N | PRO | 5 | −0.410 | 6.939 | −2.314 | 1.00 | 0.00 |
| ATOM | 57 | CA | PRO | 5 | 0.917 | 7.007 | −1.721 | 1.00 | 0.00 |
| ATOM | 58 | C | PRO | 5 | 1.505 | 5.610 | −1.509 | 1.00 | 0.00 |
| ATOM | 59 | O | PRO | 5 | 2.698 | 5.413 | −1.731 | 1.00 | 0.00 |
| ATOM | 60 | CB | PRO | 5 | 0.739 | 7.773 | −0.407 | 1.00 | 0.00 |

-continued

| | | | | | | | | | |
|---|---|---|---|---|---|---|---|---|---|
| ATOM | 61 | CG | PRO | 5 | −0.715 | 7.501 | −0.026 | 1.00 | 0.00 |
| ATOM | 62 | CD | PRO | 5 | −1.419 | 7.411 | −1.380 | 1.00 | 0.00 |
| ATOM | 63 | HA | PRO | 5 | 1.586 | 7.574 | −2.370 | 1.00 | 0.00 |
| ATOM | 64 | 1HB | PRO | 5 | 1.439 | 7.458 | 0.368 | 1.00 | 0.00 |
| ATOM | 65 | 2HB | PRO | 5 | 0.857 | 8.840 | −0.600 | 1.00 | 0.00 |
| ATOM | 66 | 1HG | PRO | 5 | −0.781 | 6.542 | 0.486 | 1.00 | 0.00 |
| ATOM | 67 | 2HG | PRO | 5 | −1.126 | 8.290 | 0.603 | 1.00 | 0.00 |
| ATOM | 68 | 1HD | PRO | 5 | −2.270 | 6.732 | −1.322 | 1.00 | 0.00 |
| ATOM | 69 | 2HD | PRO | 5 | −1.752 | 8.405 | −1.683 | 1.00 | 0.00 |
| ATOM | 70 | N | LEU | 6 | 0.670 | 4.646 | −1.098 | 1.00 | 0.00 |
| ATOM | 71 | CA | LEU | 6 | 1.043 | 3.246 | −0.926 | 1.00 | 0.00 |
| ATOM | 72 | C | LEU | 6 | 0.520 | 2.418 | −2.110 | 1.00 | 0.00 |
| ATOM | 73 | O | LEU | 6 | 0.206 | 1.241 | −1.944 | 1.00 | 0.00 |
| ATOM | 74 | CB | LEU | 6 | 0.497 | 2.733 | 0.422 | 1.00 | 0.00 |
| ATOM | 75 | CG | LEU | 6 | 1.343 | 3.106 | 1.651 | 1.00 | 0.00 |
| ATOM | 76 | CD1 | LEU | 6 | 1.406 | 4.613 | 1.920 | 1.00 | 0.00 |
| ATOM | 77 | CD2 | LEU | 6 | 0.748 | 2.411 | 2.883 | 1.00 | 0.00 |
| ATOM | 78 | H | LEU | 6 | −0.298 | 4.883 | −0.937 | 1.00 | 0.00 |
| ATOM | 79 | HA | LEU | 6 | 2.127 | 3.131 | −0.913 | 1.00 | 0.00 |
| ATOM | 80 | 1HB | LEU | 6 | −0.520 | 3.095 | 0.556 | 1.00 | 0.00 |
| ATOM | 81 | 2HB | LEU | 6 | 0.465 | 1.645 | 0.409 | 1.00 | 0.00 |
| ATOM | 82 | HG | LEU | 6 | 2.359 | 2.738 | 1.507 | 1.00 | 0.00 |
| ATOM | 83 | 2HD1 | LEU | 6 | 1.891 | 4.795 | 2.879 | 1.00 | 0.00 |
| ATOM | 84 | 3HD1 | LEU | 6 | 1.994 | 5.109 | 1.150 | 1.00 | 0.00 |
| ATOM | 85 | 1HD1 | LEU | 6 | 0.400 | 5.032 | 1.947 | 1.00 | 0.00 |
| ATOM | 86 | 2HD2 | LEU | 6 | 1.368 | 2.612 | 3.757 | 1.00 | 0.00 |
| ATOM | 87 | 3HD2 | LEU | 6 | −0.261 | 2.780 | 3.069 | 1.00 | 0.00 |
| ATOM | 88 | 1HD2 | LEU | 6 | 0.707 | 1.332 | 2.728 | 1.00 | 0.00 |
| ATOM | 89 | N | GLN | 7 | 0.441 | 3.001 | −3.316 | 1.00 | 0.00 |
| ATOM | 90 | CA | GLN | 7 | 0.009 | 2.262 | −4.497 | 1.00 | 0.00 |
| ATOM | 91 | C | GLN | 7 | 1.046 | 1.194 | −4.848 | 1.00 | 0.00 |
| ATOM | 92 | O | GLN | 7 | 0.696 | 0.030 | −5.022 | 1.00 | 0.00 |
| ATOM | 93 | CB | GLN | 7 | −0.227 | 3.214 | −5.677 | 1.00 | 0.00 |
| ATOM | 94 | CG | GLN | 7 | −0.648 | 2.494 | −6.968 | 1.00 | 0.00 |
| ATOM | 95 | CD | GLN | 7 | −1.990 | 1.773 | −6.841 | 1.00 | 0.00 |
| ATOM | 96 | OE1 | GLN | 7 | −3.015 | 2.295 | −7.270 | 1.00 | 0.00 |
| ATOM | 97 | NE2 | GLN | 7 | −1.991 | 0.566 | −6.271 | 1.00 | 0.00 |
| ATOM | 98 | H | GLN | 7 | 0.702 | 3.971 | −3.428 | 1.00 | 0.00 |
| ATOM | 99 | HA | GLN | 7 | −0.936 | 1.778 | −4.245 | 1.00 | 0.00 |
| ATOM | 100 | 1HB | GLN | 7 | −1.007 | 3.925 | −5.415 | 1.00 | 0.00 |
| ATOM | 101 | 2HB | GLN | 7 | 0.690 | 3.769 | −5.878 | 1.00 | 0.00 |
| ATOM | 102 | 1HG | GLN | 7 | −0.742 | 3.247 | −7.752 | 1.00 | 0.00 |
| ATOM | 103 | 2HG | GLN | 7 | 0.120 | 1.787 | −7.282 | 1.00 | 0.00 |
| ATOM | 104 | 1HE2 | GLN | 7 | −2.855 | 0.049 | −6.189 | 1.00 | 0.00 |
| ATOM | 105 | 2HE2 | GLN | 7 | −1.129 | 0.171 | −5.919 | 1.00 | 0.00 |
| ATOM | 106 | N | TRP | 8 | 2.319 | 1.596 | −4.940 | 1.00 | 0.00 |
| ATOM | 107 | CA | TRP | 8 | 3.449 | 0.700 | −5.154 | 1.00 | 0.00 |
| ATOM | 108 | C | TRP | 8 | 3.434 | −0.449 | −4.141 | 1.00 | 0.00 |
| ATOM | 109 | O | TRP | 8 | 3.652 | −1.602 | −4.505 | 1.00 | 0.00 |
| ATOM | 110 | CB | TRP | 8 | 4.756 | 1.500 | −5.048 | 1.00 | 0.00 |
| ATOM | 111 | CG | TRP | 8 | 5.026 | 2.107 | −3.702 | 1.00 | 0.00 |
| ATOM | 112 | CD1 | TRP | 8 | 4.543 | 3.290 | −3.263 | 1.00 | 0.00 |
| ATOM | 113 | CD2 | TRP | 8 | 5.753 | 1.533 | −2.573 | 1.00 | 0.00 |
| ATOM | 114 | NE1 | TRP | 8 | 4.896 | 3.483 | −1.944 | 1.00 | 0.00 |
| ATOM | 115 | CE2 | TRP | 8 | 5.643 | 2.425 | −1.466 | 1.00 | 0.00 |
| ATOM | 116 | CE3 | TRP | 8 | 6.450 | 0.324 | −2.354 | 1.00 | 0.00 |
| ATOM | 117 | CZ2 | TRP | 8 | 6.203 | 2.134 | −0.213 | 1.00 | 0.00 |
| ATOM | 118 | CZ3 | TRP | 8 | 7.061 | 0.049 | −1.117 | 1.00 | 0.00 |
| ATOM | 119 | CH2 | TRP | 8 | 6.933 | 0.948 | −0.045 | 1.00 | 0.00 |
| ATOM | 120 | H | TRP | 8 | 2.521 | 2.575 | −4.803 | 1.00 | 0.00 |
| ATOM | 121 | HA | TRP | 8 | 3.378 | 0.286 | −6.161 | 1.00 | 0.00 |
| ATOM | 122 | 1HB | TRP | 8 | 5.585 | 0.835 | −5.293 | 1.00 | 0.00 |
| ATOM | 123 | 2HB | TRP | 8 | 4.739 | 2.297 | −5.793 | 1.00 | 0.00 |
| ATOM | 124 | HD1 | TRP | 8 | 3.930 | 3.966 | −3.841 | 1.00 | 0.00 |
| ATOM | 125 | HE1 | TRP | 8 | 4.624 | 4.279 | −1.384 | 1.00 | 0.00 |
| ATOM | 126 | HE3 | TRP | 8 | 6.504 | −0.411 | −3.142 | 1.00 | 0.00 |
| ATOM | 127 | HZ2 | TRP | 8 | 6.053 | 2.799 | 0.624 | 1.00 | 0.00 |
| ATOM | 128 | HZ3 | TRP | 8 | 7.623 | −0.862 | −0.986 | 1.00 | 0.00 |
| ATOM | 129 | HH2 | TRP | 8 | 7.382 | 0.719 | 0.911 | 1.00 | 0.00 |
| ATOM | 130 | N | LEU | 9 | 3.164 | −0.117 | −2.872 | 1.00 | 0.00 |
| ATOM | 131 | CA | LEU | 9 | 3.155 | −1.044 | −1.753 | 1.00 | 0.00 |
| ATOM | 132 | C | LEU | 9 | 2.024 | −2.054 | −1.956 | 1.00 | 0.00 |
| ATOM | 133 | O | LEU | 9 | 2.239 | −3.260 | −1.862 | 1.00 | 0.00 |
| ATOM | 134 | CB | LEU | 9 | 3.025 | −0.233 | −0.448 | 1.00 | 0.00 |
| ATOM | 135 | CG | LEU | 9 | 3.830 | −0.813 | 0.726 | 1.00 | 0.00 |
| ATOM | 136 | CD1 | LEU | 9 | 3.898 | 0.197 | 1.877 | 1.00 | 0.00 |
| ATOM | 137 | CD2 | LEU | 9 | 3.197 | −2.091 | 1.264 | 1.00 | 0.00 |
| ATOM | 138 | H | LEU | 9 | 2.975 | 0.853 | −2.669 | 1.00 | 0.00 |
| ATOM | 139 | HA | LEU | 9 | 4.112 | −1.567 | −1.754 | 1.00 | 0.00 |

-continued

| | | | | | | | | |
|---|---|---|---|---|---|---|---|---|
| ATOM | 140 | 1HB | LEU | 9 | 3.418 | 0.768 | −0.625 | 1.00 | 0.00 |
| ATOM | 141 | 2HB | LEU | 9 | 1.977 | −0.133 | −0.166 | 1.00 | 0.00 |
| ATOM | 142 | HG | LEU | 9 | 4.846 | −1.031 | 0.399 | 1.00 | 0.00 |
| ATOM | 143 | 3HD1 | LEU | 9 | 4.523 | −0.200 | 2.678 | 1.00 | 0.00 |
| ATOM | 144 | 1HD1 | LEU | 9 | 4.326 | 1.137 | 1.535 | 1.00 | 0.00 |
| ATOM | 145 | 2HD1 | LEU | 9 | 2.899 | 0.384 | 2.267 | 1.00 | 0.00 |
| ATOM | 146 | 2HD2 | LEU | 9 | 3.808 | −2.482 | 2.077 | 1.00 | 0.00 |
| ATOM | 147 | 3HD2 | LEU | 9 | 2.197 | −1.867 | 1.630 | 1.00 | 0.00 |
| ATOM | 148 | 1HD2 | LEU | 9 | 3.135 | −2.835 | 0.479 | 1.00 | 0.00 |
| ATOM | 149 | N | CYS | 10 | 0.830 | −1.551 | −2.288 | 1.00 | 0.00 |
| ATOM | 150 | CA | CYS | 10 | −0.347 | −2.351 | −2.581 | 1.00 | 0.00 |
| ATOM | 151 | C | CYS | 10 | −0.090 | −3.354 | −3.706 | 1.00 | 0.00 |
| ATOM | 152 | O | CYS | 10 | −0.370 | −4.536 | −3.533 | 1.00 | 0.00 |
| ATOM | 153 | CB | CYS | 10 | −1.528 | −1.430 | −2.894 | 1.00 | 0.00 |
| ATOM | 154 | SG | CYS | 10 | −3.024 | −2.270 | −3.462 | 1.00 | 0.00 |
| ATOM | 155 | H | CYS | 10 | 0.733 | −0.547 | −2.354 | 1.00 | 0.00 |
| ATOM | 156 | HA | CYS | 10 | −0.598 | −2.913 | −1.684 | 1.00 | 0.00 |
| ATOM | 157 | 1HB | CYS | 10 | −1.764 | −0.865 | −1.995 | 1.00 | 0.00 |
| ATOM | 158 | 2HB | CYS | 10 | −1.251 | −0.720 | −3.670 | 1.00 | 0.00 |
| ATOM | 159 | 1LG | CYS | 10 | −2.931 | −2.146 | −4.124 | 1.00 | 0.00 |
| ATOM | 160 | 2LG | CYS | 10 | −3.134 | −2.620 | −2.887 | 1.00 | 0.00 |
| ATOM | 161 | N | GLU | 11 | 0.449 | −2.907 | −4.846 | 1.00 | 0.00 |
| ATOM | 162 | CA | GLU | 11 | 0.729 | −3.800 | −5.964 | 1.00 | 0.00 |
| ATOM | 163 | C | GLU | 11 | 1.792 | −4.838 | −5.593 | 1.00 | 0.00 |
| ATOM | 164 | O | GLU | 11 | 1.609 | −6.024 | −5.859 | 1.00 | 0.00 |
| ATOM | 165 | CB | GLU | 11 | 1.168 | −3.009 | −7.206 | 1.00 | 0.00 |
| ATOM | 166 | CG | GLU | 11 | 0.102 | −2.037 | −7.727 | 1.00 | 0.00 |
| ATOM | 167 | CD | GLU | 11 | −1.243 | −2.716 | −7.973 | 1.00 | 0.00 |
| ATOM | 168 | OE1 | GLU | 11 | −1.333 | −3.451 | −8.980 | 1.00 | 0.00 |
| ATOM | 169 | OE2 | GLU | 11 | −2.154 | −2.493 | −7.146 | 1.00 | 0.00 |
| ATOM | 170 | H | GLU | 11 | 0.669 | −1.924 | −4.942 | 1.00 | 0.00 |
| ATOM | 171 | HA | GLU | 11 | −0.182 | −4.348 | −6.204 | 1.00 | 0.00 |
| ATOM | 172 | 1HB | GLU | 11 | 2.075 | −2.446 | −6.979 | 1.00 | 0.00 |
| ATOM | 173 | 2HB | GLU | 11 | 1.396 | −3.721 | −8.001 | 1.00 | 0.00 |
| ATOM | 174 | 1HG | GLU | 11 | −0.034 | −1.231 | −7.014 | 1.00 | 0.00 |
| ATOM | 175 | 2HG | GLU | 11 | 0.452 | −1.601 | −8.663 | 1.00 | 0.00 |
| ATOM | 176 | N | LYS | 12 | 2.909 | −4.388 | −5.010 | 1.00 | 0.00 |
| ATOM | 177 | CA | LYS | 12 | 4.080 | −5.221 | −4.779 | 1.00 | 0.00 |
| ATOM | 178 | C | LYS | 12 | 3.824 | −6.277 | −3.701 | 1.00 | 0.00 |
| ATOM | 179 | O | LYS | 12 | 4.069 | −7.459 | −3.936 | 1.00 | 0.00 |
| ATOM | 180 | CB | LYS | 12 | 5.280 | −4.325 | −4.444 | 1.00 | 0.00 |
| ATOM | 181 | CG | LYS | 12 | 6.590 | −5.123 | −4.400 | 1.00 | 0.00 |
| ATOM | 182 | CD | LYS | 12 | 7.820 | −4.206 | −4.385 | 1.00 | 0.00 |
| ATOM | 183 | CE | LYS | 12 | 7.961 | −3.450 | −3.061 | 1.00 | 0.00 |
| ATOM | 184 | NZ | LYS | 12 | 9.120 | −2.542 | −3.084 | 1.00 | 0.00 |
| ATOM | 185 | H | LYS | 12 | 2.989 | −3.401 | −4.803 | 1.00 | 0.00 |
| ATOM | 186 | HA | LYS | 12 | 4.306 | −5.736 | −5.715 | 1.00 | 0.00 |
| ATOM | 187 | 1HB | LYS | 12 | 5.366 | −3.568 | −5.225 | 1.00 | 0.00 |
| ATOM | 188 | 2HB | LYS | 12 | 5.107 | −3.827 | −3.490 | 1.00 | 0.00 |
| ATOM | 189 | 1HG | LYS | 12 | 6.604 | −5.776 | −3.526 | 1.00 | 0.00 |
| ATOM | 190 | 2HG | LYS | 12 | 6.650 | −5.743 | −5.296 | 1.00 | 0.00 |
| ATOM | 191 | 1HD | LYS | 12 | 8.711 | −4.820 | −4.529 | 1.00 | 0.00 |
| ATOM | 192 | 2HD | LYS | 12 | 7.754 | −3.496 | −5.210 | 1.00 | 0.00 |
| ATOM | 193 | 1HE | LYS | 12 | 7.068 | −2.857 | −2.869 | 1.00 | 0.00 |
| ATOM | 194 | 2HE | LYS | 12 | 8.098 | −4.170 | −2.255 | 1.00 | 0.00 |
| ATOM | 195 | 2HZ | LYS | 12 | 9.000 | −1.861 | −3.820 | 1.00 | 0.00 |
| ATOM | 196 | 3HZ | LYS | 12 | 9.192 | −2.066 | −2.196 | 1.00 | 0.00 |
| ATOM | 197 | 1HZ | LYS | 12 | 9.962 | −3.073 | −3.250 | 1.00 | 0.00 |
| ATOM | 198 | N | TYR | 13 | 3.345 | −5.856 | −2.524 | 1.00 | 0.00 |
| ATOM | 199 | CA | TYR | 13 | 3.118 | −6.740 | −1.388 | 1.00 | 0.00 |
| ATOM | 200 | C | TYR | 13 | 1.704 | −7.312 | −1.433 | 1.00 | 0.00 |
| ATOM | 201 | O | TYR | 13 | 1.537 | −8.530 | −1.445 | 1.00 | 0.00 |
| ATOM | 202 | CB | TYR | 13 | 3.347 | −5.993 | −0.069 | 1.00 | 0.00 |
| ATOM | 203 | CG | TYR | 13 | 4.787 | −5.600 | 0.198 | 1.00 | 0.00 |
| ATOM | 204 | CD1 | TYR | 13 | 5.300 | −4.391 | −0.305 | 1.00 | 0.00 |
| ATOM | 205 | CD2 | TYR | 13 | 5.596 | −6.412 | 1.016 | 1.00 | 0.00 |
| ATOM | 206 | CE1 | TYR | 13 | 6.582 | −3.958 | 0.070 | 1.00 | 0.00 |
| ATOM | 207 | CE2 | TYR | 13 | 6.896 | −6.000 | 1.354 | 1.00 | 0.00 |
| ATOM | 208 | CZ | TYR | 13 | 7.385 | −4.766 | 0.892 | 1.00 | 0.00 |
| ATOM | 209 | OH | TYR | 13 | 8.639 | −4.357 | 1.241 | 1.00 | 0.00 |
| ATOM | 210 | H | TYR | 13 | 3.140 | −4.873 | −2.402 | 1.00 | 0.00 |
| ATOM | 211 | HA | TYR | 13 | 3.826 | −7.571 | −1.417 | 1.00 | 0.00 |
| ATOM | 212 | 1HB | TYR | 13 | 2.720 | −5.102 | −0.042 | 1.00 | 0.00 |
| ATOM | 213 | 2HB | TYR | 13 | 3.018 | −6.640 | 0.745 | 1.00 | 0.00 |
| ATOM | 214 | HD1 | TYR | 13 | 4.707 | −3.781 | −0.968 | 1.00 | 0.00 |
| ATOM | 215 | HD2 | TYR | 13 | 5.218 | −7.350 | 1.396 | 1.00 | 0.00 |
| ATOM | 216 | HE1 | TYR | 13 | 6.948 | −3.005 | −0.278 | 1.00 | 0.00 |
| ATOM | 217 | HE2 | TYR | 13 | 7.514 | −6.626 | 1.982 | 1.00 | 0.00 |
| ATOM | 218 | HH | TYR | 13 | 8.872 | −3.497 | 0.883 | 1.00 | 0.00 |

-continued

| | | | | | | | | | |
|---|---|---|---|---|---|---|---|---|---|
| ATOM | 219 | N | PHE | 14 | 0.685 | −6.443 | −1.441 | 1.00 | 0.00 |
| ATOM | 220 | CA | PHE | 14 | −0.707 | −6.851 | −1.269 | 1.00 | 0.00 |
| ATOM | 221 | C | PHE | 14 | −1.342 | −7.174 | −2.628 | 1.00 | 0.00 |
| ATOM | 222 | O | PHE | 14 | −2.470 | −6.768 | −2.906 | 1.00 | 0.00 |
| ATOM | 223 | CB | PHE | 14 | −1.488 | −5.752 | −0.525 | 1.00 | 0.00 |
| ATOM | 224 | CG | PHE | 14 | −0.808 | −5.116 | 0.680 | 1.00 | 0.00 |
| ATOM | 225 | CD1 | PHE | 14 | 0.044 | −5.862 | 1.519 | 1.00 | 0.00 |
| ATOM | 226 | CD2 | PHE | 14 | −1.039 | −3.756 | 0.964 | 1.00 | 0.00 |
| ATOM | 227 | CE1 | PHE | 14 | 0.722 | −5.231 | 2.578 | 1.00 | 0.00 |
| ATOM | 228 | CE2 | PHE | 14 | −0.370 | −3.129 | 2.027 | 1.00 | 0.00 |
| ATOM | 229 | CZ | PHE | 14 | 0.523 | −3.862 | 2.826 | 1.00 | 0.00 |
| ATOM | 230 | H | PHE | 14 | 0.882 | −5.453 | −1.475 | 1.00 | 0.00 |
| ATOM | 231 | HA | PHE | 14 | −0.751 | −7.755 | −0.659 | 1.00 | 0.00 |
| ATOM | 232 | 1HB | PHE | 14 | −1.708 | −4.956 | −1.237 | 1.00 | 0.00 |
| ATOM | 233 | 2HB | PHE | 14 | −2.441 | −6.169 | −0.195 | 1.00 | 0.00 |
| ATOM | 234 | HD1 | PHE | 14 | 0.196 | −6.918 | 1.352 | 1.00 | 0.00 |
| ATOM | 235 | HD2 | PHE | 14 | −1.733 | −3.185 | 0.367 | 1.00 | 0.00 |
| ATOM | 236 | HE1 | PHE | 14 | 1.396 | −5.800 | 3.201 | 1.00 | 0.00 |
| ATOM | 237 | HE2 | PHE | 14 | −0.539 | −2.080 | 2.228 | 1.00 | 0.00 |
| ATOM | 238 | HZ | PHE | 14 | 1.053 | −3.370 | 3.629 | 1.00 | 0.00 |
| ATOM | 239 | N | GLY | 15 | −0.607 | −7.896 | −3.480 | 1.00 | 0.00 |
| ATOM | 240 | CA | GLY | 15 | −0.995 | −8.181 | −4.849 | 1.00 | 0.00 |
| ATOM | 241 | C | GLY | 15 | 0.182 | −8.794 | −5.604 | 1.00 | 0.00 |
| ATOM | 242 | O | GLY | 15 | 1.159 | −9.233 | −4.999 | 1.00 | 0.00 |
| ATOM | 243 | H | GLY | 15 | 0.302 | −8.231 | −3.186 | 1.00 | 0.00 |
| ATOM | 244 | 1HA | GLY | 15 | −1.832 | −8.881 | −4.853 | 1.00 | 0.00 |
| ATOM | 245 | 2HA | GLY | 15 | −1.295 | −7.254 | −5.340 | 1.00 | 0.00 |
| ATOM | 246 | N | NH2 | 16 | 0.095 | −8.822 | −6.935 | 1.00 | 0.00 |
| ATOM | 247 | 1HN | NH2 | 16 | −0.720 | −8.445 | −7.397 | 1.00 | 0.00 |
| ATOM | 248 | 2HN | NH2 | 16 | 0.854 | −9.209 | −7.476 | 1.00 | 0.00 |

Example 9

Displacement of IGF-I From IGFBPs Using (Leu$^{24}$, Ala$^{31}$)hIGF

This example shows that the IGF mutant (Leu$^{24}$,Ala$^{31}$) hIGF used in the above animal studies can displace IGF-I tracer from IGFBPs present in human serum.

To determine if the IGF mutant could displace IGF-I from endogenous IGFBPs present in human serum, the following experiment was performed. Radiolabeled rhIGF-I ($^{125}$I-IGF-I) was incubated with normal human serum samples at a concentration of 33 ng/ml for 16 hr at 4° C. to allow for the formation of $^{125}$I-IGF-I:IGFBP complexes. Following complex formation, the IGF mutant (Leu$^{24}$,Ala$^{31}$)hIGF (40 μg/ml) was added to the incubations for 0, 0.5, 3, or 16 hr. The samples (n=3) were then analyzed by FPLC size-exclusion chromatography (FPLC-SEC) to determine the relative size and amounts of the $^{125}$I-IGF-I:IGFBP complexes.

Figure 41:
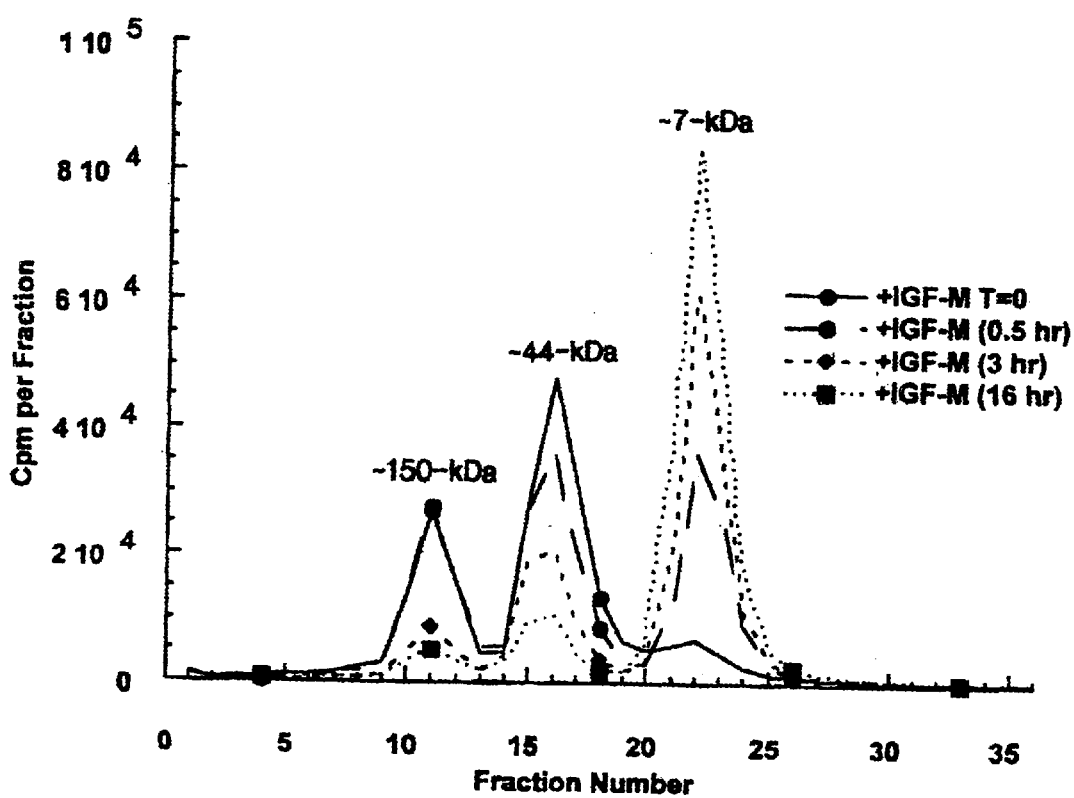
FIG. 41 is a chromatogram demonstrating the ability of the mutant ($Leu^{24}$,$Ala^{31}$)hIGF-I to displace $^{125}$I-IGF-I from endogenous IGFBPs present in serum from normal humans. Data are expressed as cpm per fraction (n=1). In the figure, the solid lines with circles are the mutant at time 0 of incubation, the long dashed lines with circles are the mutant at time 0.5 hr of incubation, the shorter dashed lines with diamonds are the mutant at time 3 hr of incubation, and the shortest dotted lines with squares are the mutant at time 16 hr of incubation.

FIG. 41 is a chromatogram demonstrating the ability of the IGF mutant to displace $^{125}$I-IGF-I from endogenous IGFBPs present in serum from normal humans. Data are expressed as cpm per fraction (n=1). This experiment was repeated three times, was quantitated, and is presented in Table IX.

TABLE IX

Quantitation of FPLC-SEC Data Demonstrating
Ability of IGF Mutant to Displace $^{125}$I-IGF-I
From Endogenous IGFBPs in Normal Human Serum*

| | ~150 kDa | ~44 kDa | Free (~7 kDa) |
|---|---|---|---|
| IGF Mutant (0 hr) | 30.3 ± 1.4 | 60.5 ± 0.8 | 9.3 ± 2.3 |
| IGF Mutant (0.5 hr) | 24.4 ± 0.8 | 37.3 ± 2.9 | 38.2 ± 3.7 |

TABLE IX-continued

Quantitation of FPLC-SEC Data Demonstrating
Ability of IGF Mutant to Displace $^{125}$I-IGF-I
From Endogenous IGFBPs in Normal Human Serum*

| | ~150 kDa | ~44 kDa | Free (~7 kDa) |
|---|---|---|---|
| IGF Mutant (3 hr) | 10.3 ± 1.1 | 27.8 ± 1.5 | 61.9 ± 2.6 |
| IGF Mutant (24 hr) | 5.5 ± 0.1 | 12.6 ± 0.4 | 81.9 ± 0.5 |

*Data (mean ± SD, n = 3) are expressed as percent of total radioactivity, calculated by dividing the amount of radioactivity in each molecular weight range by total radioactivity in all three molecular weight ranges.

Figure 42:
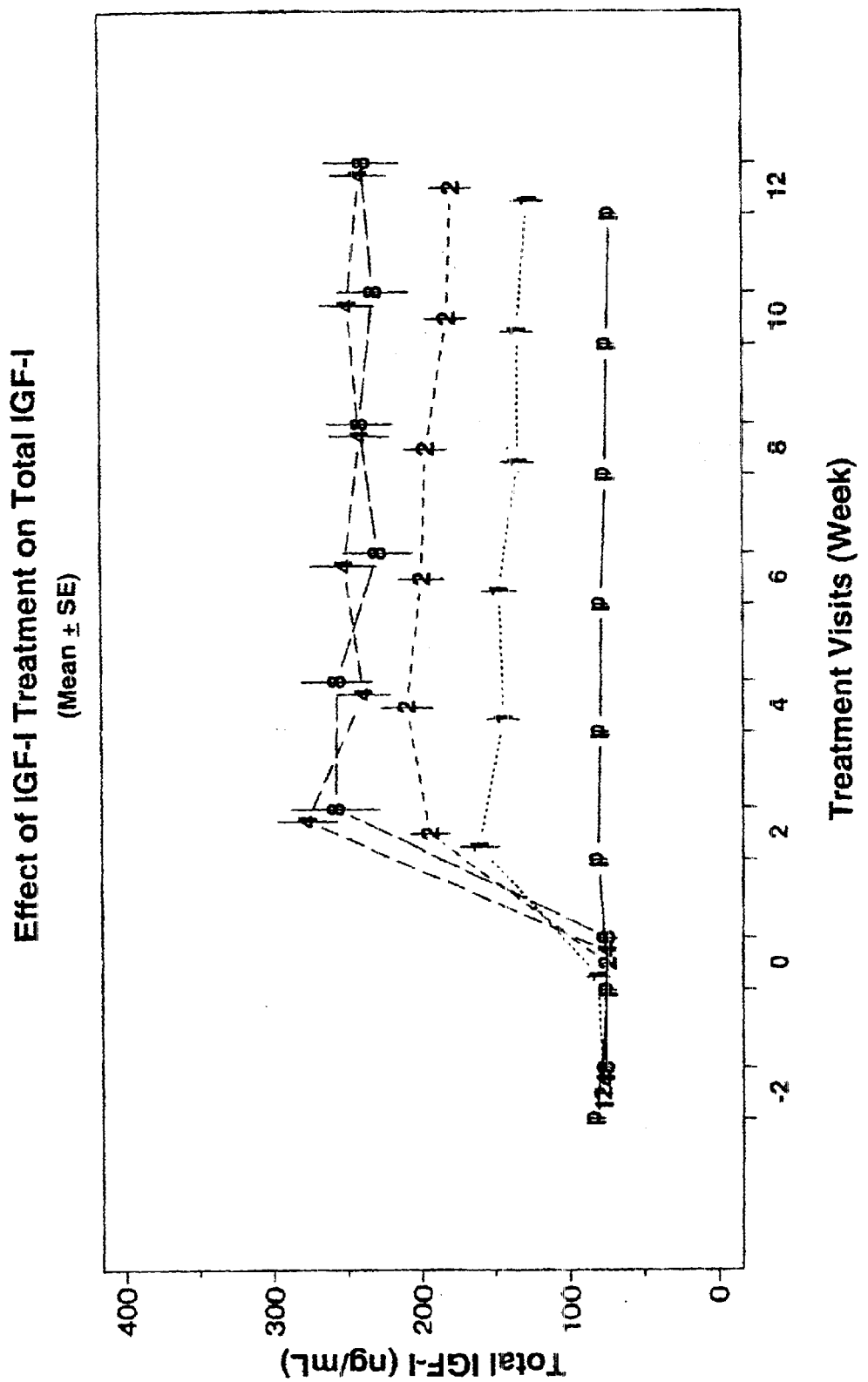
FIG. 42 shows the concentrations of IGF-I in the blood of type II diabetic patients treated with placebo (p) or 10 (1), 20 (2), 40 (4), or 80 (8) μg/kg of rhIGF-I for 12 weeks by twice daily subcutaneous injection.

After incubation of normal human serum with $^{125}$I-IGF-I for 16 hr, three peaks of radioactivity were observed following FPLC-SEC (FIG. 42). These peaks likely correspond to the following $^{125}$I-IGF-I complexes: ~150 kDa ($^{125}$I-IGF-I:IGFBP-3:ALS); ~44 kDa ($^{125}$I-IGF-I:IGFBPs 1-4); ~7 kDa (free $^{125}$I-IGF-I). As can be seen in FIG. 42, addition of the IGF mutant to the serum resulted in a time-dependent decrease in $^{125}$I-IGF-I associated with the $^{125}$I-IGF-I:IGFBP complexes and an increase in the amount of free $^{125}$I-IGF-I. These results are outlined in the above table. The $^{125}$-I-IGF-I was more readily displaced from the ~44 kDa than the ~150 kDa $^{125}$I-IGF-I:IGFBP complex, suggesting that IGF-I bound to the lower molecular weight IGFBPs is in a more bioavailable form. These data clearly indicate that the IGF mutant has the ability to displace IGF-I from endogenous IGFBPs present in normal human serum and therefore is likely to be active in vivo in humans.

In conclusion, this evidence shows that one would expect the molecules of the nature of the mutant to demonstrate the activities in humans that have been shown in rats.

Example 10

Displacement of IGF-I From IGFBPs Using BP15

This Example tests an IGFBP-3-specific peptide, BP15, for its ability to block the binding of $^{125}$I-IGF-I in human serum. Human serum was incubated with $^{125}$I-IGF-I±the peptide and the amount of tracer bound to IGFBPs via size-exclusion chromatography was measured. Addition of the peptide resulted in an approximate 42% decrease in $^{125}$I-IGF-I associated with the 150-KD IGF/IGFBP-3/ALS complex and a 59% increase in the amount of free $^{125}$I-IGF-I. The peptide did not decrease $^{125}$I-IGF-I binding to the 44-KD IGFBPs (in fact, it slightly increased it), indicating that the peptide only competes with IGF-I for binding to IGFBP-3.

These results indicate that the analog (at 0.2 mM) can compete with IGF-I for binding to IGFBP-3 in human serum.

Example 11

Treatment of Humans With Human IGF-I

This example shows the principle of how an exogenously administered compound that binds to one or more of the IGFBPs acts to displace endogenous IGFs and how to dose an IGF agonist for use in humans.

In this study human Type II diabetics were administered recombinant human IGF-I or placebo by twice daily injection at four doses (10, 20, 40 or 80 μg/kg) for 12 weeks. Blood samples were drawn, before, every two weeks during, and after (EP) the 12 weeks of treatment. The concentrations of IGF-I, IGF-II, and IGFBP-3 were measured in all the samples, with the exception of IGF-II not being measured in the samples taken from the patients treated with 10 μg/day of IGF-I.

Figure 43:
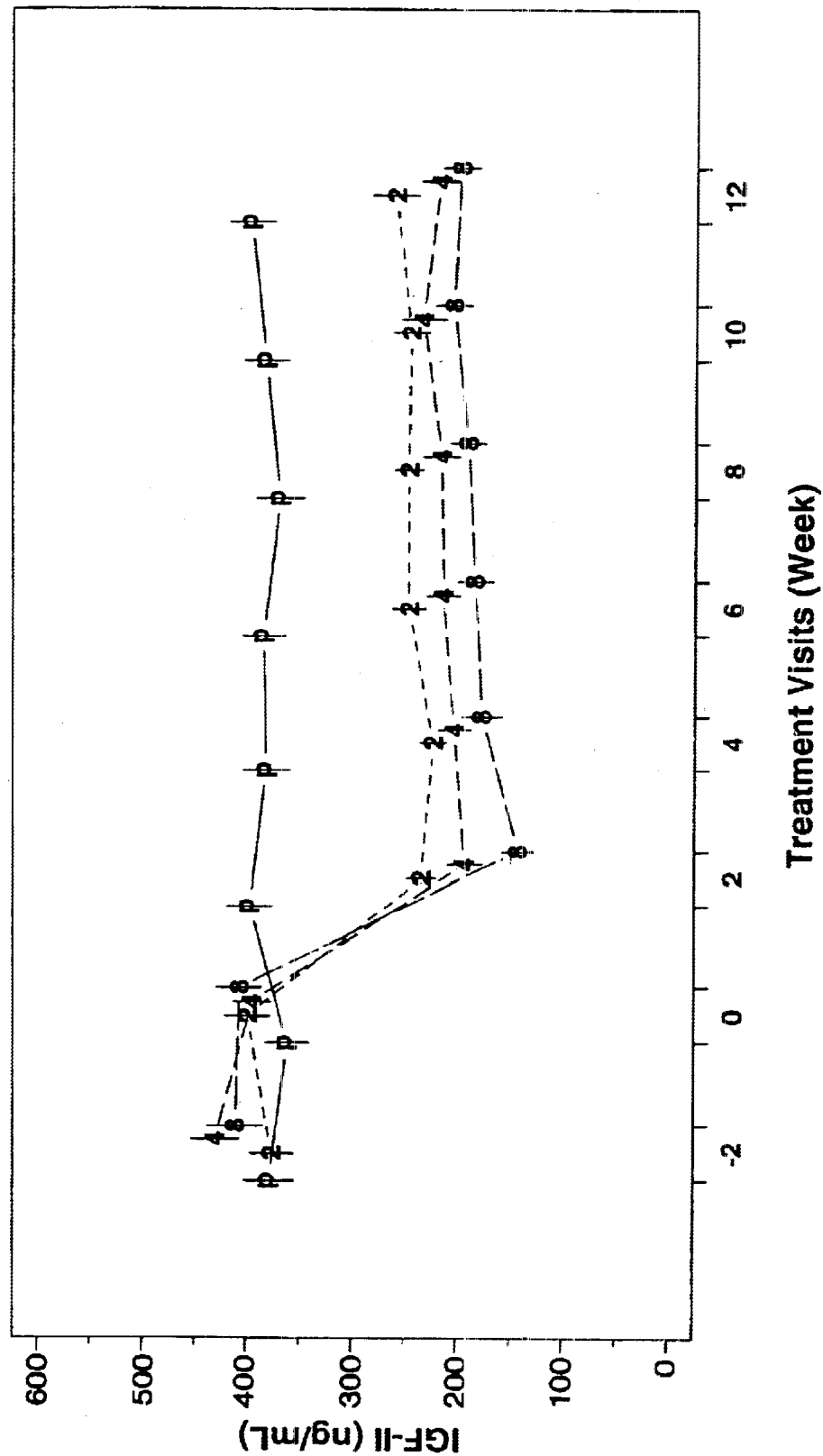
FIG. 43 shows the concentrations of IGF-II in the blood of the patients treated as described for FIG. 42.

FIG. 43 shows the concentrations of IGF-I in the blood of the patients. The unexpected finding was the "plateau" effect of administering 40 and 80 μg of IGF-I; the same total blood concentration of IGF-I was reached with these two doses.

FIG. 44 shows the concentrations of IGF-II in the blood of the patients. In contrast to the rising levels of IGF-I, the levels of IGF-II fell in almost a mirror image pattern to the rise in IGF-I concentrations. As with the plateauing of the rising IGF-I concentrations, the falling IGF-II concentrations also reached a plateau.

FIG. 45 shows the concentrations of IGFBP-3 in the blood of the patients. In contrast to the clear changes in the patterns of IGF-I and IGF-II in the blood, the concentrations of IGFBP-3 showed no statistically significant or clear pattern of change.

Inspection of FIGS. 43 and 44 reveals that the total IGF concentrations (IGF-I plus IGF-II) showed little change with treatment. This was because the rise in the concentrations of IGF-I closely matched the fall in the concentrations of IGF-II. Inspection of all three Figures shows that the dose-related changes in the concentrations of IGF-I and IGF-II in the blood of the patients were not accompanied by a reduced IGFBP-3 binding protein capacity (IGFBP-3 is the major binding protein in blood).

The obvious explanation for the fall in the concentration of IGF-II, and the plateauing of IGF-I and IGF-II concentrations, is that there is a finite amount of IGF binding protein capacity and in this experiment the doses of IGF-I used caused a dose-related displacement of IGF-II from the binding proteins.

It is a logical extension of the observations in this Example to expect that any molecule with the ability to enhance levels of active IGF would show activities similar to those shown for IGF-I in this Example. In addition, from the doses of IGF-I used and the concentrations of IGFBP and IGF-I and IGF-II demonstrated, it is simple to calculate how much of an IGF agonist should be given to increase levels of active endogenous IGF. The molar size relative to IGF-I, the affinity of the IGF agonist for the IGFBP, and its bioavailability would be other variables taken into account to arrive at doses that increased active IGF in a human.

Example 12

Structure/function of bp1-01 and Affinity Maturation

A. Kinetics of bp1-01 Binding to IGFBP-1

The kinetics of bp1-01 peptide variants were examined in a BIAcore™ (BIAcore, Inc., Piscataway, N.J.) assay using IGFBP-1 covalently coupled via EDC/NHS (as described by the manufacturer) to a dextran chip. Peptide bp1-01 (SEQ ID NO:15) displayed dissociation kinetics too rapid to measure. However, bp1-02, the 19-mer variant (SEQ ID NO:16) displayed measurable kinetics. The association rate constant was $2.30 \times 10^5$ M$^{-1}$ sec$^{-1}$ and the dissociation rate constant was $5.03 \times 10^{-2}$ sec$^{-1}$. The latter implies a half-life for peptide dissociation from IGFBP-1 of approximately 28 sec. The association rate constant is moderately fast, consistent with the notion that the peptide may not undergo significant conformation change upon binding to IGFBP-1.

B. Scanning Mutagenesis of bp1-01 Peptides

Two series of synthetic peptide variants were generated to determine which side chains of the bp1-01 peptide might contribute directly to binding IGFBP-1. In the first series an alanine-scanning approach (Cunningham and Wells, *Science*, 244: 1081–1085 (1989)) was used to remove that portion of each side chain beyond the beta carbon. The contribution of these atoms to the free energy of binding of the peptide to IGFBP-1 was then assessed by measuring the potency (IC50) of the variant for inhibiting IGFBP-1 binding to IGF-I or IGF-II in a BIAcore™ competition assay, analogous to that described for IGFBP-3 (see Example 7). The results are shown in Table X.

A second series of peptides made use of non-natural amino acids to probe whether other structural features such as an added methyl group at the alpha carbon, or an isomer (D-alanine) could affect peptide binding to IGFBP-1. The potencies of these peptides were measured by biotinylated-IGFBP-1 ELISA assay, with the results shown in Table XI. These results confirm the importance of side chains L6, L9, W8, and Y13 in the binding of bp1-01 to IGFBP-1. Structural contributions are also suggested by the effects of substitutions at R2 and A3.

In contrast, some substitutions, such as aib substitutions at G4, Q7, E11, K12, and F14, had little or no effect upon binding affinity. Peptides including one or more of these substitutions may nevertheless by useful because non-natural amino acids often confer upon a peptide greater resistance to proteolysis (see Schumacher et al., *Science*, 271: 1854 (1996) and references therein). Such peptides may achieve a longer half-life in serum than those having only natural amino acids.

In view of the results shown in Table XI, it is expected that peptides with a D-alanine substituted at position 2, 3, or 6 of bp1-01 or with an alpha-aminoisobutyrate substituted at position 7, 8, 9, 11, 12, 13, or 14 will increase the availability of IGF-I in an in vitro cell culture assay.

Lastly, the relative affinities of various C-terminal bp1-01 variants were determined by ELISA, as shown in Table XII. These data show that the C-terminal region of the peptide is important for binding. Only peptide bp1-18 (SEQ ID NO:83) retained measurable inhibitory activity for IGF-I:IGFBP-1 binding. It is expected that this peptide will increase the availability of IGF-I in an in vitro cell culture assay.

Taken together, the structure-function data suggest that a smaller, including a non-peptidyl, compound could be designed to mimic the action of the bp1-01 peptide by including elements of the C-terminus of this peptide in combination with the side chains L6, L9, W8, and Y13.

TABLE X

Relative affinities of bp1-01 Ala-scan peptide variants by BIAcore ™

| Variant | IGF-I Inhibition IC50 (mut)/IC50 (wt) | IGF-II Inhibition IC50 (mut)/IC50 (wt) |
|---|---|---|
| C1 | n.d. | n.d. |
| R2A | 0.9 | 0.9 |
| A3 | -1- | -1- |
| G4 | n.d. | n.d. |
| P5 | n.d. | n.d. |
| L6A | 30.3 | 34.7 |
| Q7A | 0.7 | 0.6 |
| W8A | 7.4 | 6.4 |
| L9A | 33.2 | 29.7 |
| C10 | n.d. | n.d. |
| E11A | 2.9 | 2.4 |
| K12A | 7.9 | 5.3 |
| Y13A | 12.5 | 14.6 |
| F14A | 6.2 | 5.8 |
| (wt) | -1- | -1- |

TABLE XI

Relative affinities of bp1-01 non-natural peptide variants by ELISA (a = D-alanine; aib = alpha-aminoisobutyrate)

| Variant | IGF-I Inhibition IC50 (mut)/IC50 (wt) |
|---|---|
| C1 | n.d. |
| R2a | 50 |
| A3a | 34 |
| G4a | 0.6 |
| P5 | n.d. |
| L6a | 400 |
| Q7 aib | 1.6 |
| W8aib | 24 |
| L9aib | 400 |
| C10 | n.d. |
| E11aib | 1.0 |
| K12aib | 2.0 |
| Y13aib | 7.1 |
| F14aib | 3.0 |
| (wt) | -1- |

TABLE XII

Relative affinities of C-terminal bp1-01 variants by ELISA

| Variant name | Peptide seq. | IGF-I Inhibition IC50 (mut)/IC50 (wt) |
|---|---|---|
| bp1-01 | CRAGPLQWLCEKYFG (SEQ ID NO: 15) | -1- |
| bp1-04 | CRAGPLQWLCE (SEQ ID NO: 81) | >1000 |
| bp1-17 | CRAGPLQWLCEK (SEQ ID NO: 82) | >1000 |
| bp1-18 | CRAGPLQWLCEKAA (SEQ ID NO: 83) | 148 |

C. Polyvalent (g8) Selection of bp1-01 Secondary Libraries

NNS codons were used to generate diverse peptide libraries as described in Example 7. Affinity selections were performed by solution binding of phage to biotinylated IGFBP-1 (prepared as described in Example 7) in solution to minimize avidity effects. A similar strategy was used for antibody-phage selections by Hawkins et al., *J. Mol. Biol.*, 226: 889 (1992). For each round of selection, the target amount was reduced to select for enhanced affinity variants. Typically, $10^9$–$10^{10}$ purified phage were preblocked with MPBST (5% skim milk in PBS+0.05% TWEEN™ 20) for 1 hr at room temperature and screened for binding to biotinylated target. Binding conditions are described below. Phage which bound to target were captured by incubating with streptavidin-magnetic beads (Promega Corp., Madison, Wis.) for 2–5 minutes at room temperature. After binding, the beads were washed with PBS-TWEEN™/MPBST ten times before eluting with 0.1 M HCl. The eluate was immediately neutralized with 1/3 volume of 1 M TRIS, pH 8.0. The eluted phage were propagated by infecting XL1 for the next selection cycle. Rounds 1, 2, 3 were carried out with 400 nM, 200 nM, and 20 nM target, respectively, with 1-h incubations. Round 4 was carried out with 4 nM target overnight. All binding reactions were performed at room temperature.

The identified mutations are shown in Table XIII and the relative affinities by ELISA plate assay or BIAcore™ are shown in Table XIV. It can be seen that bp1-10 (SEQ ID NO:84), bp1-11 (SEQ ID NO:85), bp1-12 (SEQ ID NO:86), bp1-13 (SEQ ID NO:87), bp1-15 (SEQ ID NO:89), bp68 (SEQ ID NO:91), bp1027 (SEQ ID NO:92), bp1028 (SEQ ID NO:93), bp1029 (SEQ ID NO:94), and bp1030 (SEQ ID NO:95) are of comparable or higher affinity than bp1-02 and bp1-01, and are thus expected to increase the availability of IGF-I in an in vitro cell culture assay.

TABLE XIII

Mutations identified from polyvalent (g8) bp101 libraries and (no. sequenced)

| Position | Lib. 121(40) | Lib. 122(61) | Lib. 123(93) | Lib. 124 |
|---|---|---|---|---|
| S(-4) | | | | |
| E(-3) | | | | |
| V(-2) | | | | |
| G(-1) | | | E(27); V(13); S(10); T(6); Q(8); L(3); K(5); R(4); M(2); G(6); D(2); A(7) | |
| C1 | | | | |
| R2 | | K(22); R(16); F(4); A(3); | | |
| A3 | | | Y(2); V(2); T(2); N(3); S(3); E(2); D; H E(31); R(13); K(11); S(8); D(5); Q(6); V(5); T(4)G(3); A(4); P(2); I | |
| G4 | G(39); N | | | |
| P5 | P(32); R(3); K; A; S; V; E | | | |
| L6 | L(40) | | | |
| Q7 | | E(20); L(15); Q(7); K(5); R(2); H(5); Y(4); T; F; W | | |
| W8 | W(40) | | | |
| L9 | | L(61) | | |
| C10 | | | | |
| E11 | | E(29); V(11); L(9); D(3); N(2); Q(2); | | E(21); Q(20); K(5); P(4); V(4); L(5); |

TABLE XIII-continued

Mutations identified from polyvalent
(g8) bp101 libraries and (no. sequenced)

| Position | Lib. 121(40) | Lib. 122(61) | Lib. 123(93) | Lib. 124 |
|---|---|---|---|---|
| | | | I(2); M(2); R | R(2); N(2); M; T; D |
| K12 | | | R(31); L(28); M(21); K(8); V(3); I(2) | L(30); R(26); W(5); K(2); M(2); H |
| Y13 | | | Y(65); F(15); M(5); V(3); K(3); H; I | Y(37); F(9); V(6); M(6); I(4); L(3); H |
| F14 | | | | F(56); V(6); S(2); R; Q |

TABLE XIV

Relative affinities of g8 bp1-01 selectants
by ELISA plate assay or BIAcore ™*

| Variant name | Peptide seq. | IGF-I Inhibition IC50 (mut)/IC50 (wt) |
|---|---|---|
| bp1-02 | SEVGCRAGPLQWLCEKYFG (SEQ ID NO: 16) | 0.37 |
| bp1-01 | CRAGPLQWLCEKYFG (SEQ ID NO: 15) | -1- |
| bp1-10 | CRKGPLQWLCELYF (SEQ ID NO: 84) | 1.1* |
| bp1-11 | CRKGPLQWLCEKYF (SEQ ID NO: 85) | 1.9* |
| bp1-12 | CKEGPLQWLCEKYF (SEQ ID NO: 86) | 2.9* |
| bp1-13 | CKEGPLLWLCEKYF (SEQ ID NO: 87) | 2.5* |
| bp1-14 | SEVGCREGPLQWLCEKYF (SEQ ID NO: 88) | 0.26 |
| bp1-15 | CAAGPLQWLCEKYF (SEQ ID NO: 89) | 0.68 |
| bp67 | CRAGPLQWLCERYF (SEQ ID NO: 90) | 0.34 |
| bp68 | CRAGPLQWLCEKFF (SEQ ID NO: 91) | 0.39 |
| bp1027 | CKAGPLLWLCERFF (SEQ ID NO: 92) | 8.8 |
| bp1028 | CRAGPLQWLCERFF (SEQ ID NO: 93) | 4.6 |
| bp1029 | CREGPLQWLCERFF (SEQ ID NO: 94) | 1.7 |
| bp1030 | CKEGPLLWLCERFF (SEQ ID NO: 95) | 4.3 |

D. Monovalent (g3) Selection of bp1-01 Secondary Libraries

Monovalent (g3) selections of bp1-01 secondary libraries were carried out essentially as described in part C above. Templates contained either the TAA stop codon at the targeted sites for randomization or an entirely unrelated binding sequence from bp1-01. Selection conditions were as described below with BSA replacing milk in the blocking buffer. Phage-target complexes were captured by magnetic streptavidin beads (Promega Corp., Madison, Wis.). Biotinylated target was preincubated with phage for 1–3 h at room temperature in each round, with the target concentrations being reduced from 200–500 nM in round 1, to 50–100 nM in round 2, 10–50 nM in round 3, and 1–20 nM in round 4.

The identified mutations are shown in Table XV, and the relative affinities, as determined by BIAcore™ competition assay or by ELISA plate assay (carried out as above, except that 5% acetonitrile was used for peptide solubility) of several peptides selected are shown in Table XVI. bp1-16 (SEQ ID NO:96), a 13-residue version of bp1-01 (lacking the C-terminal Gly), had similar affinity to that of BP1-01. Substitutions at the N-terminus or C-terminus yielded affinity improvements. For example, compared with bp1-16, addition of the STY sequence at the C-terminus yielded about a 3-fold affinity improvement for peptide bp1-21B (SEQ ID NO:100). A similar effect was seen in the context of the 18-mer: namely, a 3-fold improvement was observed between bp1-14 (SEQ ID NO:88) and bp1-21A (SEQ ID NO:99). Substitution of the N-terminal S to G motif also improved affinity by 2- to 3-fold in peptides bp1-19 (SEQ ID NO:97) and bp1-20 (SEQ ID NO:98). All of these peptides had similar or improved apparent affinity for IGFBP-1 as compared with bp1-01 and bp1-02 and are thus expected to increase the availability of IGF-I in an in vitro cell culture assay.

TABLE XV

Mutations identified from
monovalent (g3) bp1-01 libraries

| Position | Lib. 126(22) | Lib. 133(10) | Lib. 135(11) | Lib. 124 |
|---|---|---|---|---|
| S(-4) | | | | E(5); Q(2); D; T; S |
| E(-3) | | | | A(3); K(2); D; E; T; S; Q |
| V(-2) | M(19) | R(9); K(1) | | |
| G(-1) | V(19) | V(5); Q(2); Q(2); S; T; I | | |
| C1 | | | | |
| R2 | | | | |
| A3 | | | | |
| G4 | | | | |
| P5 | | | | |
| L6 | | | | |
| Q7 | | | | |
| W8 | | | | |
| L9 | | | | |
| C10 | | | | |
| E11 | | | | |
| K12 | I(19) | | | |
| Y13 | | | | |
| F14 | | | | |
| 15 | | | | A(3); Q(2); S(2); K; D |
| 16 | | | | T(10) |
| 17 | | | | Y(10) |
| 18 | | | | G(9); T |

TABLE XVI

Relative affinities of g3 bp1-01 selectants
by BIAcore ™ or ELISA plate assay*

| Variant name | Peptide seq. | IGF-I Inhibition IC50 (116)/ IC50 (mut) | IGF-I Inhibition IC50 (114)/ IC50 (mut) |
|---|---|---|---|
| bp1-14 | SEVGCRAGPLQWLCEKYFG-nh2 (SEQ ID NO: 88) | 4.8 | -1- |
| bp1-16 | CRAGPLQWLCEKYF-nh2 (SEQ ID NO: 96) | -1- | 0.21 |
| bp1-19 | SEMVCRAGPLQWLCEIYF-nh2* (SEQ ID NO: 97) | 9.9 | 2.1 |
| bp1-20 | EARVCRAGPLQWLCEKYF-nh2 (SEQ ID NO: 98) | 12 | 2.6 |
| bp1-21A | SEVGCRAGPLQWLCEKYFSTY-nh2 (SEQ ID NO: 99) | 15 | 3.2 |
| bp1-21B | CRAGPLQWLCEKYFSTY-nh2 (SEQ ID NO: 100) | 3.1 | 0.67 |

Example 13

Relative Affinity of IGFBP-3 Binding Peptide Variants

The relative affinities of various bp3-01-ox variants were measured by the BIAcore™ competition assay. The results are shown in Table XVII. It can be seen that 4d3.3 (SEQ ID NO:101), bp3-30 (SEQ ID NO:102), bp3-41 (SEQ ID NO:103), bp3-40 (SEQ ID NO:10), bp3-39 (SEQ ID NO:10), bp3-28 (SEQ ID NO:104), bp3-27 (SEQ ID NO:105), and bp3-25 (SEQ ID NO:106), have affinities similar to or greater than that of bp3-01-ox and are expected to increase the availability of IGF-I in an in vitro cell culture assay. The lack of measurable activity for peptide bp3-24 (SEQ ID NO:107) indicates the critical role that the intact disulfide plays in maintaining a peptide conformation favorable for binding to IGFBP-3 for this series of peptides.

TABLE XVII

Relative affinities of bp3-01-ox variants by BIAcore™ competition assay

| Variant name | Peptide sequence | IGF-I Inhibition | |
|---|---|---|---|
| | | IC50 (uM) | IC50 (mut)/ IC50 (wt) |
| 4d3.3 | ASEEVCWPVAEWYLCNMWGR (SEQ ID NO: 101) | 5.6 | 2.8 |
| bp3-30 | ASEEVCWPVAEWYLCN (SEQ ID NO: 102) | 5.6 | 2.8 |
| bp3-41 | GPETCWPVAEWYLCN (SEQ ID NO: 103) | 4.0 | 2.0 |
| bp3-01-ox | SEEVCWPVAEWYLCNMWG (SEQ ID NO: 9) | 2.0 | -1- |
| bp3-40 | ac-SEEVCWPVAEWYLCN-nh2 (SEQ ID NO: 10) | 0.66 | 0.33 |
| bp3-39 | SEEVCWPVAEWYLCN-nh2 (SEQ ID NO: 10) | 0.66 | 0.33 |
| bp3-15 | SEEVCWPVAEWYLCN (SEQ ID NO: 10) | 0.72 | 0.36 |
| bp3-28 | EEVCWPVAEWYLCN (SEQ ID NO: 104) | 5.4 | 2.7 |
| bp3-27 | EVCWPVAEWYLCN (SEQ ID NO: 105) | 2.8 | 1.4 |
| bp3-25 | CWPVAEWYLCN (SEQ ID NO: 106) | 46 | 23 |

TABLE XVII-continued

Relative affinities of bp3-01-ox variants by BIAcore™ competition assay

| Variant name | Peptide sequence | IGF-I Inhibition | |
|---|---|---|---|
| | | IC50 (uM) | IC50 (mut)/ IC50 (wt) |
| bp3-24 | WPVAEWYLCN (SEQ ID NO: 107) | >1000 | >500 |

Example 14

Screening of Additional Libraries for Binding to IGFBP-3

Additional polyvalent (g8) peptide-phage libraries were desgined and sorted that yielded two peptides that inhibited IGFBP-3 binding to IGF-I. The results, shown in Table XVIII, indicate that bp3-107 (SEQ ID NO:108) and bp3-108 (SEQ ID NO:109) are inhibitors and they are expected to increase the availability of IGF-I in an in vitro cell culture assay.

TABLE XVIII

Peptide inhibition of IGFBP-3 binding to IGF-I by BIAcore competition

| Peptide | Phage parent | Sequence | IC50 (uM) |
|---|---|---|---|
| bp3-107 | t4H3.6 | suc-CQLVRPDLLLCQ-nh2 (SEQ ID NO: 108) | 100 |
| bp3-108 | t4H3.9 | suc-IPVSPDWFVCQ-nh2 (SEQ ID NO: 109) | 20 |

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

What is claimed is:

1. A method for determining the amount in a biological fluid of IGFBP that binds a peptide comprising an amino acid sequence that is SEQ ID NO: 15 or SEQ ID NO: 16, which comprises:
   (a) contacting the fluid with
      1) a first antibody attached to a solid-phase carrier, wherein the first antibody binds epitopes on the IGFBP such that in the presence of the antibody the IGF binding sites remain available on the IGFBP for binding to the peptide, thereby forming a complex between the first antibody and the IGFBP, and
      2) a concentration of the peptide for a period of time sufficient to saturate all available IGF binding sites on the IGFBP, thereby forming a saturated complex;
   (b) removing the unbound peptide;
   (c) contacting the saturated complex with a detectably labeled second antibody which binds epitopes on the peptide which are available for binding when the peptide is bound to the IGFBP;
   (d) removing the unbound second antibody; and
   (e) quantitatively analyzing the amount of the labeled second antibody bound as a measure of the amount of IGFBP in the biological fluid.

2. The method of claim 1 wherein the peptide comprises an amino acid sequence that is SEQ ID NO:15.

3. The method of claim 1 wherein the peptide comprises an amino acid sequence that is SEQ ID NO:16.

4. The method of claim 1 wherein the IGF binding protein is IGFBP-1.

* * * * *

UNITED STATES PATENT AND TRADEMARK OFFICE
CERTIFICATE OF CORRECTION

PATENT NO.   : 6,645,775 B1
DATED        : November 11, 2003
INVENTOR(S)  : Clark et al.

It is certified that error appears in the above-identified patent and that said Letters Patent is hereby corrected as shown below:

Column 72,
Lines 46 and 49, delete "FIG. 42" and insert -- FIG. 41 --

Column 73,
Line 32, delete "FIG. 43" and insert -- FIG. 42 --
Line 36, delete "FIG. 44" and insert -- FIG. 43 --
Line 42, delete "FIG. 45" and insert -- FIG. 44 --
Line 47, delete "FIG. 43 and FIG. 44" and insert -- FIG. 42 and FIG. 43 --

Signed and Sealed this

Twenty-sixth Day of October, 2004

JON W. DUDAS
*Director of the United States Patent and Trademark Office*